United States Patent [19]
Iwaki et al.

[11] Patent Number: 5,385,692
[45] Date of Patent: Jan. 31, 1995

[54] MESOMORPHIC COMPOUND, LIQUID CRYSTAL COMPOSITION, LIQUID CRYSTAL DEVICE, DISPLAY APPARATUS AND DISPLAY METHOD

[75] Inventors: Takashi Iwaki; Takao Takiguchi, both of Tokyo; Takeshi Togano, Yokohama; Yoko Yamada, Isehara; Shinichi Nakamura, Hadano, all of Japan

[73] Assignee: Canon Kabushiki Kaisha, Tokyo, Japan

[21] Appl. No.: 225,344

[22] Filed: Apr. 8, 1994

Related U.S. Application Data

[63] Continuation of Ser. No. 975,108, Nov. 12, 1992, abandoned.

[30] Foreign Application Priority Data

Nov. 12, 1991 [JP] Japan ................. 2-95684
Oct. 30, 1992 [JP] Japan ................. 3-16329

[51] Int. Cl.⁶ ......................... C09K 19/32; C09K 19/34
[52] U.S. Cl. ......................... 252/299.62; 252/299.61
[58] Field of Search ................. 252/299.62, 299.61

[56] References Cited

U.S. PATENT DOCUMENTS

| | | | |
|---|---|---|---|
| 4,367,924 | 1/1983 | Clark et al. | 359/56 X |
| 4,680,137 | 7/1987 | Isoyama et al. | 252/299.62 |
| 4,853,149 | 8/1989 | Krause et al. | 252/299.61 |
| 5,034,151 | 7/1991 | Shinjo et al. | 252/299.61 |
| 5,075,030 | 12/1991 | Togano et al. | 252/299.61 |
| 5,076,961 | 12/1991 | Nakamura et al. | 252/299.61 |
| 5,091,109 | 2/1992 | Takiguchi et al. | 252/299.61 |
| 5,116,530 | 5/1992 | Togano et al. | 252/299.61 |
| 5,118,441 | 6/1992 | Mori et al. | 252/299.61 |
| 5,236,619 | 8/1993 | Iwaki et al. | 252/299.61 |
| 5,244,596 | 9/1993 | Takiguchi et al. | 252/299.61 |

FOREIGN PATENT DOCUMENTS

| | | |
|---|---|---|
| 0184012 | 6/1986 | European Pat. Off. . |
| 079647 | 6/1981 | Japan . |
| 79647 | 6/1981 | Japan . |
| 83448 | 7/1981 | Japan . |
| 083448 | 7/1981 | Japan . |
| 107216 | 8/1981 | Japan . |
| 069055 | 4/1985 | Japan . |
| 69055 | 4/1985 | Japan . |
| 181247 | 8/1987 | Japan . |
| 195355 | 8/1987 | Japan . |
| 403122189 | 5/1991 | Japan . |

OTHER PUBLICATIONS

Applied Physics Letters, vol. 18, No. 4 (1971) 127:28.

*Primary Examiner*—Robert L. Stoll
*Assistant Examiner*—C. Harris
*Attorney, Agent, or Firm*—Fitzpatrick, Cella, Harper & Scinto

[57] ABSTRACT

A mesomorphic compound of the formula (I) according to claim 1 is suitable as a component for liquid crystal composition providing improved response characteristics.

36 Claims, 4 Drawing Sheets

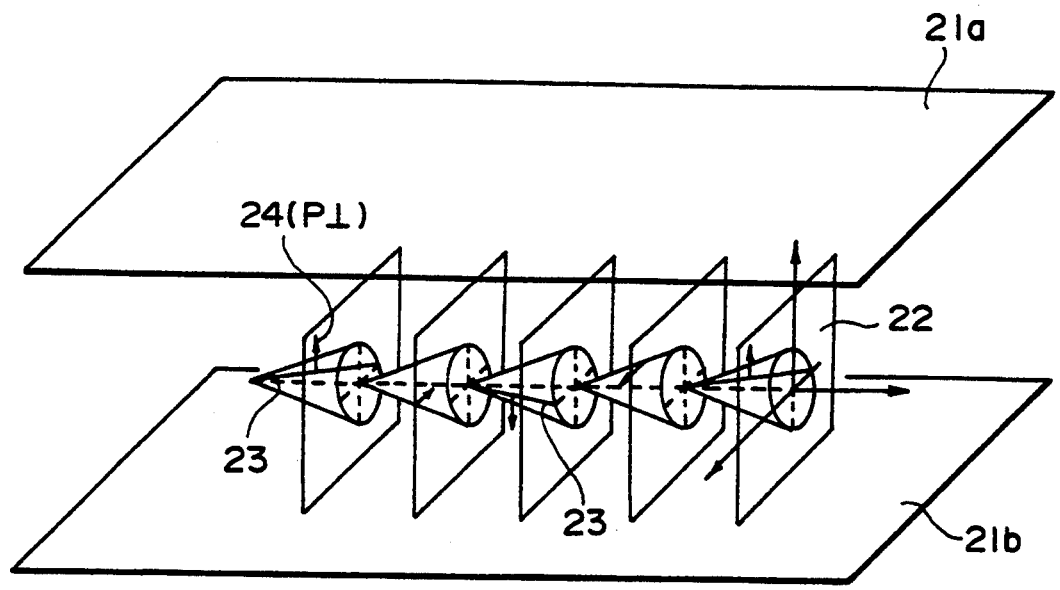
F I G. 2
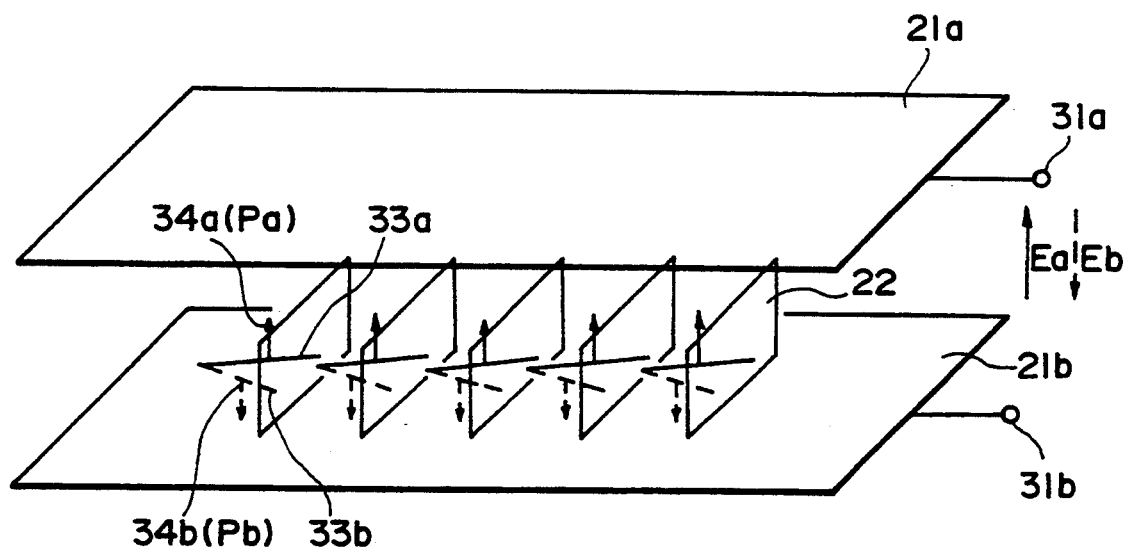
F I G. 3

MESOMORPHIC COMPOUND, LIQUID CRYSTAL COMPOSITION, LIQUID CRYSTAL DEVICE, DISPLAY APPARATUS AND DISPLAY METHOD

This application is a continuation of application Ser. No. 07/975,108, filed Nov. 12, 1992, now abandoned.

FIELD OF THE INVENTION AND RELATED ART

The present invention relates to a mesomorphic compound, a liquid crystal composition, a liquid crystal device, a display apparatus and a display method, and more particularly to a mesomorphic compound, a liquid crystal composition containing the mesomorphic compound with improved responsiveness to an electric field, a liquid crystal device using the liquid crystal composition for use in a display device, a liquid crystal-optical shutter, etc., a display apparatus using the device, and a display method of using the composition and device.

Hitherto, liquid crystal devices have been used as an electro-optical device in various fields. Most liquid crystal devices which have been put into practice use TN (twisted nematic) type liquid crystals, as shown in "Voltage-Dependent Optical Activity of a Twisted Nematic Liquid Crystal" by M. Schadt and W. Helfrich "Applied Physics Letters" Vol. 18, No. 4 (Feb. 15, 1971) pp. 127–128.

These devices are based on the dielectric alignment effect of a liquid crystal and utilize an effect that the average molecular axis direction is directed to a specific direction in response to an applied electric field because of the dielectric anisotropy of liquid crystal molecules. It is said that the limit of response speed is on the order of $\mu$sec, which is too slow for many uses. On the other hand, a simple matrix system of driving is most promising for application to a large-area flat display in view of cost, productivity, etc., in combination. In the simple matrix system, an electrode arrangement wherein scanning electrodes and signal electrodes are arranged in a matrix, and for driving, a multiplex driving scheme is adopted wherein an address signal is sequentially, periodically and selectively applied to the scanning electrodes and prescribed data signals are selectively applied in parallel to the signal electrodes in synchronism with the address signal.

When the above-mentioned TN-type liquid crystal is used in a device of such a driving system, a certain electric field is applied to regions where a scanning electrode is selected and signal electrodes are not selected (or regions where a scanning electrode is not selected and a signal electrode is selected), which regions are called "half-selected points". If the difference between a voltage applied to the selected points and a voltage applied to the half-selected points is sufficiently large, and a voltage threshold level required for allowing liquid crystal molecules to be aligned or oriented perpendicular to an electric field is set to a value therebetween, display devices normally operate. However, in fact, as the number (N) of scanning lines increases, a time (duty ratio) during which an effective electric field is applied to one selected point when a whole image area (corresponding to one frame) is scanned decreases with a ratio of 1/N. Accordingly, the larger the number of scanning lines are, the smaller is the voltage difference of an effective value applied to a selected point and non-selected points when scanning is repeatedly effected. This leads to unavoidable drawbacks of lowering of image contrast or occurrence of interference or crosstalk. These phenomena are regarded as essentially unavoidable problems appearing when a liquid crystal having no bistability (i.e. liquid crystal molecules are horizontally oriented with respect to the electrode surface as stable state and is vertically oriented with respect to the electrode surface only when an electric field is effectively applied) is driven (i.e. repeatedly scanned) by making use of a time storage effect. To overcome these drawbacks, the voltage averaging method, the two-frequency driving method, the multiple matrix method, etc. has been already proposed.. However, any method is not sufficient to overcome the above-mentioned drawbacks. As a result, the development of large image area or high packaging density in respect to display elements is delayed because it is difficult to sufficiently increase the number of scanning lines.

To overcome drawbacks with such prior art liquid crystal devices, the use of liquid crystal devices having bistability has been proposed by Clark and Lagerwall (e.g. Japanese Laid-Open Patent Appln. No. 56-107216; U.S. Pat. No. 4,367,924, etc.). In this instance, as the liquid crystals having bistability, ferroelectric liquid crystals having chiral smectic C-phase (SmC*) or H-phase (SmH*) are generally used. These liquid crystals have bistable states of first and second stable states with respect to an electric field applied thereto. Accordingly, as different from optical modulation devices in which the above-mentioned TN-type liquid crystals are used, the bistable liquid crystal molecules are oriented to first and second optically stable states with respect to one and the other electric field vectors, respectively. Further, this type of liquid crystal has a property (bistability) of assuming either one of the two stable states in response to an applied electric and retaining the resultant state in the absence of an electric field.

In addition to the above-described characteristic of showing bistability, such a ferroelectric liquid crystal (hereinafter sometimes abbreviated as "FLC") has an excellent property, i.e., a high-speed responsiveness. This is because the spontaneous polarization of the ferroelectric liquid crystal and an applied electric field directly interact with each other to induce transition of orientation states. The resultant response speed is faster than the response speed due to the interaction between dielectric anisotropy and an electric field by 3 to 4 digits.

Thus, a ferroelectric liquid crystal potentially has very excellent characteristics, and by making use of these properties, it is possible to provide essential improvements to many of the above-mentioned problems with the conventional TN-type devices. Particularly, the application to a high-speed optical shutter and a display of a high density and a large picture is expected. For this reason, there has been made extensive research with respect to liquid crystal materials showing ferroelectricity. However, previous ferroelectric liquid crystal materials do not sufficiently satisfy characteristics required for a liquid crystal device including low-temperature operation characteristic, high-speed responsiveness, etc. Among a response time $\gamma$, the magnitude of spontaneous polarization Ps and viscosity $\eta$, the following relationship exists: $\gamma = \eta/(Ps \cdot E)$, where E is an applied voltage. Accordingly, a high response speed can be obtained by (a) increasing the spontaneous polarization Ps, (b) lowering the viscosity $\eta$, or (c) increasing the applied voltage E. However, the driving voltage has a certain upper limit in view of driving with IC, etc., and should desirably be as low as possible. Accordingly, it is actually necessary to lower the viscosity or increase the spontaneous polarization.

A ferroelectric chiral smectic liquid crystal having a large spontaneous polarization generally provides a large internal electric field in a cell given by the spontaneous polarization and is liable to pose many constraints on the device construction giving bistability. Further, an excessively large spontaneous polarization is liable to accompany an increase in viscosity, so that remarkable increase in response speed may not be attained as a result.

Moreover, if it is assumed that the operation temperature of an actual display device is 5°-40° C., the response speed changes by a factor of about 20, so that it actually exceeds the range controllable by driving voltage and frequency.

Thus, as described hereinabove, commercialization of a ferroelectric liquid crystal device requires a liquid crystal composition assuming a chiral smectic phase which has a high-speed responsiveness and a small temperature-dependence of response speed.

In order to afford uniform switching characteristics at display, a good view-angle characteristic, a good storage stability at a low temperature, a decrease in a load to a driving IC (integrated circuit), etc. to the above-mentioned ferroelectric liquid crystal device or a display apparatus including the ferroelectric liquid crystal device, the above-mentioned liquid crystal composition is required to optimize its properties such as spontaneous polarization, an chiral smectic C (SmC*) pitch, a cholesteric (Ch) pitch, a temperature range showing a mesomorphic phase, optical anisotropy, a tilt angle and dielectric anisotropy.

SUMMARY OF THE INVENTION

An object of the present invention is to provide a mesomorphic compound, a liquid crystal composition, particularly a chiral smectic liquid crystal composition containing the mesomorphic compound for providing a practical ferroelectric liquid crystal device as described above, a liquid crystal device including the liquid crystal composition, a display apparatus including the device, and a display method of using the composition and device.

According to the present invention, there is provided a mesomorphic compound represented by the following formula (I):

$$R_1-A_1-X_1-A_2-X_2-A_3-R_2 \qquad (I),$$

wherein $R_1$ and $R_2$ independently denote hydrogen, halogen,

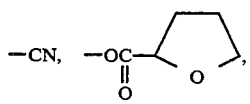

or a linear or branched alkyl group having 1-18 carbon atoms capable of including one or non-neighboring two or more —CH$_2$— groups which can be replaced with

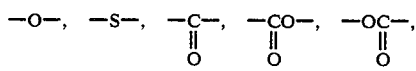

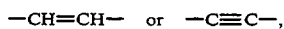

said linear or branched alkyl group being capable of including hydrogen which can be replaced with fluorine;

$X_1$ and $X_2$ independently denote a single bond,

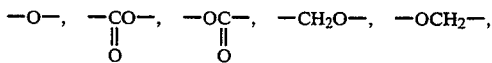

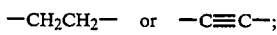

$A_1$, $A_2$ and $A_3$ independently denote a single bond

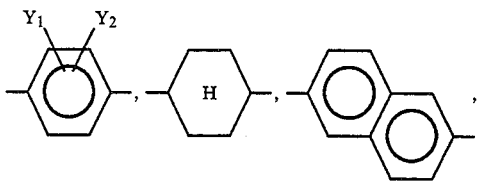

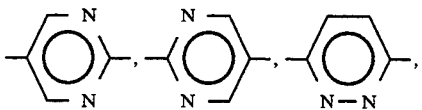

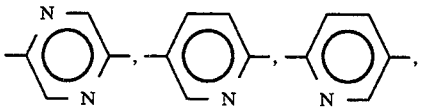

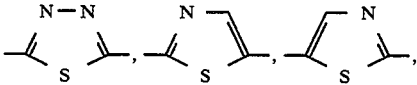

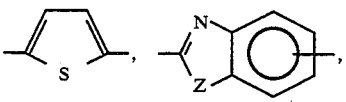

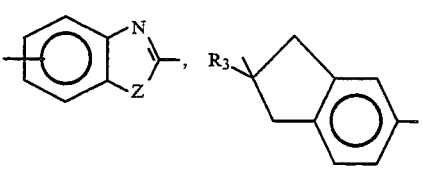

or

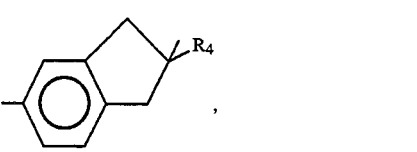

wherein $R_3$ and $R_4$ independently denote hydrogen, halogen, —CN or a linear or branched alkyl group having 1-18 carbon atoms capable of including one or non-neighboring two or more —CH$_2$— groups which can be replaced with

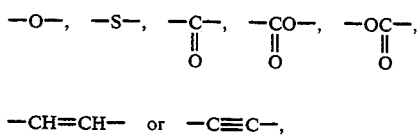

—CH=CH— or —C≡C—, said linear or branched alkyl group being capable of including hydrogen which can be replaced with fluorine; $Y_1$ and $Y_2$ independently denote, H, F, Cl, Br, —$CH_3$, —$CF_3$ or —CN; Z denotes O or S; and at least one of $A_1$, $A_2$ and $A_3$ is

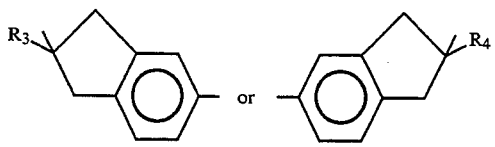

and the remaining two of $A_1$, $A_2$ and $A_3$ cannot be a single bond simultaneously; and with the proviso that:

(i) —$A_1$—$X_1$—$A_2$—$X_2$—$A_3$— is not

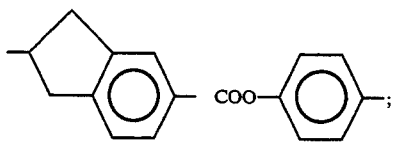

(ii) $X_1$ and $X_2$ are not an ester group simultaneously when $A_1$ is

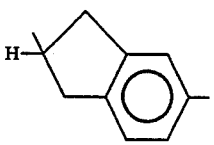

and $A_2$ and $A_3$ are

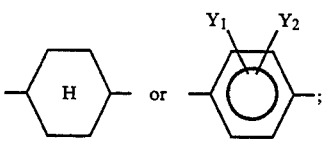

and (iii) $X_1$ and $X_2$ are not an ester group simultaneously when $A_3$ is

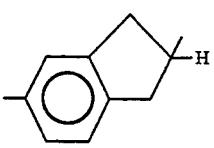

and $A_1$ and $A_2$ are

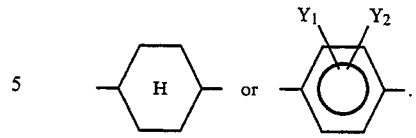

According to the present invention, there is further provided a liquid crystal composition containing at least one species of the above-mentioned mesomorphic compounds.

The present invention provides a liquid crystal device comprising a pair of electrode plates and the liquid crystal composition described above disposed between the electrode plates.

The present invention further provides a display apparatus comprising the liquid crystal device, and voltage application means for driving the liquid crystal device.

The present invention still further provides a display method using the liquid crystal composition or the liquid crystal device described above and switching the alignment direction of liquid crystal molecules by applying voltages to the liquid crystal composition to effect display.

We have found that a mesomorphic compound represented by the formula (I) having an indan skeleton is suitable as a component of a ferroelectric chiral smectic liquid crystal composition and a liquid crystal device including the liquid crystal composition which provide good display characteristics based on improvements in various characteristics such as an alignment characteristic, high speed responsiveness, and a temperature-dependence of response speed. As the mesomorphic compound of the formula (I) according to the present invention has a good compatibility with another mesomorphic compound used herein, it is possible to use the mesomorphic compound of the formula (I) for controlling properties such as spontaneous polarization, SmC* pitch, Ch pitch, a temperature range showing a mesomorphic phase, optical anisotropy, a tilt angle and dielectric anisotropy, as a liquid crystal mixture or composition.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIGS. 2 and 3 are schematic perspective views of a device cell embodiment for illustrating the operation principle of a liquid crystal device utilizing ferroelectricity of a liquid crystal composition;

Figure 1:
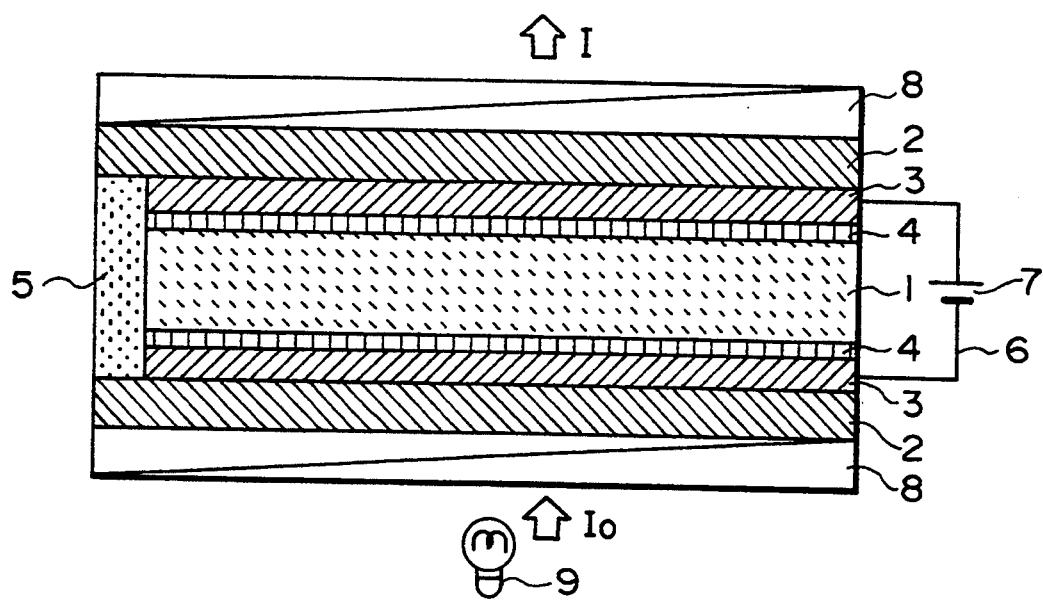
FIG. 1 is a schematic sectional view of a liquid crystal display device using a liquid crystal composition assuming a chiral smectic phase.

DETAILED DESCRIPTION OF THE INVENTION
Preferred examples-of the mesomorphic compound of the formula (I) may include those of the following formulas (Ia) to (It):
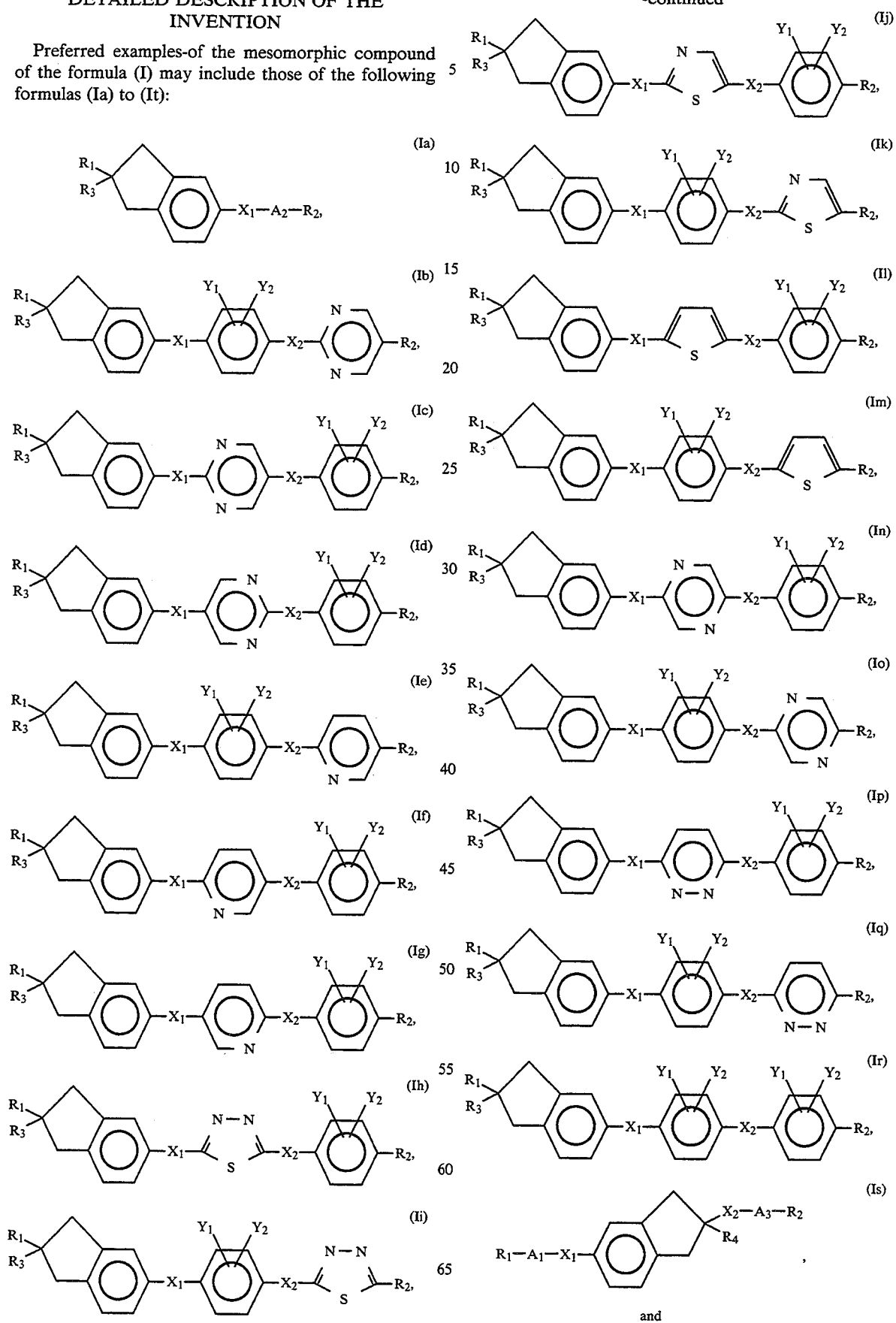
and

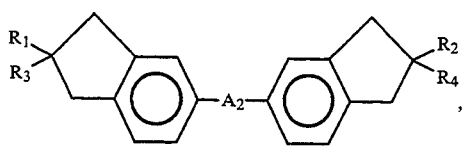 (It)

wherein $R_1$ and $R_2$ independently denote hydrogen, halogen,

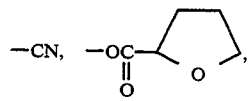

or a linear or branched alkyl group having 1–18 carbon atoms capable of including one or non-neighboring two or more —$CH_2$— groups which can be replaced with

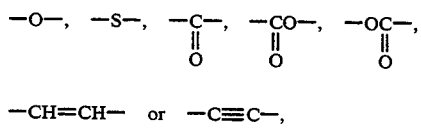

—CH=CH— or —C≡C—, said linear or branched alkyl group being capable of including hydrogen which can be replaced with fluorine;

$X_1$ and $X_2$ independently denote a single bond,

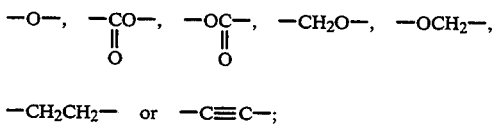

—$CH_2CH_2$— or —C≡C—;

$A_1$, $A_2$ and $A_3$ independently denote a single bond

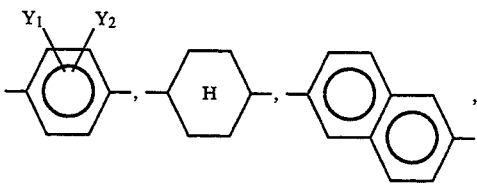

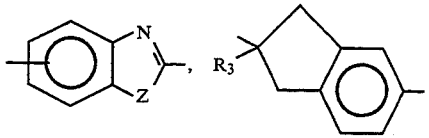

or

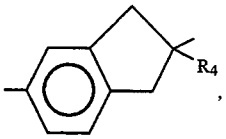

wherein $R_3$ and $R_4$ independently denote hydrogen, halogen, —CN or a linear or branched alkyl group having 1–18 carbon atoms capable of including one or non-neighboring two or more —$CH_2$— groups which can be replaced with

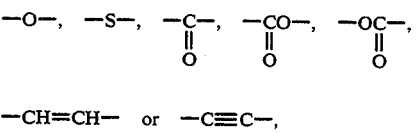

—CH=CH— or —C≡C—, said linear or branched alkyl group being capable of including hydrogen which can be replaced with fluorine; $Y_1$ and $Y_2$ independently denote, H, F, Cl, Br, —$CH_3$, —$CF_3$ or —CN; Z denotes O or S; and at least one of $A_1$, $A_2$ and $A_3$ is

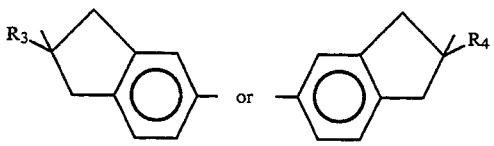

and the remaining two of $A_1$, $A_2$ and $A_3$ cannot be a single bond simultaneously; and
with the proviso that:
(i) —$A_1$—$X_1$—$A_2$—$X_2$—$A_3$— is not

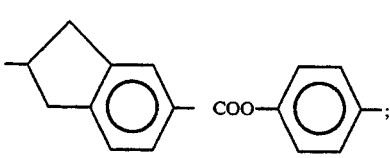

(ii) $X_1$ and $X_2$ are not an ester group simultaneously when $A_1$ is

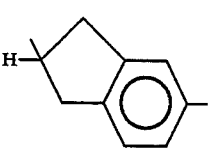

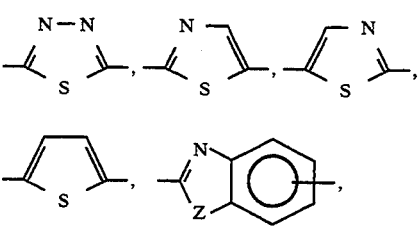

and $A_2$ and $A_3$ are

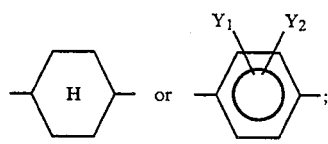
and
(iii) $X_1$ and $X_2$ are not an ester group simultaneously when $A_3$ is
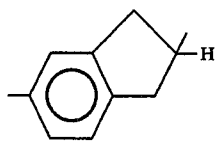
and $A_1$ and $A_2$ are
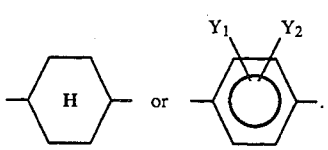
Further preferred examples of the mesomorphic compound of the formula (I) may include those of the following formulas (Iaa) to (Itg):
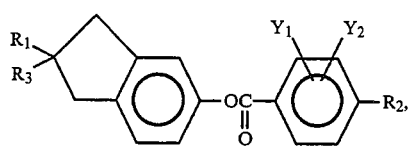 (Iaa)
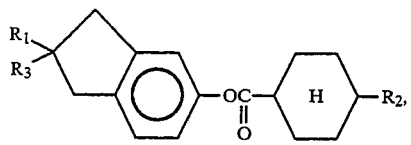 (Iab)
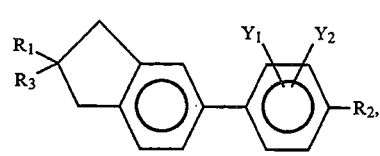 (Iac)
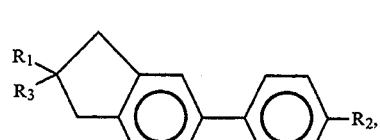 (Iad)
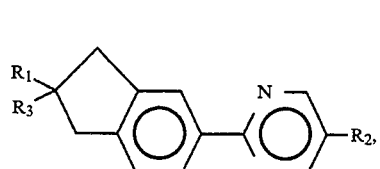 (Iae)
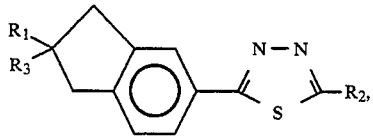 (Iaf)
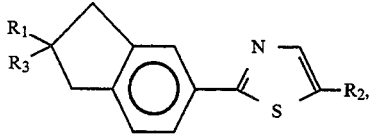 (Iag)
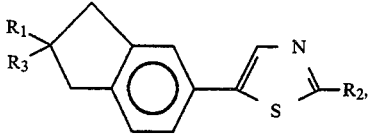 (Iah)
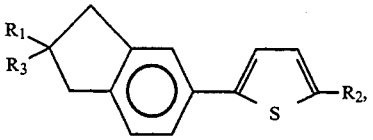 (Iai)
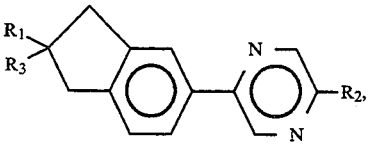 (Iaj)
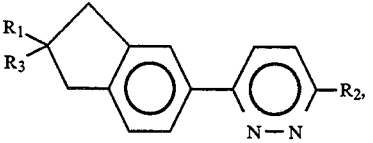 (Iak)
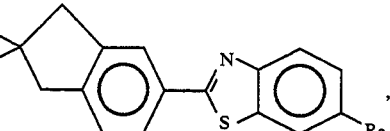 (Ial)
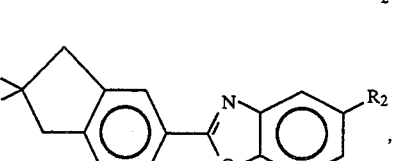 (Iam)
 (Ian)
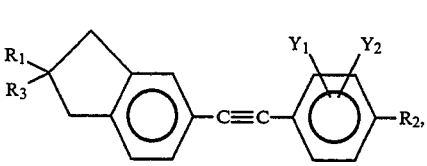 (Iao)

-continued
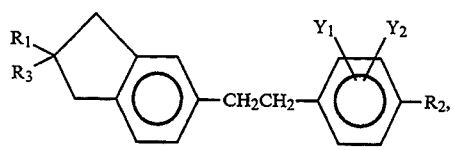 (Iap)
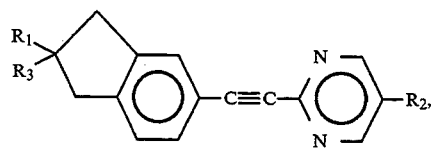 (Iaq)
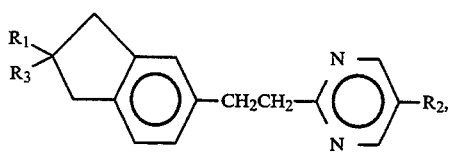 (Iar)
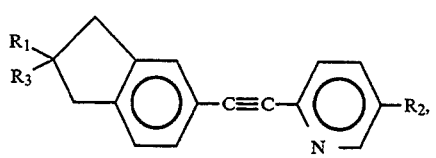 (Ias)
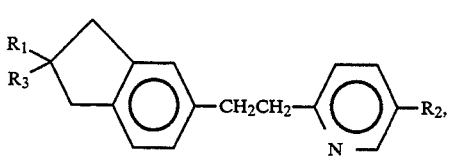 (Iat)
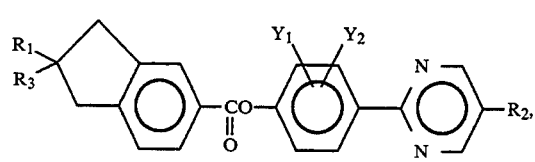 (Iba)
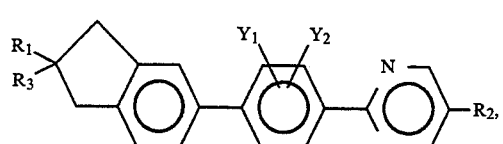 (Ibb)
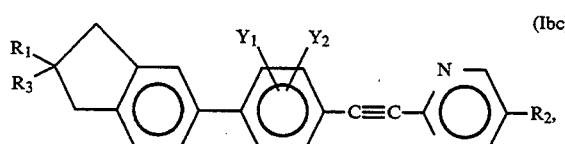 (Ibc)
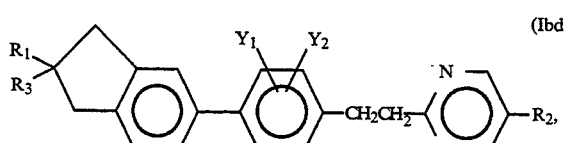 (Ibd)
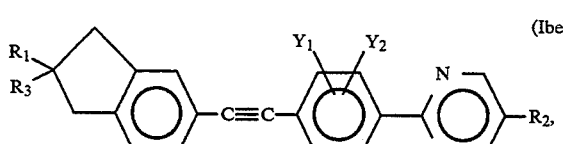 (Ibe)
-continued
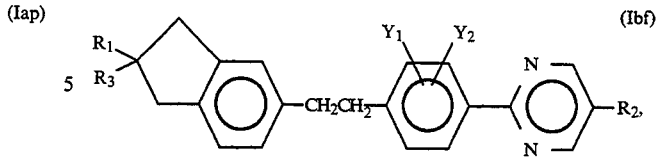 (Ibf)
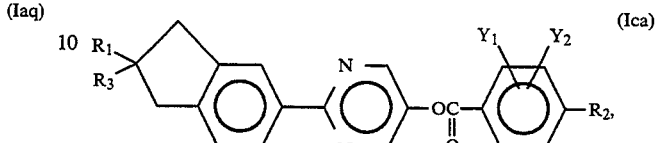 (Ica)
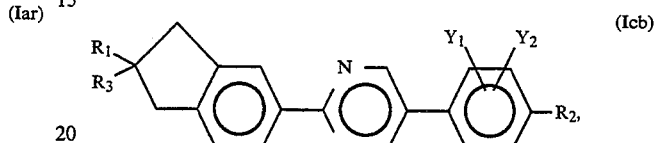 (Icb)
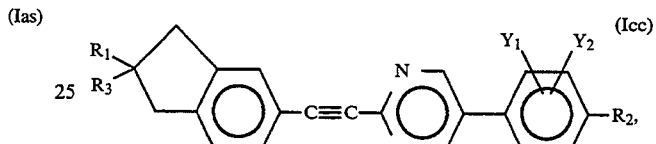 (Icc)
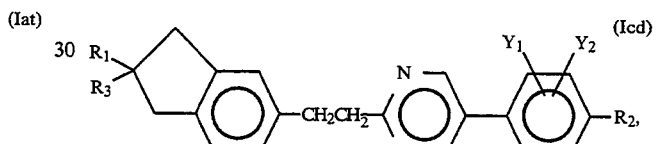 (Icd)
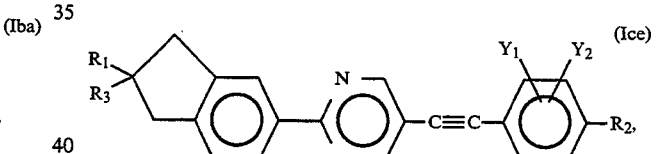 (Ice)
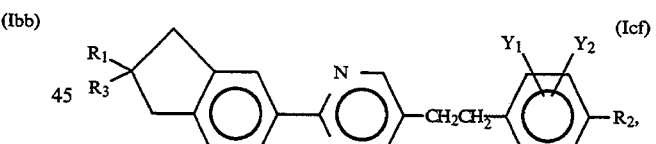 (Icf)
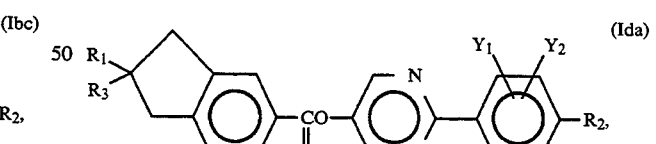 (Ida)
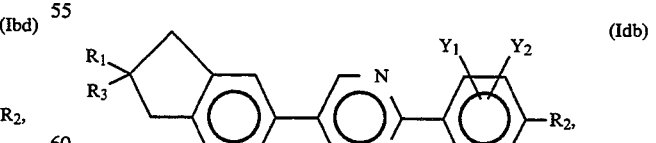 (Idb)
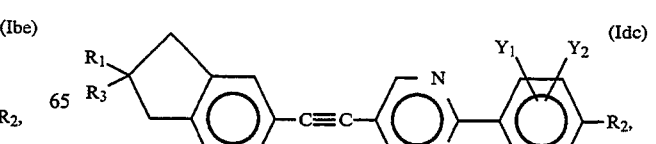 (Idc)

-continued
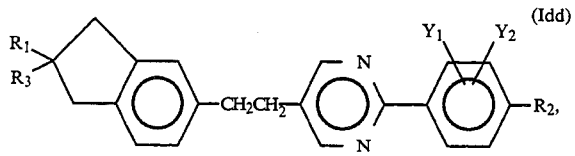 (Idd)
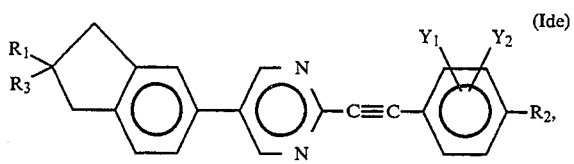 (Ide)
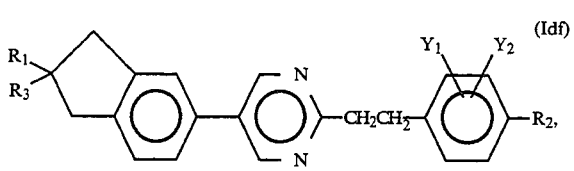 (Idf)
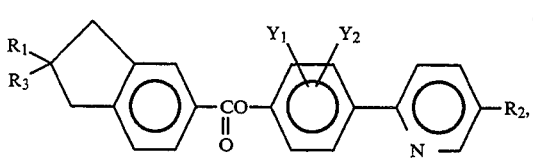 (Iea)
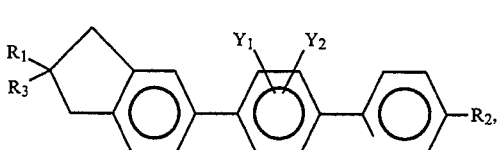 (Ieb)
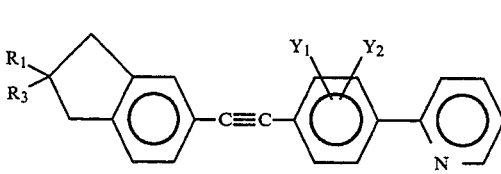 (Iec)
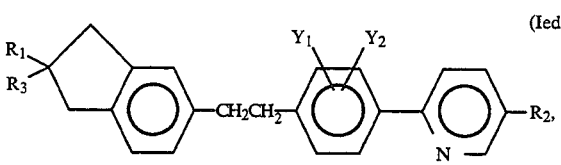 (Ied)
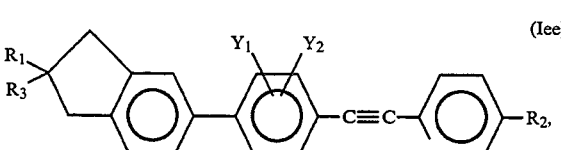 (Iee)
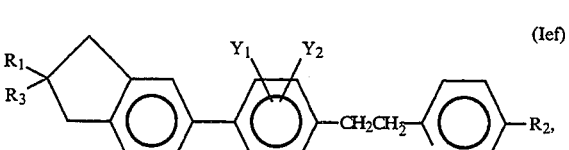 (Ief)
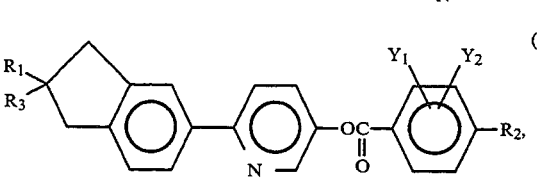 (Ifa)
-continued
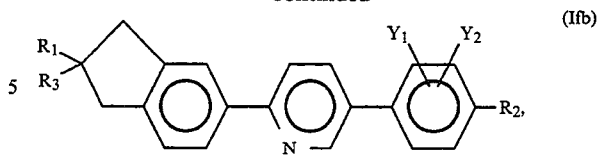 (Ifb)
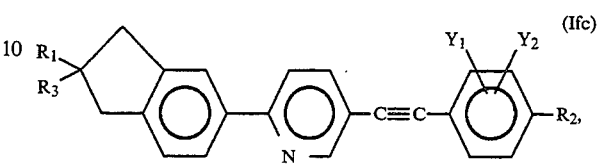 (Ifc)
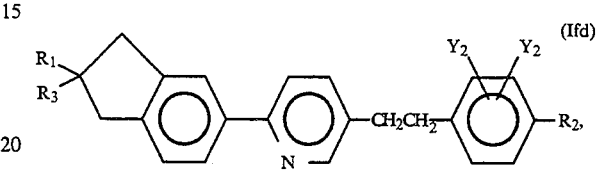 (Ifd)
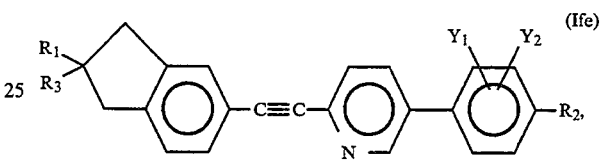 (Ife)
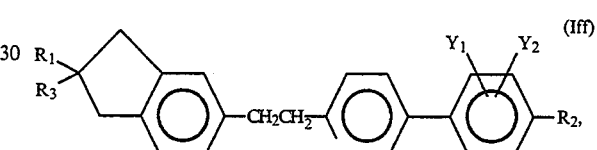 (Iff)
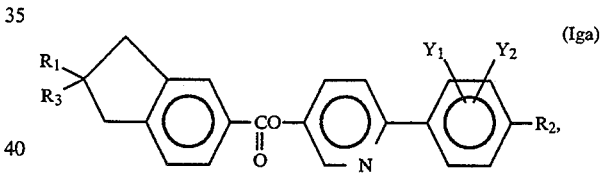 (Iga)
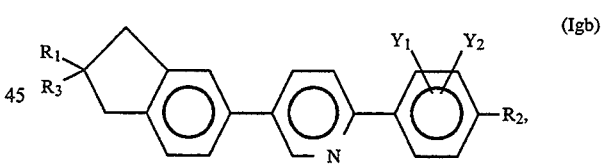 (Igb)
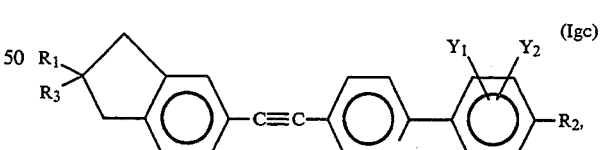 (Igc)
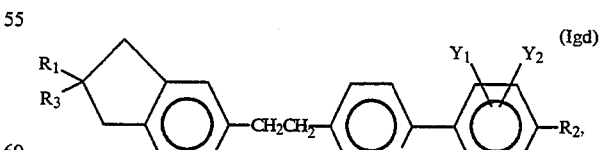 (Igd)
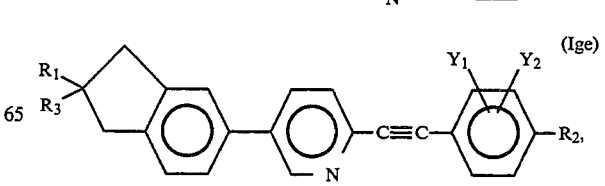 (Ige)

-continued
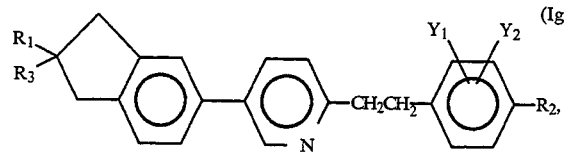 (Igf)
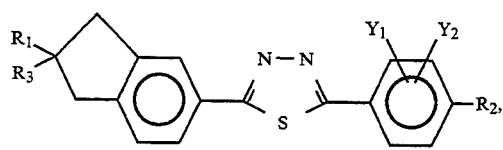 (Iha)
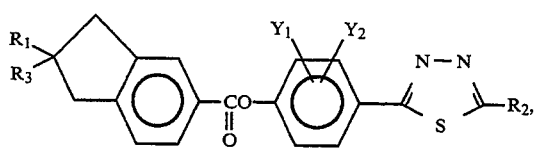 (Iia)
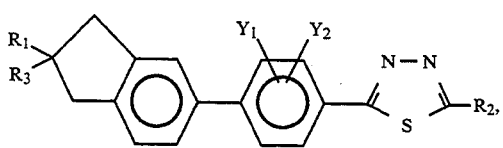 (Iib)
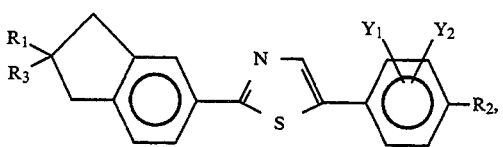 (Ija)
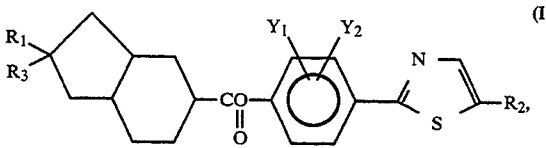 (Ika)
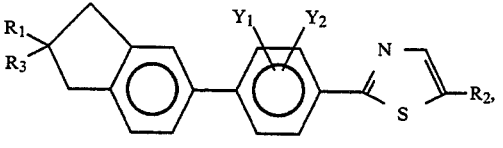 (Ikb)
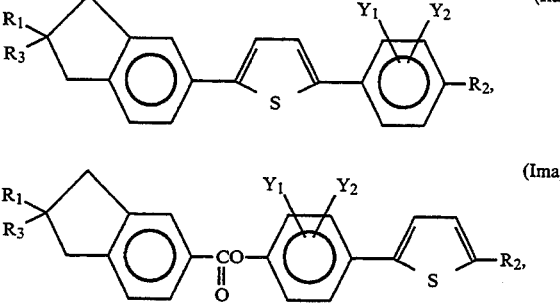 (Ila) (Ima)
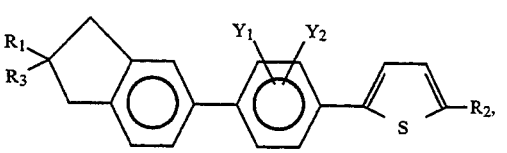 (Imb)
-continued
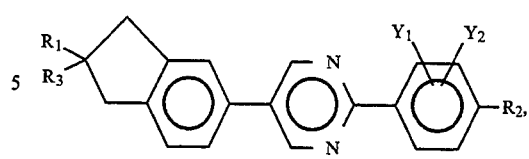 (Ina)
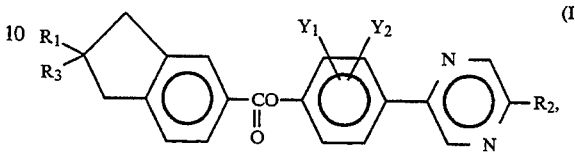 (Ioa)
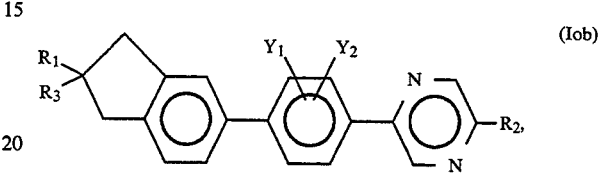 (Iob)
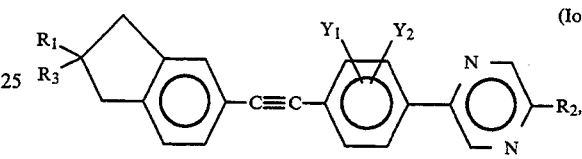 (Ioc)
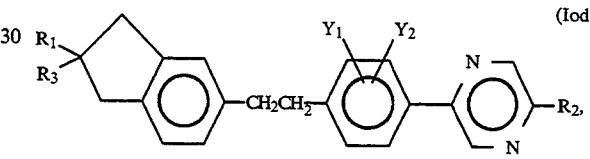 (Iod)
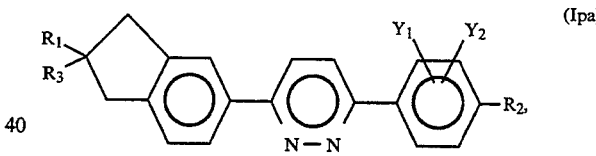 (Ipa)
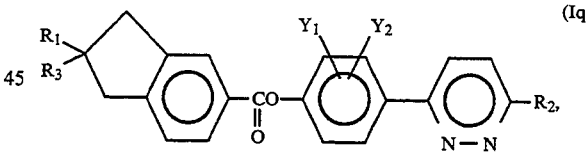 (Iqa)
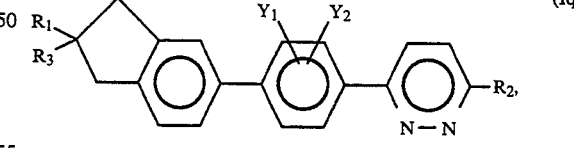 (Iqb)
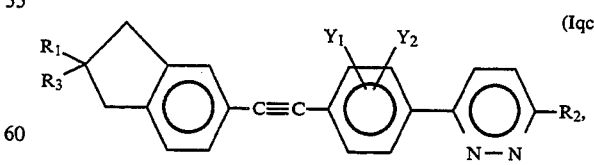 (Iqc)
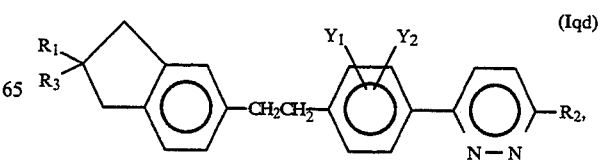 (Iqd)

-continued
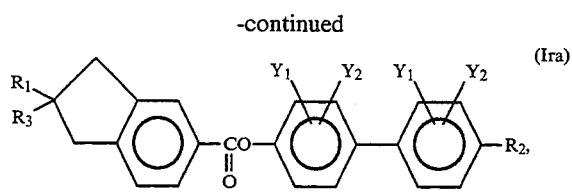 (Ira)
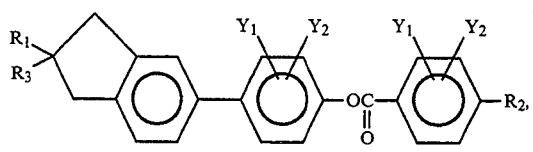 (Irb)
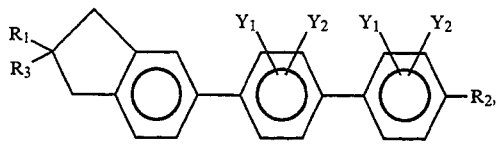 (Irc)
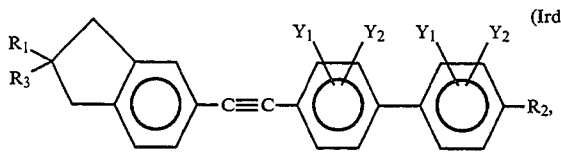 (Ird)
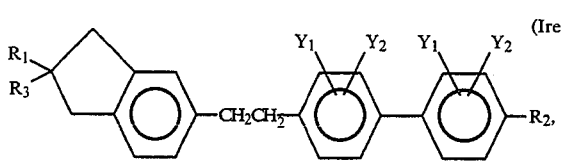 (Ire)
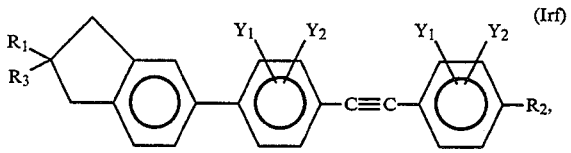 (Irf)
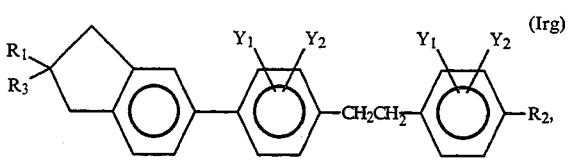 (Irg)
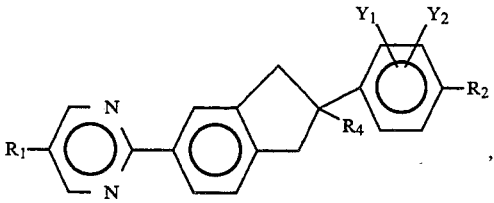 (Isa)
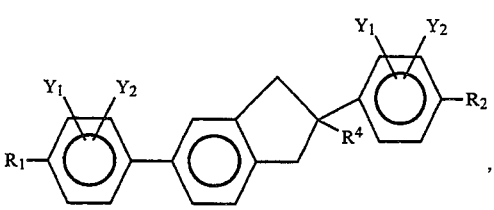 (Isb)
-continued
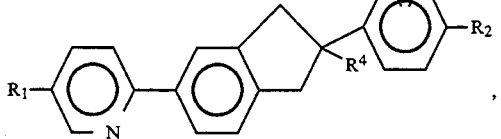 (Isc)
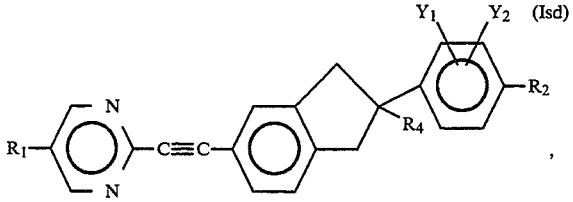 (Isd)
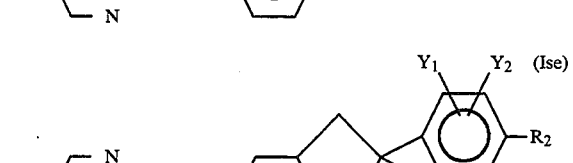 (Ise)
 (Ita)
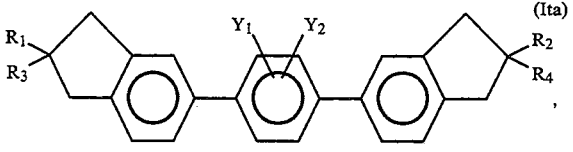 (Itb)
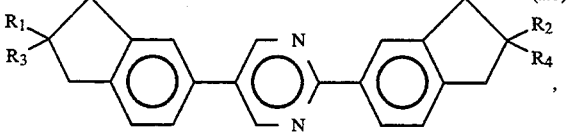 (Itc)
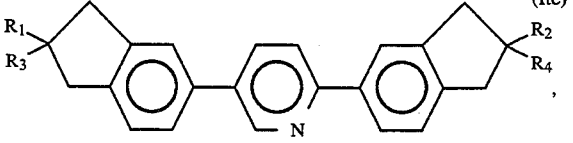 (Itd)
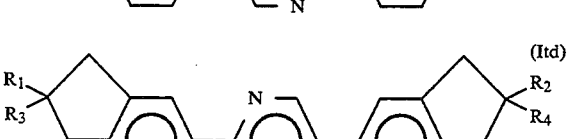 (Ite)
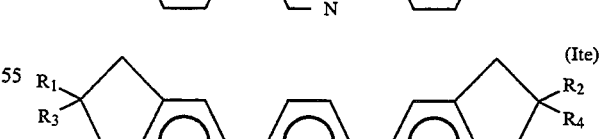 (Itf)
and

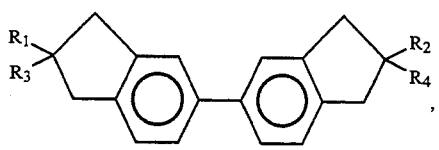 (Itg)

wherein $R_1$ and $R_2$ independently denote hydrogen, halogen,

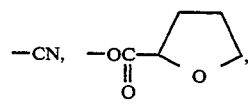

or a linear or branched alkyl group having 1-18 carbon atoms capable of including one or non-neighboring two or more —$CH_2$— groups which can be replaced with

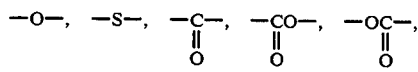

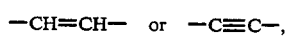

said linear or branched alkyl group being capable of including hydrogen which can be replaced with fluorine;

$R_3$ and $R_4$ independently denote hydrogen, halogen, —CN or a linear or branched alkyl group having 1-18 carbon atoms capable of including one or non-neighboring two or more —$CH_2$— groups which can be replaced with

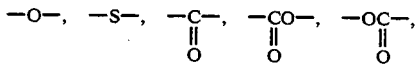

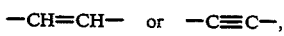

said linear or branched alkyl group being capable of including hydrogen which can be replaced with fluorine; and $Y_1$ and $Y_2$ independently denote, H, F, Cl, Br, —$CH_3$, —$CF_3$ or —CN.

In the mesomorphic compound of the formula (I), $Y_1$ and $Y_2$ may preferably be hydrogen (H), halogen (F, Cl or Br) of trifluoromethyl (—$CF_3$), particularly H or F.

$R_1$ in the formula (I) may preferably be selected from the following groups (i) to (vi):

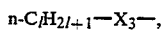     (i)

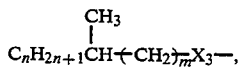     (ii)

     (iii)

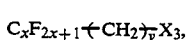     (iv)

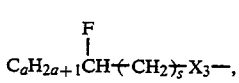     (v)

and

H,     (vi)

wherein l is an integer of 1-17; m, r and y is an integer of 0-7; n, t and x is an integer of 1-8, s is 0 or 1, a is an integer of 1-15; and $X_3$ denotes a single bond, —O—,   —OC—   or   —CO—.
           ‖             ‖
           O             O $R_1$ may more preferably be the group (i), the group (ii) or the group (v), particularly the group (i).

$X_3$ in the above groups (i) to (vi) may preferably be a single bond or —O—, particularly a single bond.

$R_2$ in the formula (I) may preferably be selected from the following groups (i) to (vii):

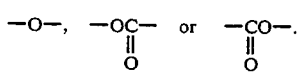     (i)

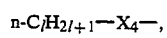     (ii)
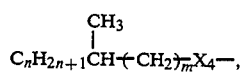

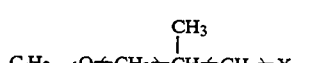     (iii)

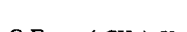     (iv)
     (v)

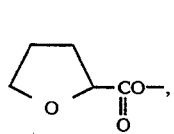     (vi)

and

F,     (vii)

wherein l is an integer of 1-17; m, r and y is an integer of 0-7; n, t and x is an integer of 1-8, s is 0 or 1, a is an integer of 1-15; and $X_4$ denotes a single bond,

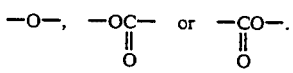

$R_2$ may more preferably be selected from the above groups (i), (ii), (v) and (vii), particularly the group (i).

$X_4$ in the above groups (i) to (vii) may preferably be a single bond,

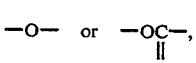

more preferably be a single bond or —O—. Further, a single bond is particularly preferred.

The mesomorphic compound of the formula (I) may also include those represented by the following formulas (II), (III) and (IV) as preferred examples:

Formula (II)

-continued

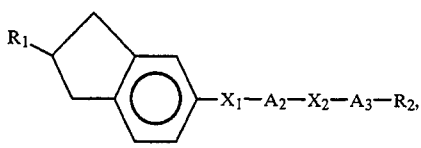 (II)

wherein

R₁ and R₂ independently denote hydrogen, halogen,

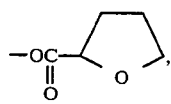

or a linear or branched alkyl group having 1-18 carbon atoms capable of including one or non-neighboring two or more —CH₂— groups which can be replaced with

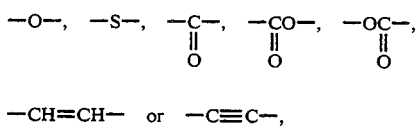

said linear or branched alkyl group being capable of including hydrogen which can be replaced with fluorine;

X₁ and X₂ independently denote a single bond,

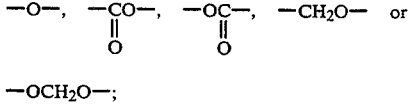

—OCH₂O—;

A₂ denotes

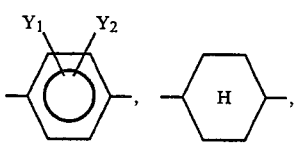

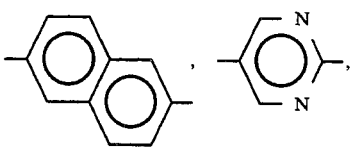

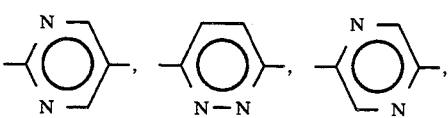

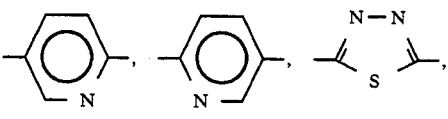

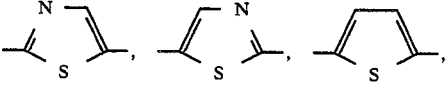

-continued

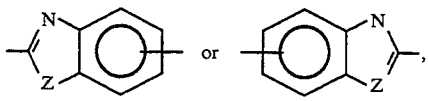

wherein Y₁ and Y₂ independently denote, H, F, Cl, Br, —CH₃, —CF₃ or —CN; and Z denotes O or S;
A₃ denotes a single bond or A₂; and
with the proviso that:
(i) A₂ is not

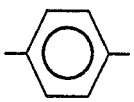

when X₁ is —COO— and A₃ is a single bond, and
(ii) X₁ and X₂ are not an ester group simultaneously when A₂ and A₃ are

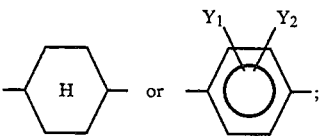

Formula (III)

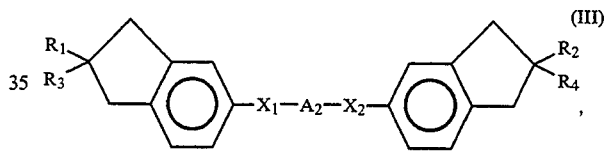 (III)

wherein
R₁, R₂, R₃ and R₄ independently denote hydrogen, halogen, —CN, or a linear or branched alkyl group having 1-18 carbon atoms capable of including one or non-neighboring two or more —CH₂— groups which can be replaced with

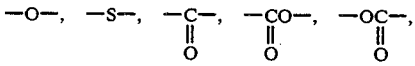

said linear or branched alkyl group being capable of including hydrogen which can be replaced with fluorine;

X₁ and X₂ independently denote a single bond,

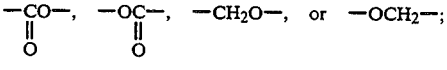

A₂ denotes a single bond,

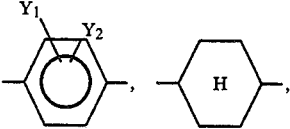

-continued

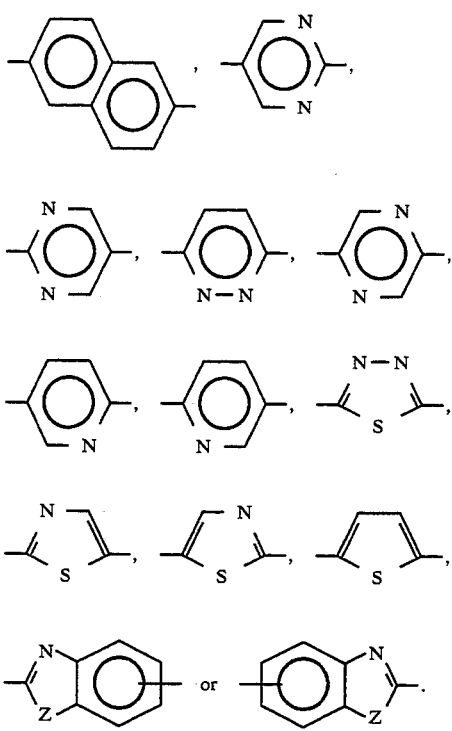

wherein Y₁ and Y₂ independently denote, H, F, Cl, Br, —CH₃, —CF₃ or —CN; and Z denotes O or S; and Formula (IV)

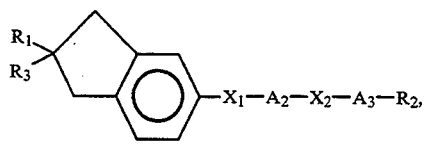

wherein

R₁ and R₂ independently denote hydrogen, halogen,

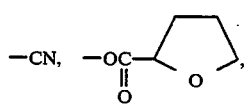

or a linear or branched alkyl group having 1-18 carbon atoms capable of including one or non-neighboring two or more —CH₂— groups which can be replaced with

—O—, —S—, —C—, —CO—, —OC—,
         ‖       ‖       ‖
         O       O       O

—CH=CH— or —C≡C—, said linear or branched alkyl group being capable of including hydrogen which can be replaced with fluorine:

R₃ denotes hydrogen, halogen, —CN, or a linear or branched alkyl group having 1-18 carbon atoms;

X₁ and X₂ independently denote a single bond,

—O—, —CO—, —OC—, —CH₂O—, —OCH₂—,
       ‖       ‖
       O       O

—CH₂CH₂— or —C≡C— with the proviso that at least one species of X₁ and X₂ is —C≡C—;

A₂ denotes

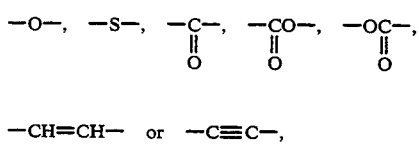

or wherein Y₁ and Y₂ independently denotes H, F, Cl, Br, —CH₃, —CF₃ or —CN; and Z denotes O or S; and A₃ denotes a single bond or A₂.

Further, the mesomorphic compound of the formula (I) may include a compound which does not show mesomorphism singly but shows mesomorphism in combination with another mesomorphic compound and/or the mesomorphic compound of the formula (I) which shows mesomorphism singly.

The mesomorphic compound of the above-mentioned formula (I) may generally be synthesized through the following reaction schemes A and B.

Scheme A
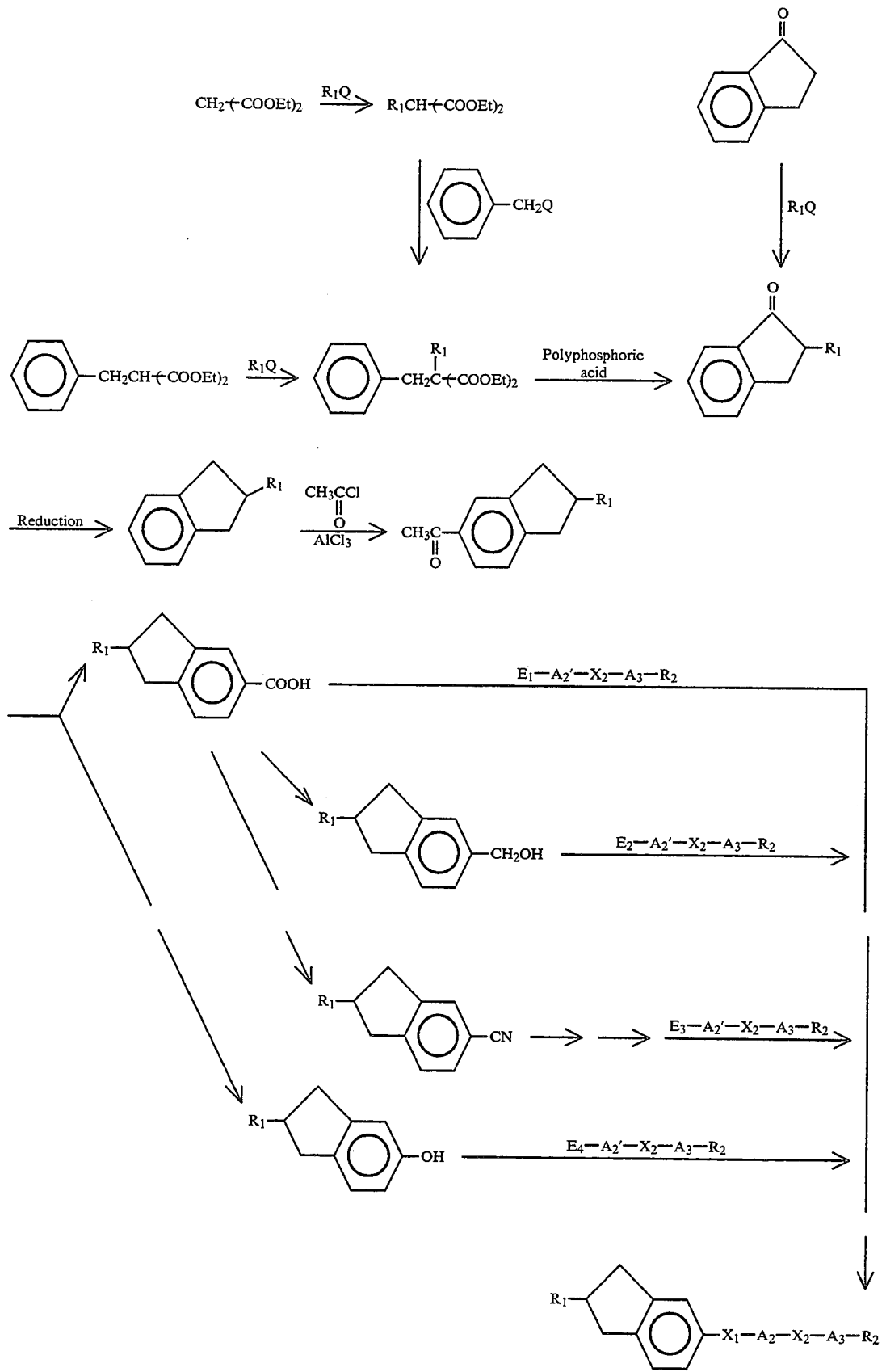

Scheme B

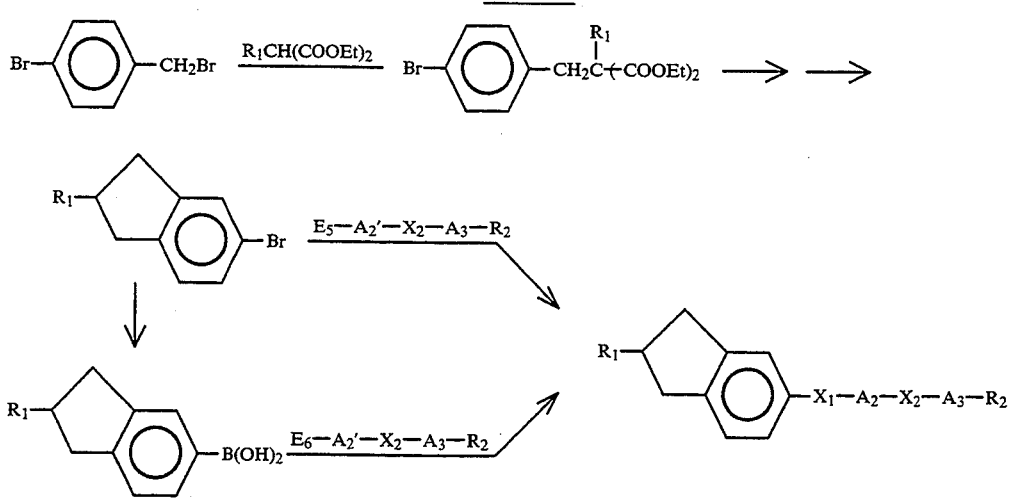

In the above reaction schemes A and B, $R_1$, $R_2$, $A_2$, $A_3$, $X_1$ and $X_2$ have the meanings given above. Q denotes

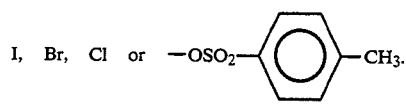

In a case where $X_1$ is not a single bond, $E_1$ to $E_6$ are appropriate groups, such as —OH, —COOH and —CH$_2$Br, for forming $X_1$ and $A_2'$ denotes $A_2$. In a case where $X_1$ is a single bond, $E_1$—$A_2'$ to $E_6$—$A_2'$ are appropriate groups, such as

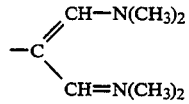 and 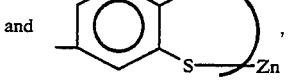, for forming $A_2$.

Specific examples of the mesomorphic compounds represented by the formula (I) may include those shown in the following structural formulas.

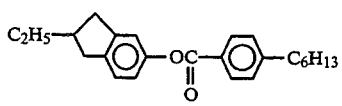 (I-1)

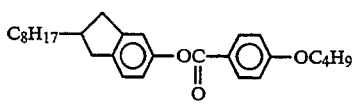 (I-2)

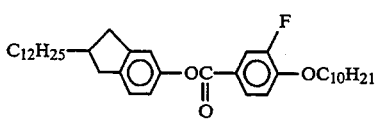 (I-3)

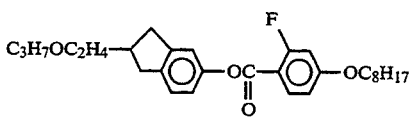 (I-4)

-continued

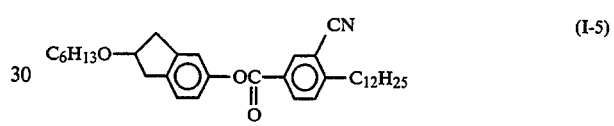 (I-5)

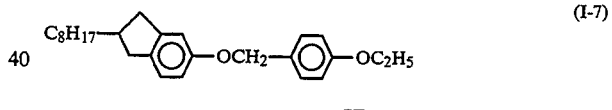 (I-6)

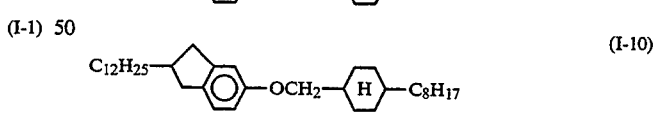 (I-7)

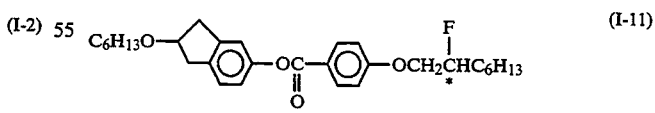 (I-8)

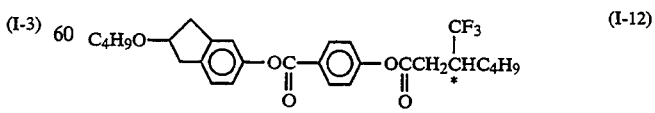 (I-9)

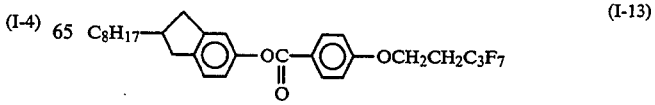 (I-10)

-continued
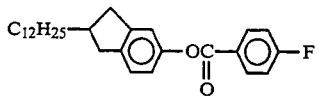 (I-14)
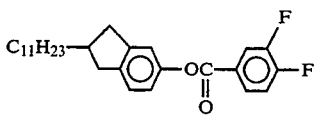 (I-15)
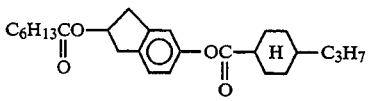 (I-16)
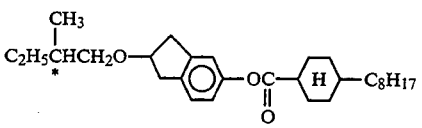 (I-17)
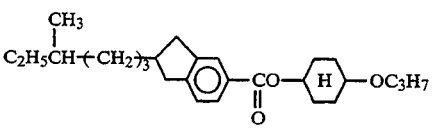 (I-18)
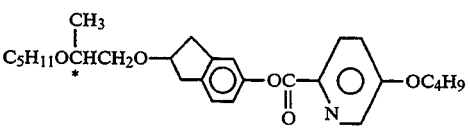 (I-19)
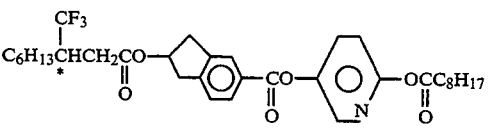 (I-20)
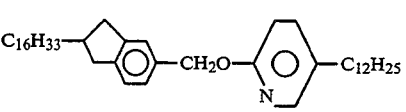 (I-21)
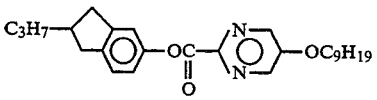 (I-22)
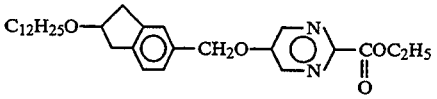 (I-23)
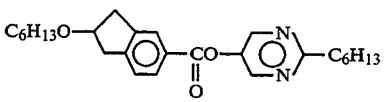 (I-24)
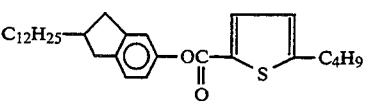 (I-25)
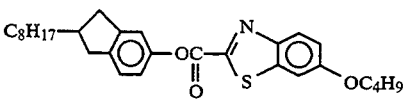 (I-26)
-continued
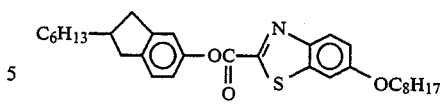 (I-27)
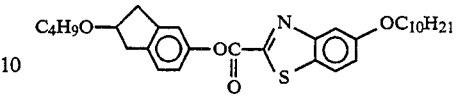 (I-28)
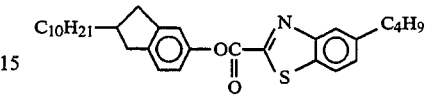 (I-29)
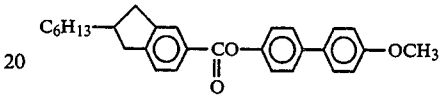 (I-30)
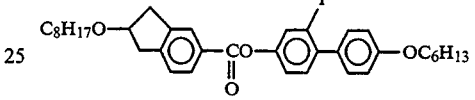 (I-31)
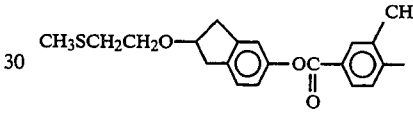 (I-32)
 (I-33)
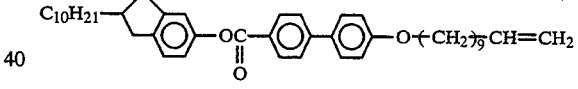 (I-34)
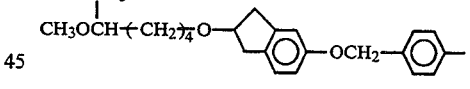 (I-35)
 (I-36)
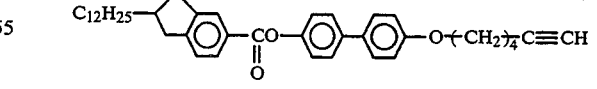 
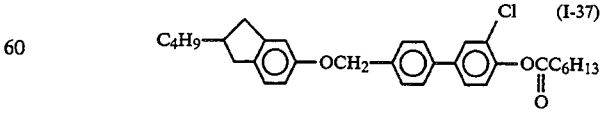 (I-37)
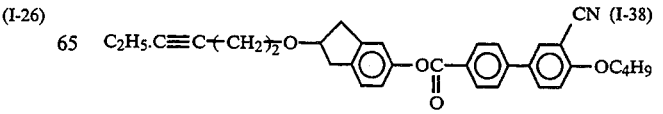 (I-38)

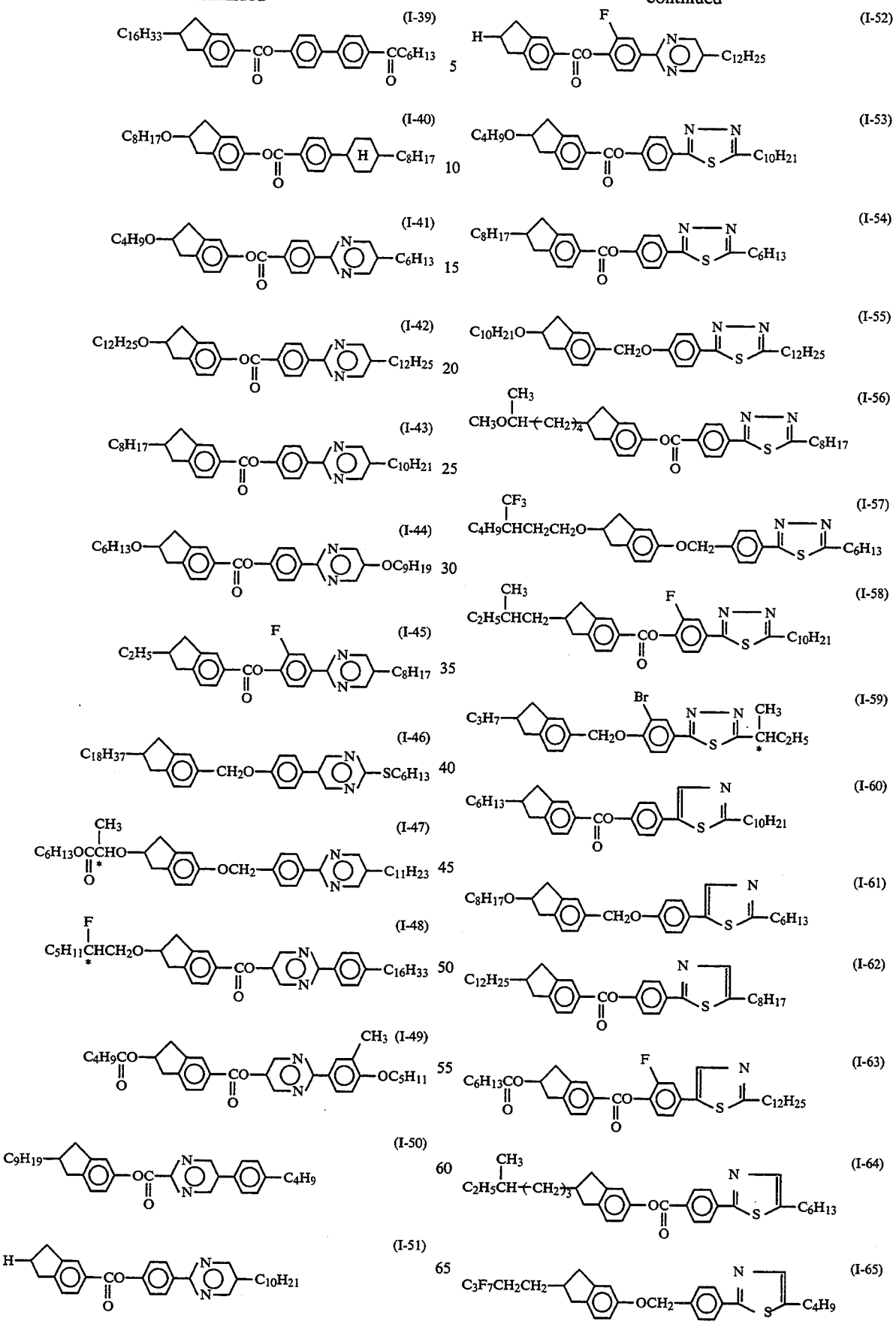

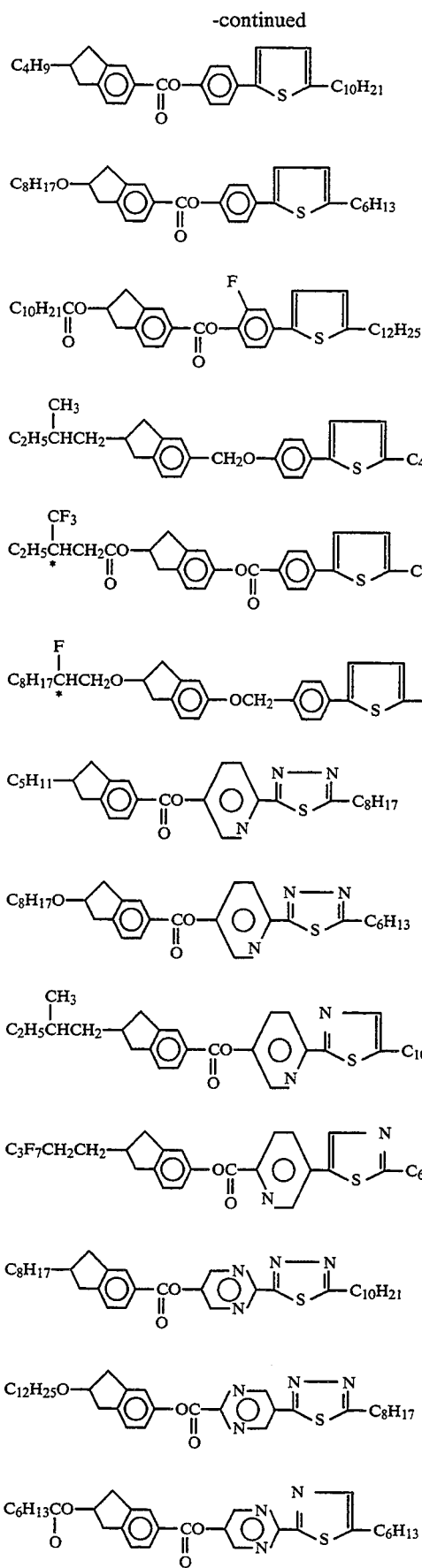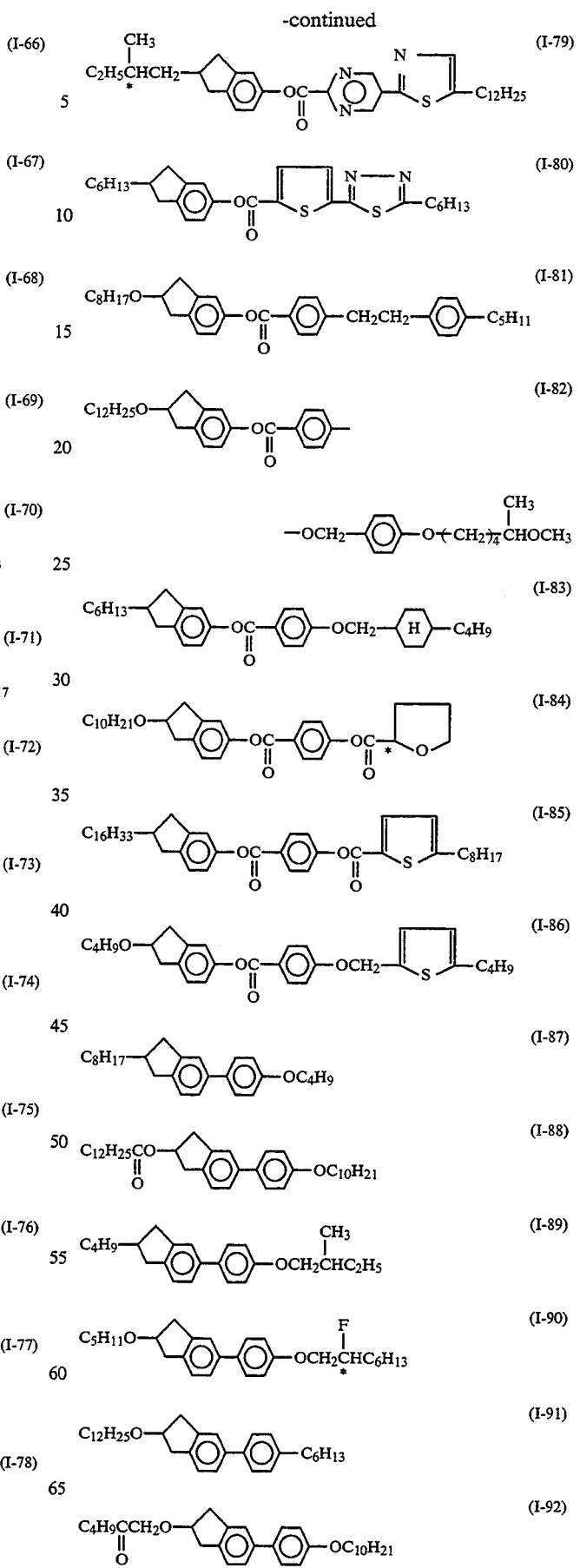

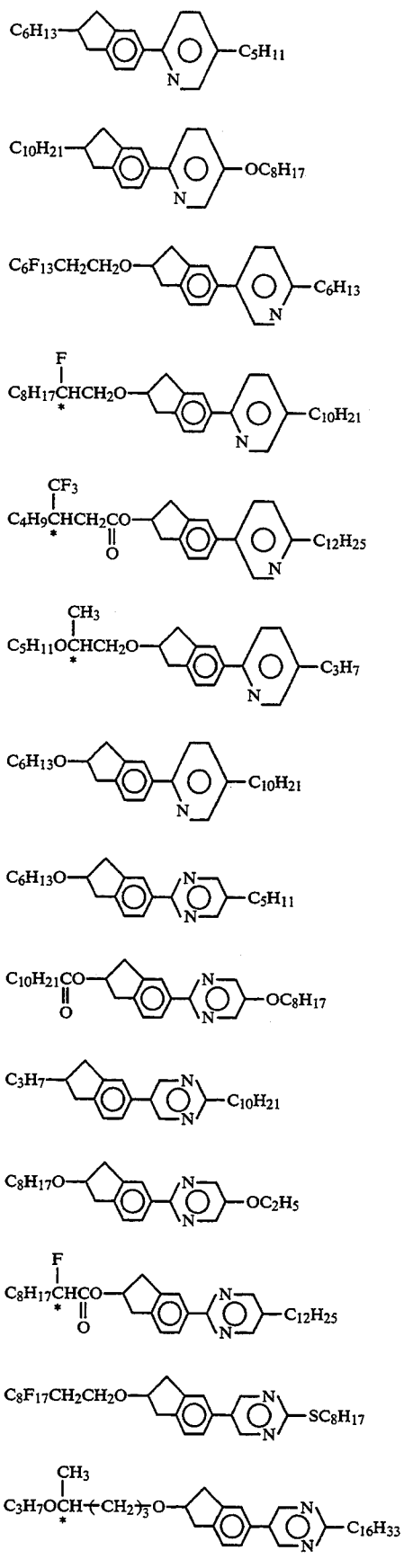
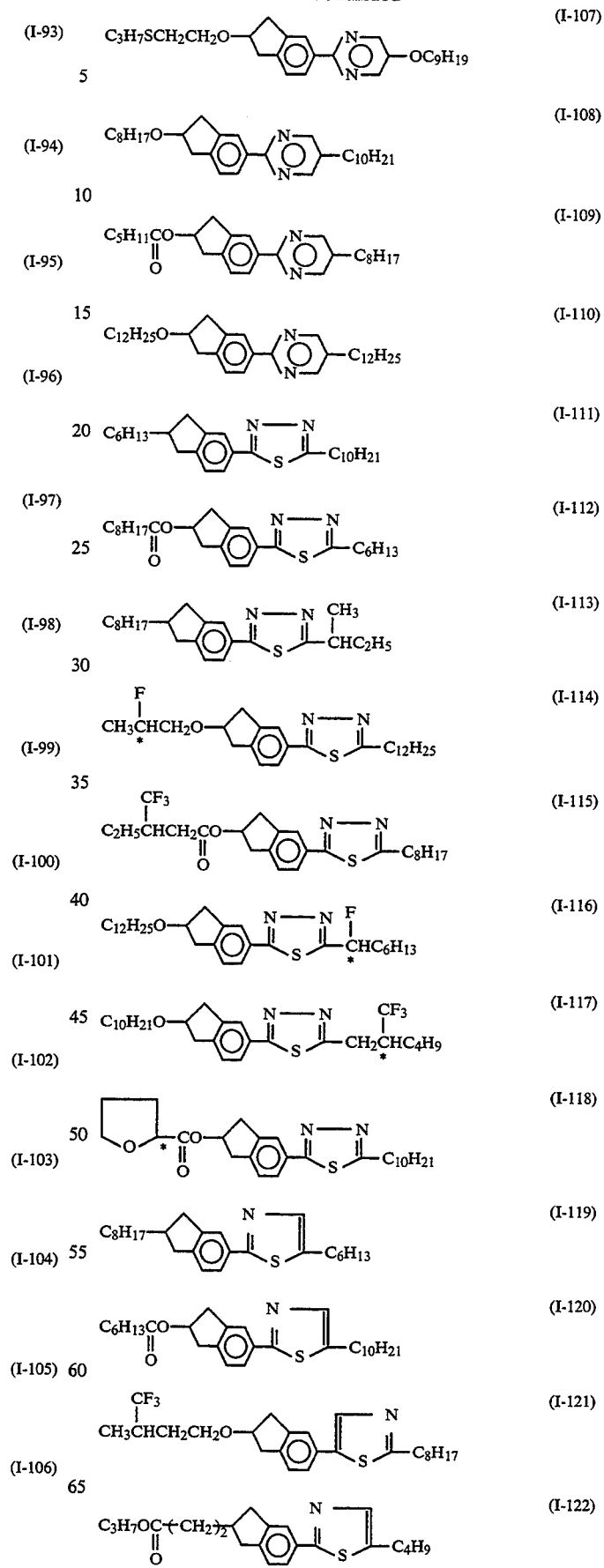

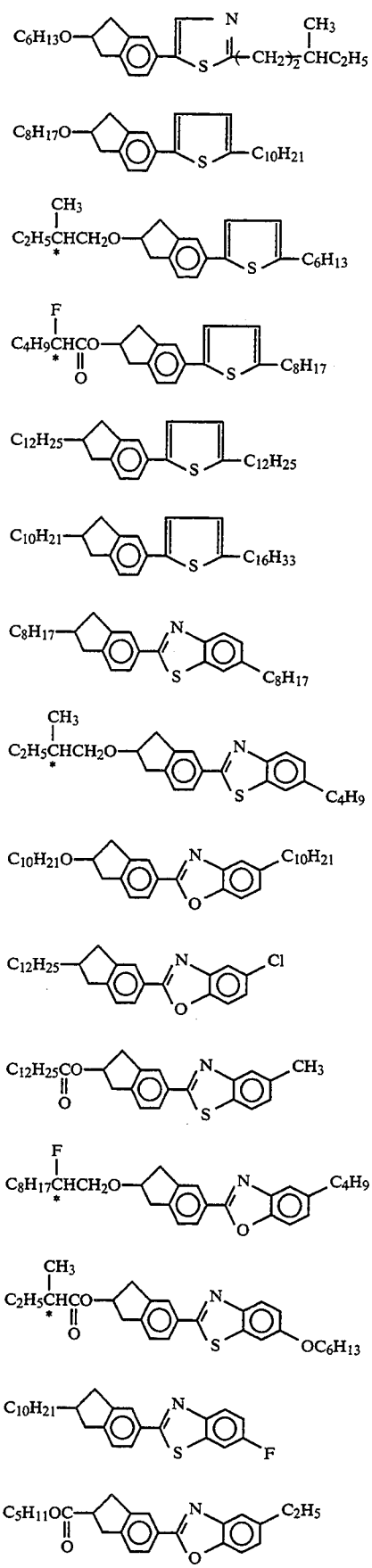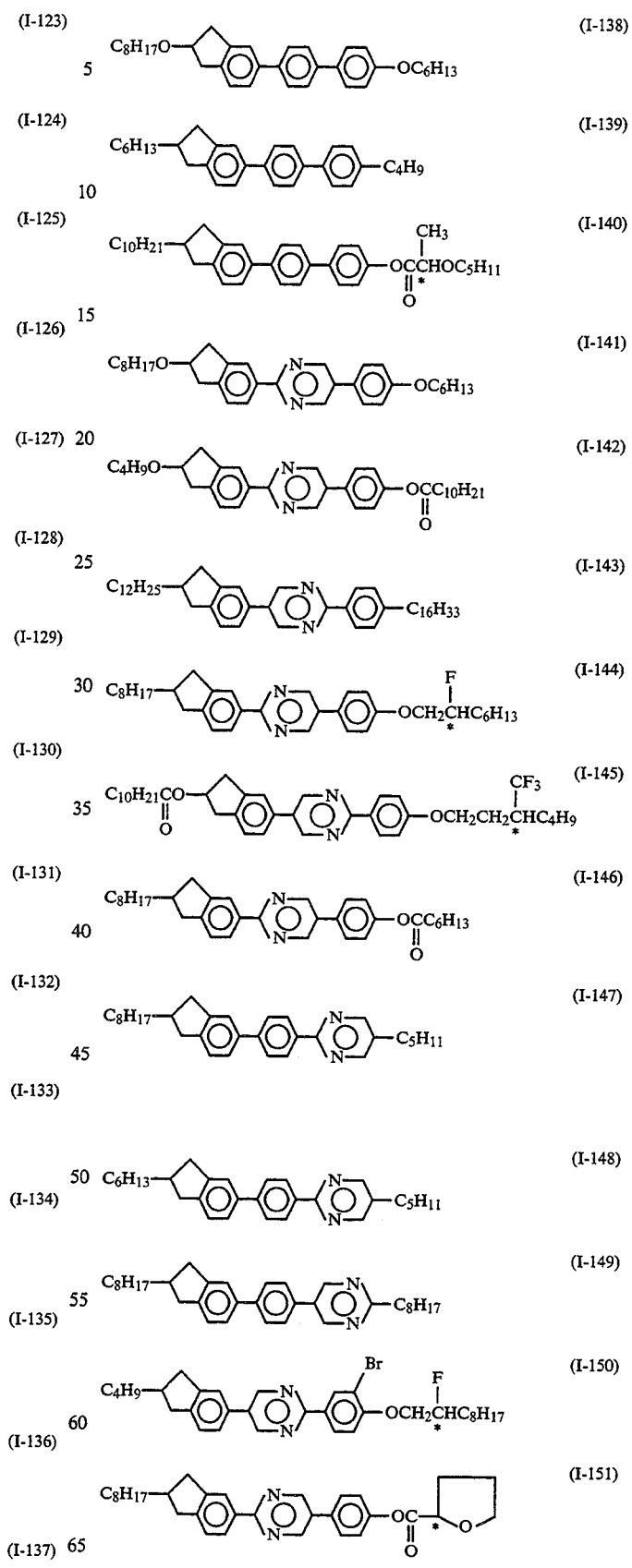

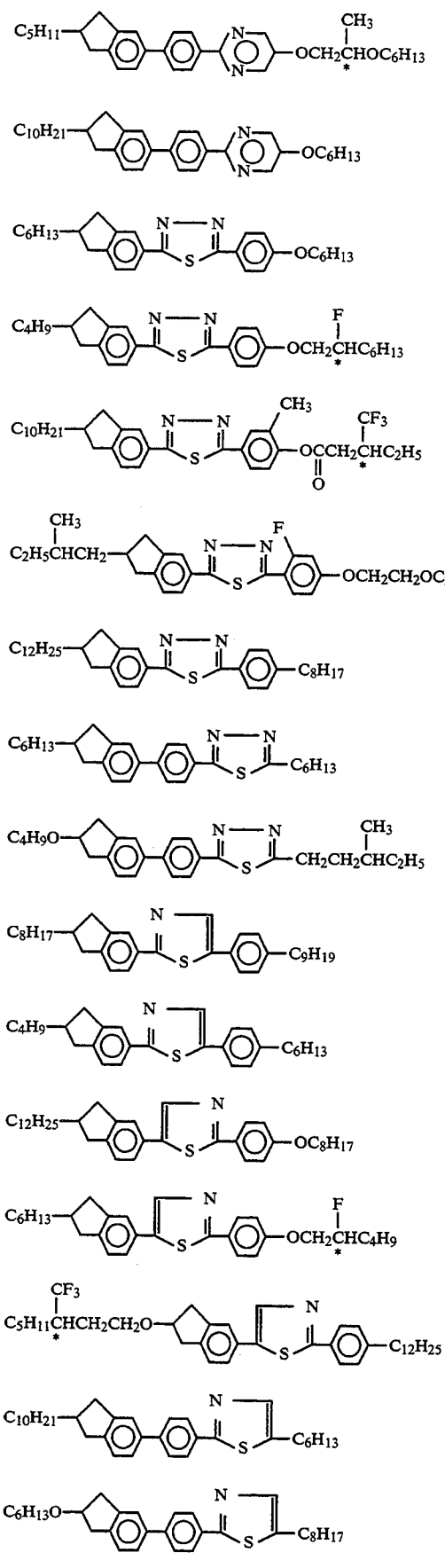
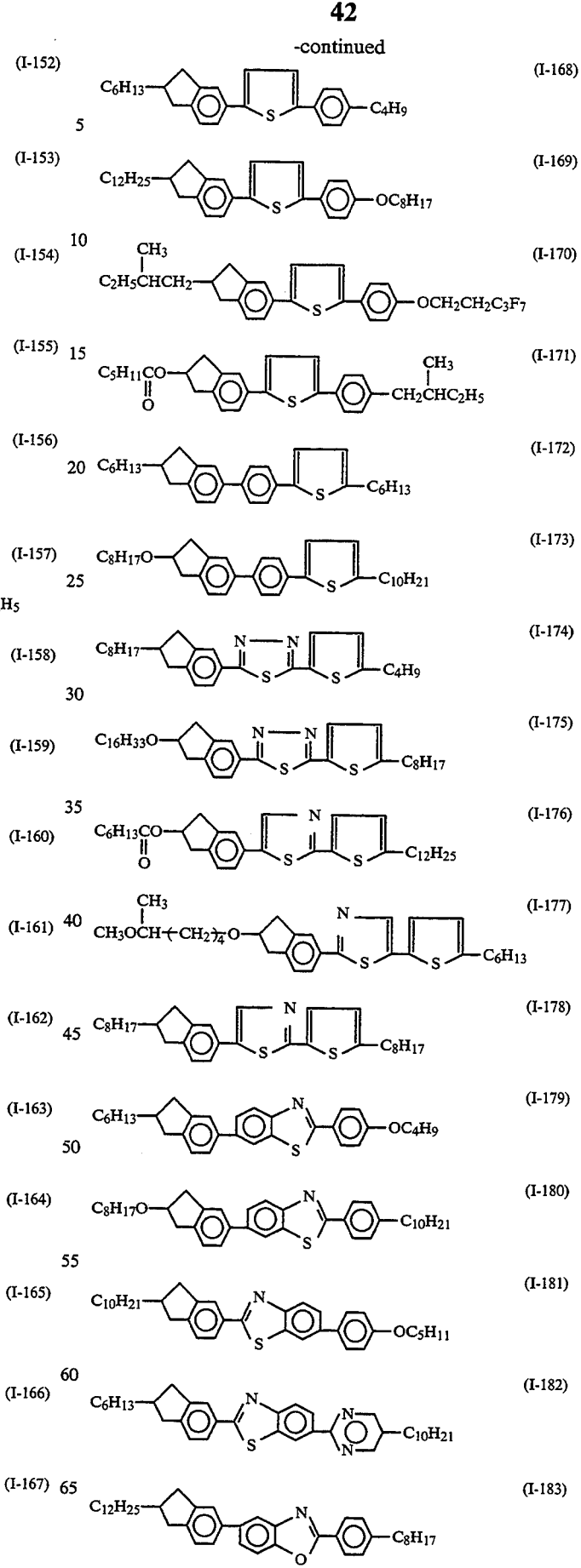

Chemical structure compounds (I-184) through (I-212) shown as structural diagrams.

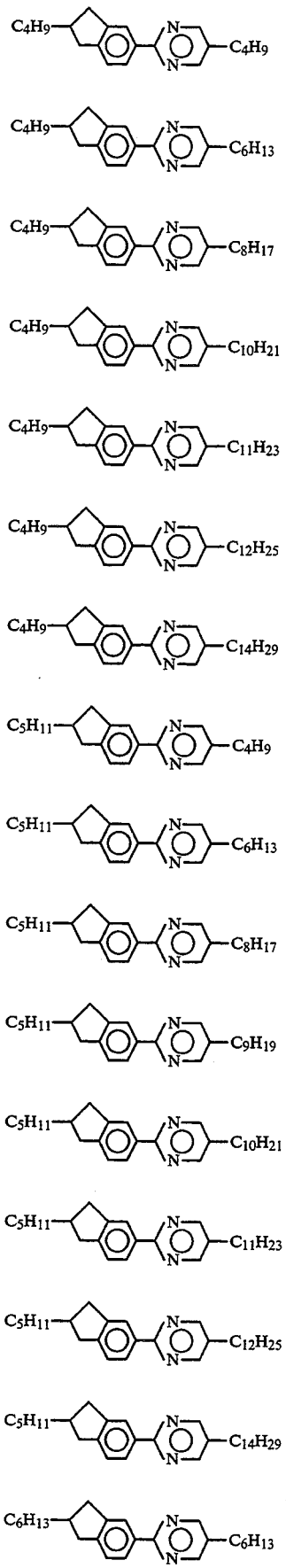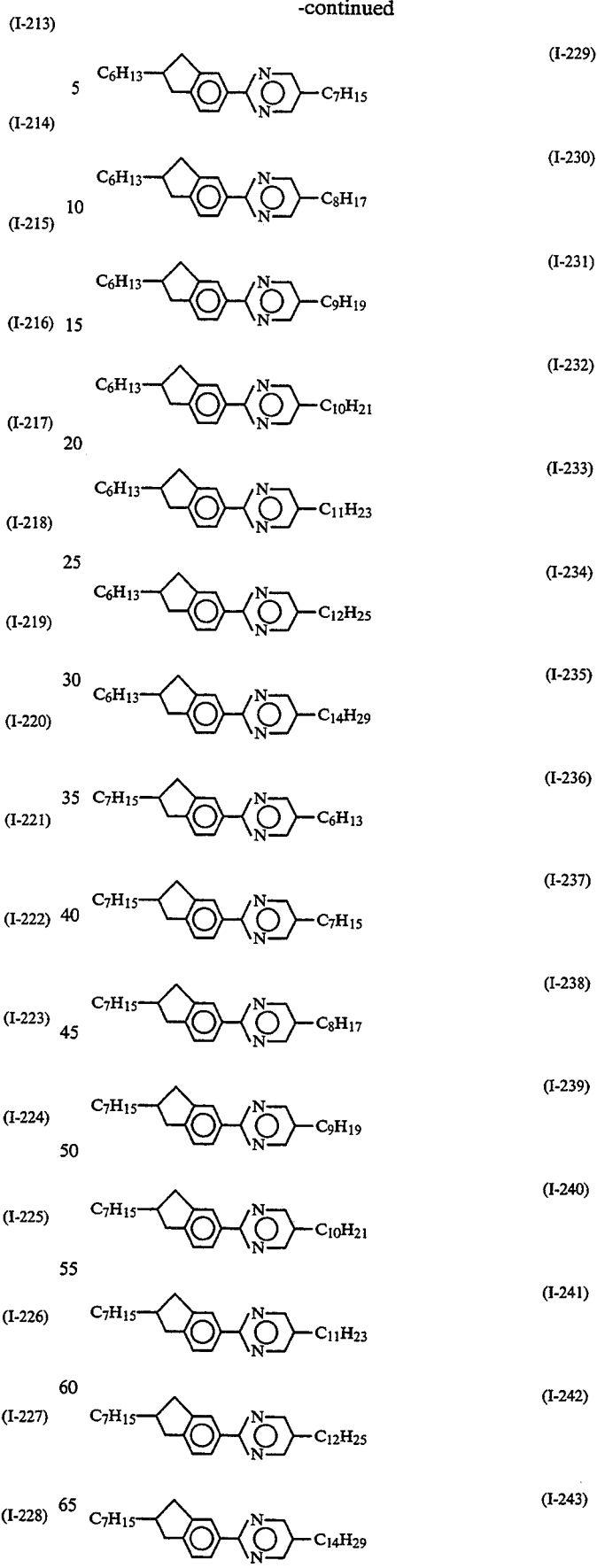

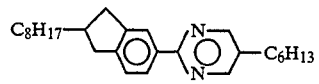 (I-205)
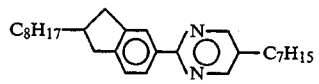 (I-206)
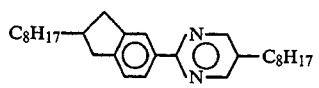 (I-207)
 (I-208)
 (I-209)
 (I-210)
 (I-211)
 (I-212)
 (I-213)
 (I-214)
 (I-215)
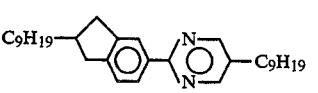 (I-216)
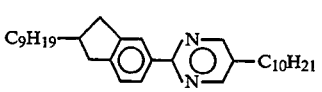 (I-217)
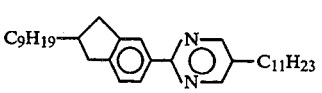 (I-218)
 (I-219)
(I-244)
(I-245)
(I-246)
(I-247)
(I-248)
(I-249)
(I-250)
(I-251)
(I-252)
(I-253)
(I-254)
(I-255)
(I-256)
(I-257)
(I-258)
(I-259)
(I-260)
(I-261)
(I-262)
(I-263)
(I-264)
(I-265)
(I-266)
(I-267)
(I-268)
(I-269)
(I-270)
(I-271)
(I-272)
(I-273)
(I-274)

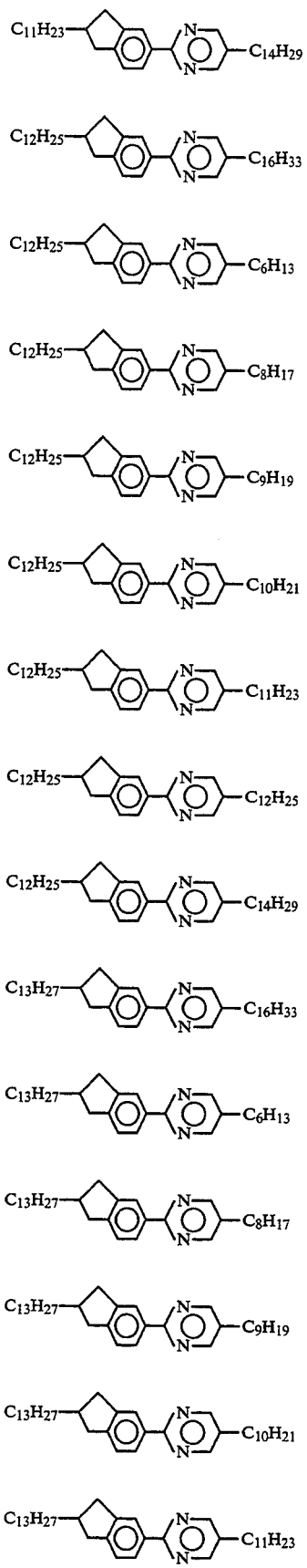
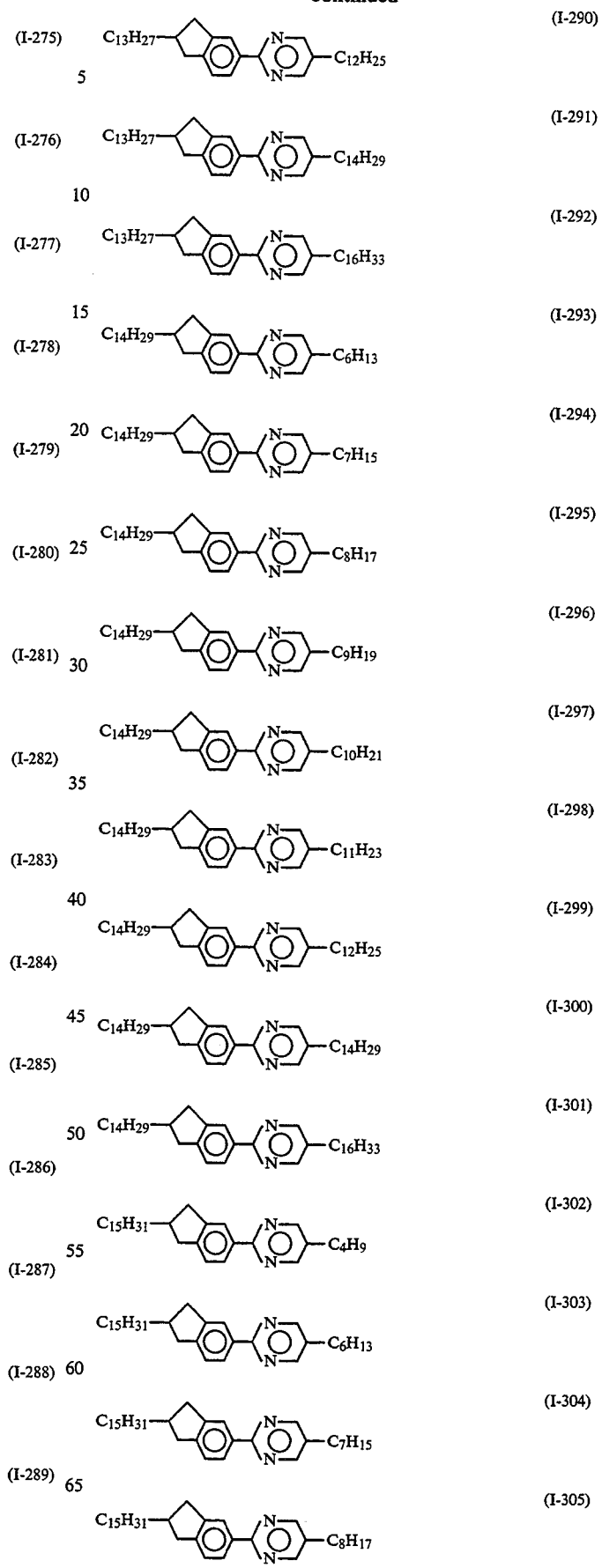

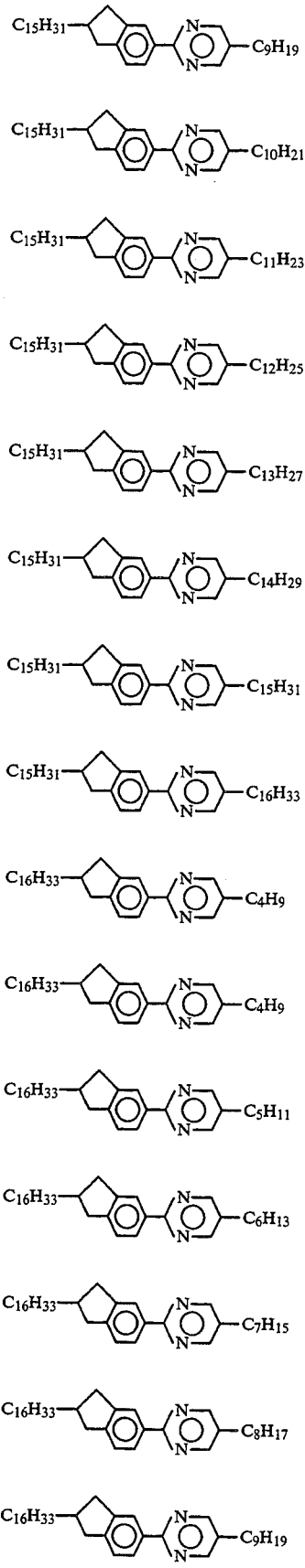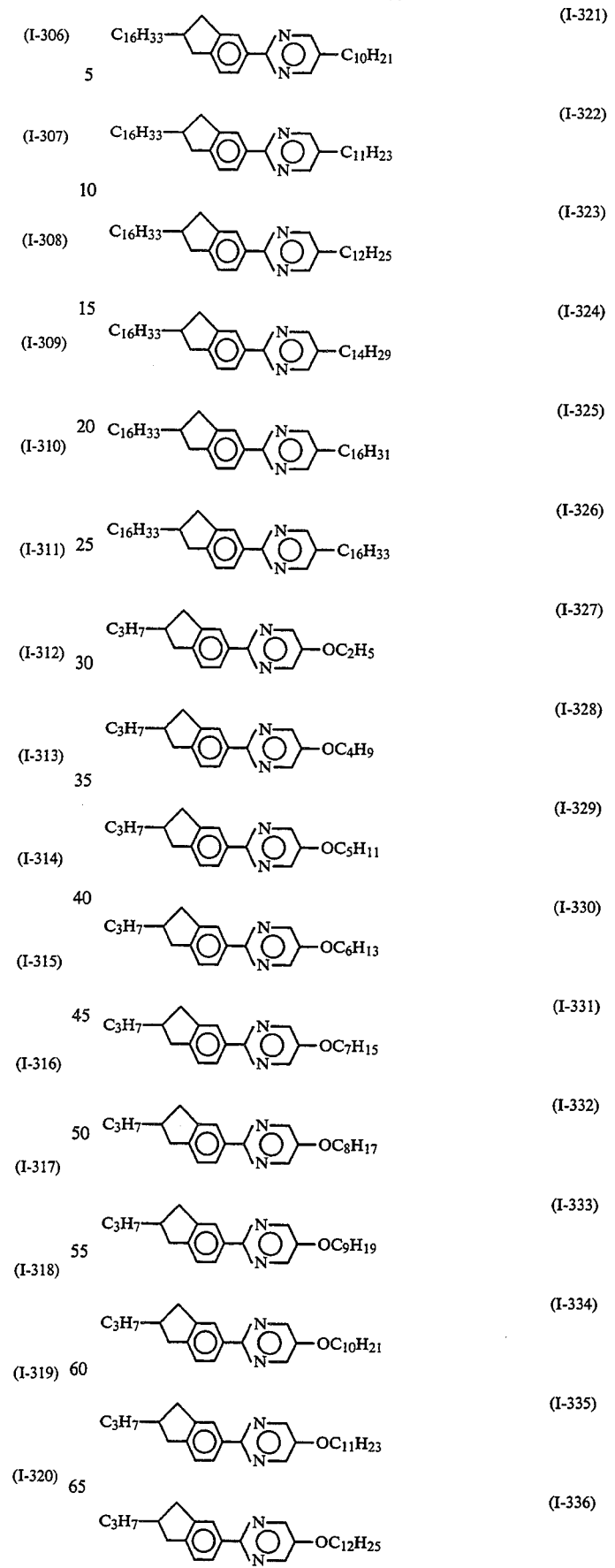

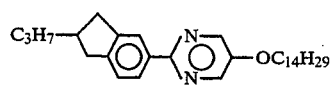 (I-337)
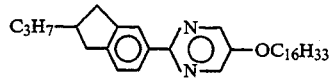 (I-338)
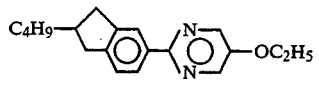 (I-339)
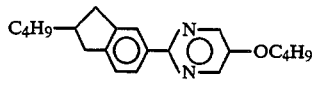 (I-340)
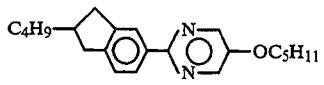 (I-341)
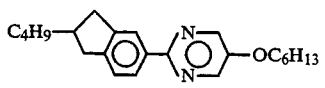 (I-342)
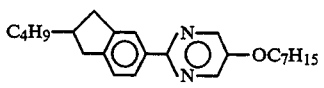 (I-343)
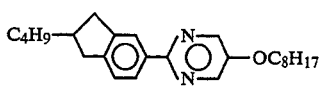 (I-344)
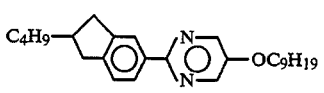 (I-345)
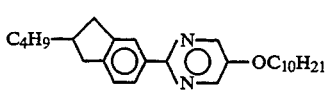 (I-346)
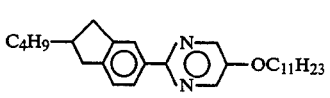 (I-347)
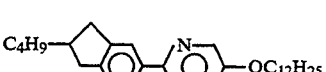 (I-348)
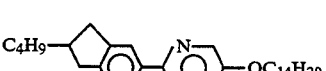 (I-349)
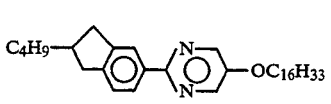 (I-350)
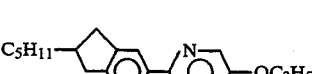 (I-351)
 (I-352)
 (I-353)
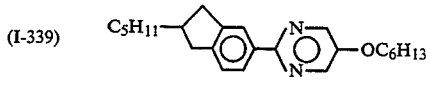 (I-354)
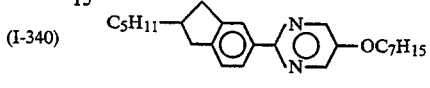 (I-355)
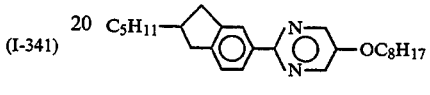 (I-356)
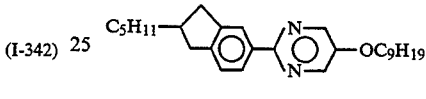 (I-357)
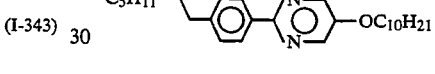 (I-358)
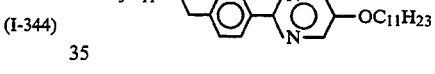 (I-359)
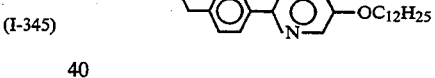 (I-360)
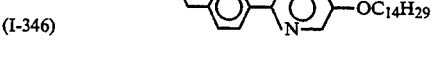 (I-361)
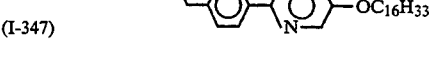 (I-362)
 (I-363)
 (I-364)
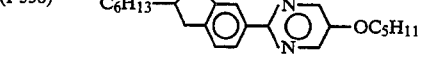 (I-365)
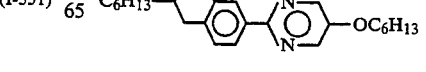 (I-366)

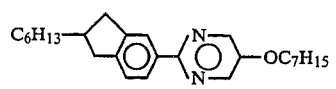 (I-367)
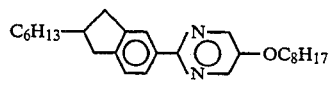 (I-368)
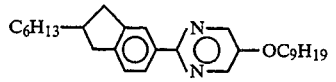 (I-369)
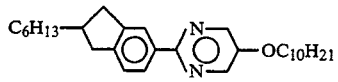 (I-370)
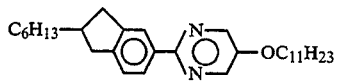 (I-371)
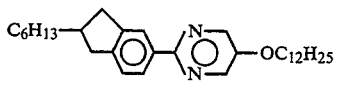 (I-372)
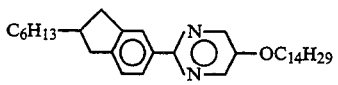 (I-373)
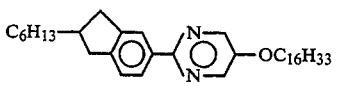 (I-374)
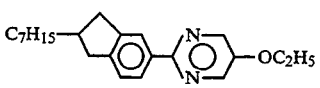 (I-375)
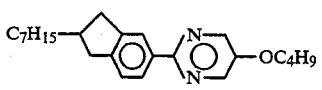 (I-376)
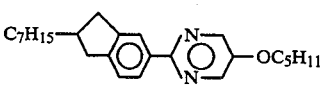 (I-377)
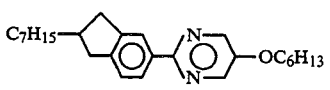 (I-378)
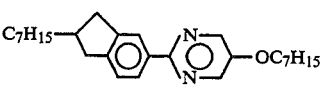 (I-379)
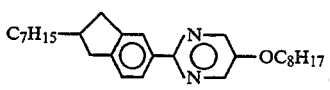 (I-380)
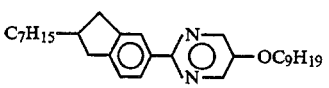 (I-381)
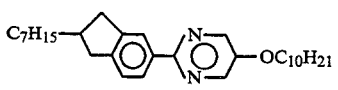 (I-382)
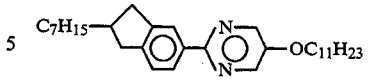 (I-383)
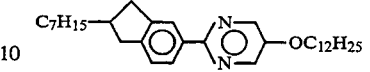 (I-384)
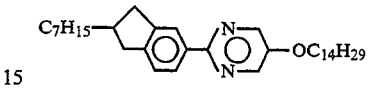 (I-385)
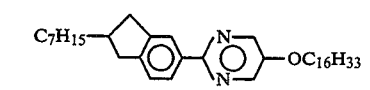 (I-386)
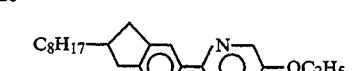 (I-387)
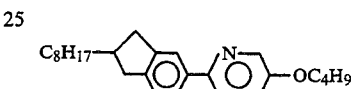 (I-388)
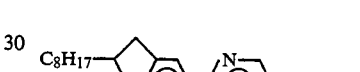 (I-389)
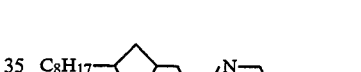 (I-390)
 (I-391)
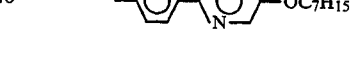 (I-392)
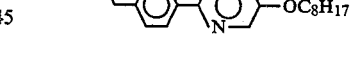 (I-393)
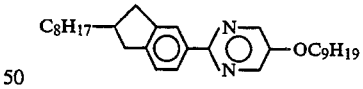 (I-394)
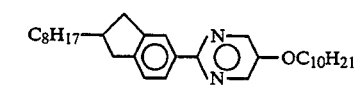 (I-395)
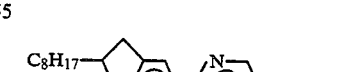 (I-396)
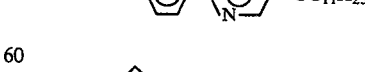 (I-397)

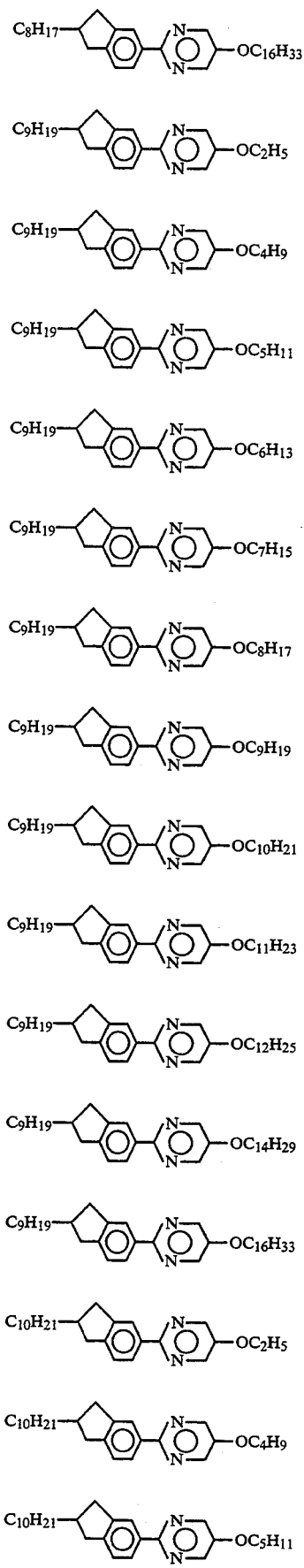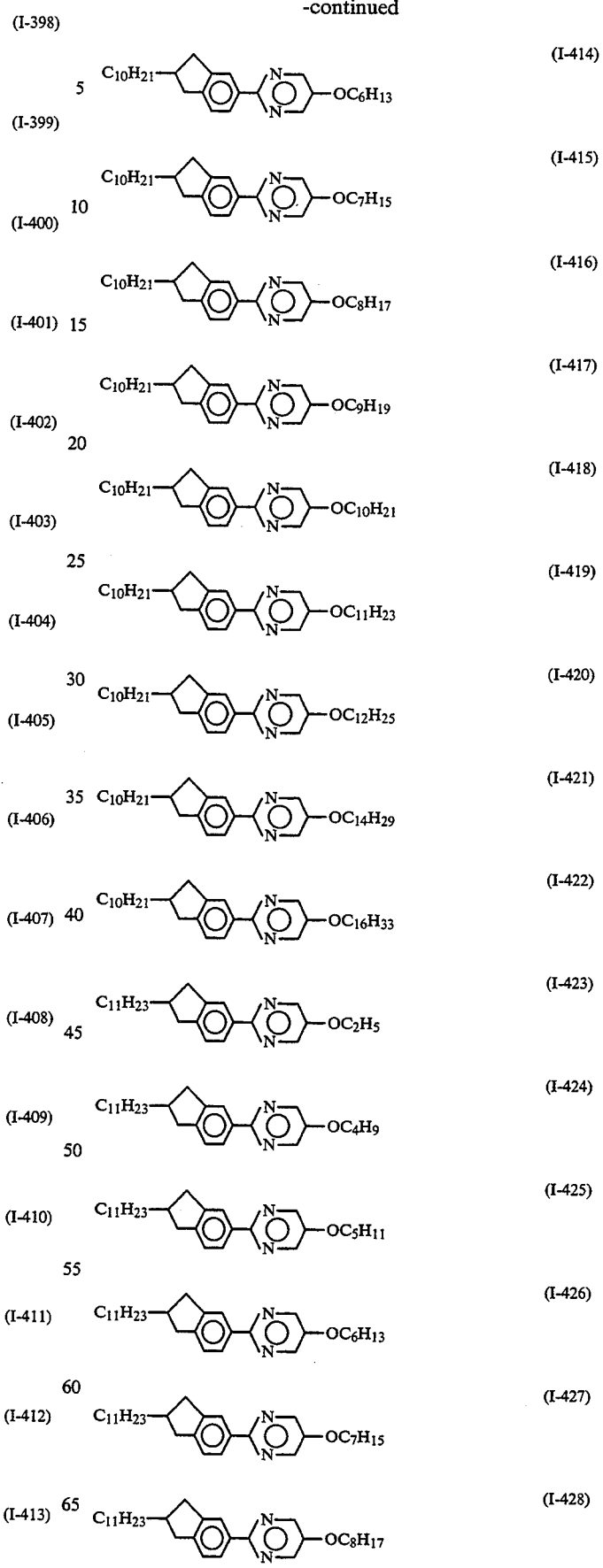

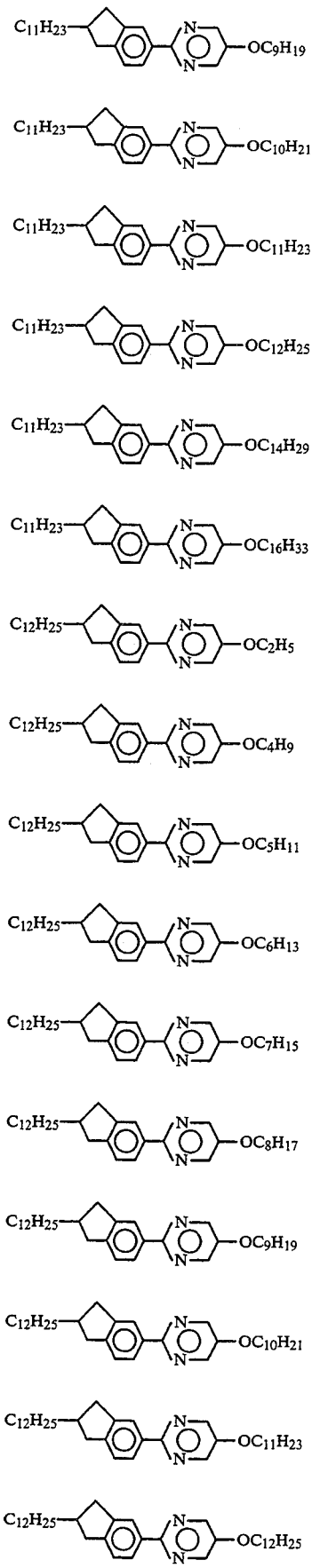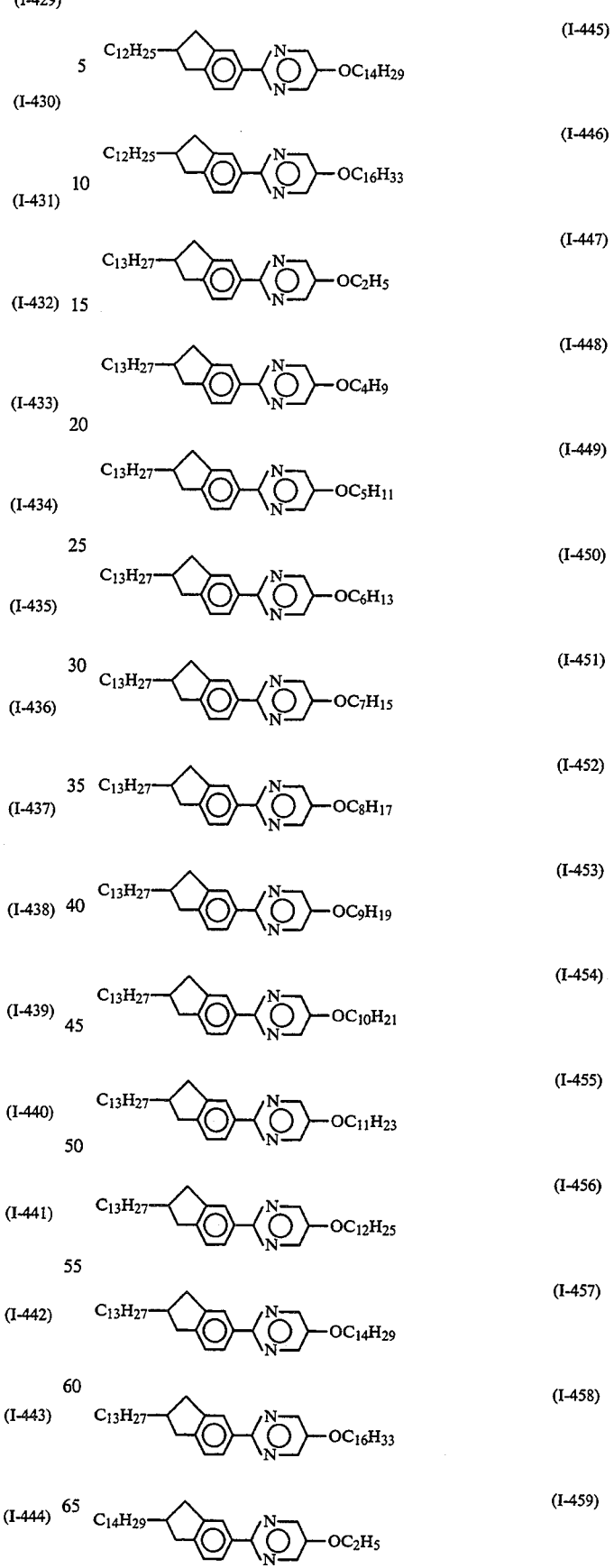

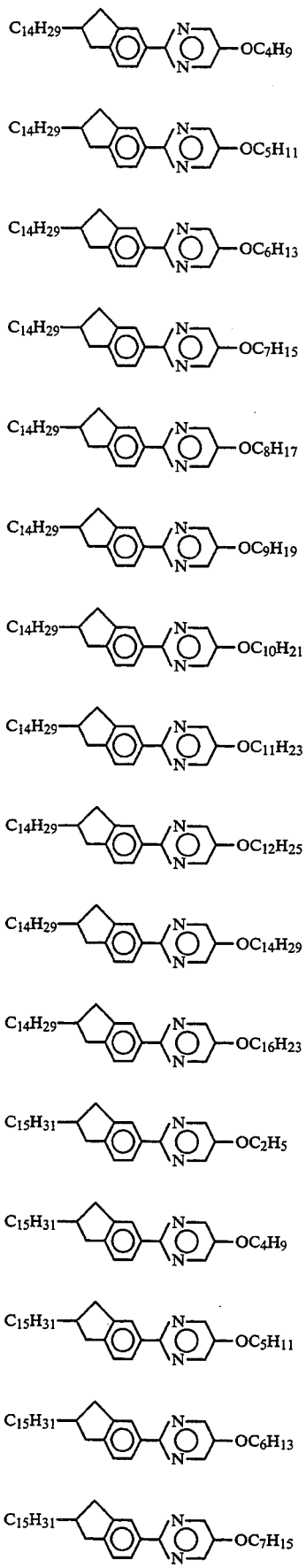
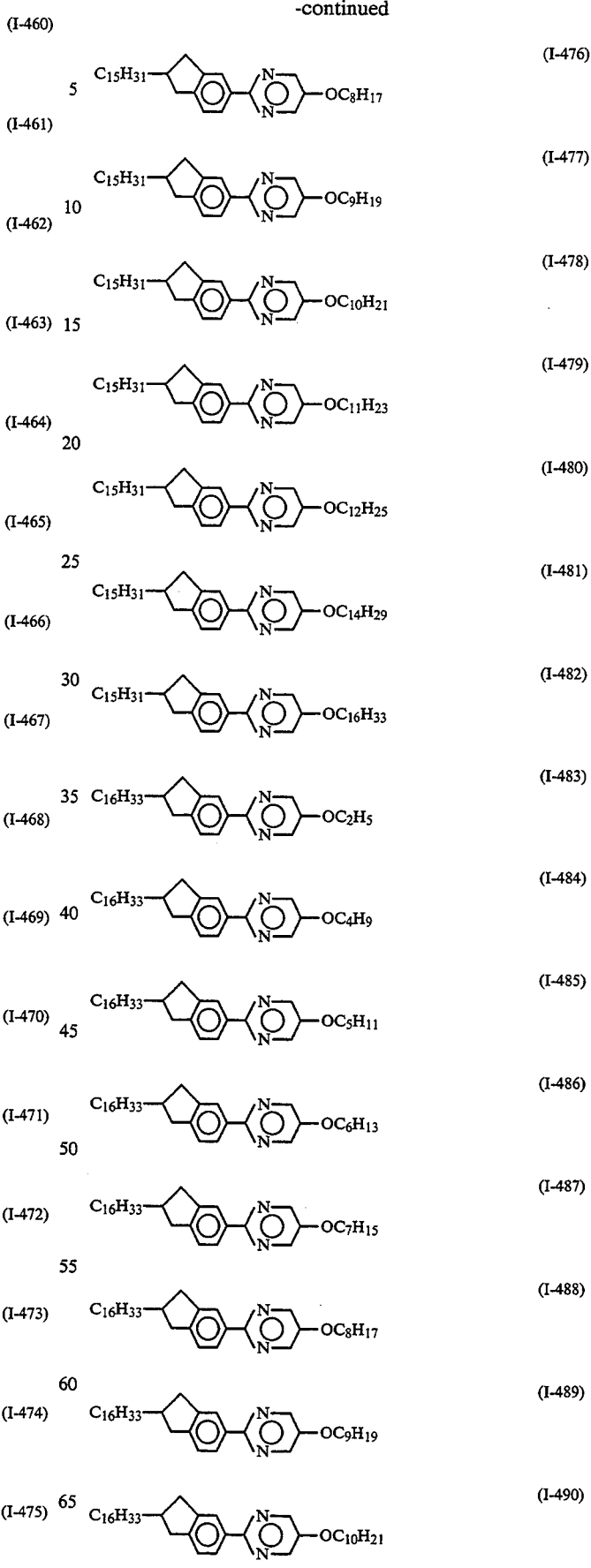

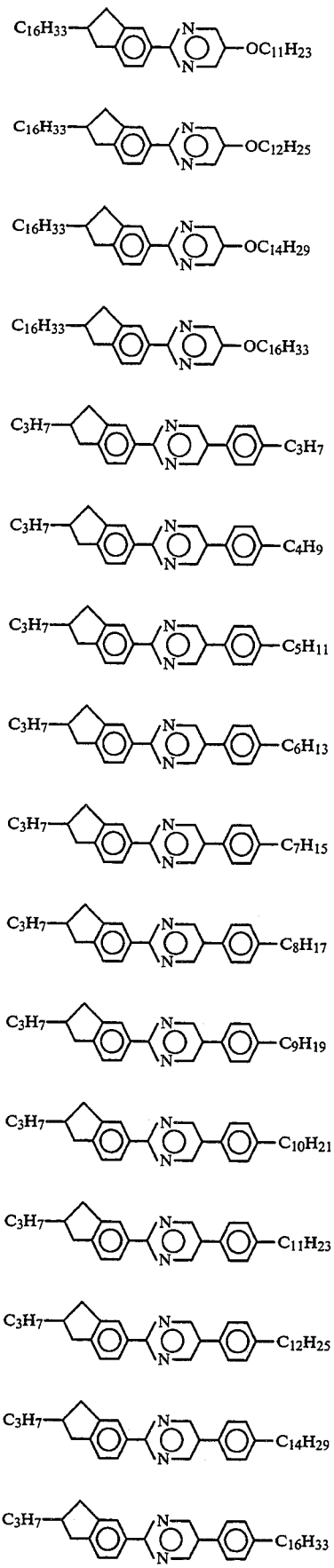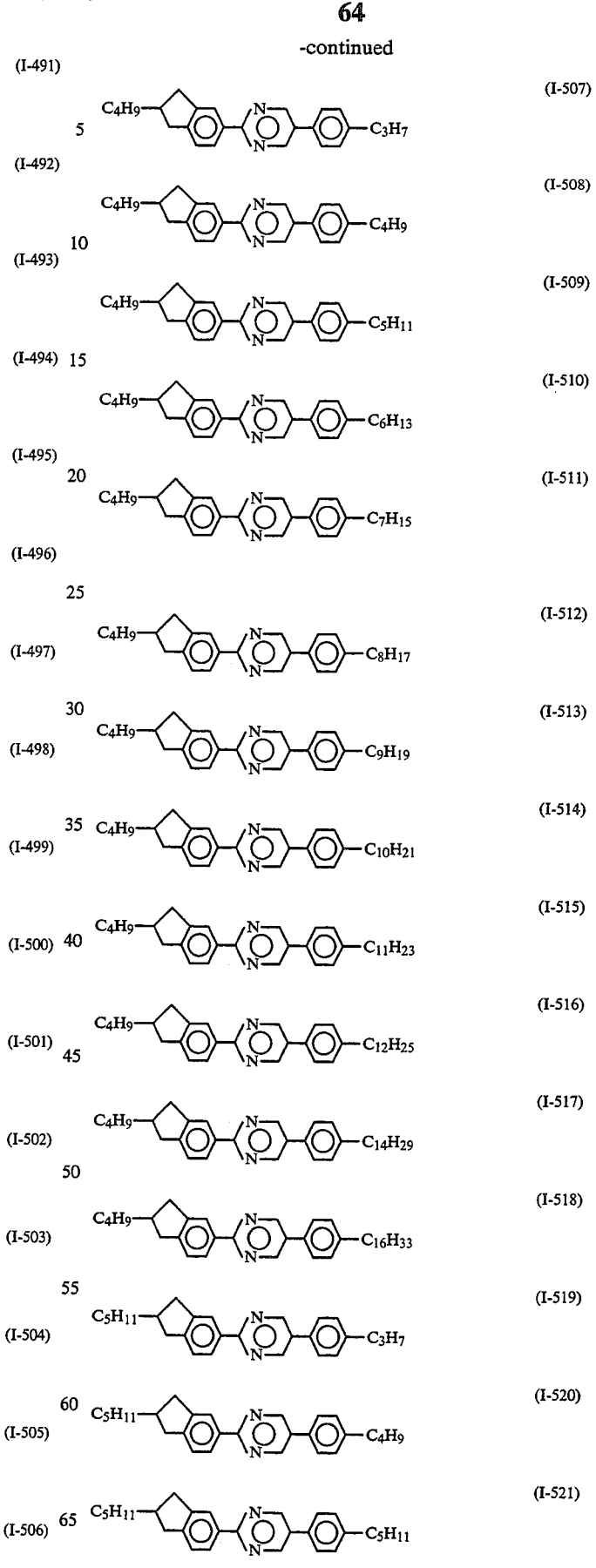

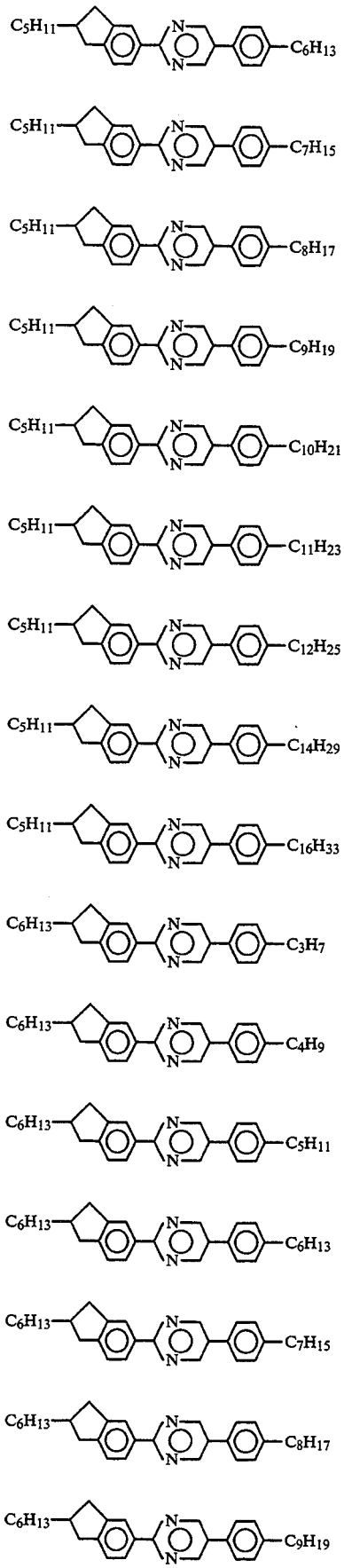
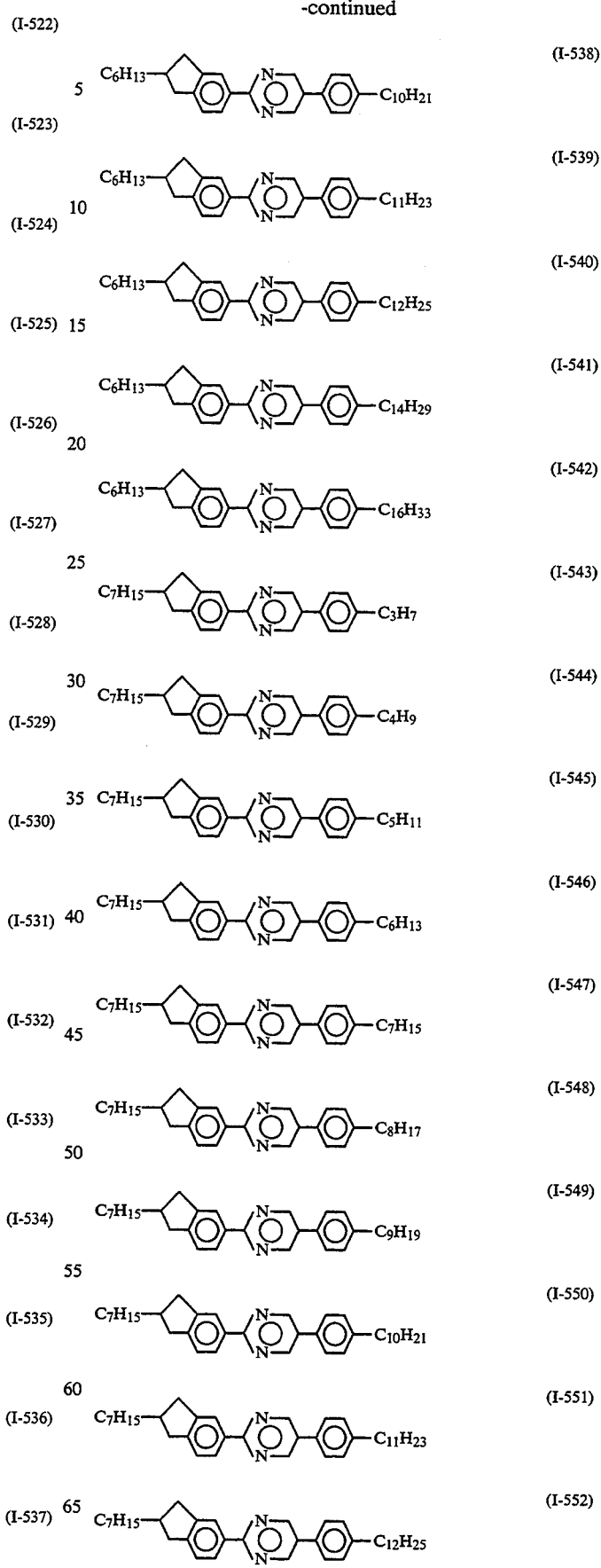

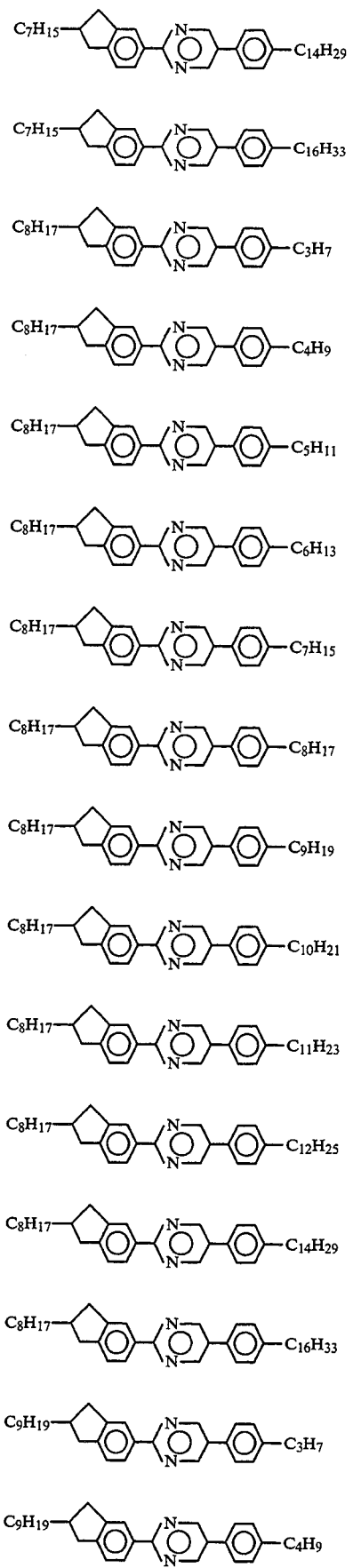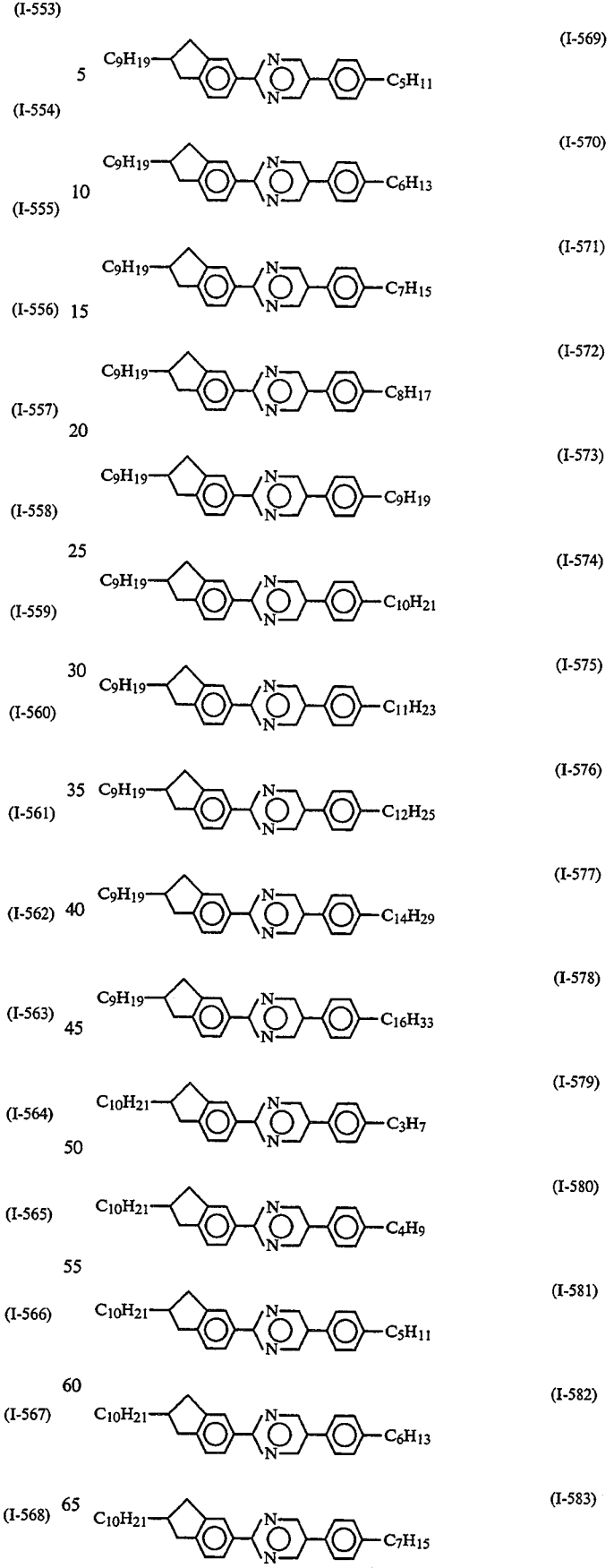

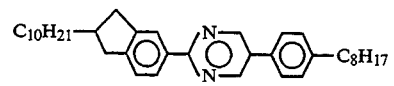 (I-569)
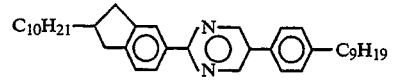 (I-570)
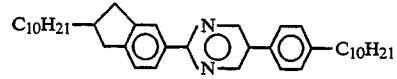 (I-571)
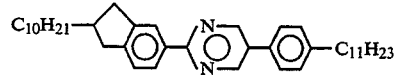 (I-572)
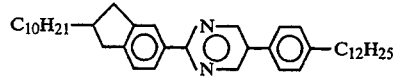 (I-573)
 (I-574)
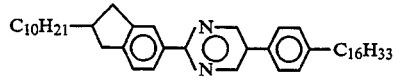 (I-575)
 (I-576)
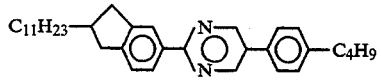 (I-577)
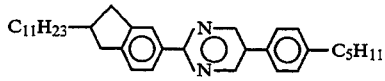 (I-578)
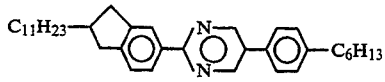 (I-579)
 (I-580)
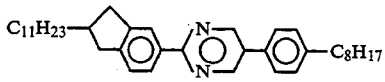 (I-581)
 (I-582)
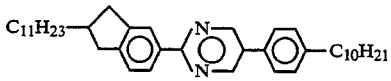 (I-583)
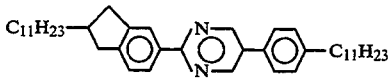 (I-584)
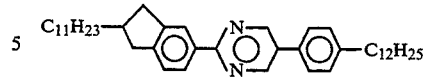 (I-585)
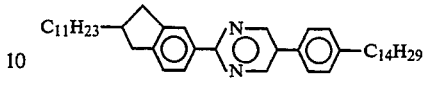 (I-586)
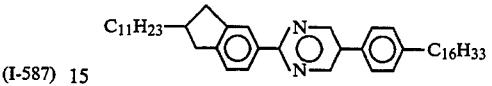 (I-587)
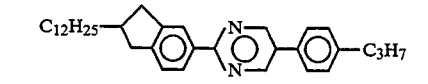 (I-588)
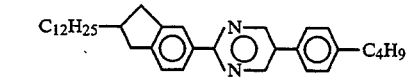 (I-589)
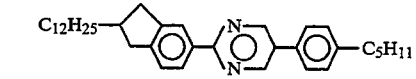 (I-590)
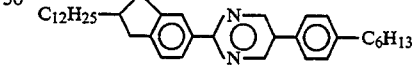 (I-591)
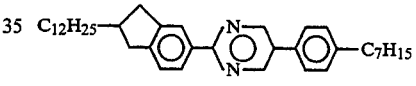 (I-592)
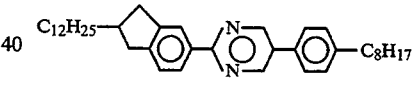 (I-593)
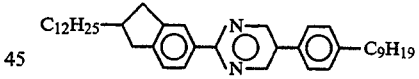 (I-594)
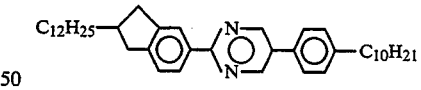 (I-595)
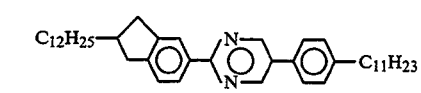 (I-596)
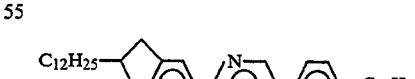 (I-597)
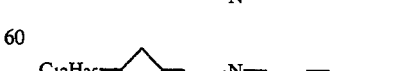 (I-598)

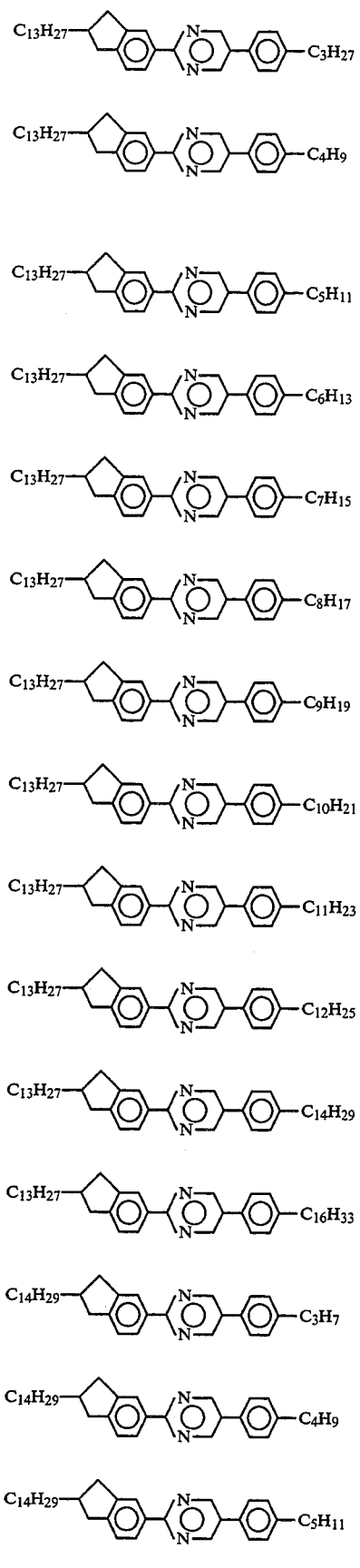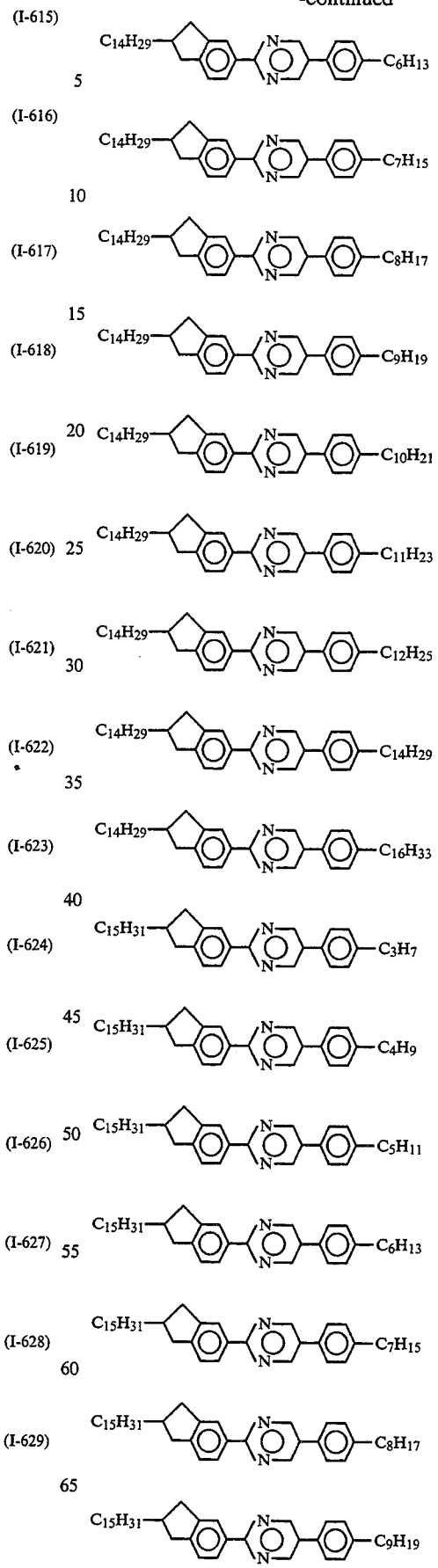

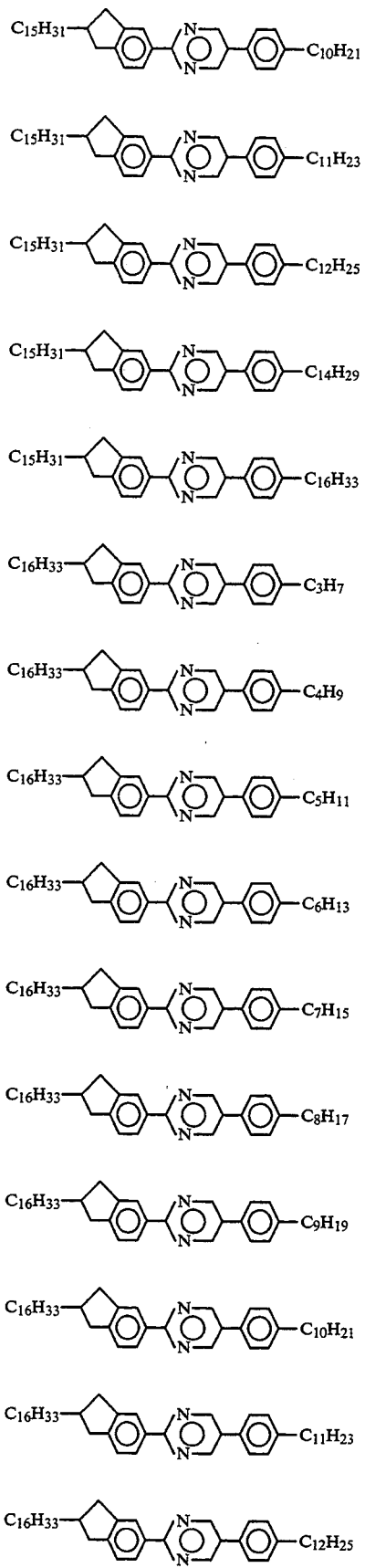
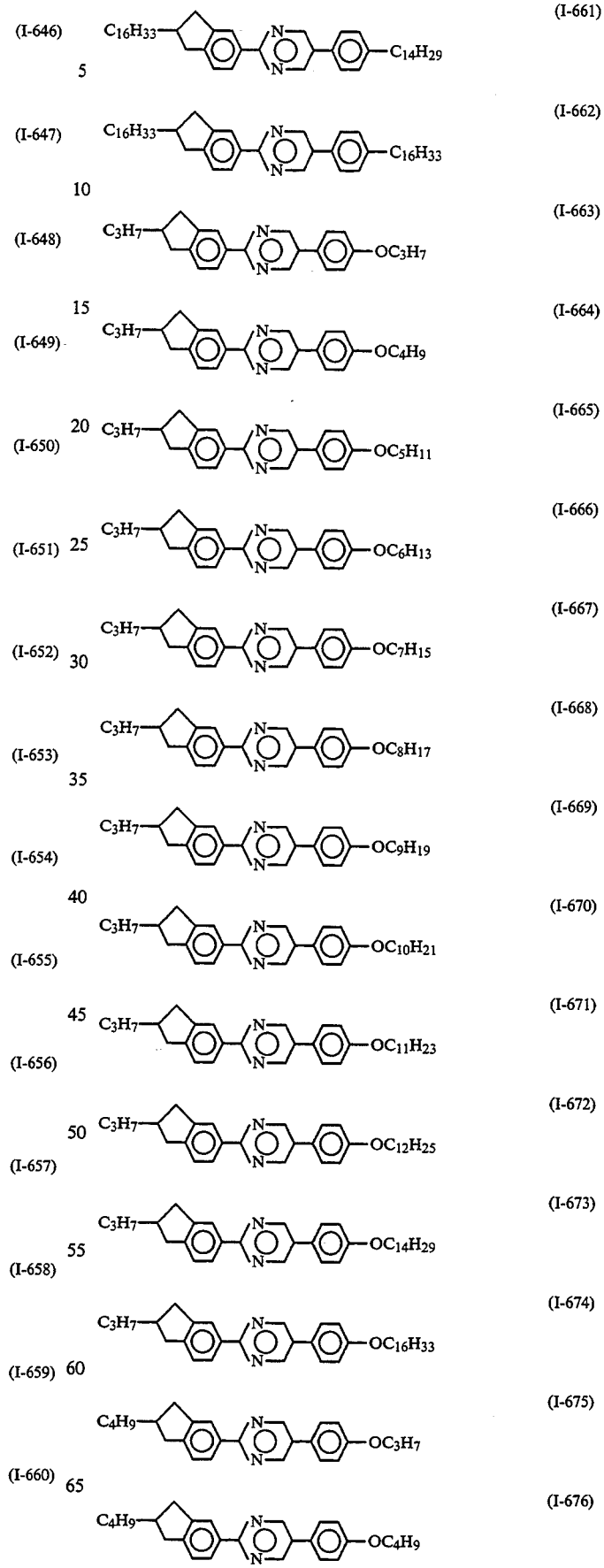

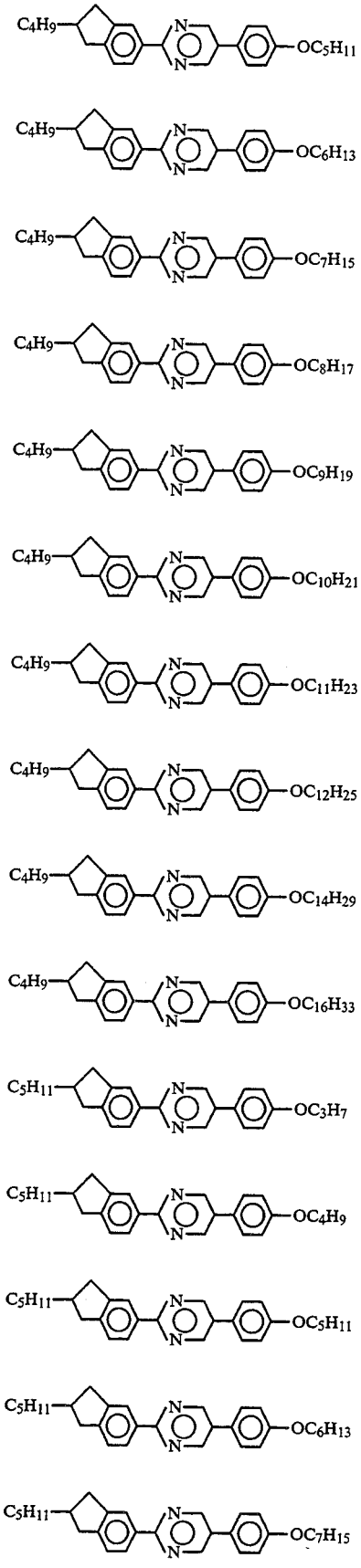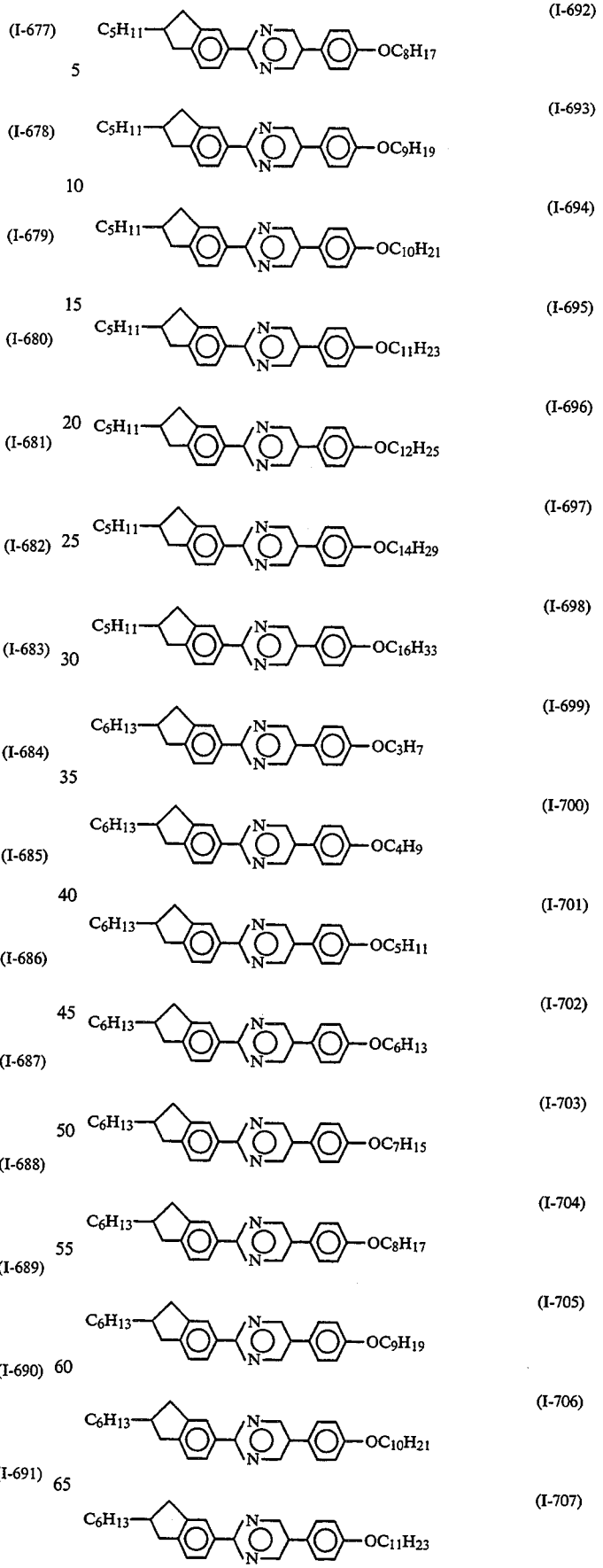

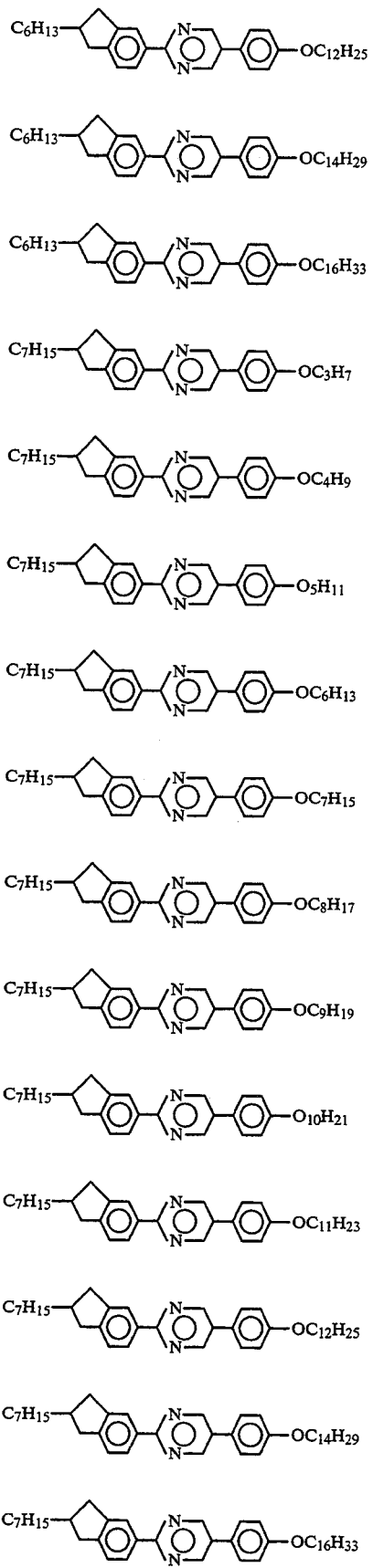
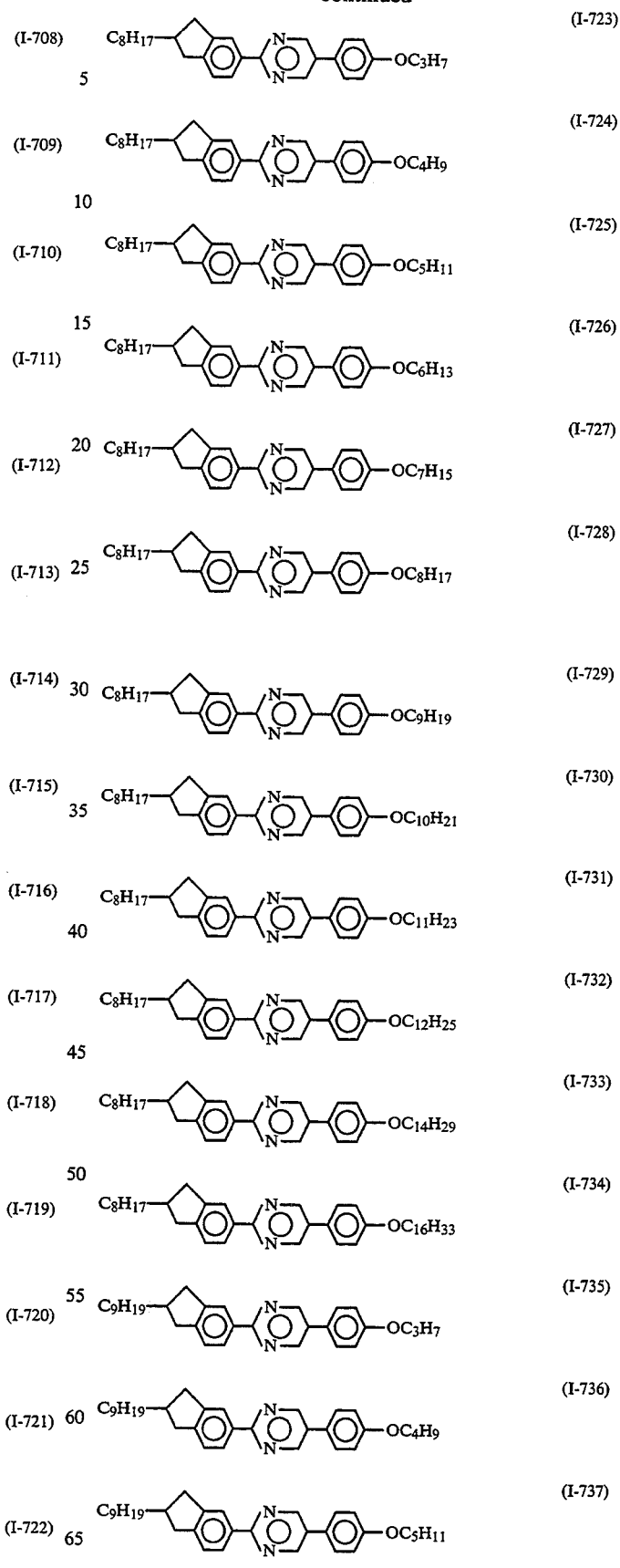

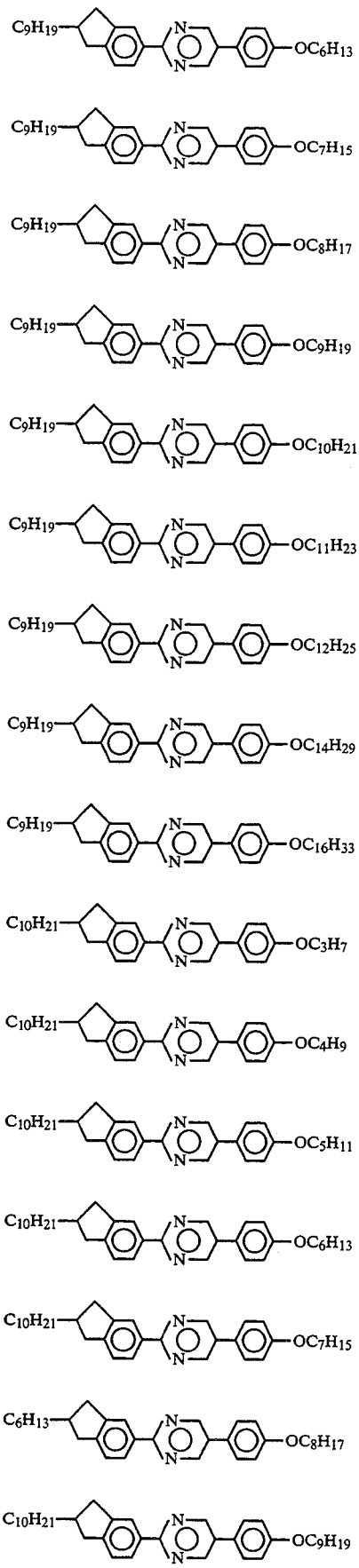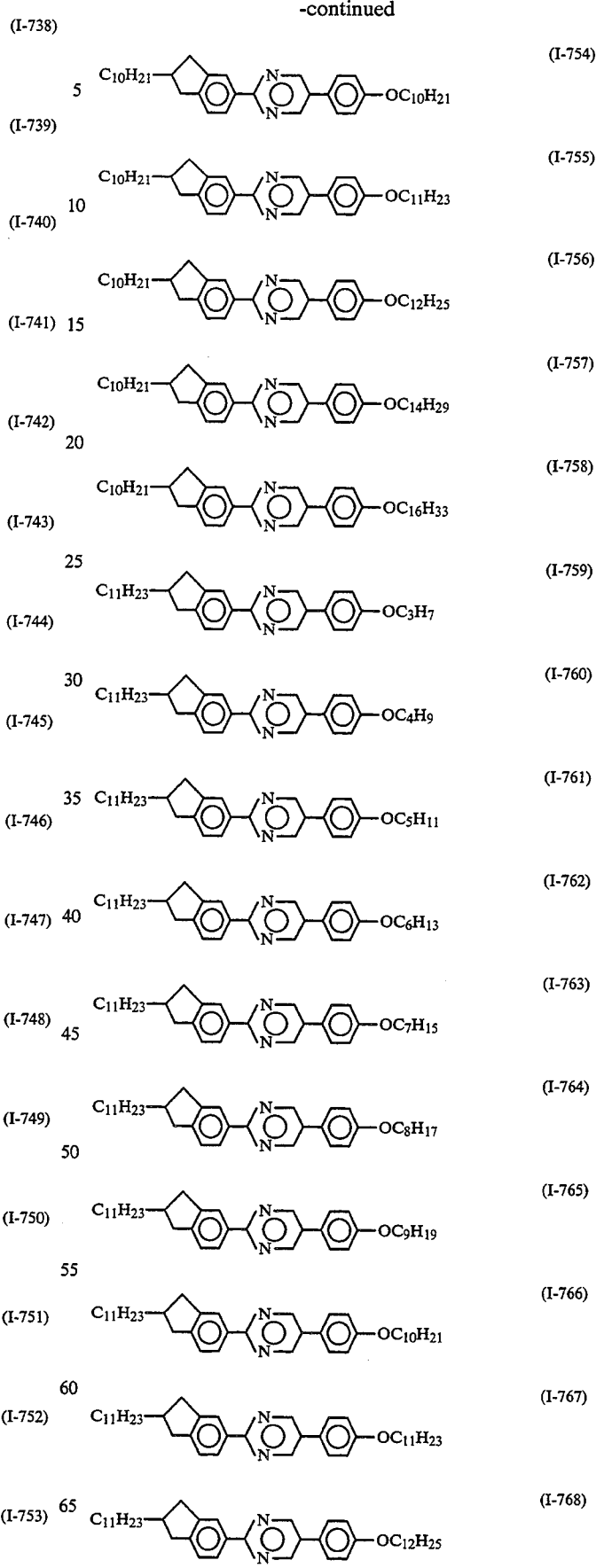

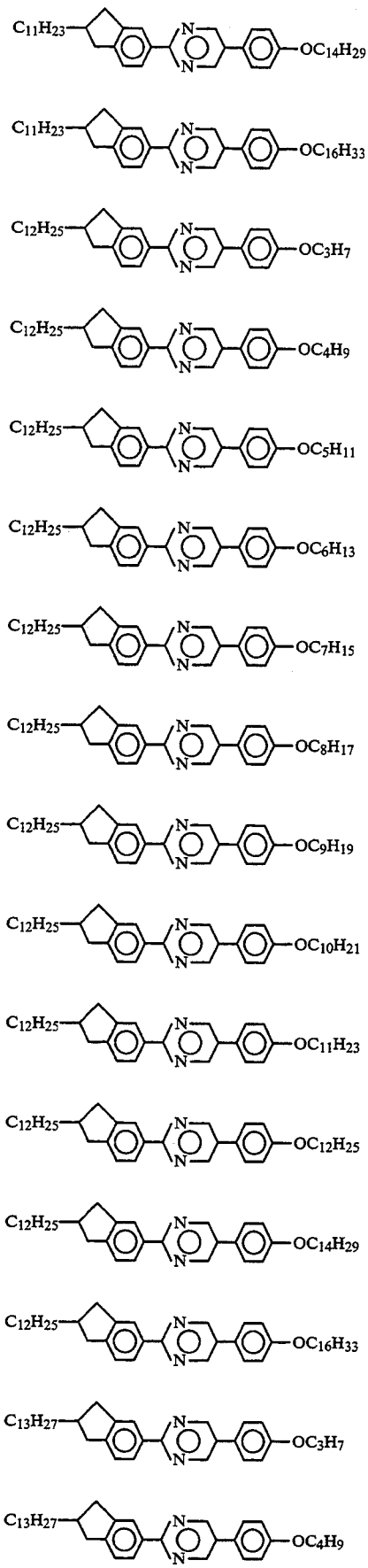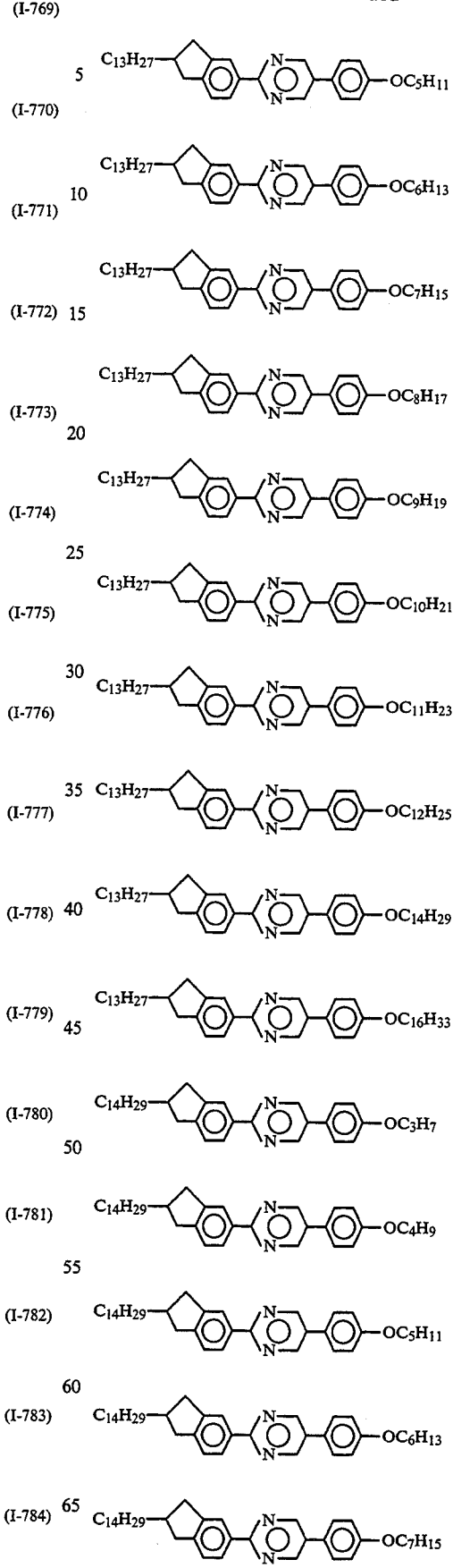

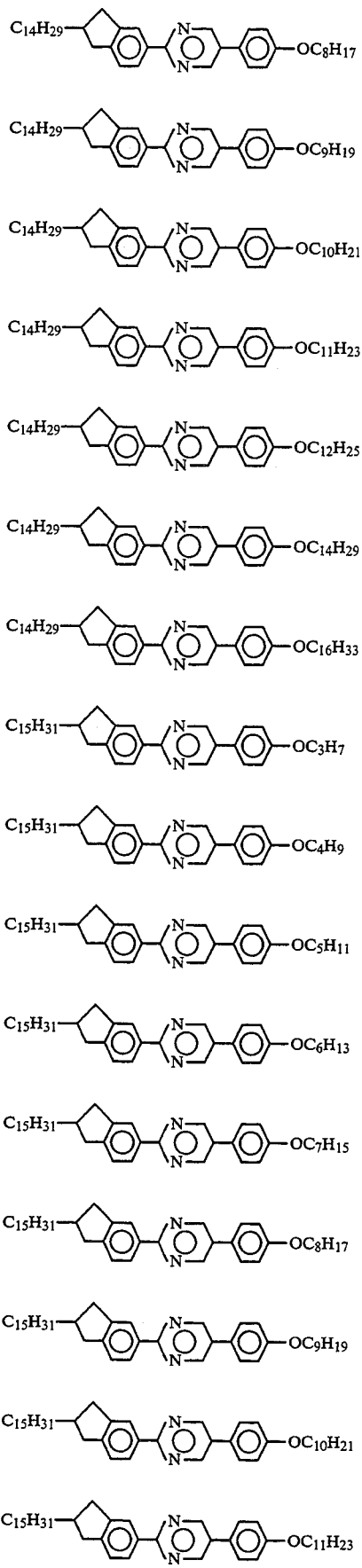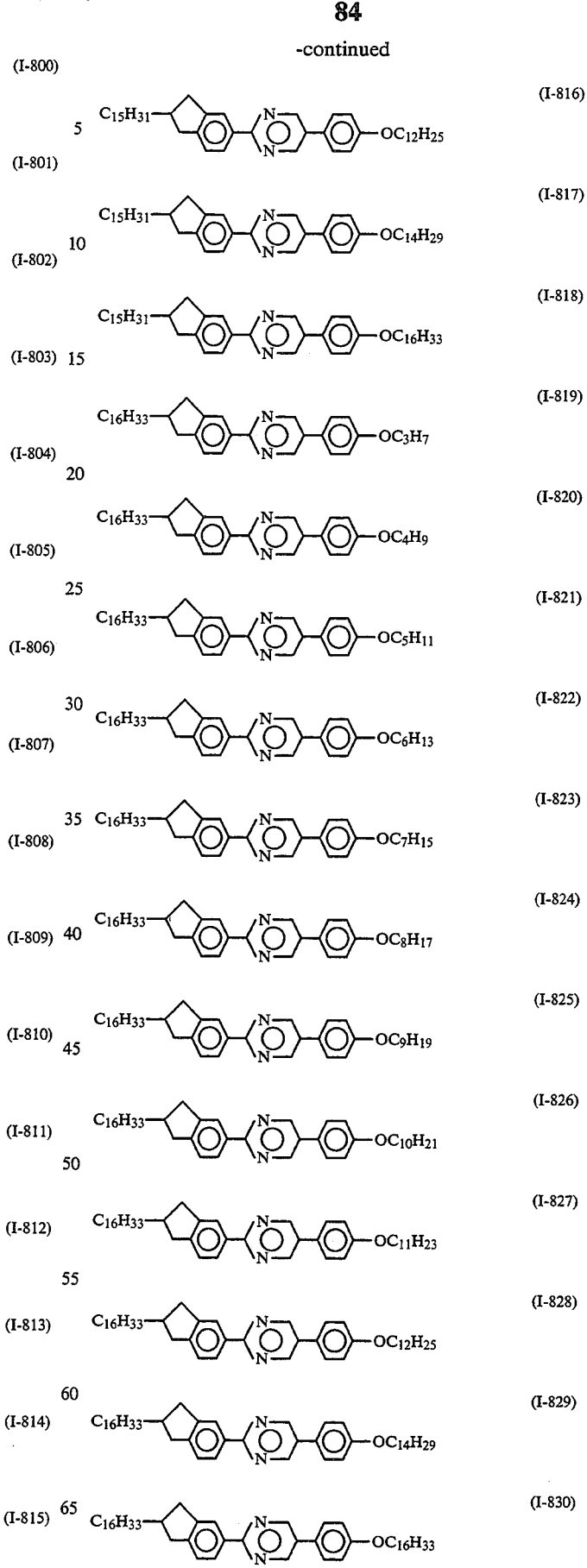

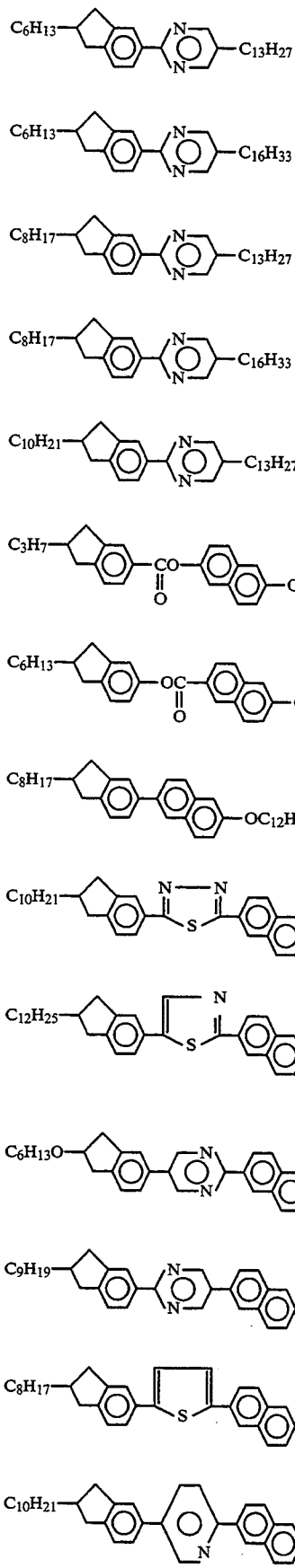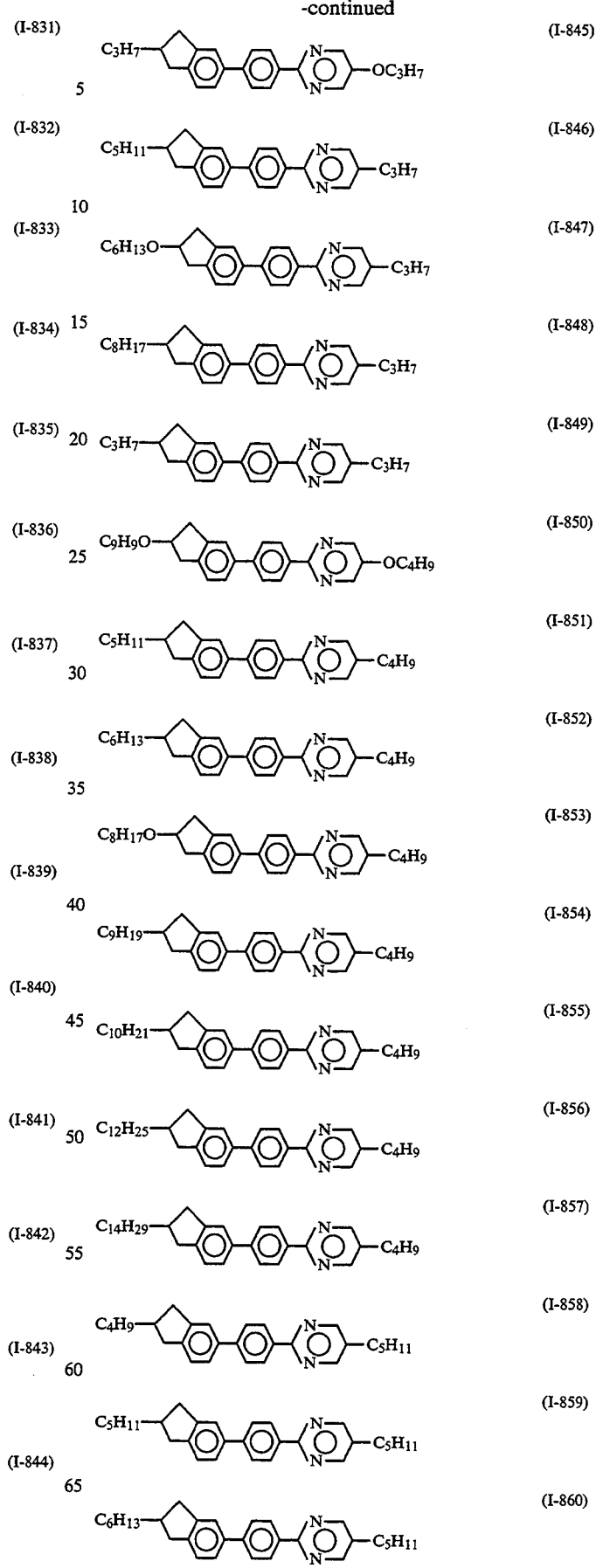

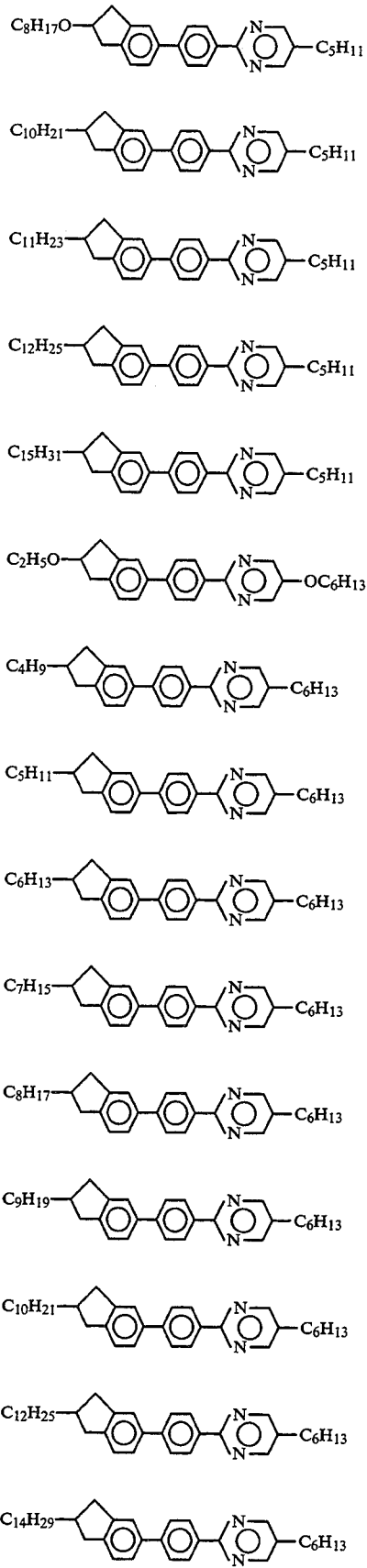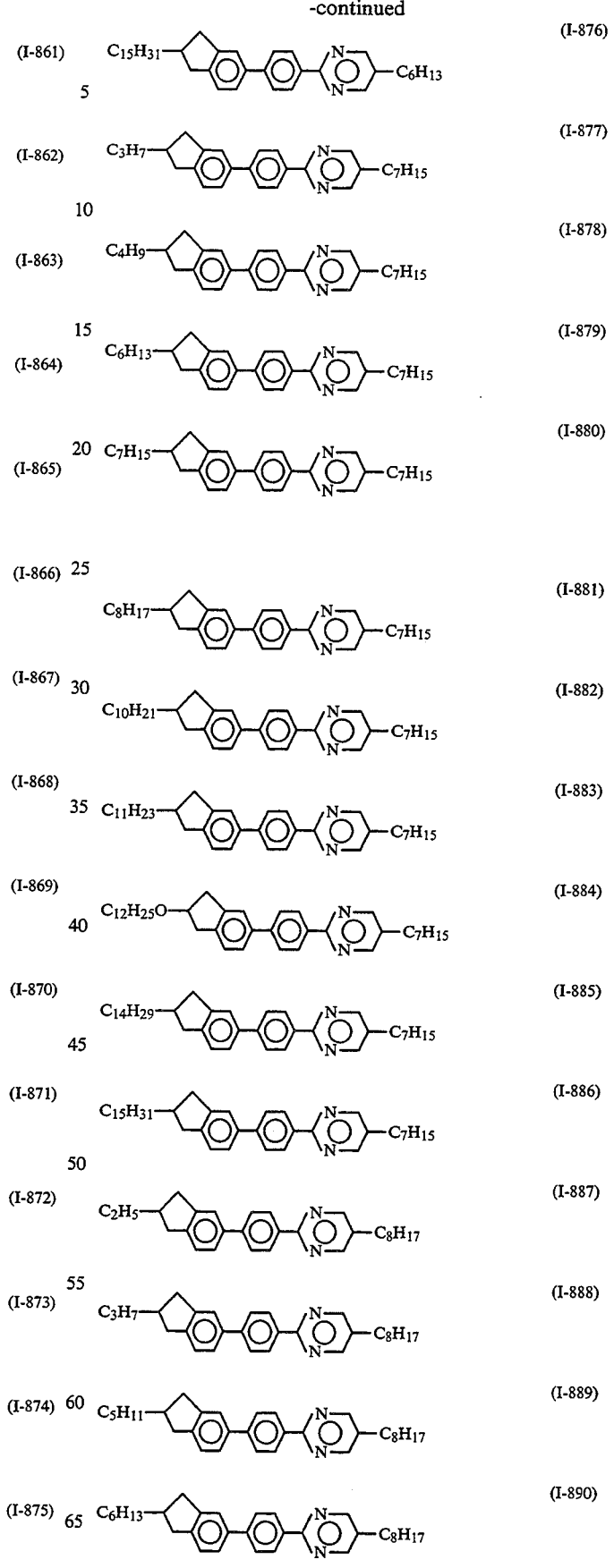

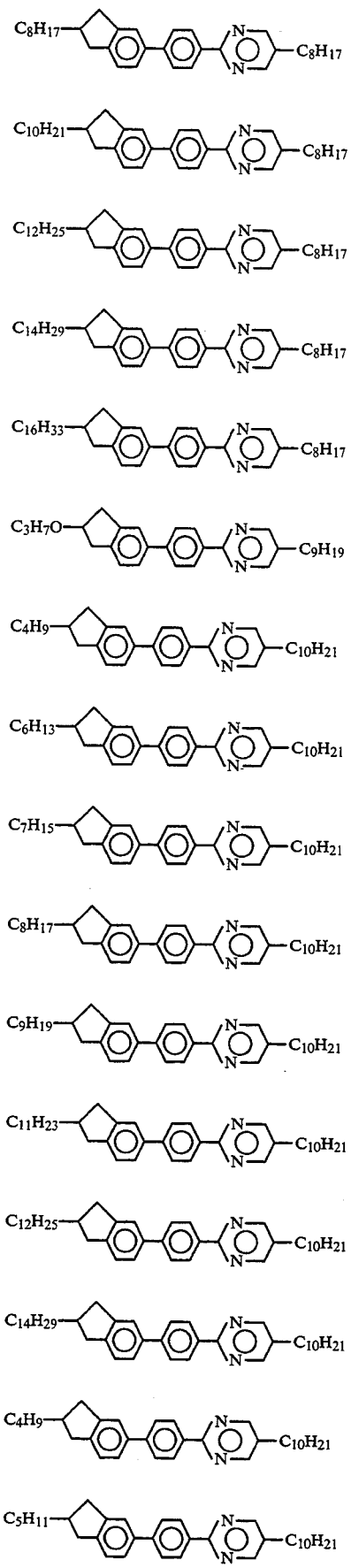
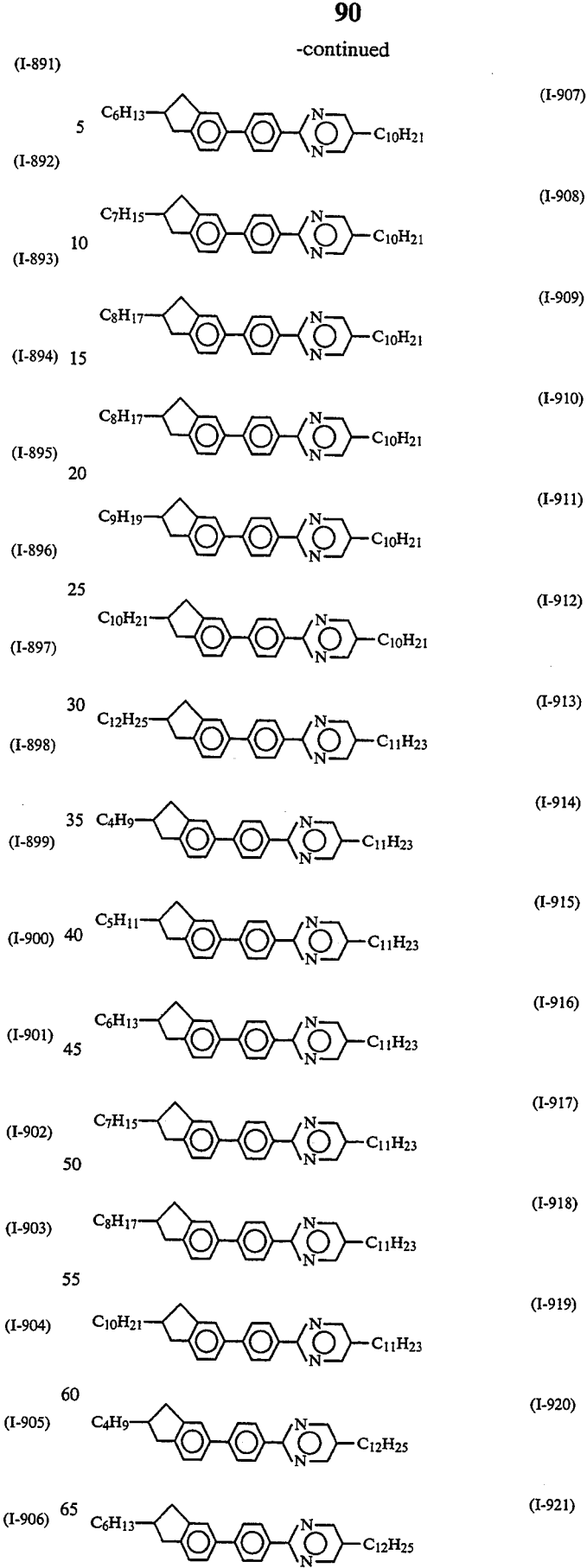

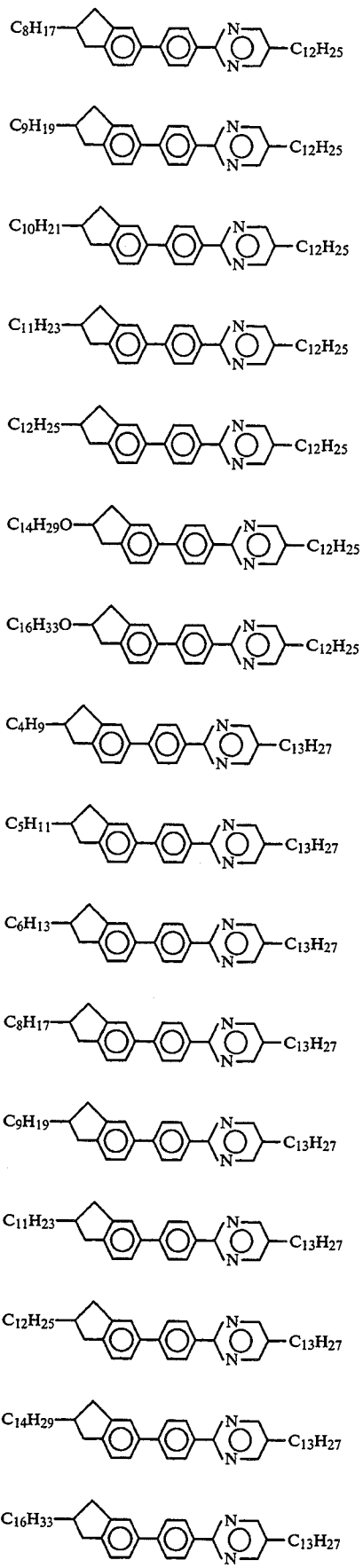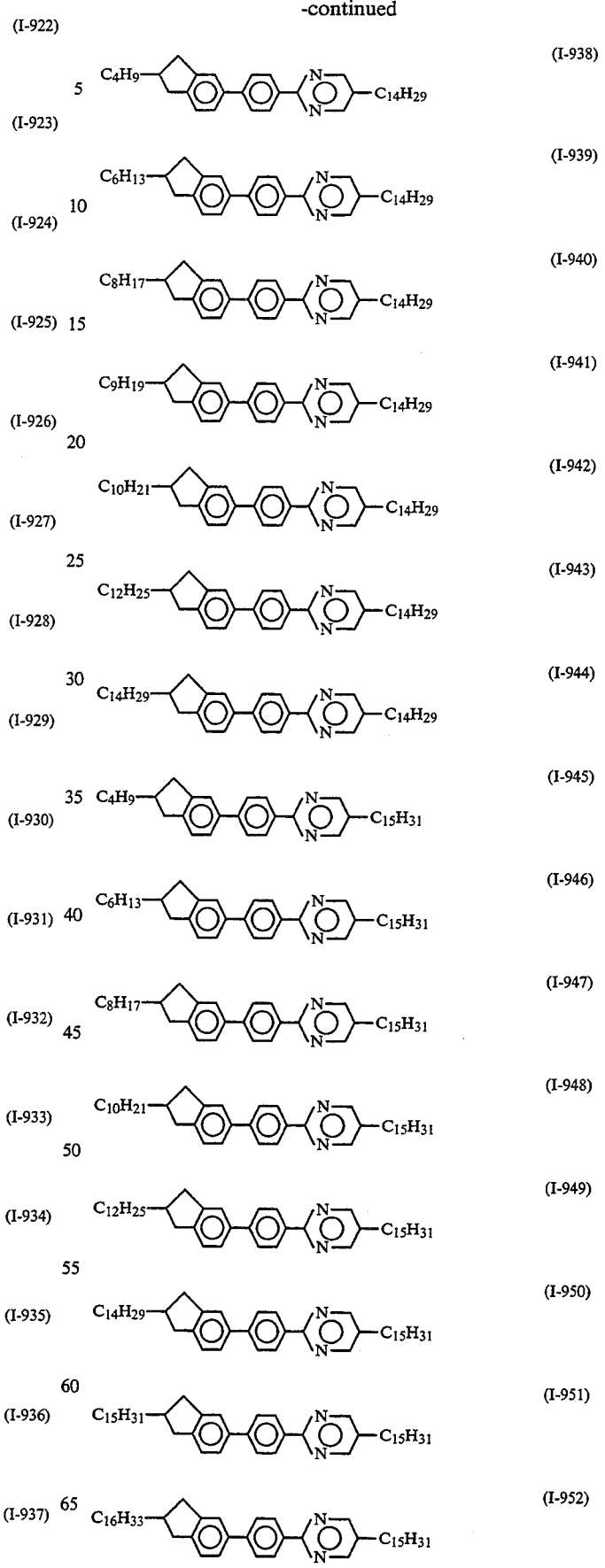

-continued (I-953) C₄H₉—⟨indane⟩—⟨phenyl⟩—⟨pyrimidine⟩—C₁₆H₃₃

(I-954) C₆H₁₃—⟨indane⟩—⟨phenyl⟩—⟨pyrimidine⟩—C₁₆H₃₃

(I-955) C₈H₁₇—⟨indane⟩—⟨phenyl⟩—⟨pyrimidine⟩—C₁₆H₃₃

(I-956) C₁₀H₂₁—⟨indane⟩—⟨phenyl⟩—⟨pyrimidine⟩—C₁₆H₃₃

(I-957) C₁₂H₂₅—⟨indane⟩—⟨phenyl⟩—⟨pyrimidine⟩—C₁₆H₃₃

(I-958) C₁₃H₂₇—⟨indane⟩—⟨phenyl⟩—⟨pyrimidine⟩—C₁₆H₃₃

(I-959) C₁₅H₃₁—⟨indane⟩—⟨phenyl⟩—⟨pyrimidine⟩—C₁₆H₃₃

(I-960) C₁₆H₃₃—⟨indane⟩—⟨phenyl⟩—⟨pyrimidine⟩—C₁₆H₃₃

(I-961) C₃H₇—⟨indane⟩—⟨phenyl-F⟩—⟨pyrimidine⟩—C₃H₇

(I-962) C₅H₁₁—⟨indane⟩—⟨phenyl-F⟩—⟨pyrimidine⟩—C₃H₇

(I-963) C₆H₁₃—⟨indane⟩—⟨phenyl-F⟩—⟨pyrimidine⟩—C₃H₇

(I-964) C₆H₁₃—⟨indane⟩—⟨phenyl-F,F⟩—⟨pyrimidine⟩—C₃H₇

(I-965) C₆H₁₃—⟨indane⟩—⟨phenyl-F⟩—⟨pyrimidine⟩—C₃H₇

(I-966) C₈H₁₇—⟨indane⟩—⟨phenyl-F⟩—⟨pyrimidine⟩—C₃H₇

(I-967) C₆H₁₃—⟨indane⟩—⟨phenyl-F⟩—⟨pyrimidine⟩—C₃H₇

(I-968) C₇H₁₅—⟨indane⟩—⟨phenyl-F⟩—⟨pyrimidine⟩—C₄H₉

(I-969) C₈H₁₇—⟨indane⟩—⟨phenyl-F⟩—⟨pyrimidine⟩—C₄H₉

(I-970) C₁₀H₂₁—⟨indane⟩—⟨phenyl-F⟩—⟨pyrimidine⟩—C₄H₉

(I-971) C₁₂H₂₅—⟨indane⟩—⟨phenyl-F,F⟩—⟨pyrimidine⟩—C₄H₉

(I-972) C₄H₉—⟨indane⟩—⟨phenyl-F⟩—⟨pyrimidine⟩—C₅H₁₁

(I-973) C₅H₁₁—⟨indane⟩—⟨phenyl-F⟩—⟨pyrimidine⟩—C₅H₁₁

(I-974) C₆H₁₃—⟨indane⟩—⟨phenyl-F⟩—⟨pyrimidine⟩—C₅H₁₁

(I-975) C₈H₁₇—⟨indane⟩—⟨phenyl-F,F⟩—⟨pyrimidine⟩—C₅H₁₁

(I-976) C₁₀H₂₁—⟨indane⟩—⟨phenyl-F⟩—⟨pyrimidine⟩—C₅H₁₁

(I-977) C₁₂H₂₅—⟨indane⟩—⟨phenyl-F⟩—⟨pyrimidine⟩—C₅H₁₁

(I-978) C₄H₉—⟨indane⟩—⟨phenyl-F⟩—⟨pyrimidine⟩—C₆H₁₃

(I-979) C₆H₁₃—⟨indane⟩—⟨phenyl-F⟩—⟨pyrimidine⟩—C₆H₁₃

(I-980) C₈H₁₇—⟨indane⟩—⟨phenyl-F⟩—⟨pyrimidine⟩—C₆H₁₃

(I-981) C₈H₁₇—⟨indane⟩—⟨phenyl-F,F⟩—⟨pyrimidine⟩—C₆H₁₃

(I-982) C₁₀H₂₁—⟨indane⟩—⟨phenyl-F⟩—⟨pyrimidine⟩—C₆H₁₃

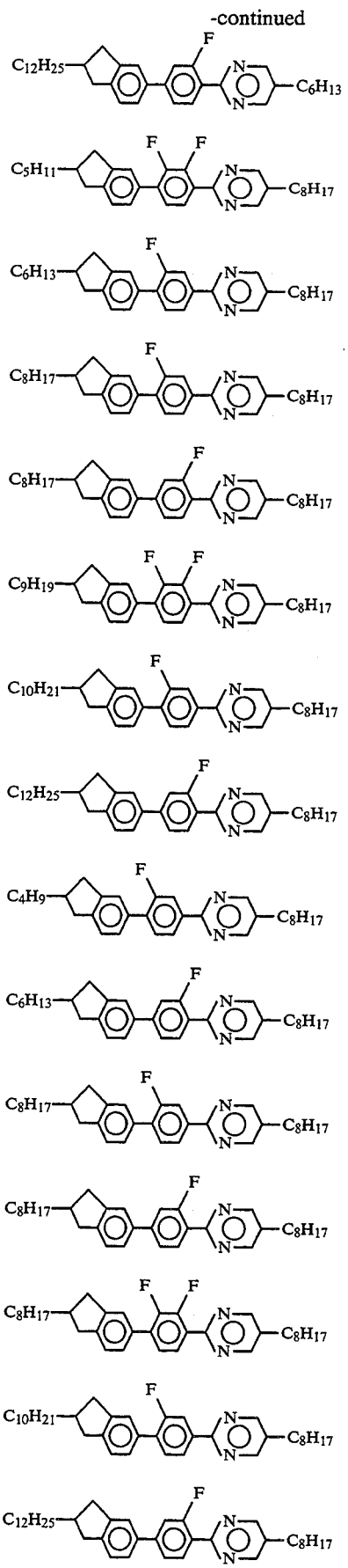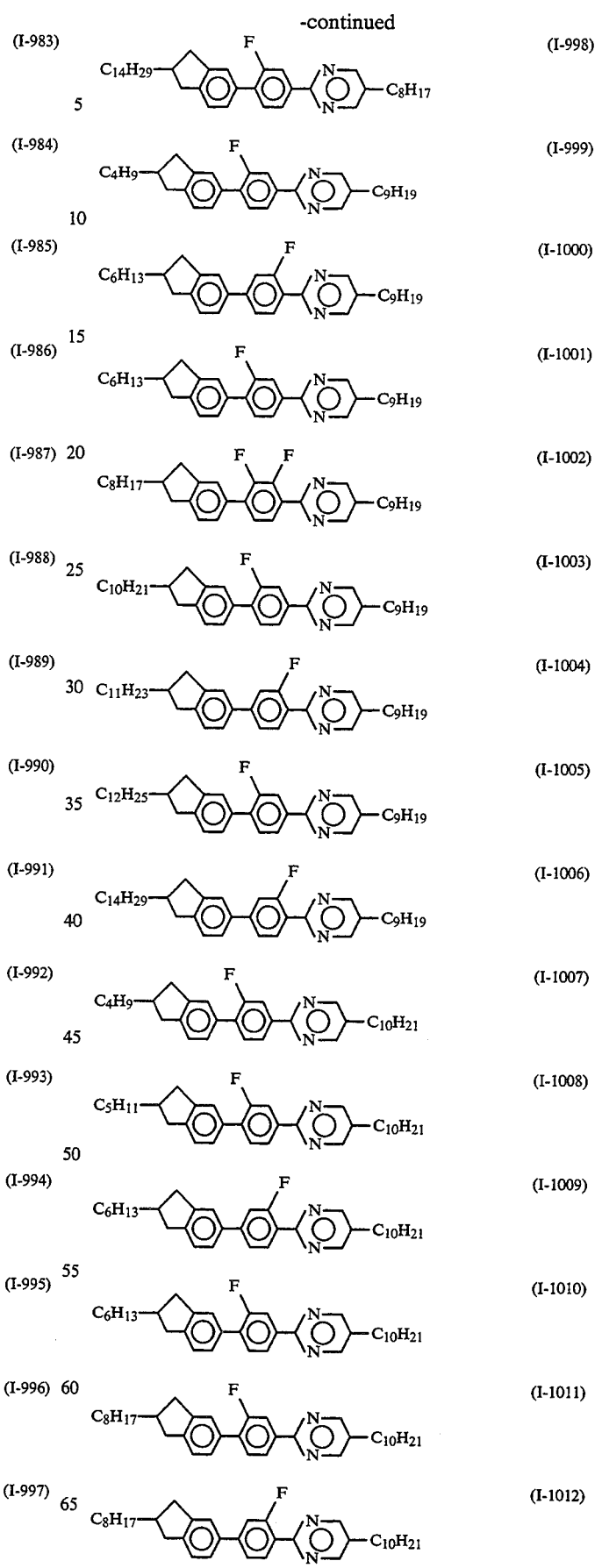

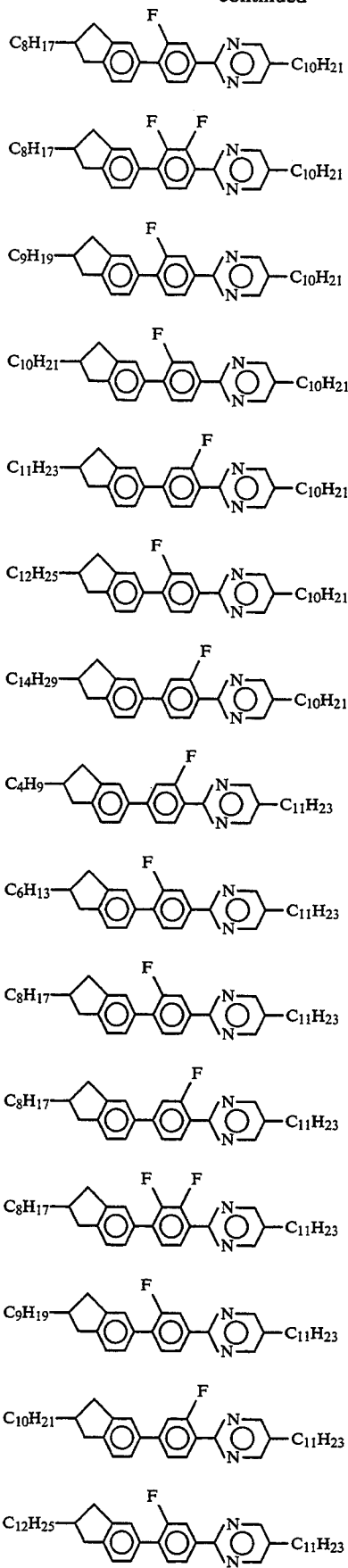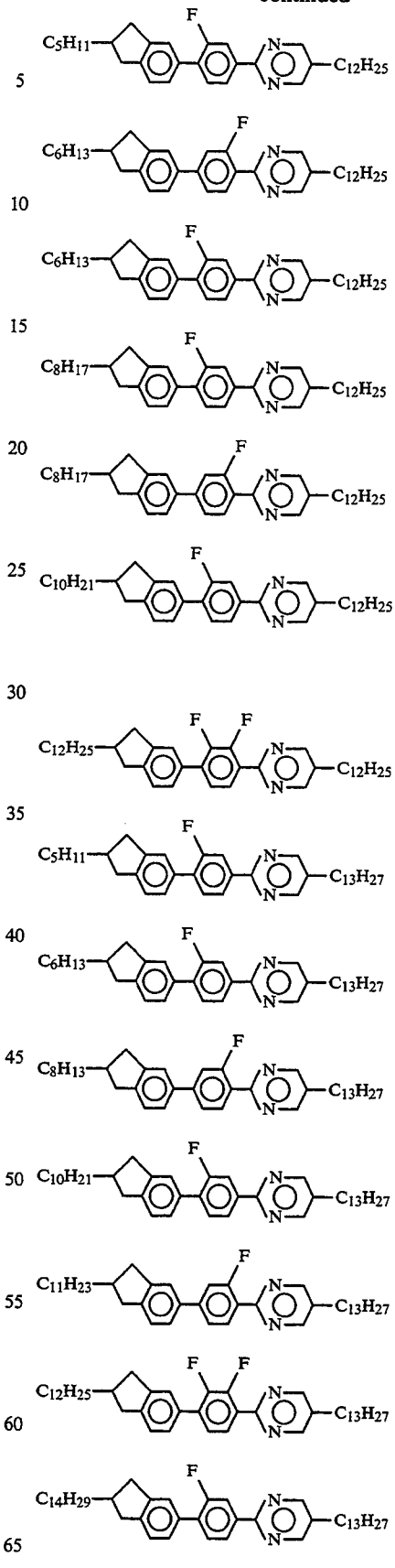

-continued (I-1042) C₄H₉–⟨indane⟩–⟨C₆H₃(F)⟩–⟨pyrimidine⟩–C₁₄H₂₉

(I-1043) C₅H₁₁–⟨indane⟩–⟨C₆H₃(F)⟩–⟨pyrimidine⟩–C₁₄H₂₉

(I-1044) C₆H₁₃–⟨indane⟩–⟨C₆H₃(F)⟩–⟨pyrimidine⟩–C₁₄H₂₉

(I-1045) C₈H₁₇–⟨indane⟩–⟨C₆H₃(F)⟩–⟨pyrimidine⟩–C₁₄H₂₉

(I-1046) C₉H₁₉–⟨indane⟩–⟨C₆H₃(F)⟩–⟨pyrimidine⟩–C₁₄H₂₉

(I-1047) C₁₀H₂₁–⟨indane⟩–⟨C₆H₂(F,F)⟩–⟨pyrimidine⟩–C₁₄H₂₉

(I-1048) C₁₁H₂₃–⟨indane⟩–⟨C₆H₃(F)⟩–⟨pyrimidine⟩–C₁₄H₂₉

(I-1049) C₁₂H₂₅–⟨indane⟩–⟨C₆H₃(F)⟩–⟨pyrimidine⟩–C₁₄H₂₉

(I-1050) C₁₄H₂₉–⟨indane⟩–⟨C₆H₃(F)⟩–⟨pyrimidine⟩–C₁₄H₂₉

(I-1051) C₈H₁₇–⟨indane⟩–⟨C₆H₃(F)⟩–⟨pyrimidine⟩–C₁₅H₃₁

(I-1052) C₁₀H₂₁–⟨indane⟩–⟨C₆H₃(F)⟩–⟨pyrimidine⟩–C₁₅H₃₁

(I-1053) C₁₂H₂₅–⟨indane⟩–⟨C₆H₂(F,F)⟩–⟨pyrimidine⟩–C₁₅H₃₁

(I-1054) C₈H₁₇–⟨indane⟩–⟨C₆H₃(F)⟩–⟨pyrimidine⟩–C₁₆H₃₃

(I-1055) C₁₀H₂₁–⟨indane⟩–⟨C₆H₃(F)⟩–⟨pyrimidine⟩–C₁₆H₃₃

(I-1056) C₁₀H₂₁–⟨indane⟩–⟨C₆H₂(F,F)⟩–⟨pyrimidine⟩–C₁₆H₃₃

(I-1057) C₁₂H₂₅–⟨indane⟩–⟨C₆H₃(F)⟩–⟨pyrimidine⟩–C₁₆H₃₃

(I-1058) C₁₄H₂₉–⟨indane⟩–⟨C₆H₃(F)⟩–⟨pyrimidine⟩–C₁₆H₃₃

(I-1059) C₂H₅–⟨indane⟩–⟨pyridine⟩–C₄H₉

(I-1060) C₃H₇–⟨indane⟩–⟨pyridine⟩–C₆H₁₃

(I-1061) C₅H₁₁–⟨indane⟩–⟨pyridine⟩–C₆H₁₃

(I-1062) C₆H₁₃–⟨indane⟩–⟨pyridine⟩–C₆H₁₃

(I-1063) C₆H₁₃–⟨indane⟩–⟨pyridine⟩–OC₆H₁₃

(I-1064) C₇H₁₅–⟨indane⟩–⟨pyridine⟩–OC(O)C₆H₁₃

(I-1065) C₈H₁₇–⟨indane⟩–⟨pyridine⟩–C₆H₁₃

(I-1066) C₉H₁₉O–⟨indane⟩–⟨pyridine⟩–C₆H₁₃

(I-1067) C₁₀H₂₁C(O)O–⟨indane⟩–⟨pyridine⟩–C₆H₁₃

(I-1068) C₁₂H₂₅–⟨indane⟩–⟨pyridine⟩–C₆H₁₃

(I-1069) C₆H₁₃–⟨indane⟩–⟨pyridine⟩–C₇H₁₅

(I-1070) C₁₀H₂₁–⟨indane⟩–⟨pyridine⟩–C₇H₁₅

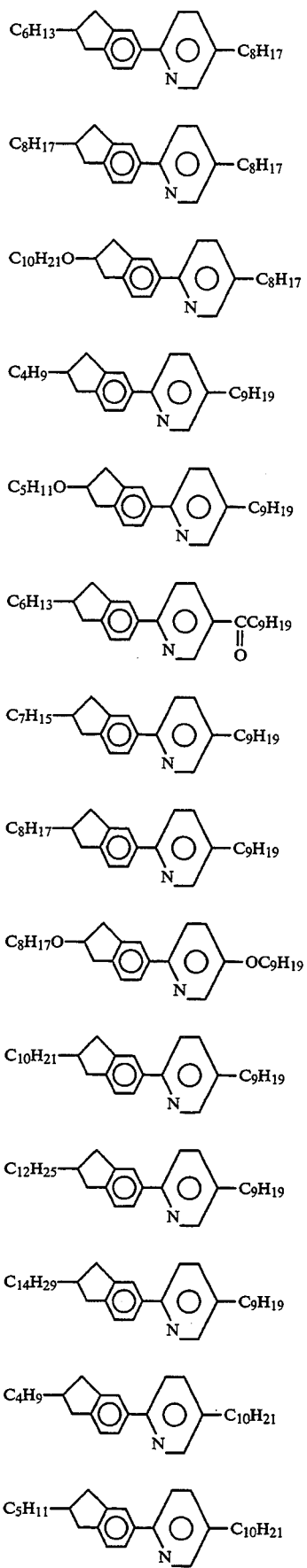
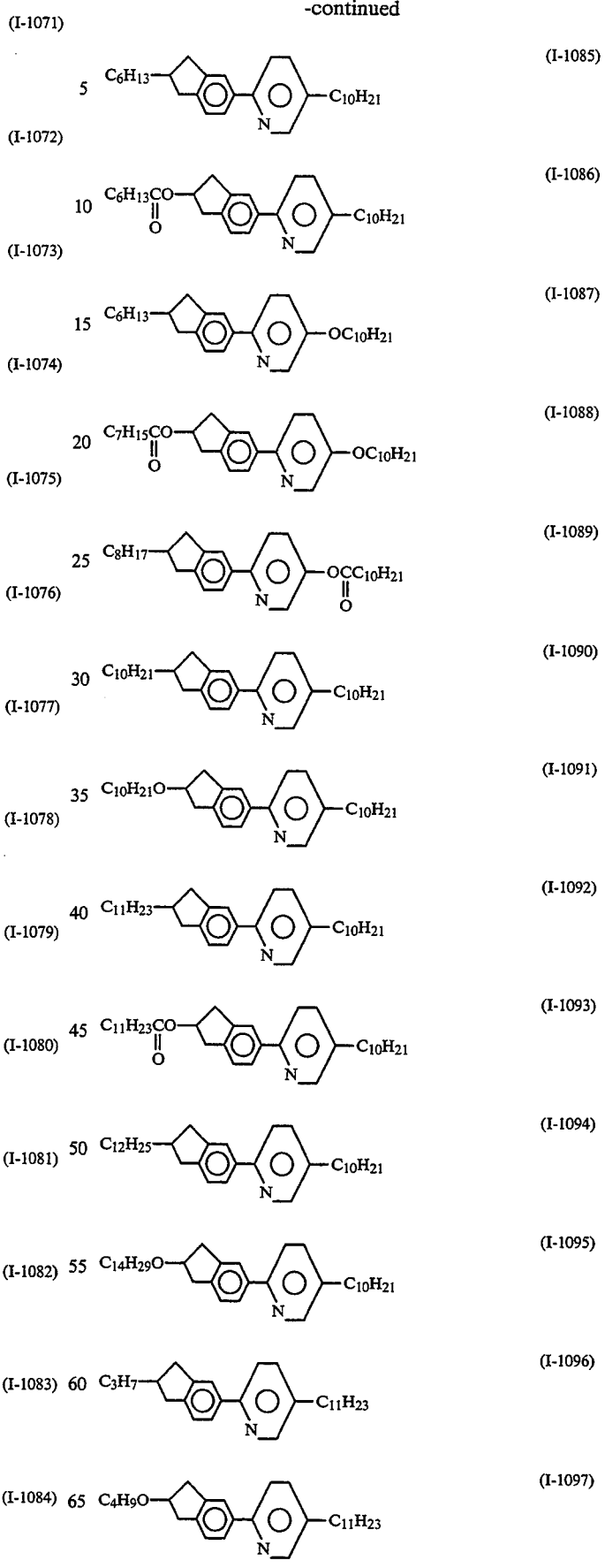

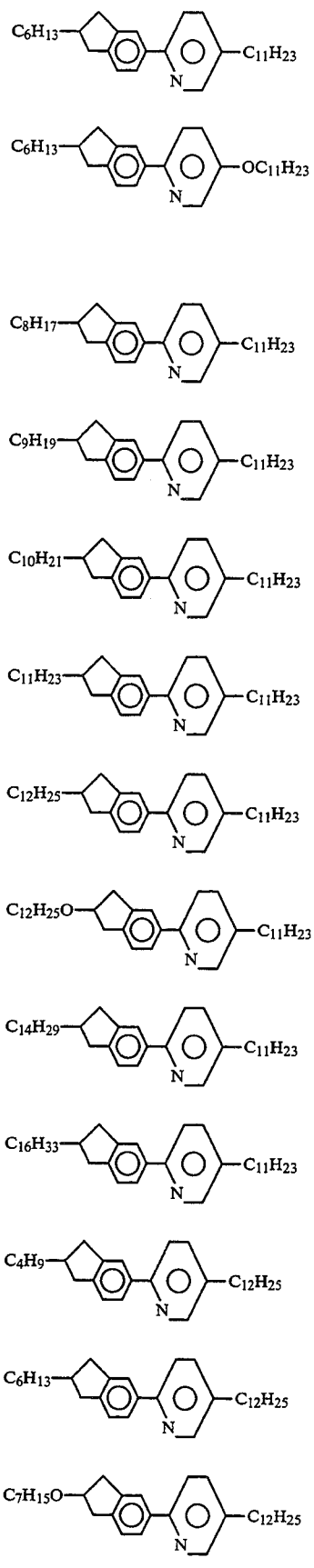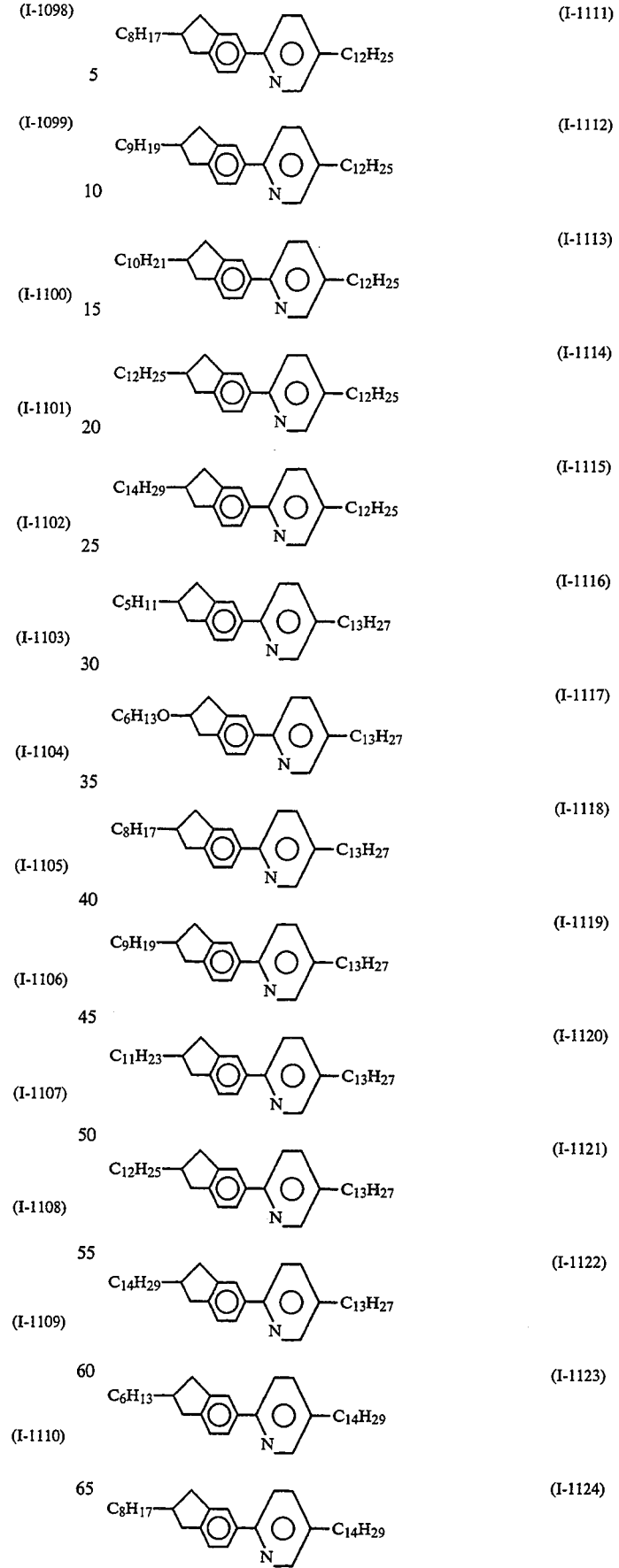

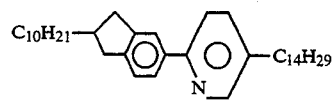 (I-1125)
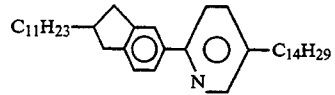 (I-1126)
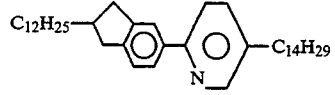 (I-1127)
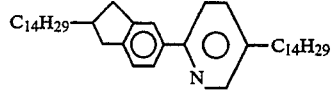 (I-1128)
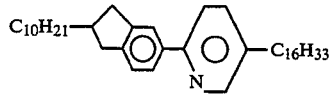 (I-1129)
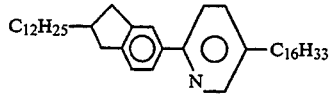 (I-1130)
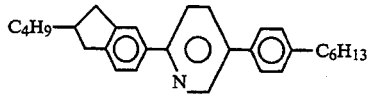 (I-1131)
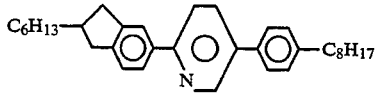 (I-1132)
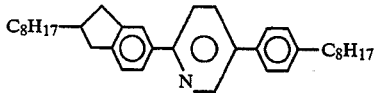 (I-1133)
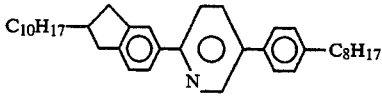 (I-1134)
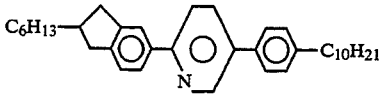 (I-1135)
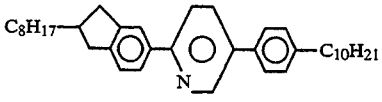 (I-1136)
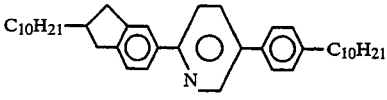 (I-1137)
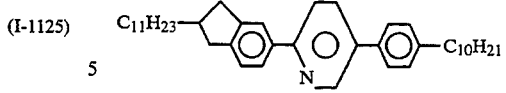 (I-1138)
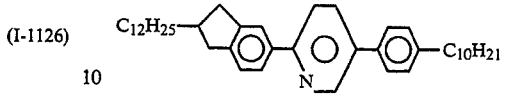 (I-1139)
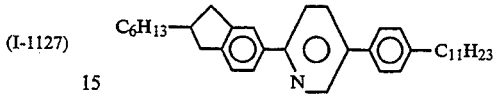 (I-1140)
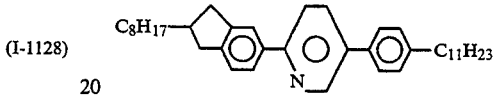 (I-1141)
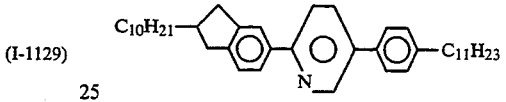 (I-1142)
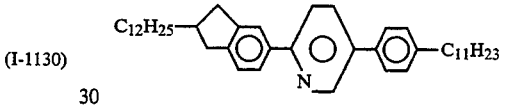 (I-1143)
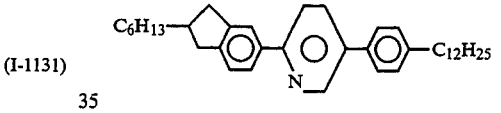 (I-1144)
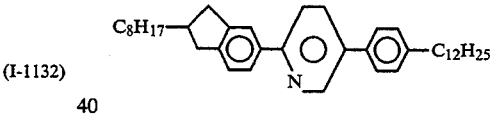 (I-1145)
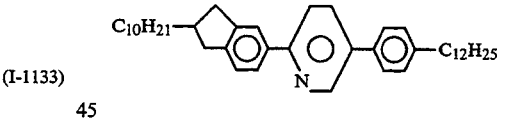 (I-1146)
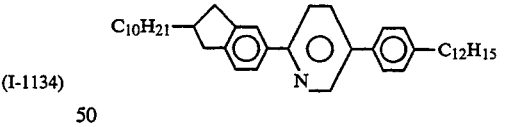 (I-1147)
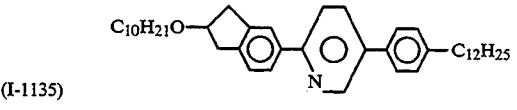 (I-1148)
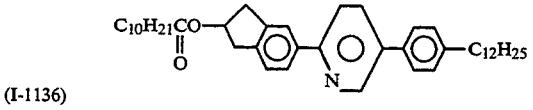 (I-1149)
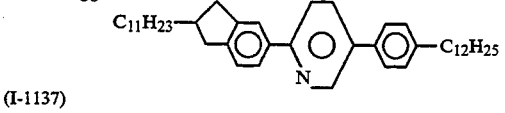 (I-1150)
(I-1151)

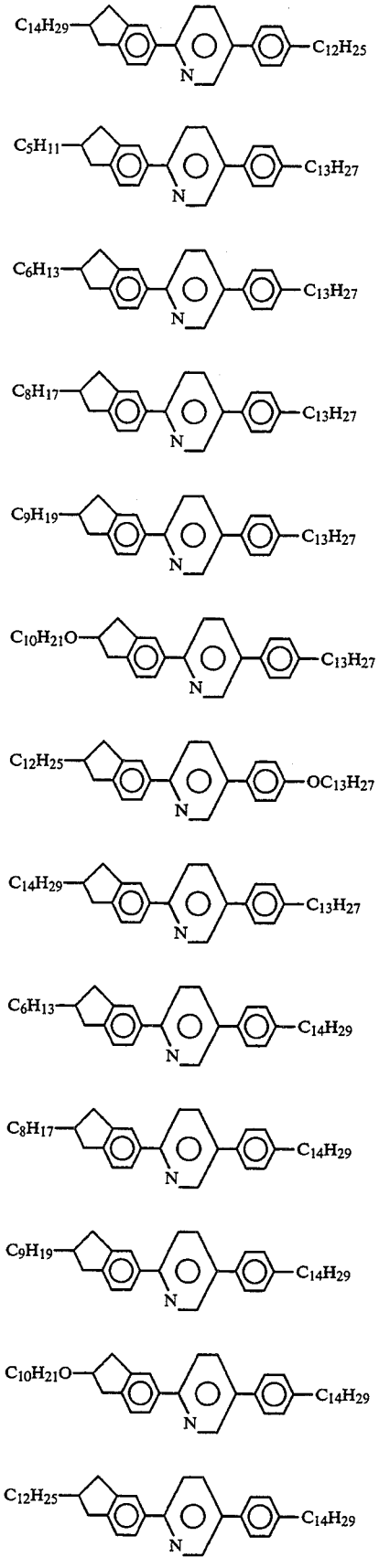
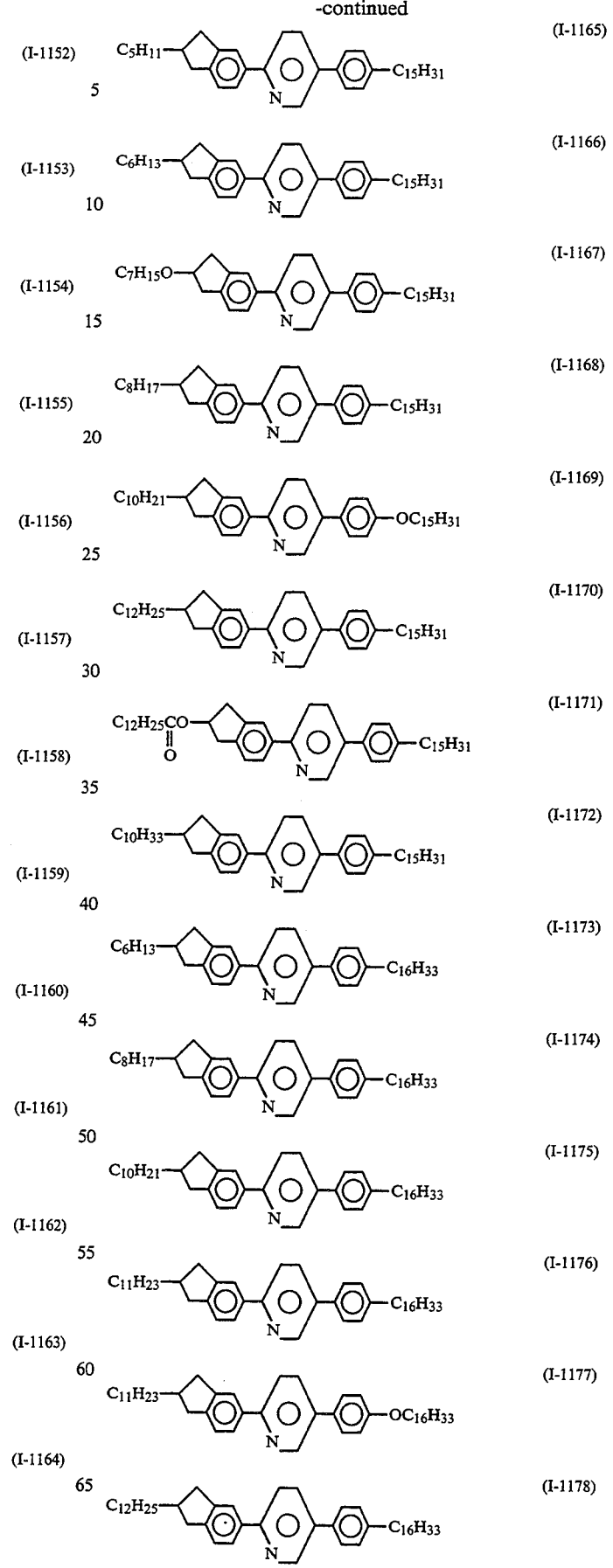

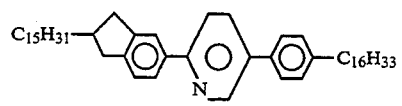 (I-1179)
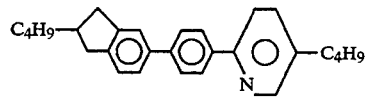 (I-1180)
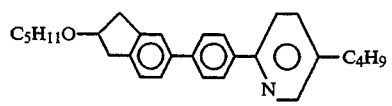 (I-1181)
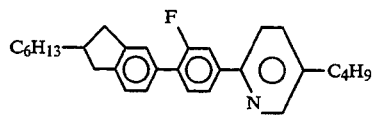 (I-1182)
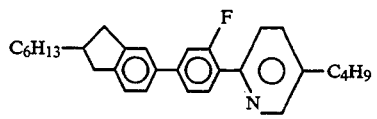 (I-1183)
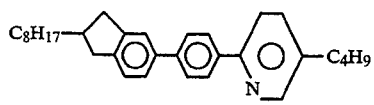 (I-1184)
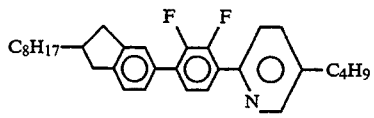 (I-1185)
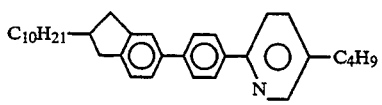 (I-1186)
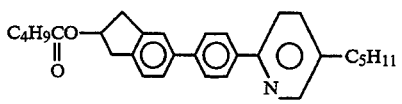 (I-1187)
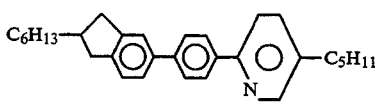 (I-1188)
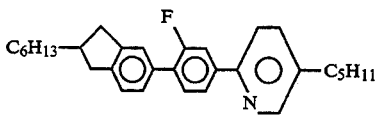 (I-1189)
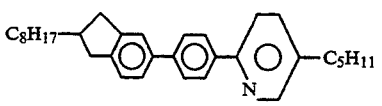 (I-1190)
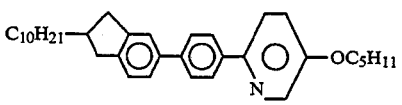 (I-1191)
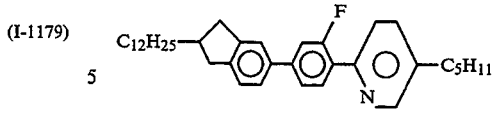 (I-1192)
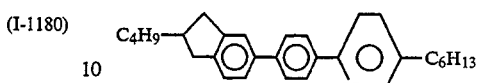 (I-1193)
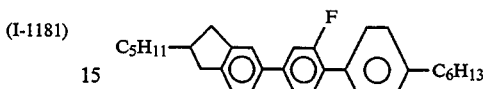 (I-1194)
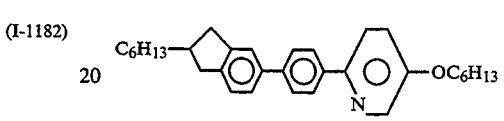 (I-1195)
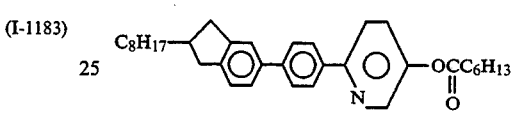 (I-1196)
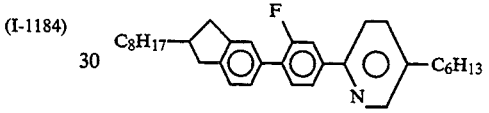 (I-1197)
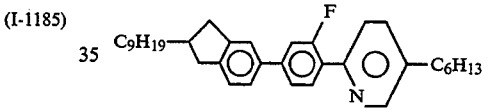 (I-1198)
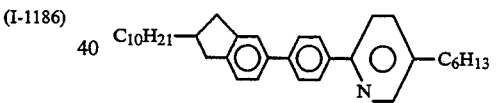 (I-1199)
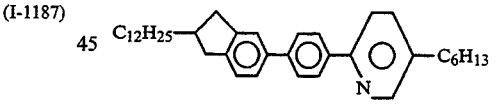 (I-1200)
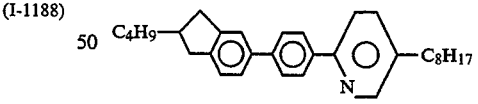 (I-1201)
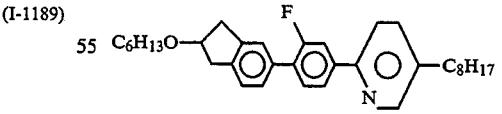 (I-1202)
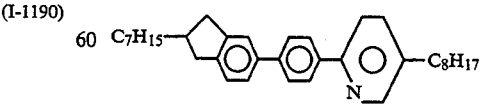 (I-1203)
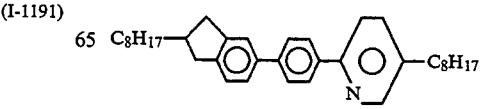 (I-1204)

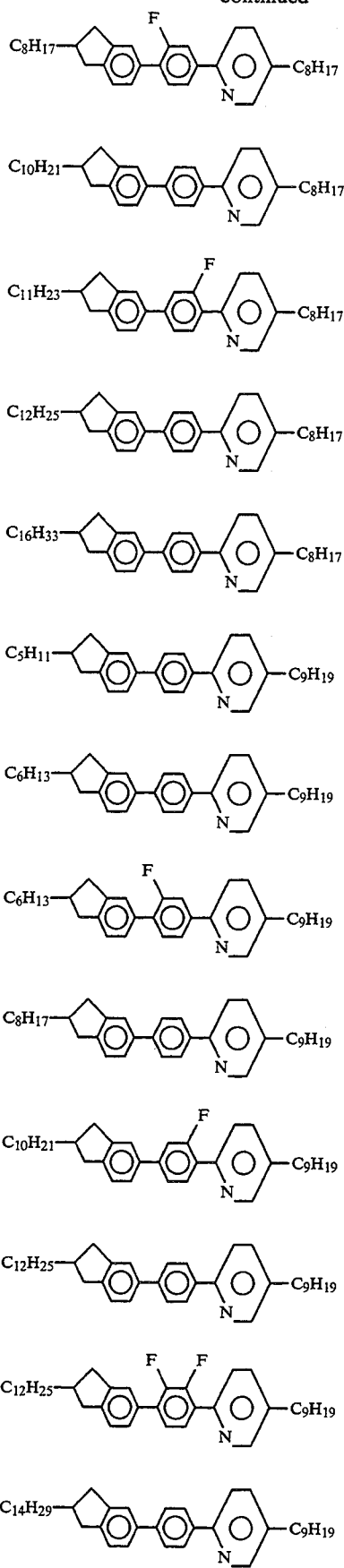
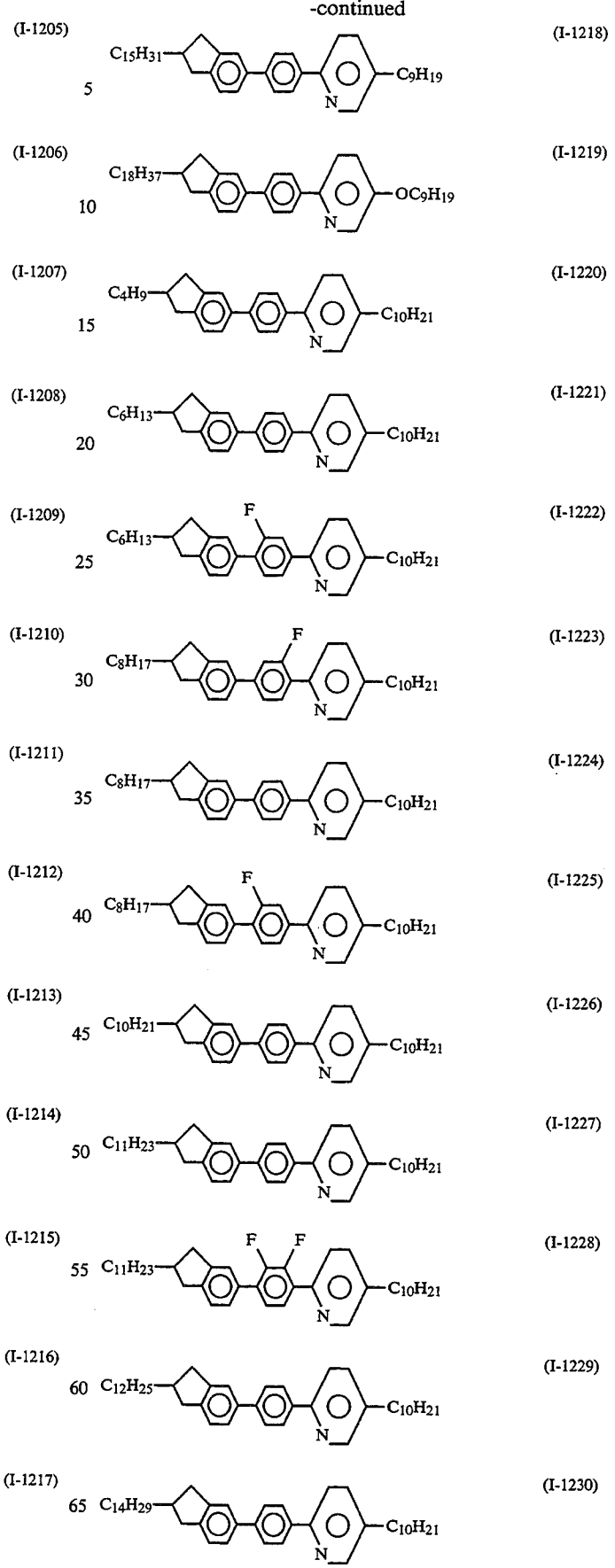

-continued
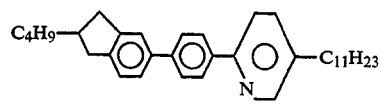 (I-1231)
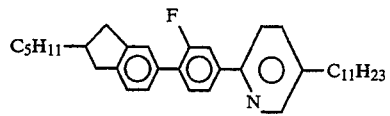 (I-1232)
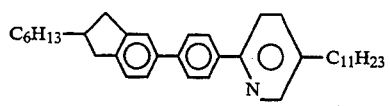 (I-1233)
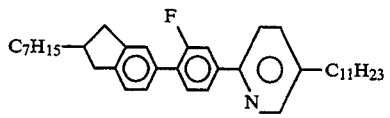 (I-1234)
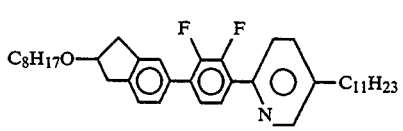 (I-1235)
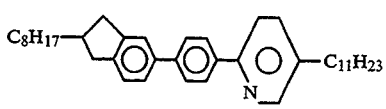 (I-1236)
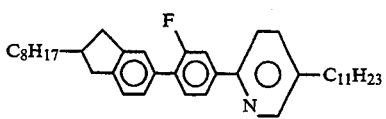 (I-1237)
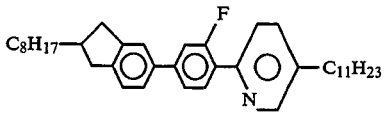 (I-1238)
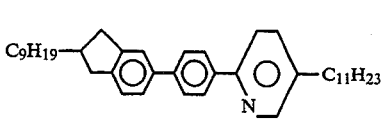 (I-1239)
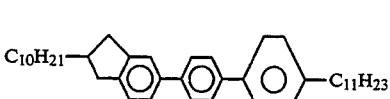 (I-1240)
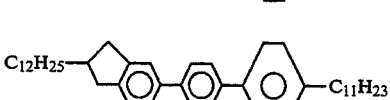 (I-1241)
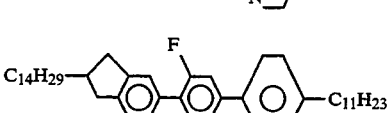 (I-1242)
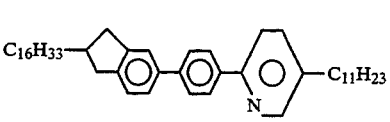 (I-1243)
-continued
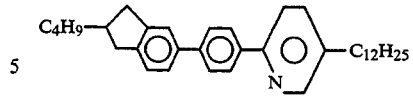 (I-1244)
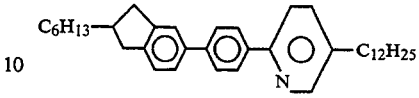 (I-1245)
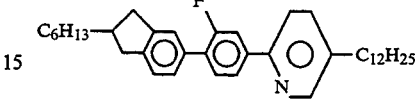 (I-1246)
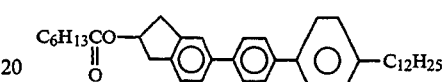 (I-1247)
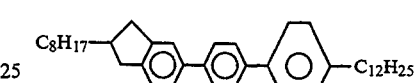 (I-1248)
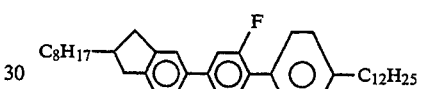 (I-1249)
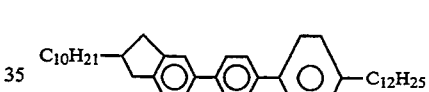 (I-1250)
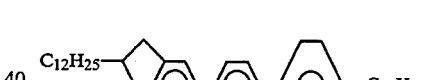 (I-1251)
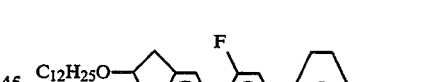 (I-1252)
 (I-1253)
 (I-1254)
 (I-1255)
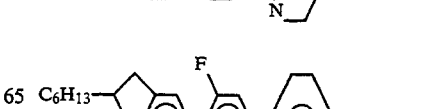 (I-1256)

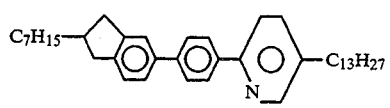 (I-1257)
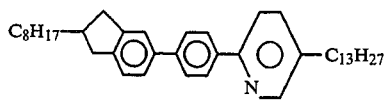 (I-1258)
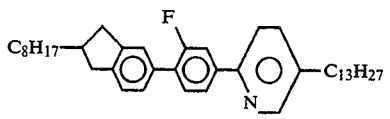 (I-1259)
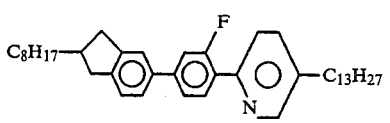 (I-1260)
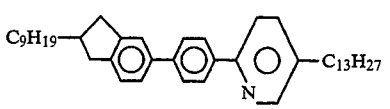 (I-1261)
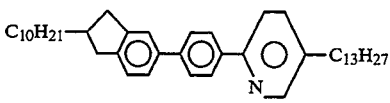 (I-1262)
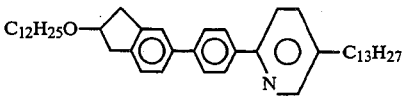 (I-1263)
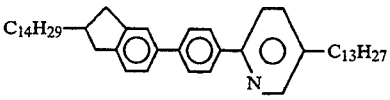 (I-1264)
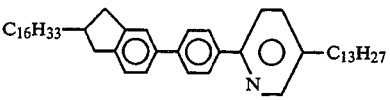 (I-1265)
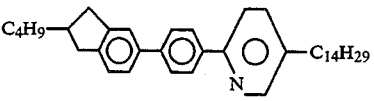 (I-1266)
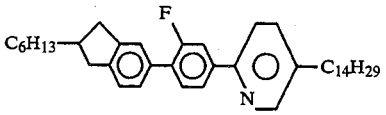 (I-1267)
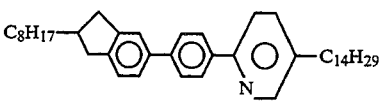 (I-1268)
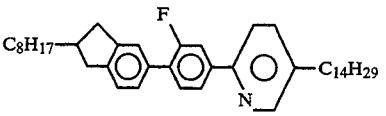 (I-1269)
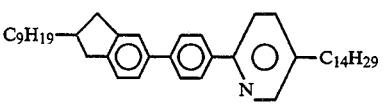 (I-1270)
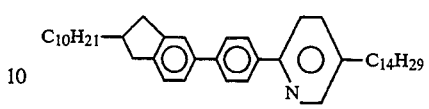 (I-1271)
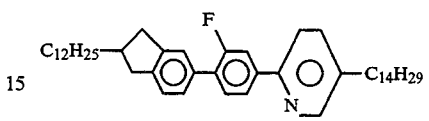 (I-1272)
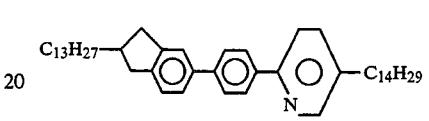 (I-1273)
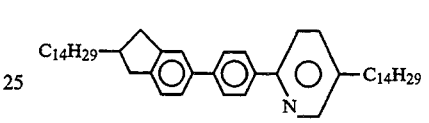 (I-1274)
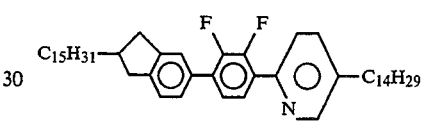 (I-1275)
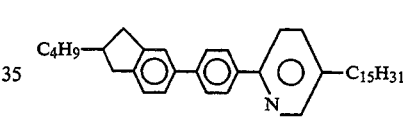 (I-1276)
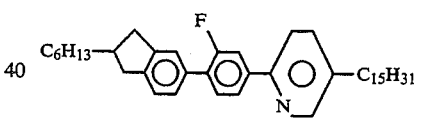 (I-1277)
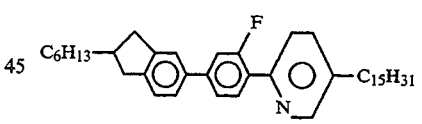 (I-1278)
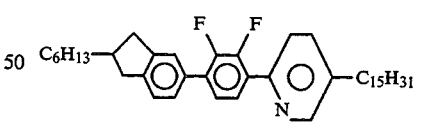 (I-1279)
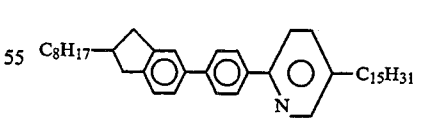 (I-1280)
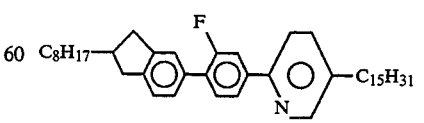 (I-1281)
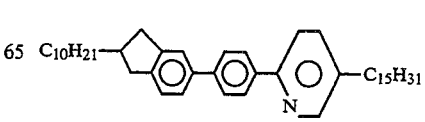 (I-1282)

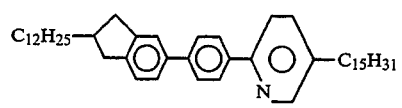 (I-1283)
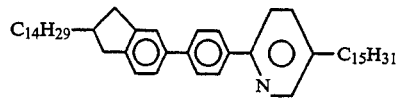 (I-1284)
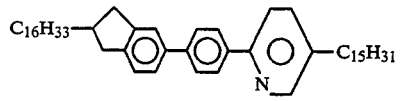 (I-1285)
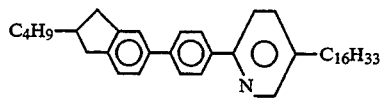 (I-1286)
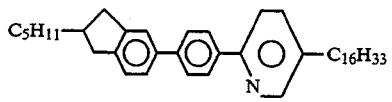 (I-1287)
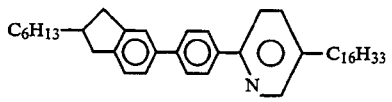 (I-1288)
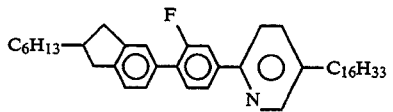 (I-1289)
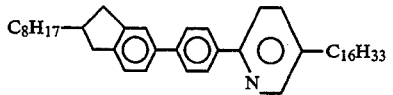 (I-1290)
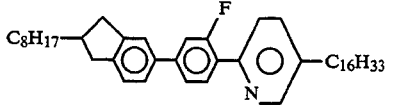 (I-1291)
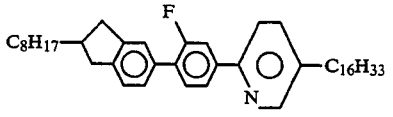 (I-1292)
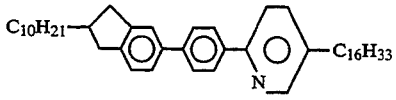 (I-1293)
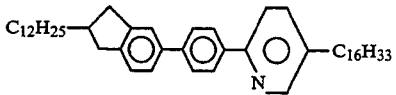 (I-1294)
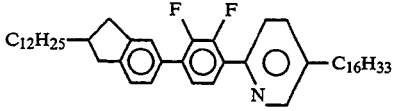 (I-1295)
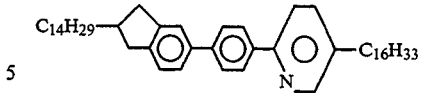 (I-1296)
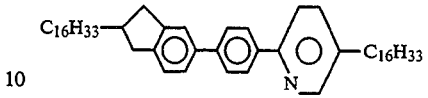 (I-1297)
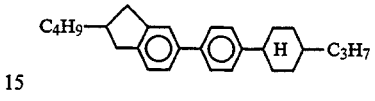 (I-1298)
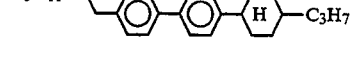 (I-1299)
 (I-1300)
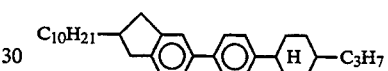 (I-1301)
 (I-1302)
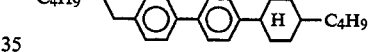 (I-1303)
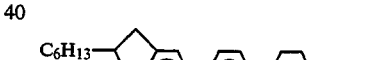 (I-1304)
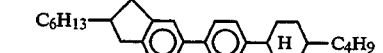 (I-1305)
 (I-1306)
 (I-1307)
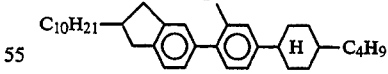 (I-1308)
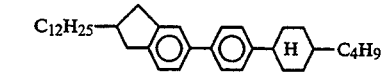 (I-1309)
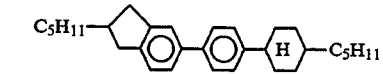 (I-1310)
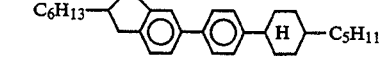 (I-1311)

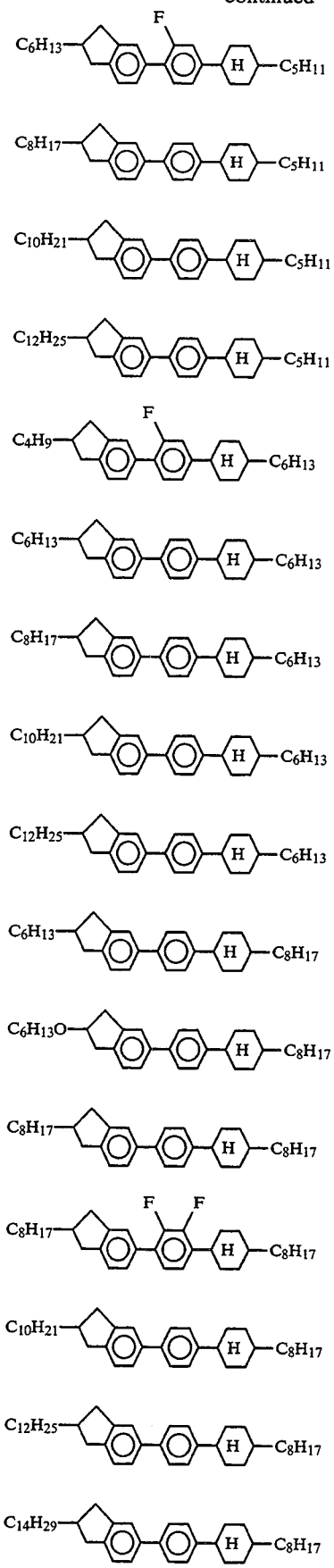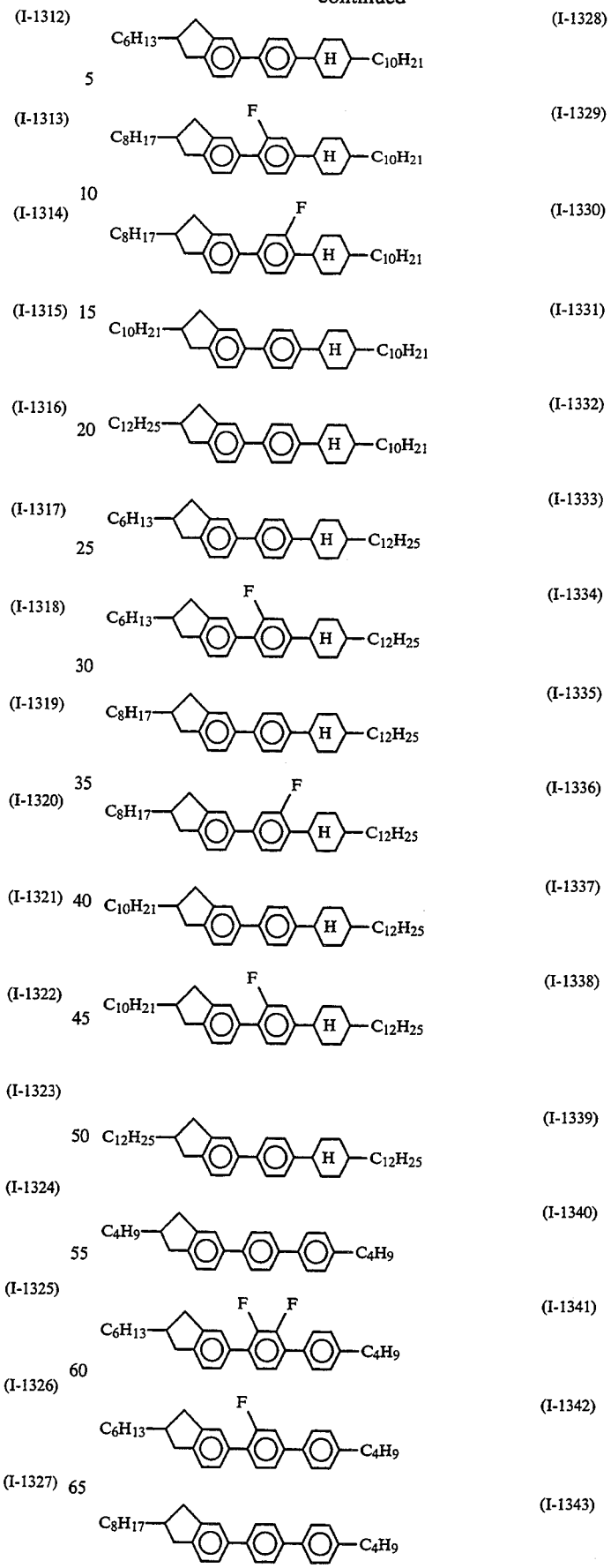

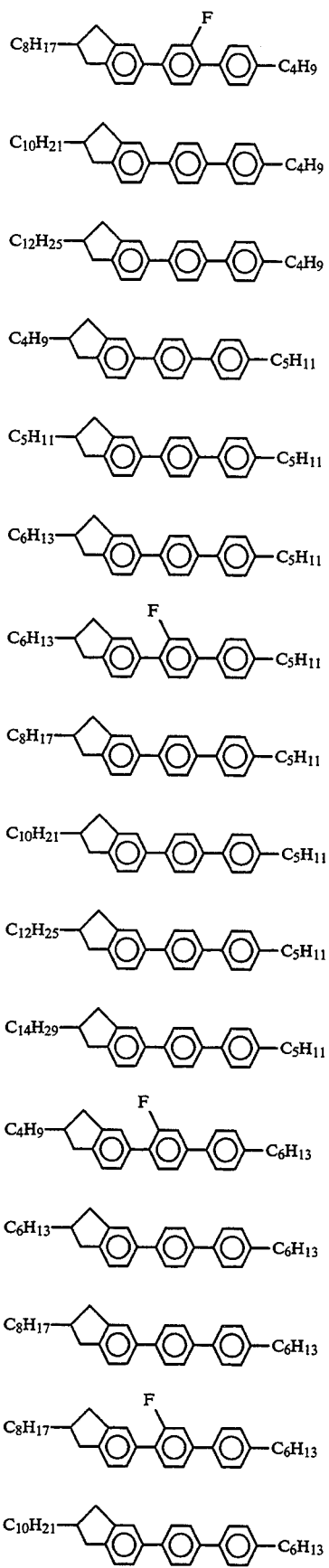
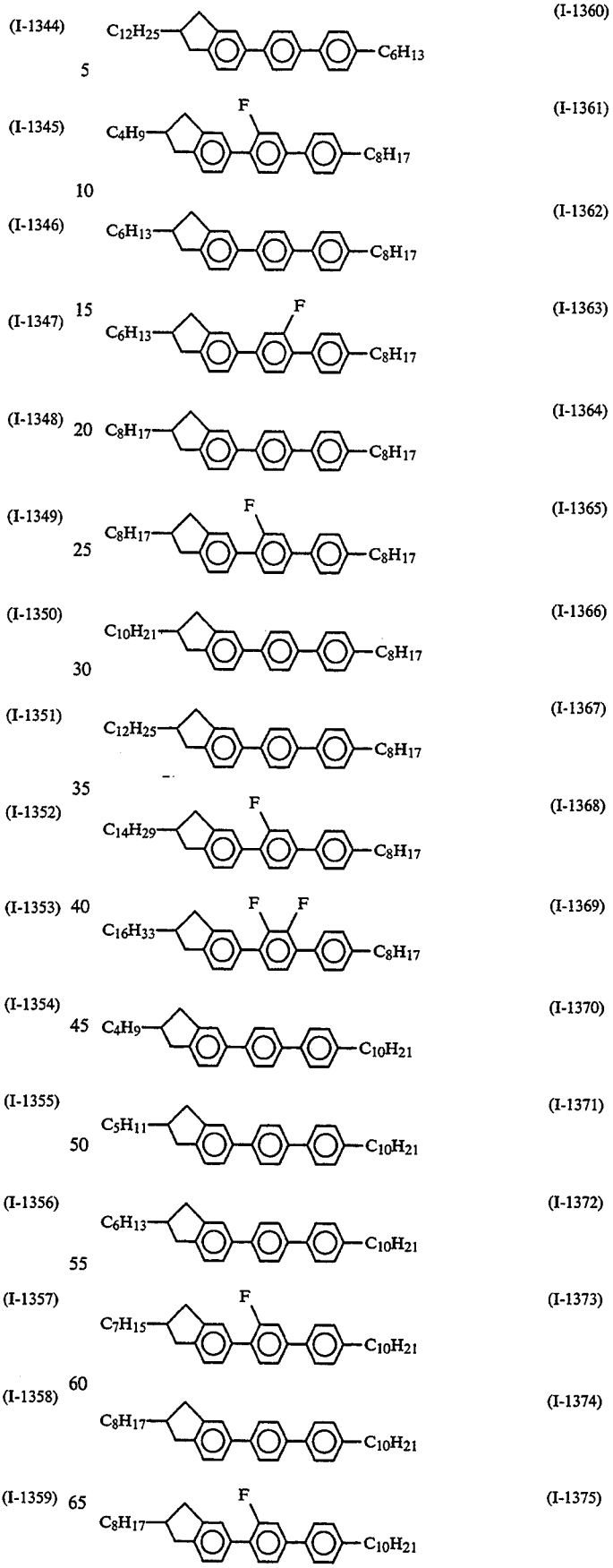

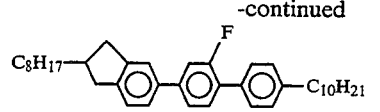 (I-1376)
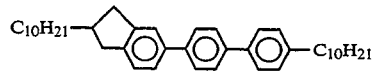 (I-1377)
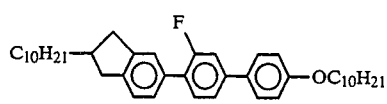 (I-1378)
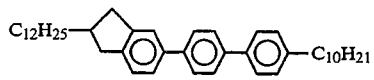 (I-1379)
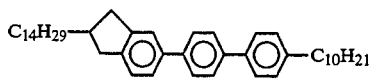 (I-1380)
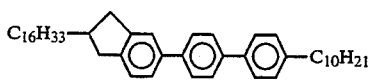 (I-1381)
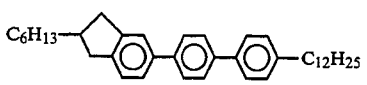 (I-1382)
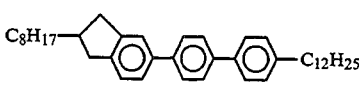 (I-1383)
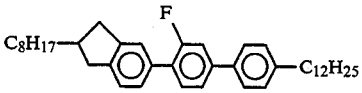 (I-1384)
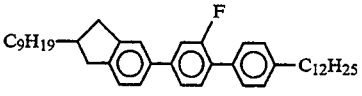 (I-1385)
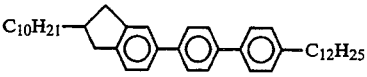 (I-1386)
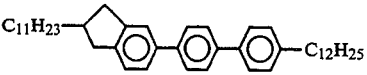 (I-1387)
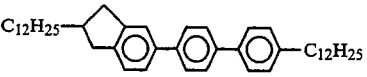 (I-1388)
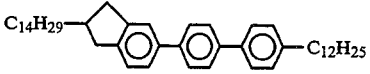 (I-1389)
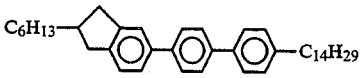 (I-1390)
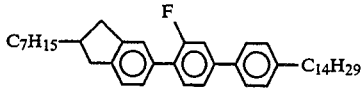 (I-1391)

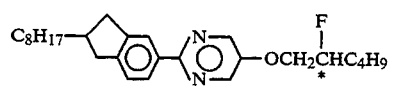 (I-1408)
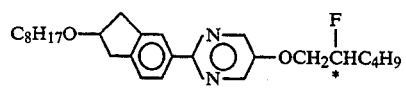 (I-1409)
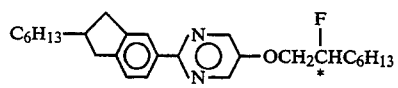 (I-1410)
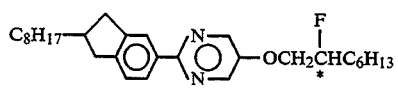 (I-1411)
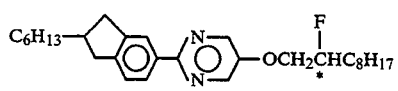 (I-1412)
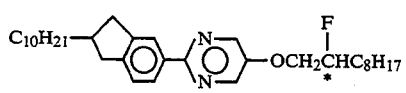 (I-1413)
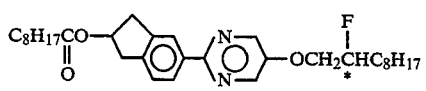 (I-1414)
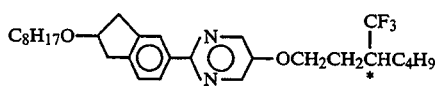 (I-1415)
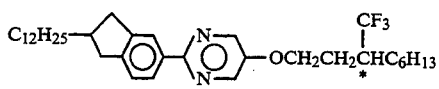 (I-1416)
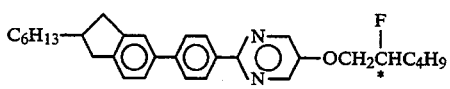 (I-1417)
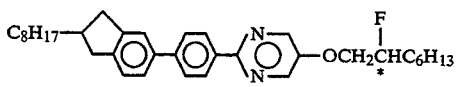 (I-1418)
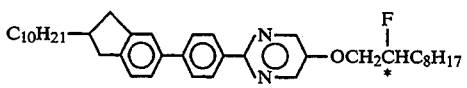 (I-1419)
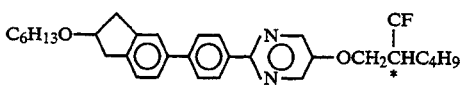 (I-1420)
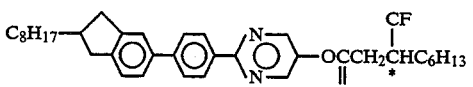 (I-1421)
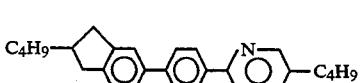 (I-1422)
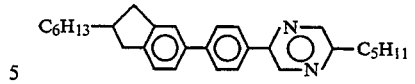 (I-1423)
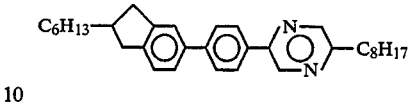 (I-1424)
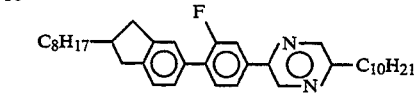 (I-1425)
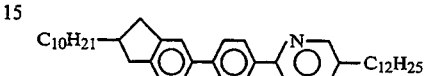 (I-1426)
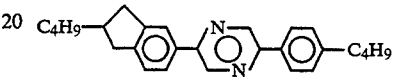 (I-1427)
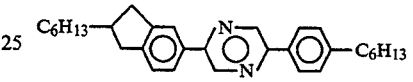 (I-1428)
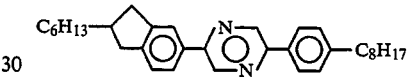 (I-1429)
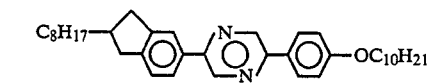 (I-1430)
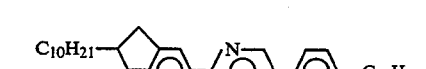 (I-1431)
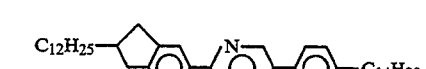 (I-1432)
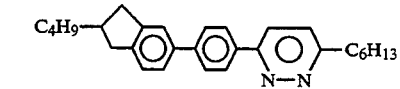 (I-1433)
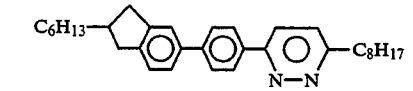 (I-1434)
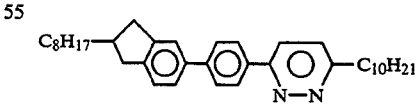 (I-1435)
 (I-1436)
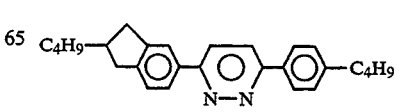 (I-1437)

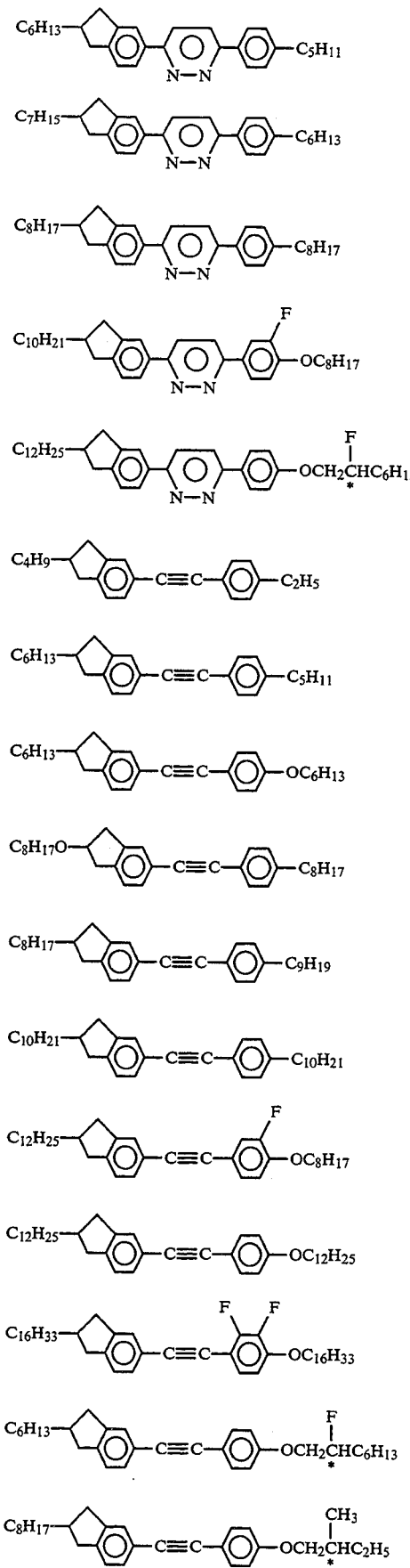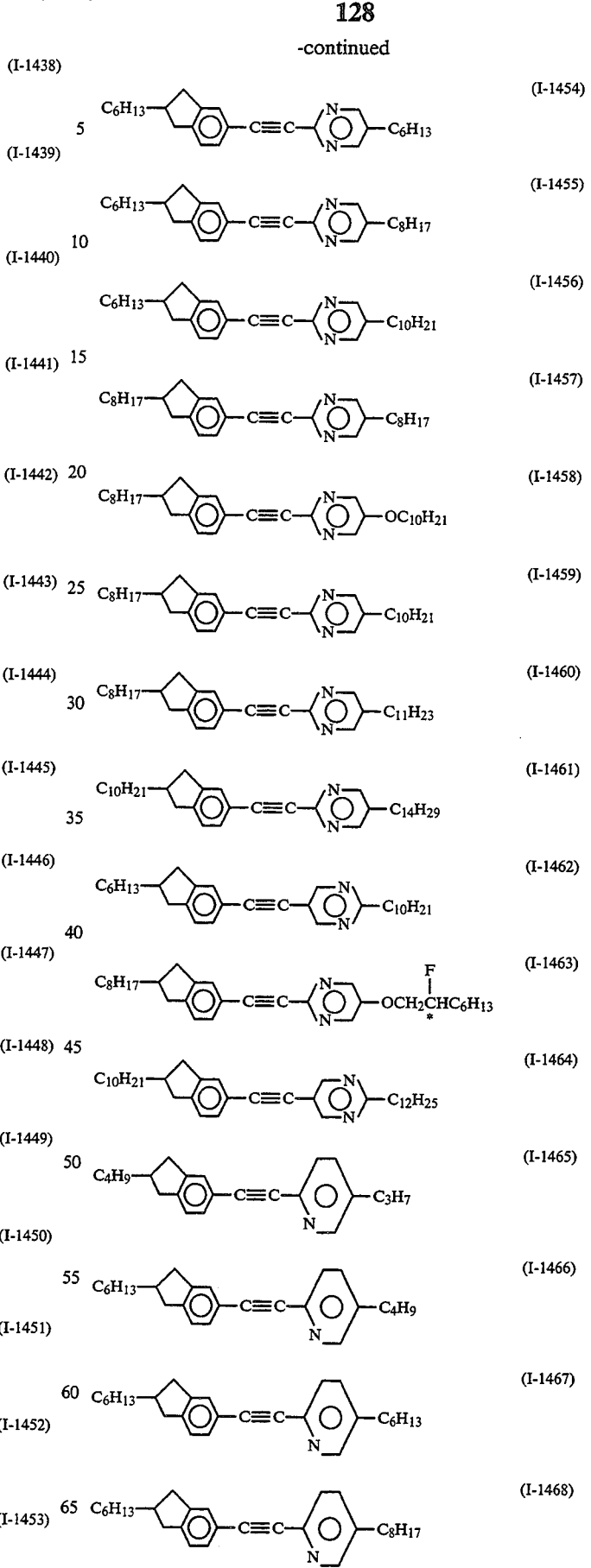

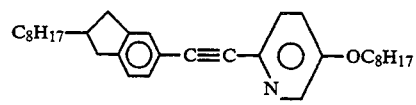 (I-1469)
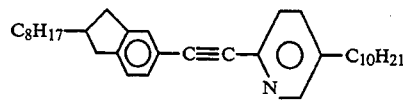 (I-1470)
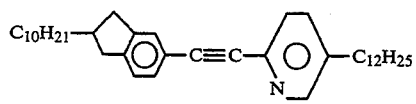 (I-1471)
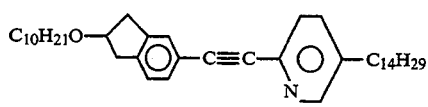 (I-1472)
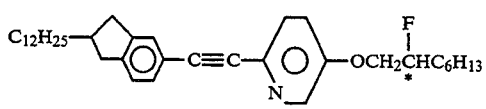 (I-1473)
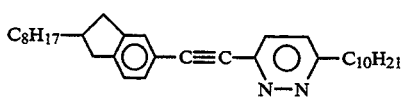 (I-1474)
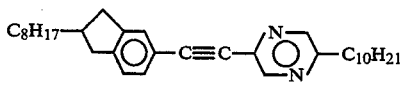 (I-1475)
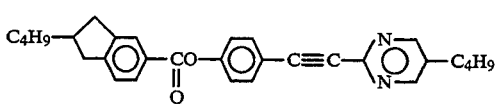 (I-1476)
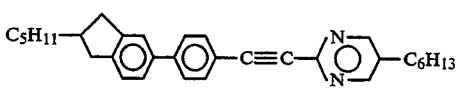 (I-1477)
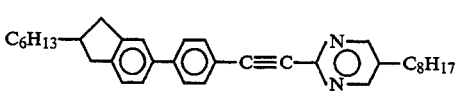 (I-1478)
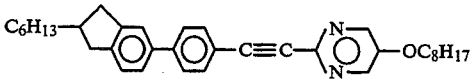 (I-1479)
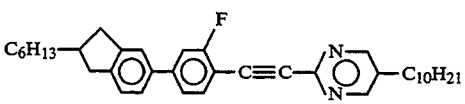 (I-1480)
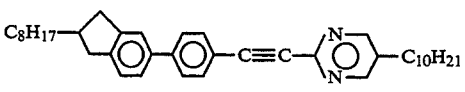 (I-1481)
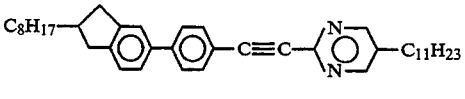 (I-1482)
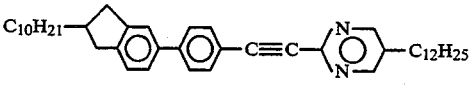 (I-1483)
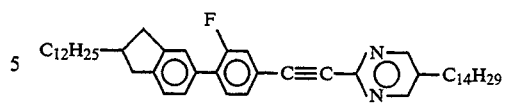 (I-1484)
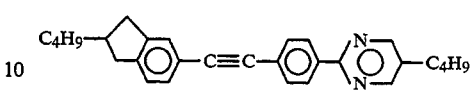 (I-1485)
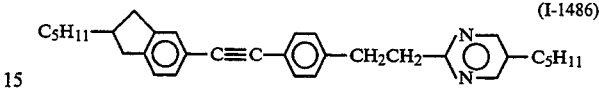 (I-1486)
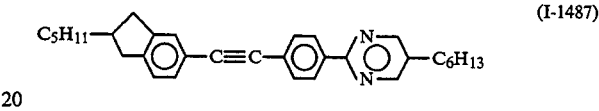 (I-1487)
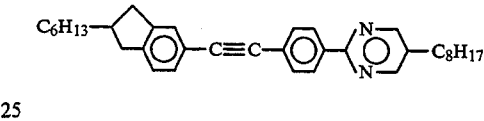 (I-1488)
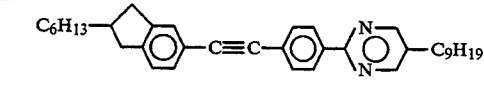 (I-1489)
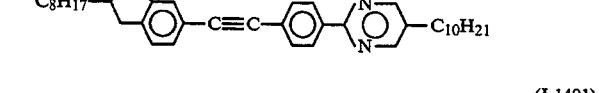 (I-1490)
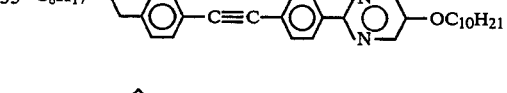 (I-1491)
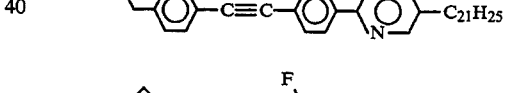 (I-1492)
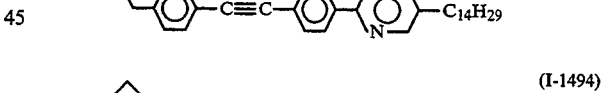 (I-1493)
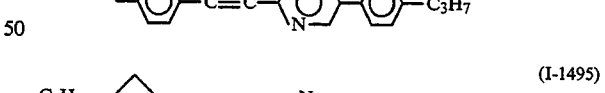 (I-1494)
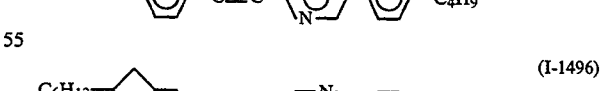 (I-1495)
 (I-1496)
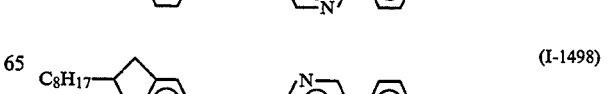 (I-1497)
(I-1498)

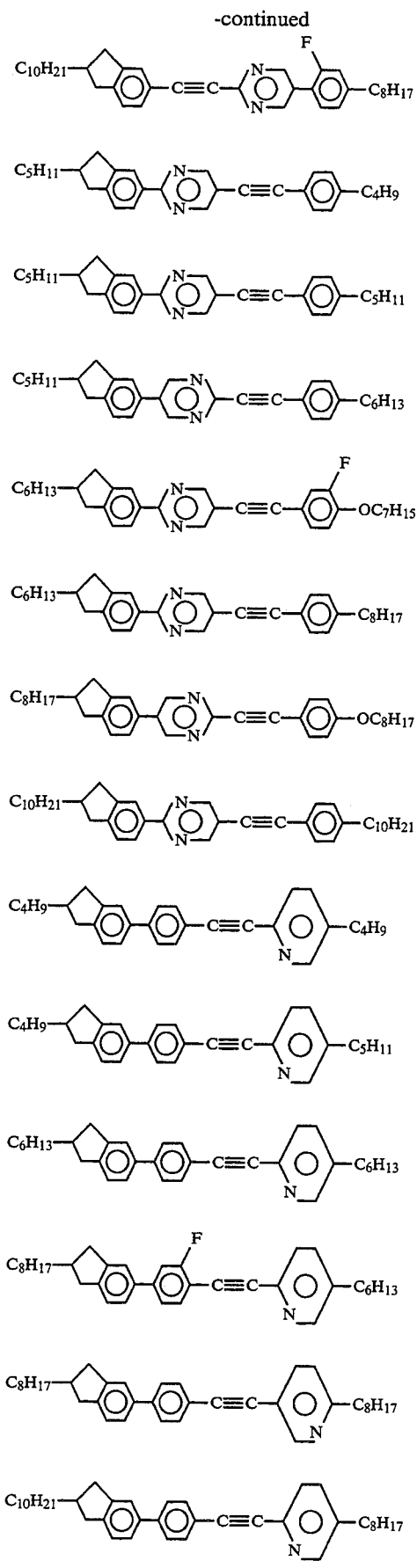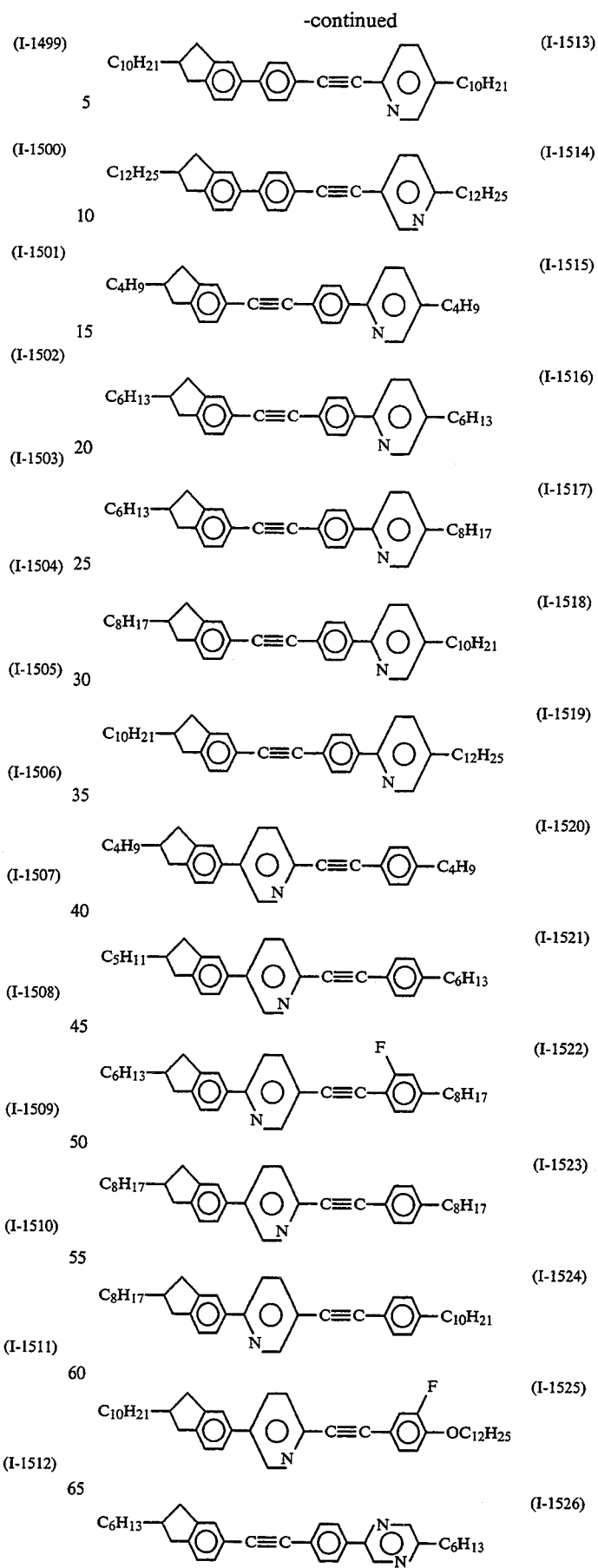

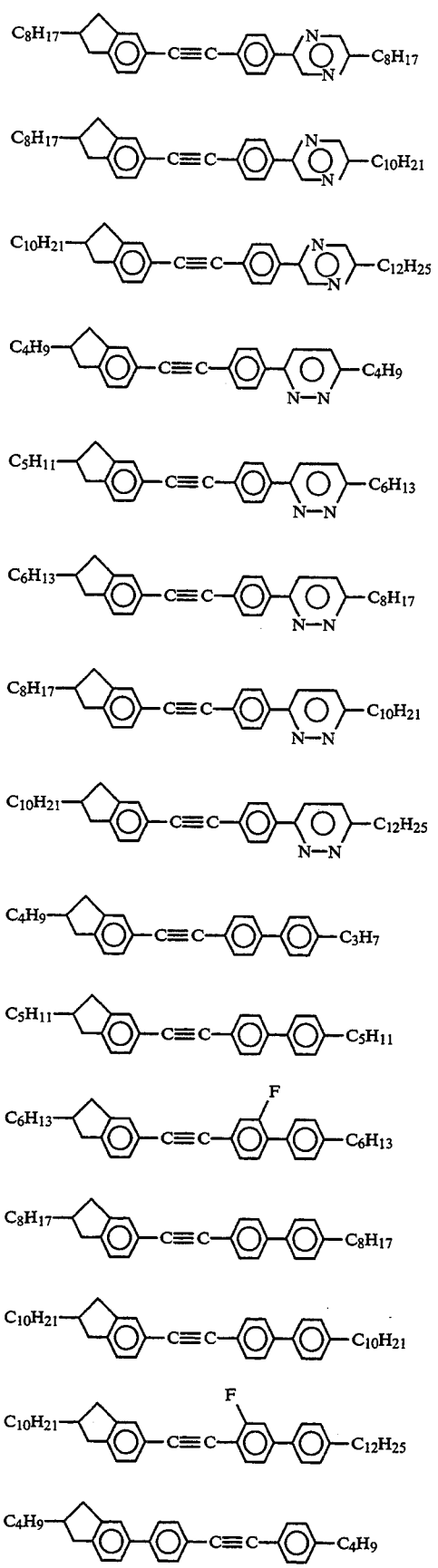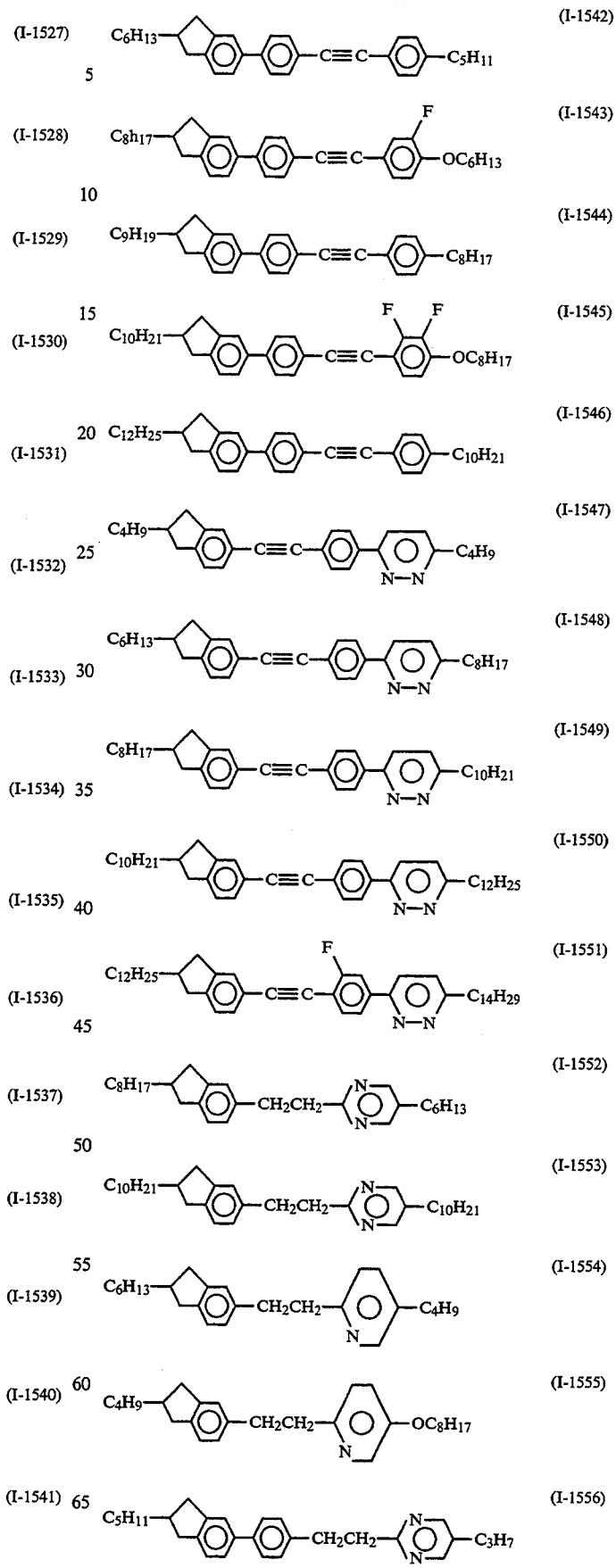

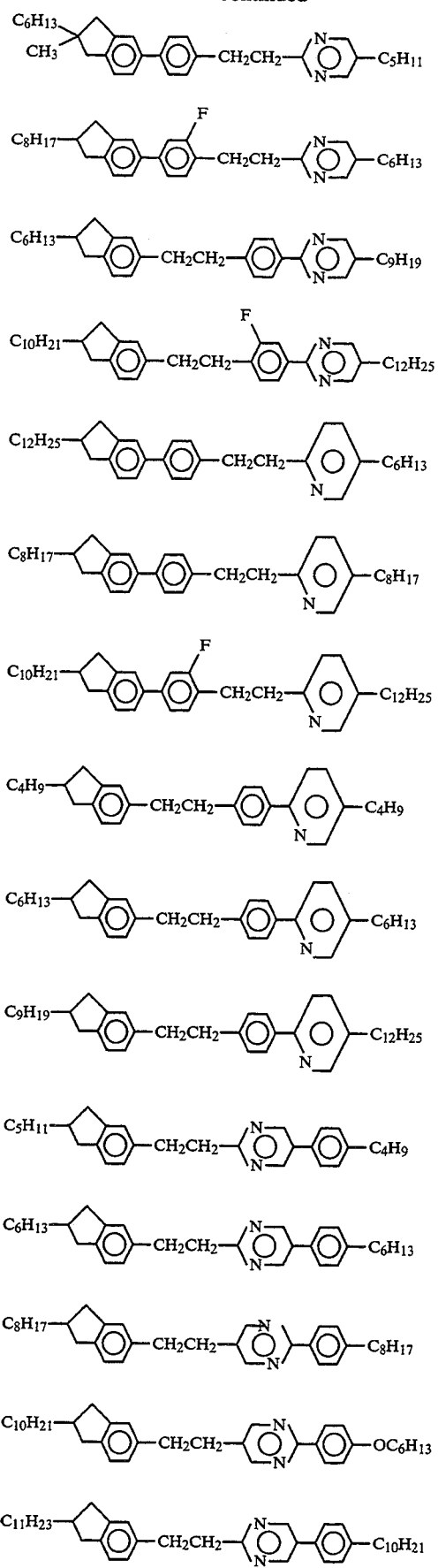
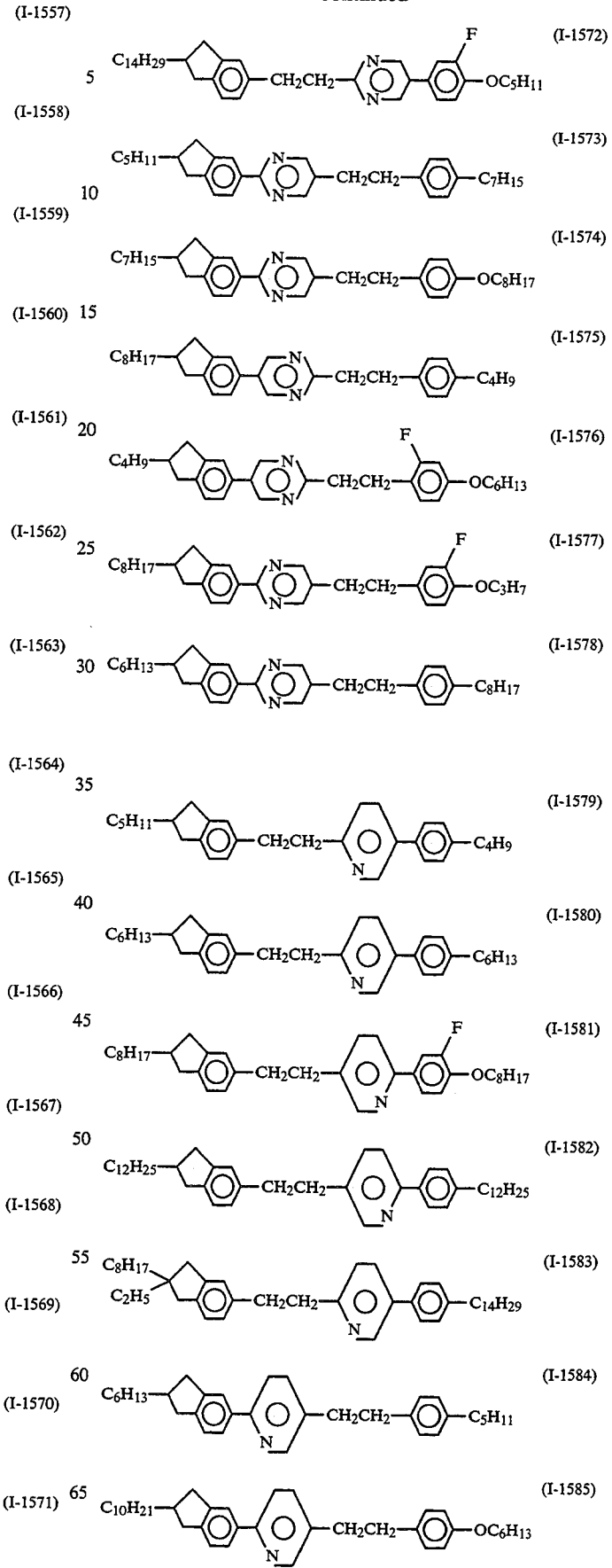

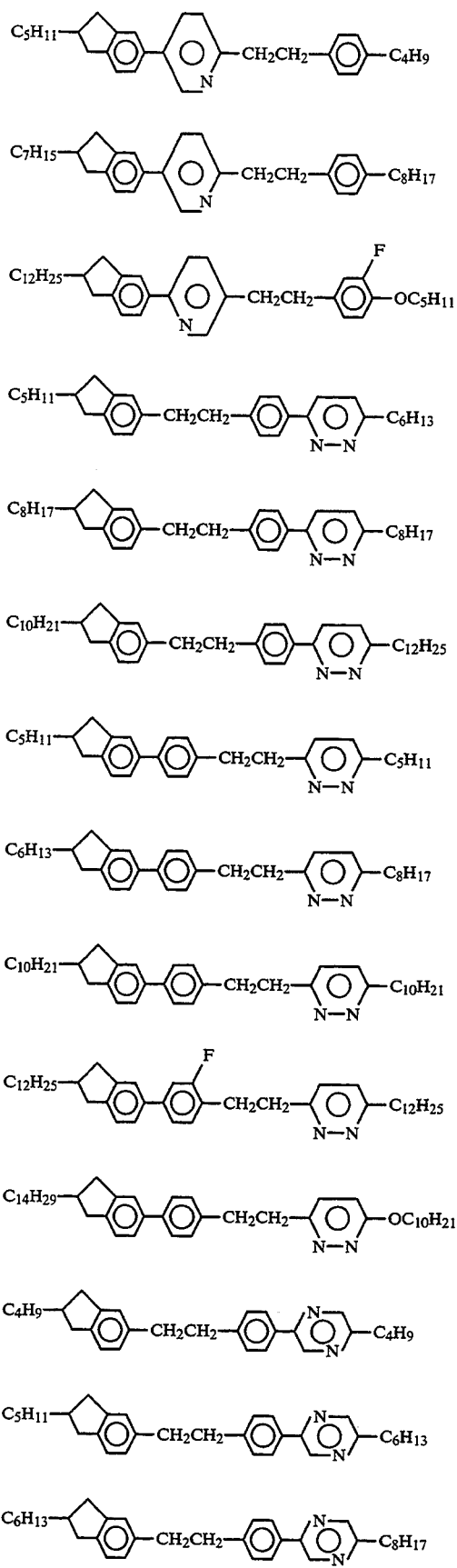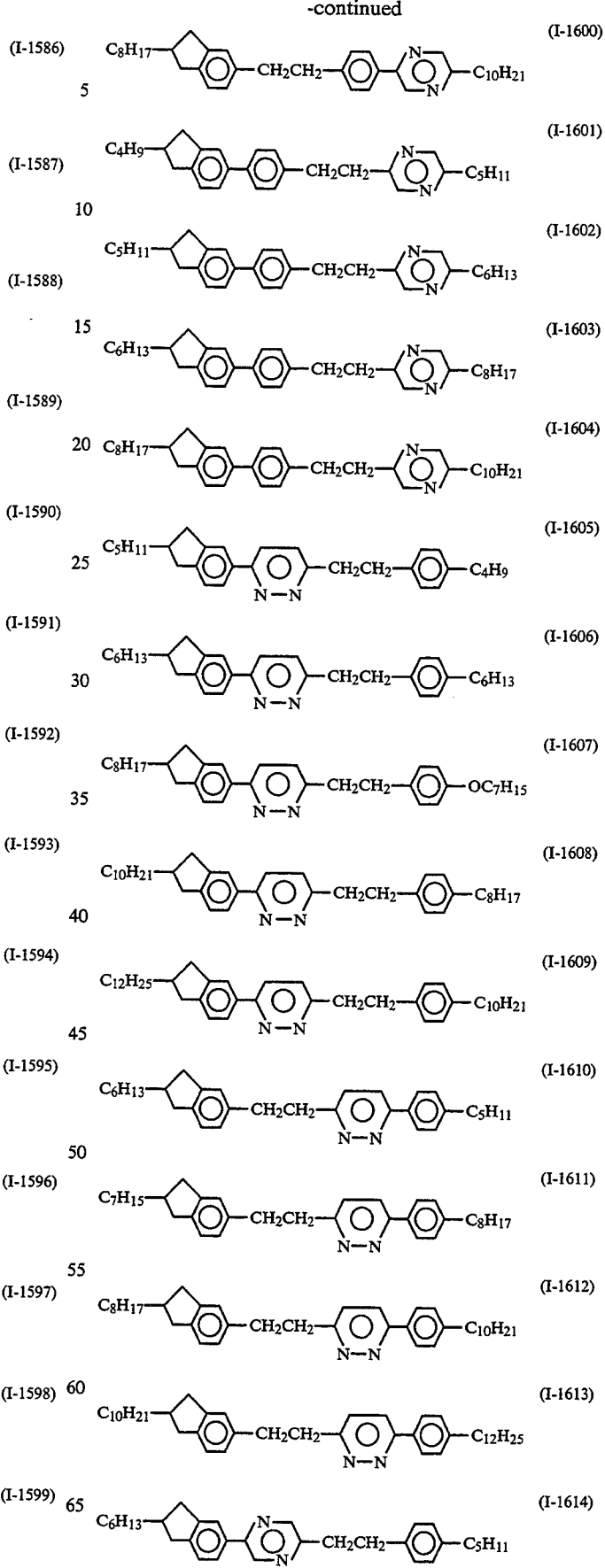

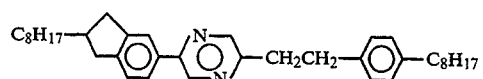 (I-1615)
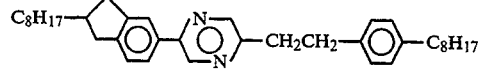 (I-1616)
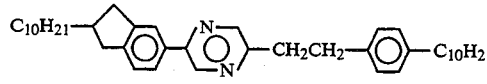 (I-1617)
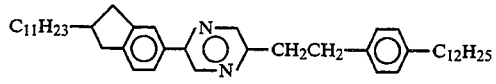 (I-1618)
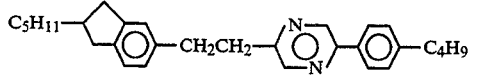 (I-1619)
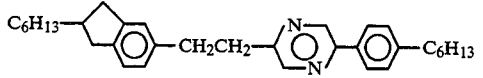 (I-1620)
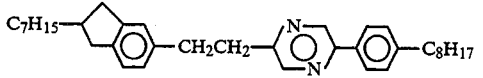 (I-1621)
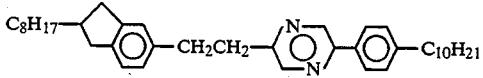 (I-1622)
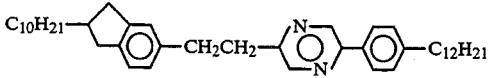 (I-1623)
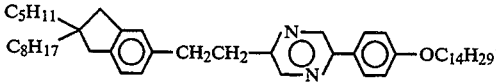 (I-1624)
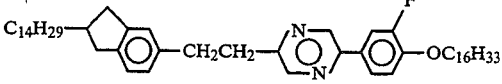 (I-1625)
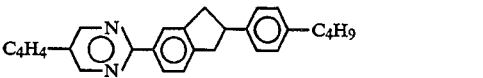 (I-1626)
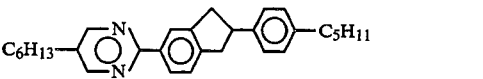 (I-1627)
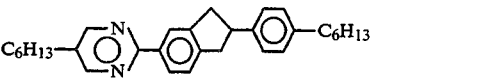 (I-1628)
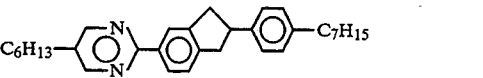 (I-1629)
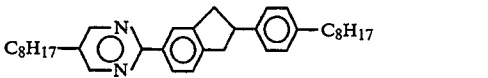 (I-1630)
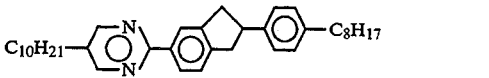 (I-1631)
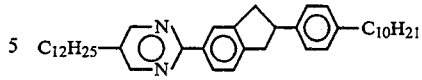 (I-1632)
(I-1633)
(I-1634)
(I-1635)
(I-1636)
(I-1637)
(I-1638)
(I-1639)
(I-1640)
(I-1641)
(I-1642)
(I-1643)
(I-1644)

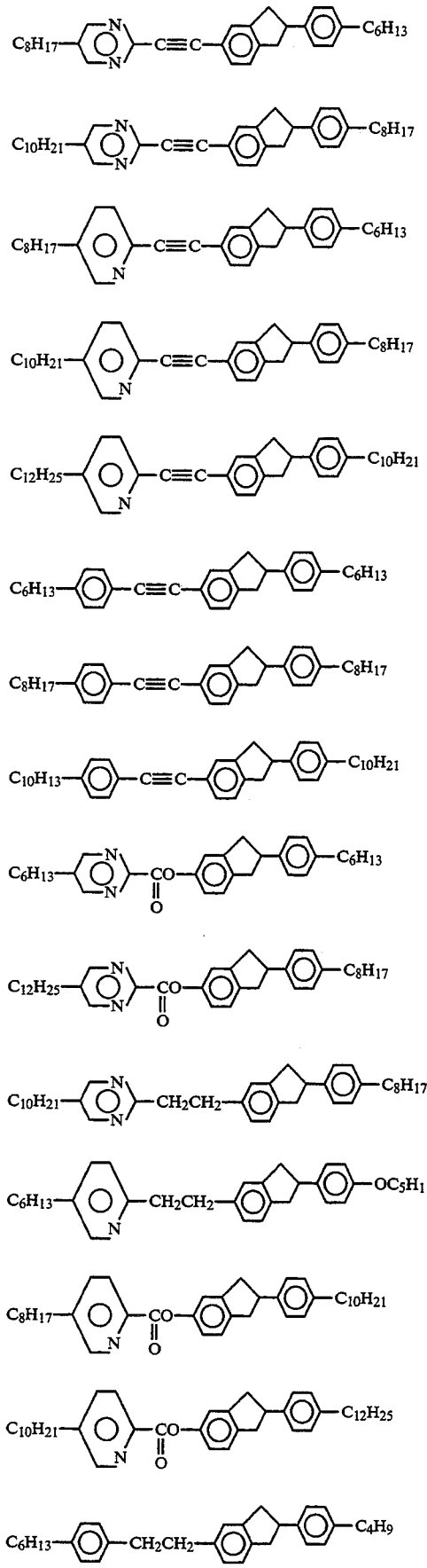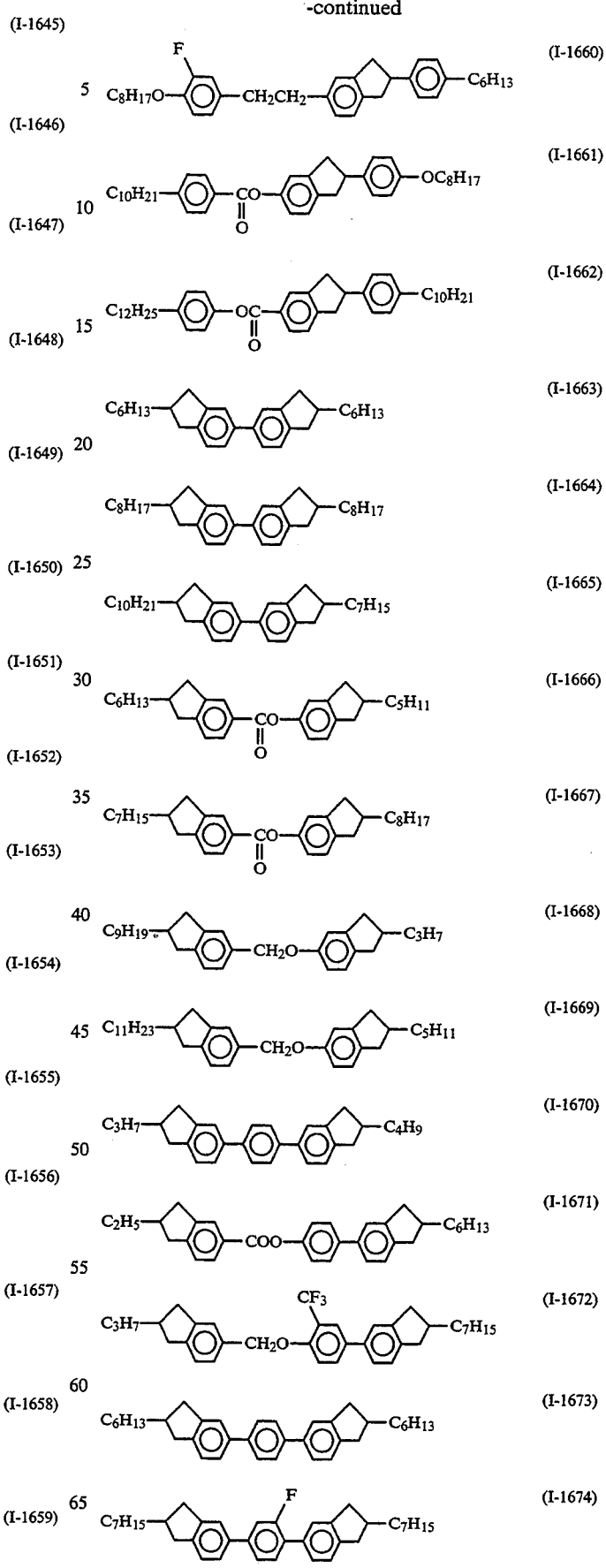

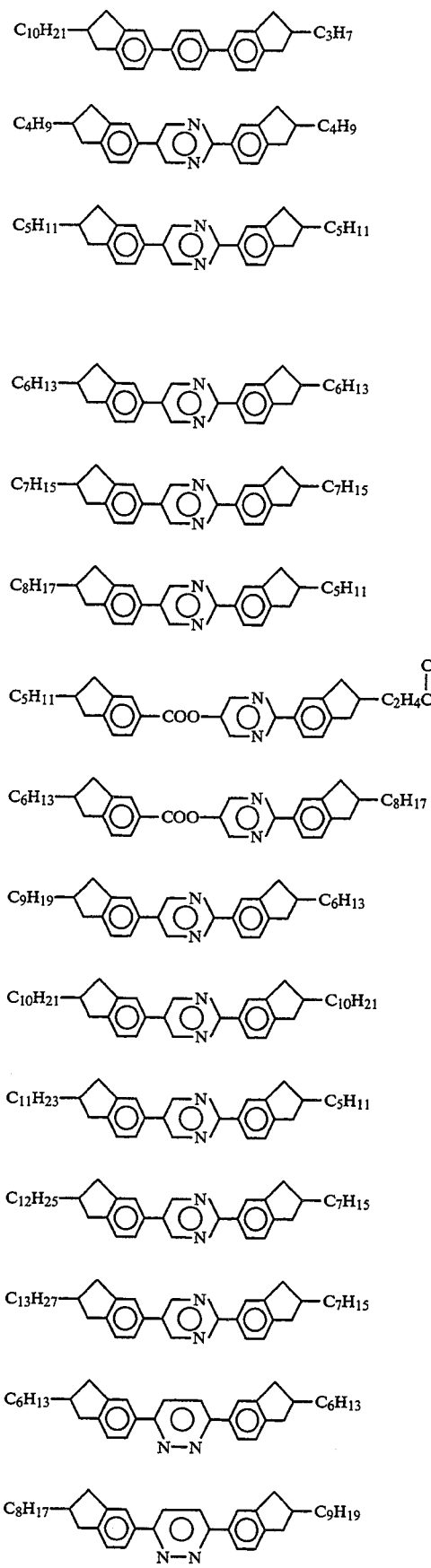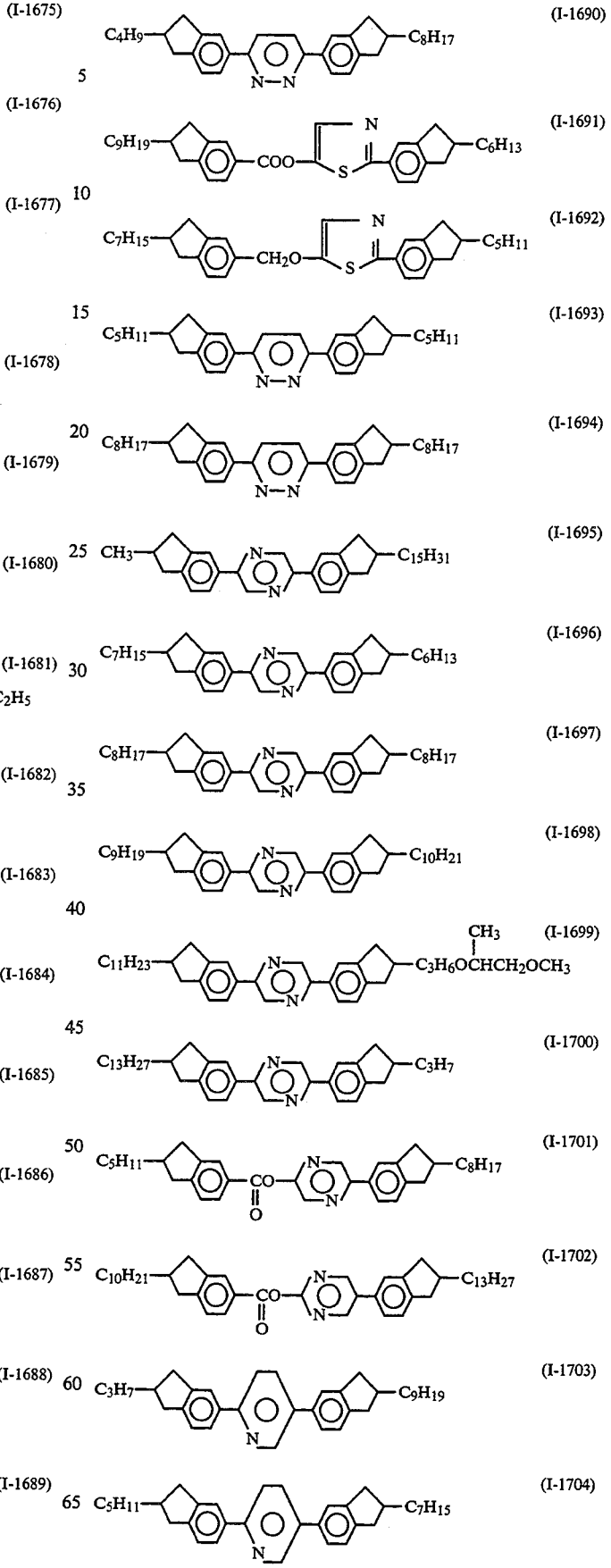

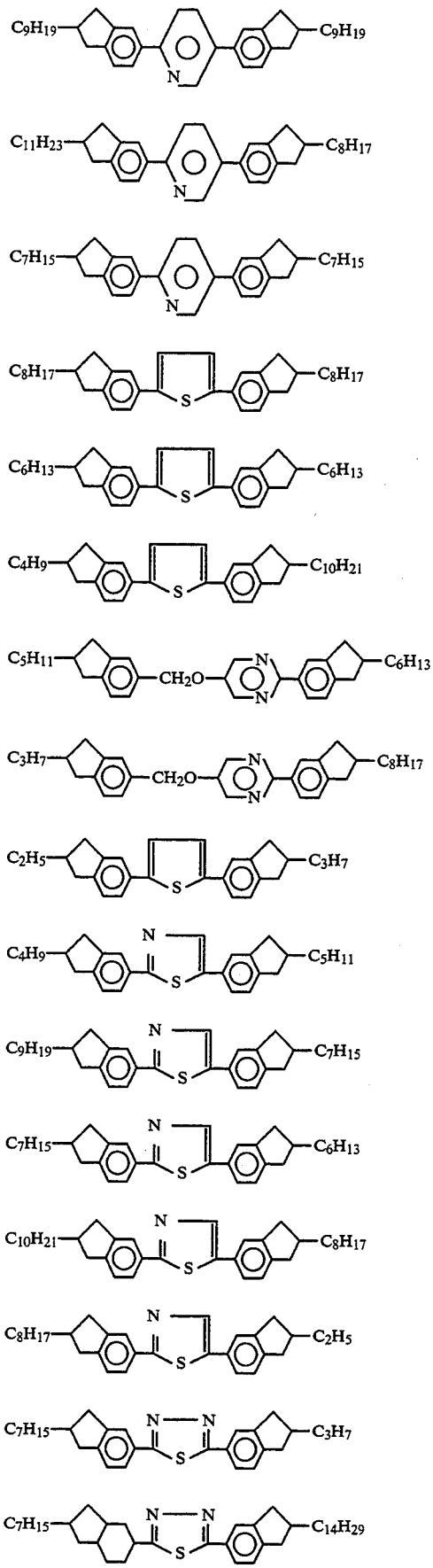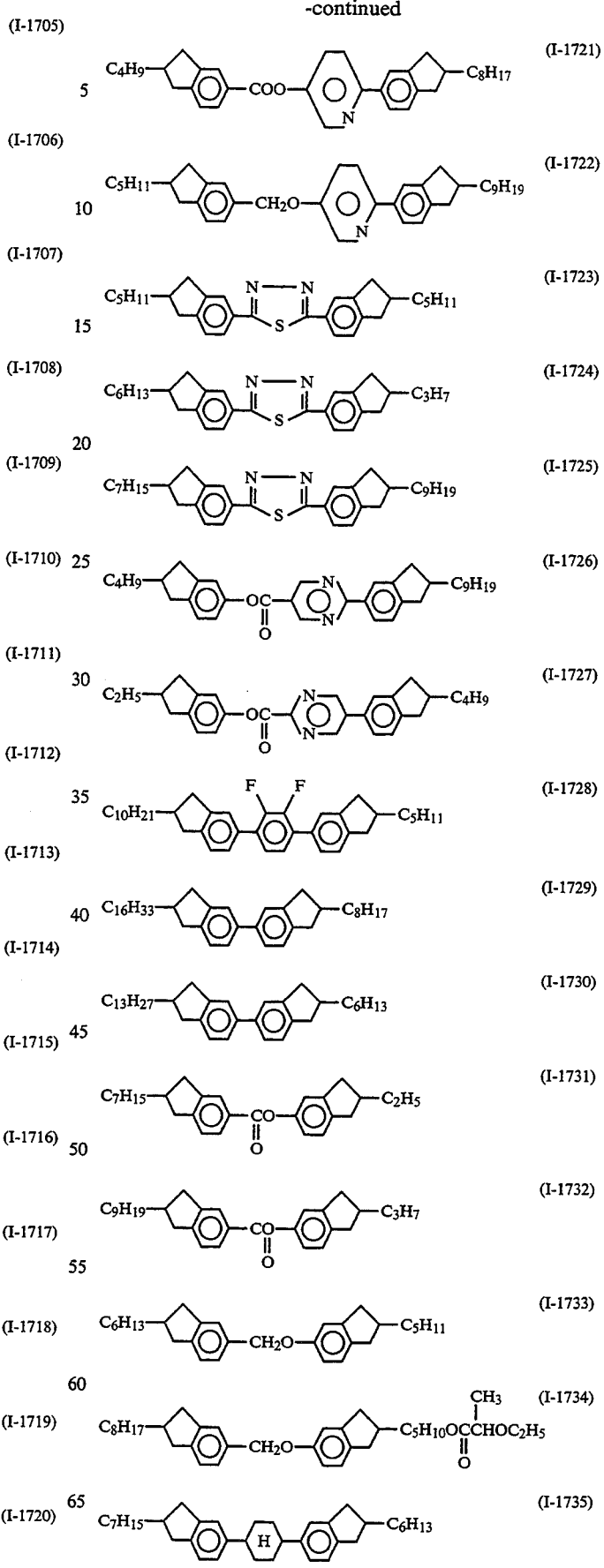

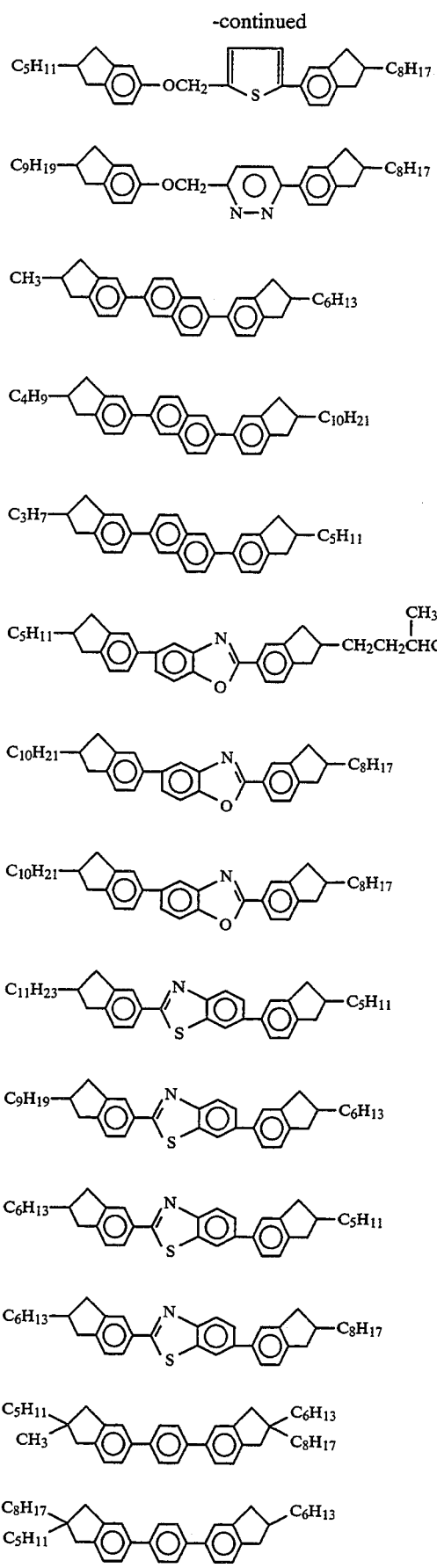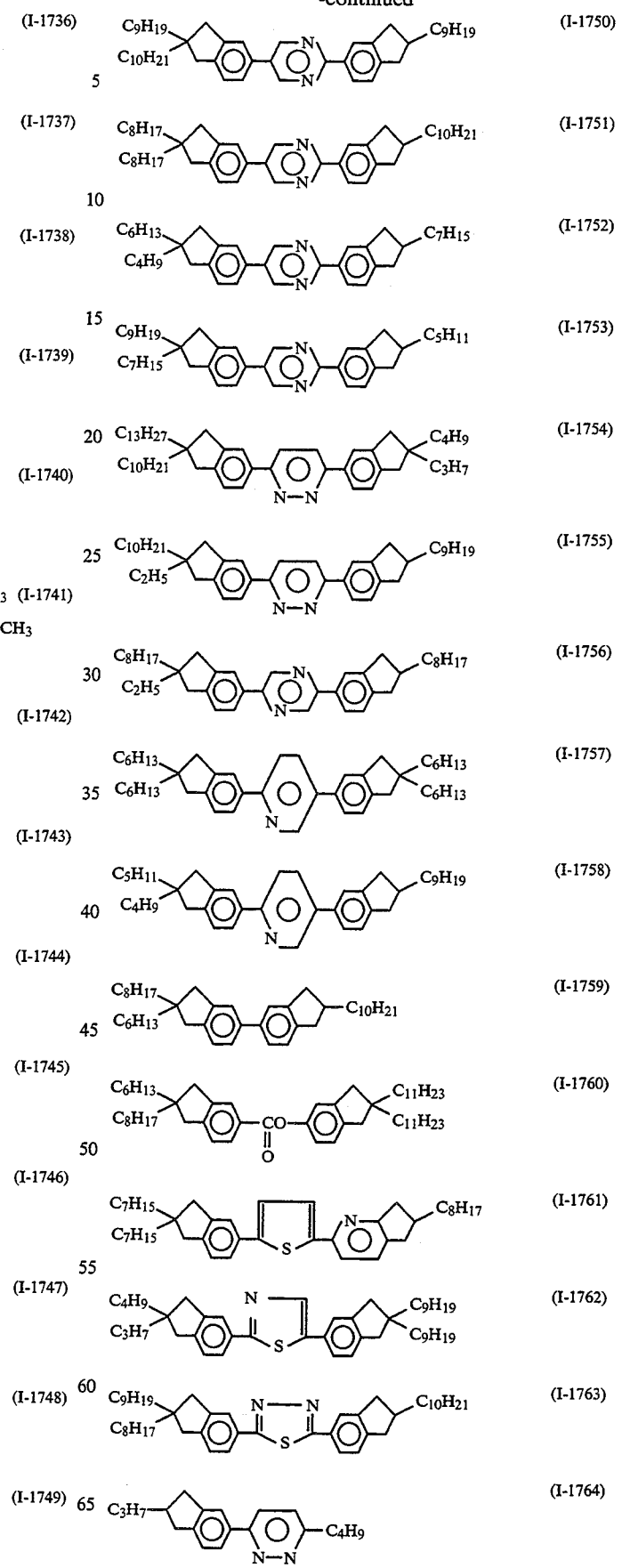

-continued (I-1765) 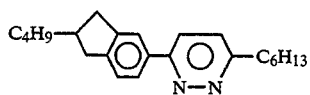

(I-1766) 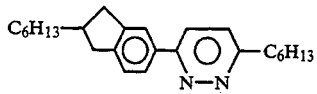

(I-1767) 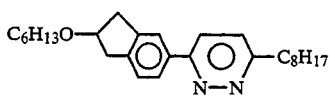

(I-1768) 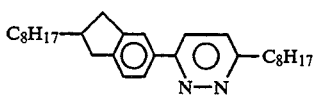

(I-1769) 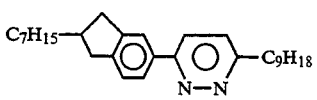

(I-1770) 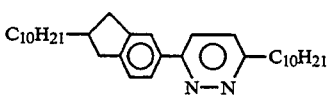

(I-1771) 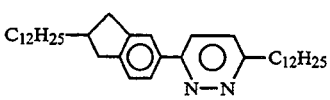

(I-1772) 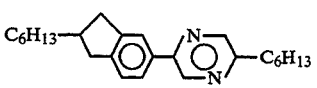

(I-1773) 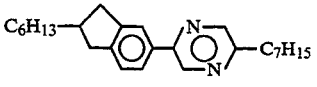

(I-1774) 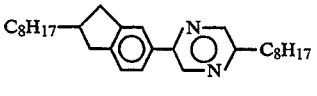

(I-1775) 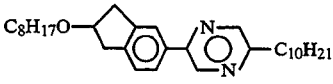

(I-1776) 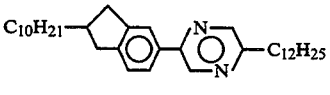

(I-1777) 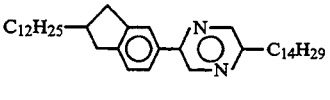

The liquid crystal composition according to the present invention may be obtained by mixing at least one species of the mesomorphic compound represented by the formula (I) and at least one species of another mesomorphic compound in appropriate proportions. The liquid crystal composition according to the present invention may preferably be formulated as a liquid crystal composition capable of showing ferroelectricity, particularly a liquid crystal composition showing a chiral smectic phase.

Specific examples of another mesomorphic compound as described above may include those denoted by the following formulas (V) to (XVI).

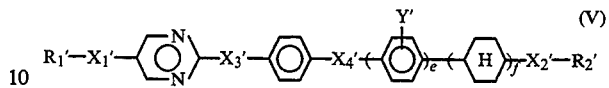 (V)

wherein e denotes 0 or 1 and f denotes 0 or 1 with proviso that e+f=0 or 1; Y' denotes H, halogen, $CH_3$ or $CF_3$; $X_1'$ and $X_2'$ respectively denote a single bond, $$-\underset{\underset{O}{\|}}{C}O-, \quad -O\underset{\underset{O}{\|}}{C}-, \quad -O- \quad \text{or} \quad -O\underset{\underset{O}{\|}}{C}O-;$$

and $X_3'$ and $X_4'$ respectively denote a single bond, $$-\underset{\underset{O}{\|}}{C}O-, \quad -O\underset{\underset{O}{\|}}{C}-, \quad OCH_2 \quad \text{or} \quad -CH_2O-.$$

In the formula (V), preferred compounds thereof may include those represented by the following formulas (Va) to (Vd):

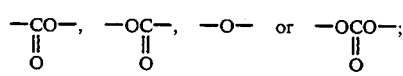 (Va)

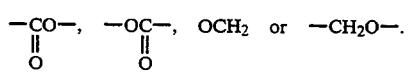 (Vb)

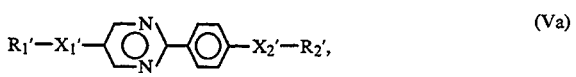 (Vc)

and

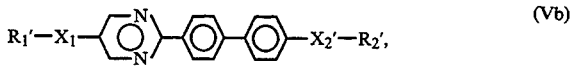 (Vd)

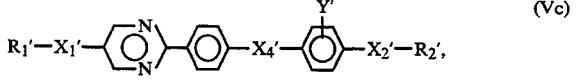 (VI)

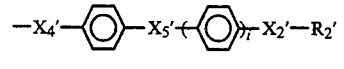

wherein g and h respectively denote 0 or 1 with proviso that g+h 0 or 1; i denotes 0 or 1; $X_1'$ and $X_2'$ respectively denote a single bond, $$-\underset{\underset{O}{\|}}{C}O-, \quad -O\underset{\underset{O}{\|}}{C}-, \quad -O- \quad \text{or} \quad -O\underset{\underset{O}{\|}}{C}O-;$$

and $X_3'$, $X_4'$ and $X_5'$ respectively denote a single bond, $$-\underset{\underset{O}{\|}}{C}O-, \quad -O\underset{\underset{O}{\|}}{C}-, \quad -CH_2O- \quad \text{or} \quad -OCH_2-.$$

In the formula (VI), preferred compounds thereof may include those represented by the following formulas (VIa) to (VIc):

 (VIa)

 (VIb)

and

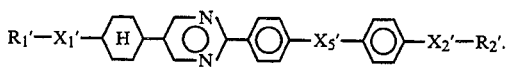 (VIc)

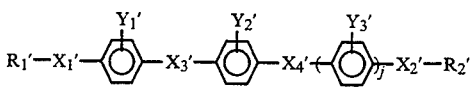 (VII)

wherein j denotes 0 or 1; $Y_1'$, $Y_2'$ and $Y_3'$ respectively denote H, halogen, $CH_3$ or $CF_3$; $X_1'$ and $X_2'$ respectively denote a single bond, $$-\underset{\underset{O}{\|}}{C}O-,\quad -O\underset{\underset{O}{\|}}{C}-,\quad -O-\quad \text{and}\quad -O\underset{\underset{O}{\|}}{C}O-;$$

and $X_3'$ and $X_4'$ respectively denote a single bond,

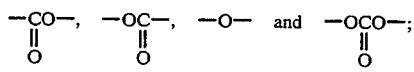

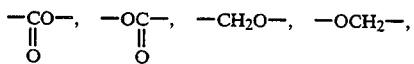

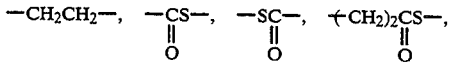

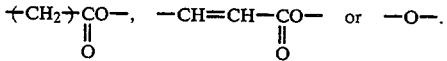

In the formula (VII), preferred compounds thereof may include those represented by the following formulas (VIIa) and (VIIb):

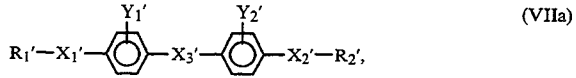 (VIIa)

and

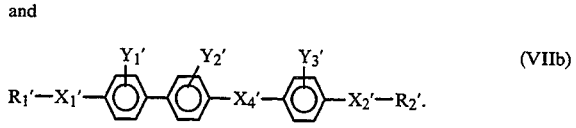 (VIIb)

 (VIII)

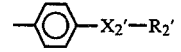

wherein k, l and m respectively denote 0 or 1 with proviso that k+l+m=0, 1 or 2; $X_1'$ and $X_2'$ respectively denote a single bond,

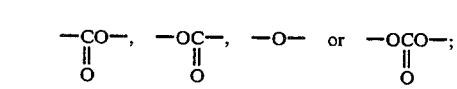

and $X_3'$ and $X_4'$ respectively denote a single bond,

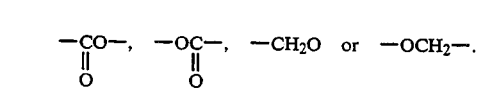

In the formula (VIII), preferred compounds thereof may include those represented by the following formulas (VIIIa) to (VIIIf):

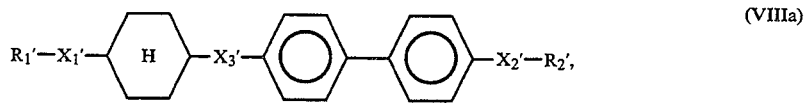 (VIIIa)

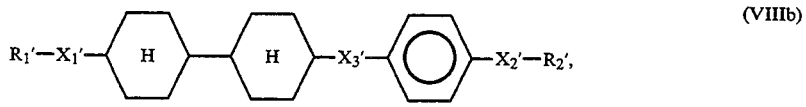 (VIIIb)

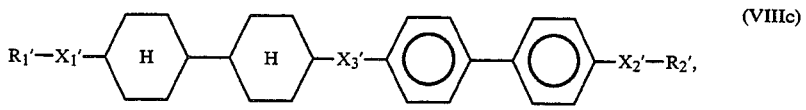 (VIIIc)

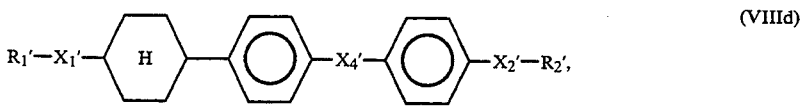 (VIIId)

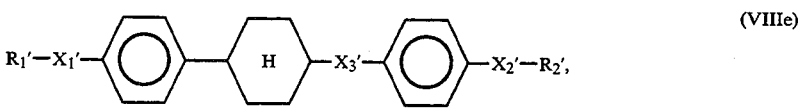 (VIIIe)

and

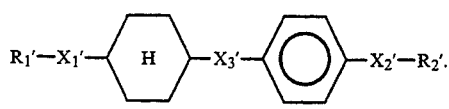

Herein, $R_1'$ and $R_2'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of

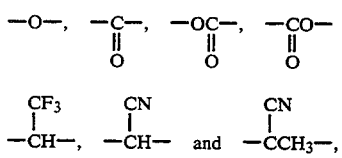

with proviso that $R_1'$ and $R_2'$ respectively do not connect to a ring structure by a single bond when $R_1'$ and $R_2'$ respectively denote a halogenated alkyl group containing one methylene group replaced with —CH halogen— or —CH(CF$_3$)—.

Further, preferred examples of $R_1'$ and $R_2'$ may respectively include those represented by the following groups (i) to (xi):

i) a linear alkyl group having 1-15 carbon atoms;

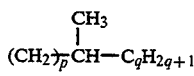  ii)

wherein p denotes an integer of 0-5 and q denotes an integer of 2-11 (optically active or inactive);

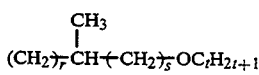  iii)

wherein r denotes an integer of 0-6, s denotes 0 or 1, and t denotes an integer of 1-14 (optically active or inactive);

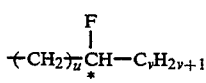  iv)

wherein u denotes 0 or 1 and v denotes an integer of 1-16;

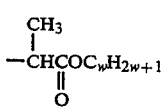  v)

wherein w denotes an integer of 1-15 (optically active or inactive);

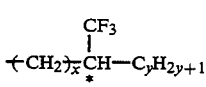  vi)

wherein x denotes an integer of 0-2 and y denotes an integer of 1-5.

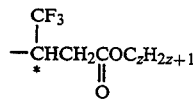  vii)

wherein z denotes an integer of 1-15.

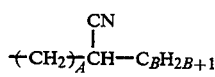  viii)

wherein A denotes an integer of 0-2 and B denotes an integer of 1-15 (optically active or inactive);

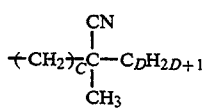  xi)

wherein C denotes an integer of 0-2 and D denotes an integer of 1-15 (optically active or inactive).

(x) hydrogen (H), and
(xi) fluorine (F).

In the above-mentioned formula (V), more preferred compounds thereof may include those represented by the formulas (Vaa) to (Vdc):

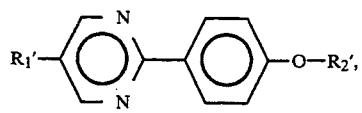 (Vaa)

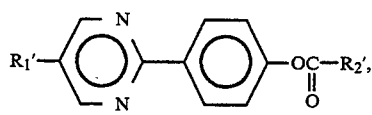 (Vab)

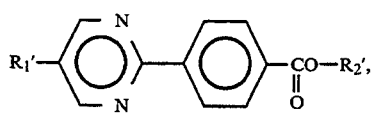 (Vac)

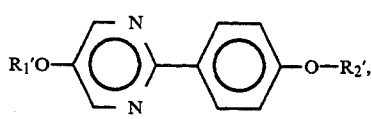 (Vad)

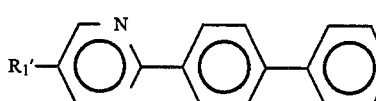 (Vba)

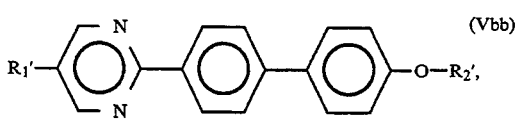 (Vbb)

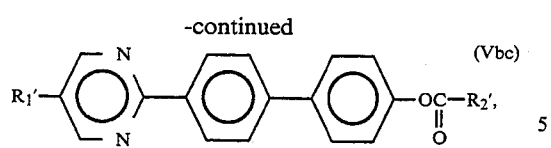(Vbc)

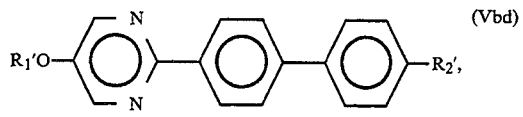(Vbd)

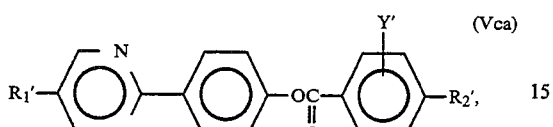(Vca)

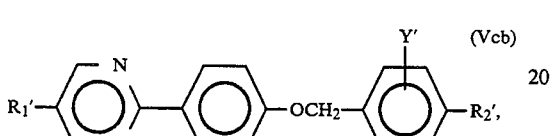(Vcb)

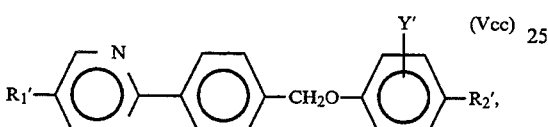(Vcc)

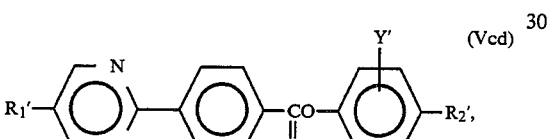(Vcd)

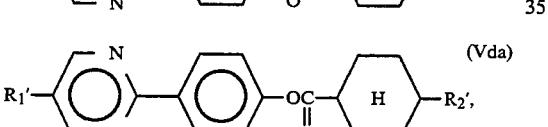(Vda)

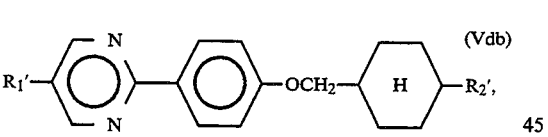(Vdb)

and

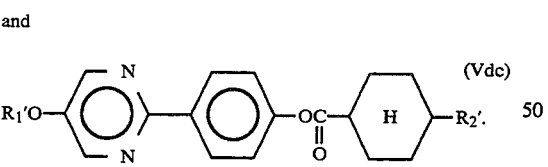(Vdc)

In the above-mentioned formula (VI), more preferred compounds thereof may include those represented by the formulas (VIaa) to (VIcd):

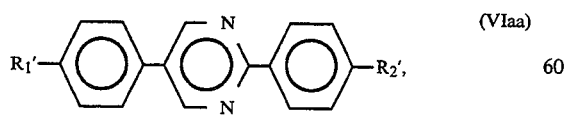(VIaa)

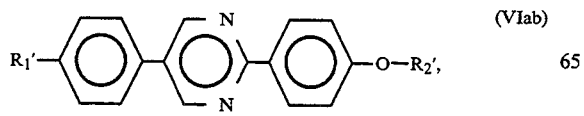(VIab)

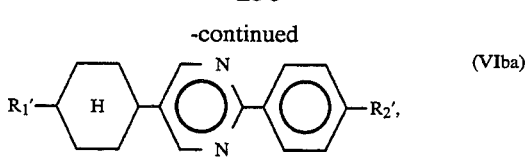(VIba)

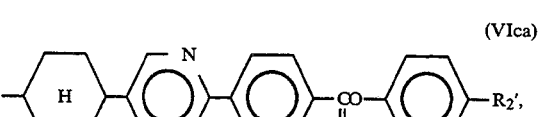(VIca)

and

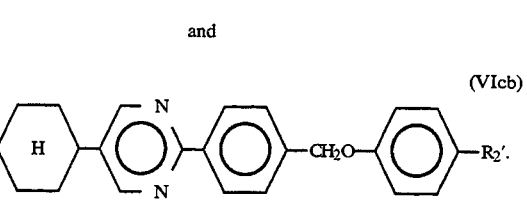(VIcb)

In the above-mentioned formula (VII), more preferred compounds thereof may include those represented by the formulas (VIIaa) to (VIIbf):

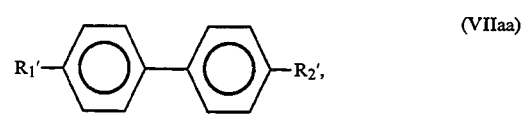(VIIaa)

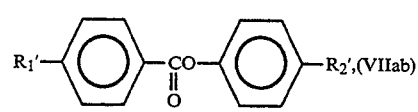(VIIab)

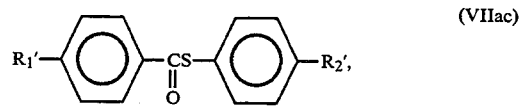(VIIac)

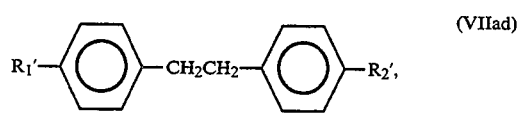(VIIad)

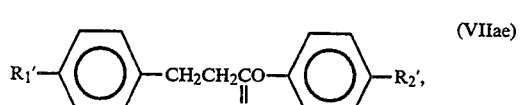(VIIae)

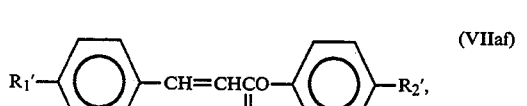(VIIaf)

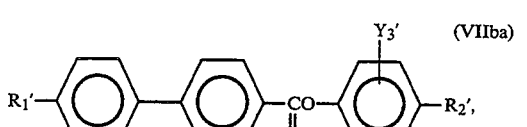(VIIba)

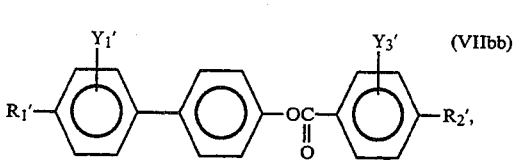(VIIbb)

-continued

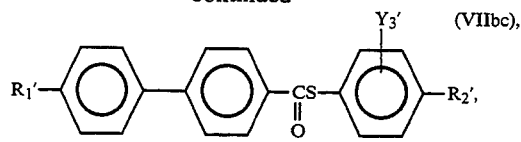 (VIIbc),

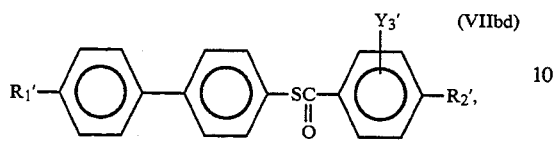 (VIIbd),

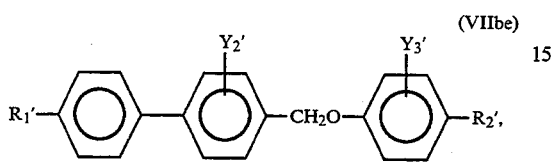 (VIIbe), and

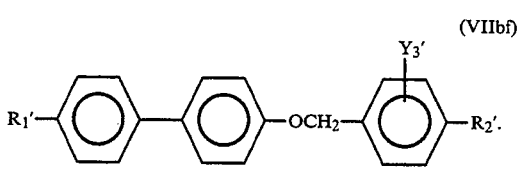 (VIIbf)

-continued

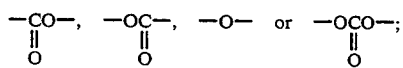 (VIIIea), and

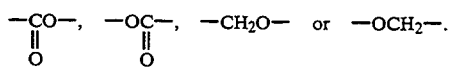 (VIIIfa).

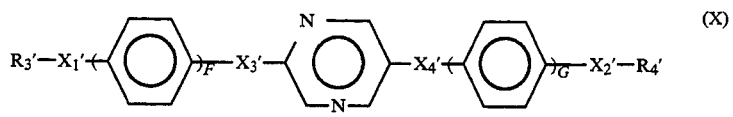 (IX)

wherein E denotes 0 or 1; $X_1'$ and $X_2'$ respectively denote a single bond,

—CO—, —OC—, —O— or —OCO—;
 ‖            ‖                    ‖
 O            O                    O and $X_3'$ denotes a single bond, —CO—, —OC—, —CH$_2$O— or —OCH$_2$—.
 ‖            ‖
 O            O

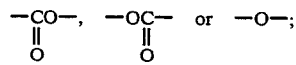 (X)

In the above-mentioned formula (VIII), more preferred compounds thereof may include those represented by the formulas (VIIIaa) to (VIIIfa):

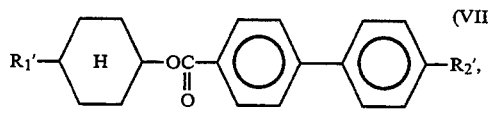 (VIIIaa)

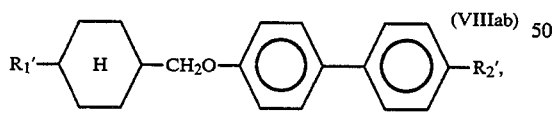 (VIIIab)

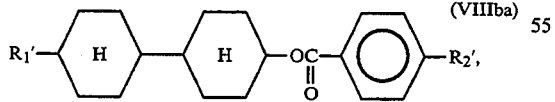 (VIIIba)

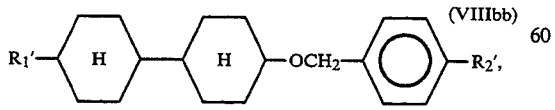 (VIIIbb)

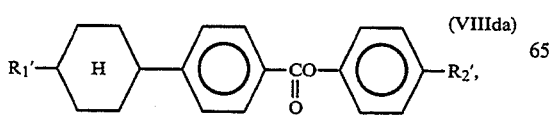 (VIIIda)

wherein F and G respectively denote 0 or 1; $X_1'$ and $X_2'$ respectively denote a single bond, —CO—, —OC— or —O—;
 ‖            ‖
 O            O and $X_3'$ and $X_4'$ respectively denote a single bond, —CO—, —OC—, —CH$_2$O— or —OCH$_2$—.
 ‖            ‖
 O            O In the above formula (IX), preferred compounds thereof may include those represented by the following formulas (IXa) and (IXb):

 (IXa)

and

-continued

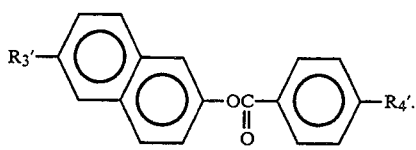

In the above formula (X), preferred compounds thereof may include those represented by the following formulas (Xa) and (Xb).

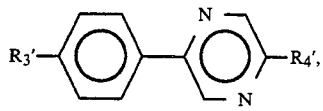

and

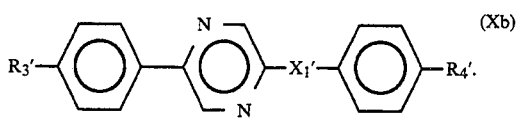

More preferred compounds of the formula (X) may include those represented by the formulas (Xba) to (Xbb):

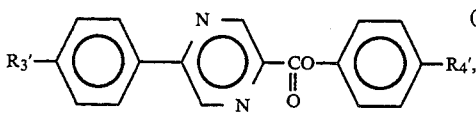

and

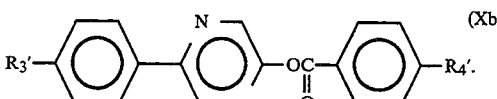

Herein, $R_3'$ and $R_4'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of

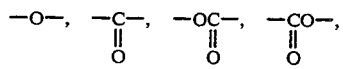

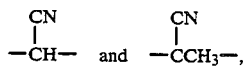

with proviso that $R_3'$ and $R_4'$ respectively do not connect to a ring structure by a single bond when $R_3'$ and $R_4'$ respectively denote a halogenated alkyl group containing one methylene group replaced with —CH halogen—.

Further, preferred examples of $R_3'$ and $R_4'$ may respectively include those represented by the following groups (i) to (vii):

i) a linear alkyl group having 1-15 carbon atoms;

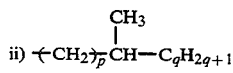

wherein p denotes an integer of 0-5 and q denotes an integer of 2-11 (optically active or inactive);

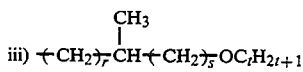

wherein r denotes an integer of 0-6, s denotes 0 or 1, and t denotes an integer of 1-14 (optically active or inactive);

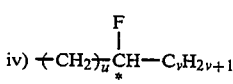

wherein u denotes an integer of 0 or 1 and v denotes an integer of 1-16;

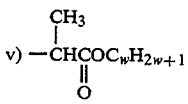

wherein w denotes an integer of 1-15 (optically active or inactive);

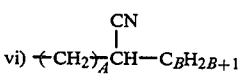

wherein A denotes an integer of 0-2 and B denotes an integer of 1-15 (optically active or inactive); and

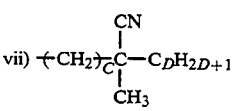

wherein C denotes an integer of 0-2 and D denotes an integer of 1-15 (optically active or inactive).

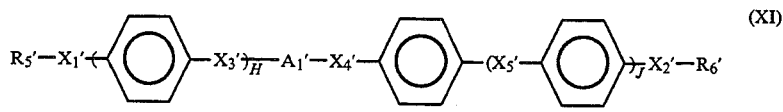

wherein H and J respectively denote 0 or 1 with proviso that H+J=0 or 1; $X_1'$ and $X_2'$ respectively denote a single bond,

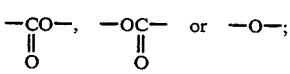

$A_1'$ denotes

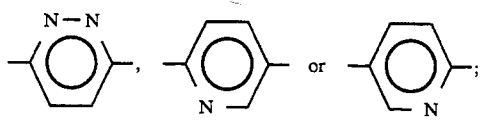

and $X_3'$ and $X_4'$ respectively denote a single bond,

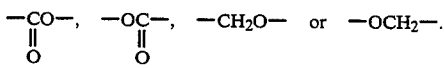

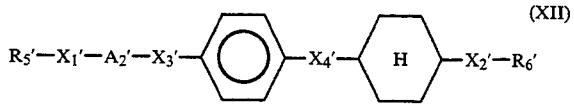 (XII)

wherein $X_1'$ and $X_2'$ respectively denote a single bond,

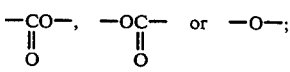

$A_2'$ denotes

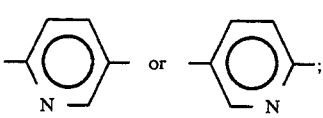

and $X_3'$ and $X_4'$ respectively denote a single bond,

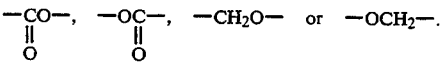

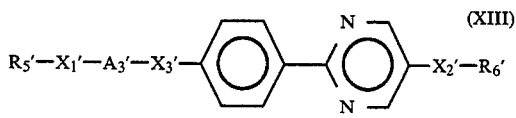 (XIII)

wherein $X_1'$ and $X_2'$ respectively denote a single bond,

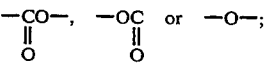

$A_3'$ denotes

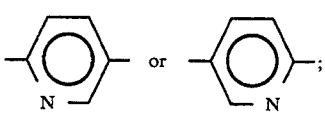

and $X_3'$ respectively denotes a single bond,

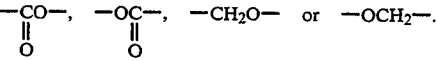

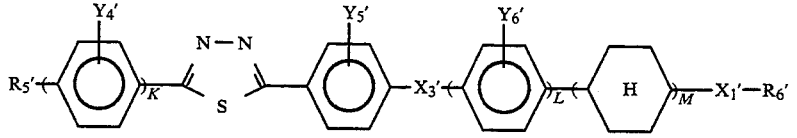 (XIV)

wherein K, L and M respectively denote 0 or 1 with the proviso that K+L+M=0 or 1; $X_1'$ denotes a single bond,

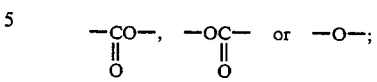

$X_3'$ denotes a single bond,

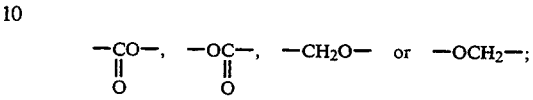

and $Y_4'$, $Y_5'$ and $Y_6'$ respectively denote H or F.

In the above formula (XI), preferred compounds thereof may include those represented by the following formulas (XIa) to (XIc):

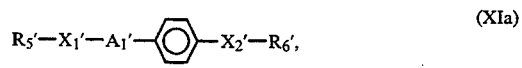 (XIa)

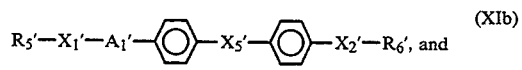 (XIb)

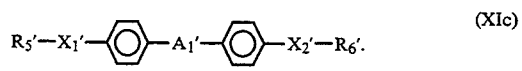 (XIc)

In the above formula (XII), preferred compounds thereof may include those represented by the following formulas (XIIa) and (XIIb):

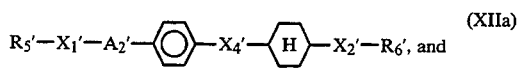 (XIIa)

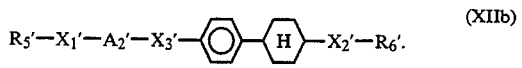 (XIIb)

In the above formula (XIV), preferred compounds thereof may include those represented by the following formulas (XIVa) and (XIVd):

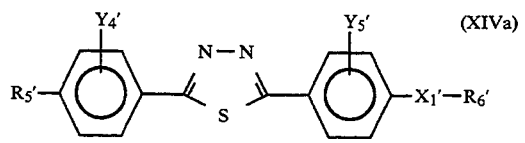 (XIVa)

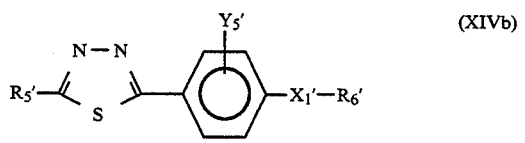 (XIVb)

-continued

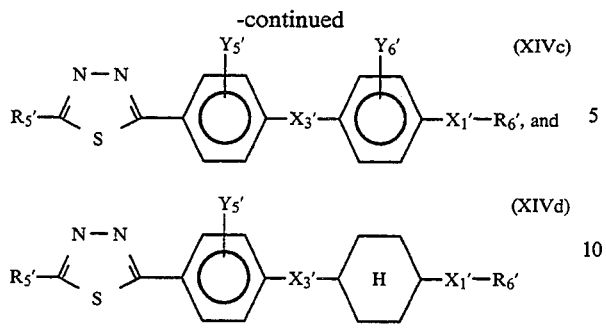

In the above-mentioned formula (XI), more preferred compounds thereof may include those represented by the formulas (XIaa) to (XIcc):

In the above-mentioned formula (XII), more preferred compounds thereof may include those represented by the formulas (XIIaa) to (XIIbb):

In the above formula (XIII), preferred compounds thereof may include those represented by the following formulas (XIIIa) to (XIIIg):

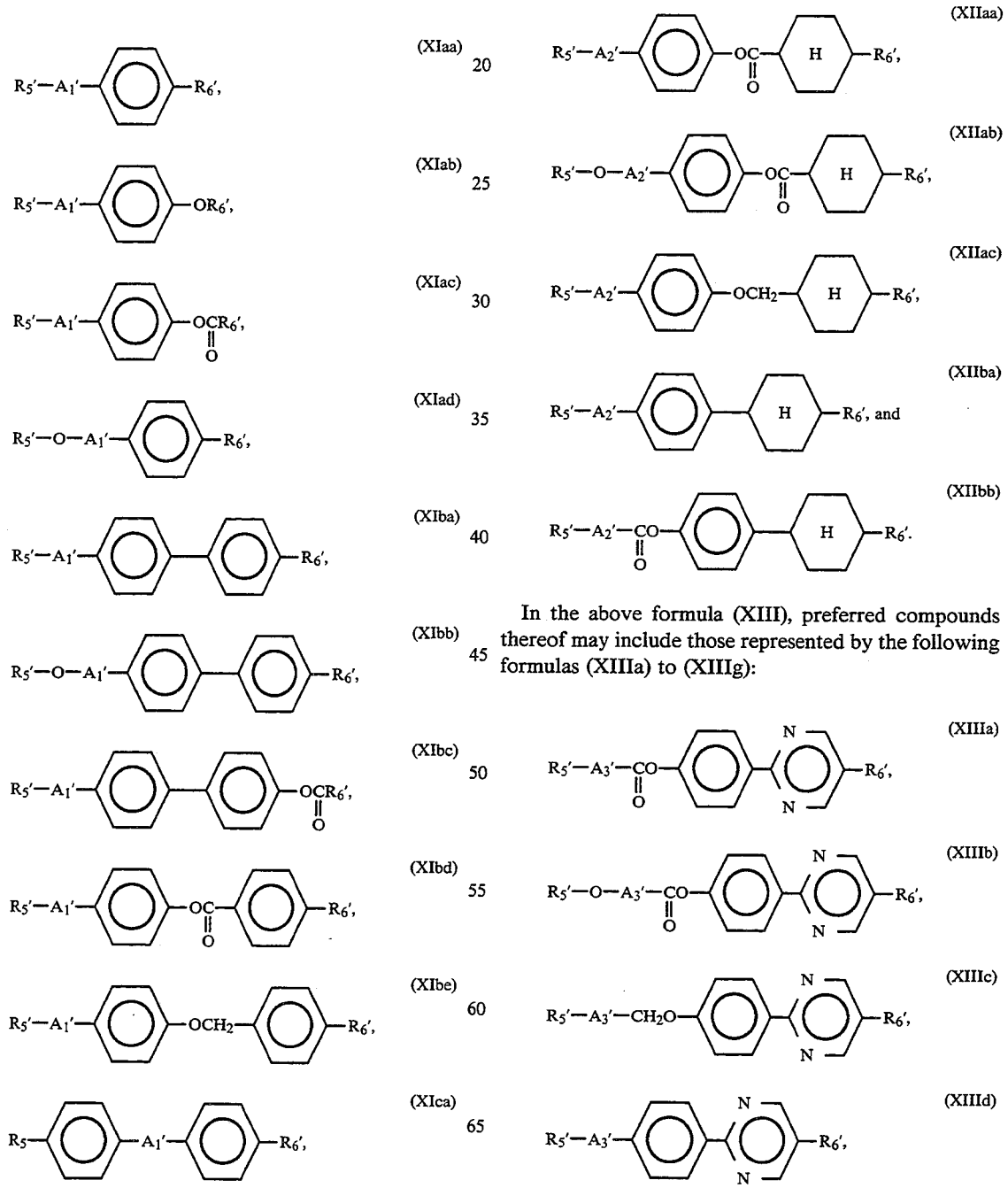

-continued

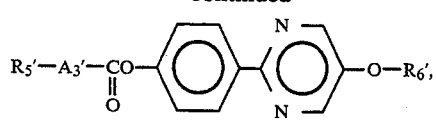 (XIIIe)

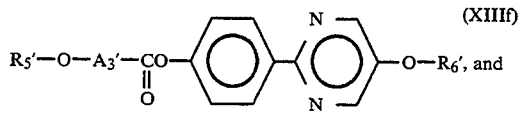 (XIIIf)

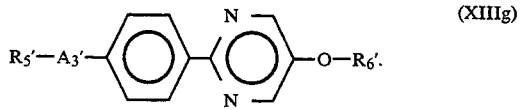 (XIIIg)

In the above-mentioned formula (XIV), more preferred compounds thereof may include those represented by the formula (XIVaa) to (XIVdb):

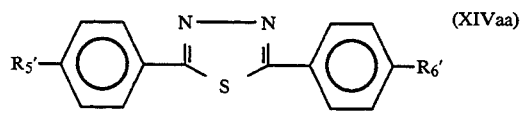 (XIVaa)

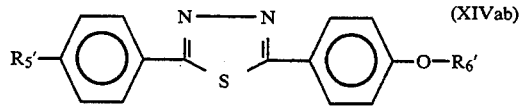 (XIVab)

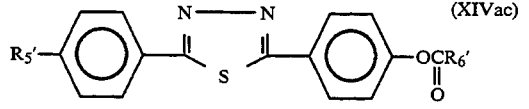 (XIVac)

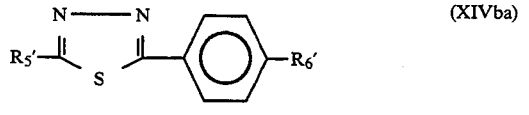 (XIVba)

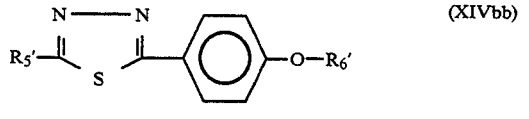 (XIVbb)

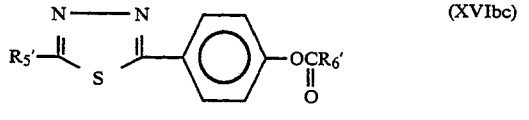 (XVIbc)

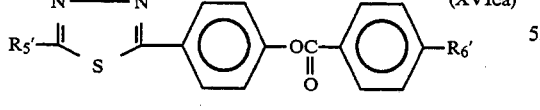 (XVIca)

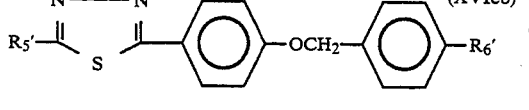 (XVIcb)

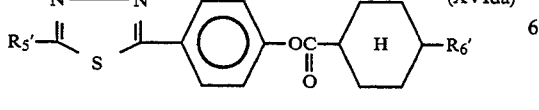 (XVIda)

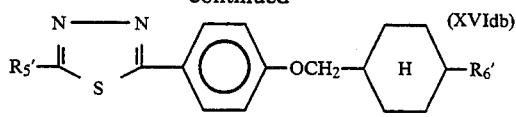 (XVIdb)

Herein, $R_5'$ and $R_6'$ respectively denote a linear or branched alkyl group having 1-18 carbon atoms capable of including one non-neighboring two or more methylene groups other than those directly connected to $X_1'$ or $X_2'$ which can be replaced with at least one species of

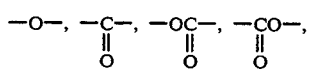

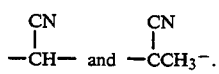

Further, preferred examples of $R_5'$ and $R_6'$ may respectively include those represented by the following groups (i) to (vi):

i) a linear alkyl group having 1-15 carbon atoms;

 ii)

wherein p denotes an integer of 0-5 and q denotes an integer of 2-11 (optically active or inactive);

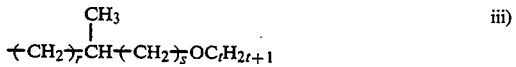 iii)

wherein r denotes an integer of 0-6, s denotes 0 or 1, and t denotes an integer of 1-14 (optically active or inactive);

 iv)

wherein w denotes an integer of 1-15 (optically active or inactive);

 v)

wherein A denotes an integer of 0-2 and B denotes an integer of 1-15 (optically active or inactive); and

 vi)

wherein C denotes an integer of 0-2 and D denotes an integer of 1-15 (optically active or inactive).

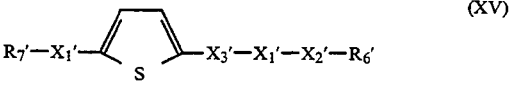 (XV)

$A_1'$ denotes $-A_2'-$ or $-A_2'-A_3'-$ wherein $A_2'$ and $A_3'$ respectively denote

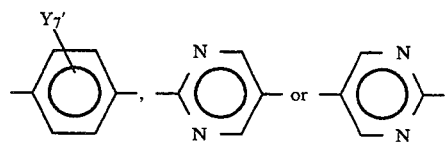

and $Y_7'$ is H or F; $X_1'$ and $X_2'$ respectively denote a single bond,

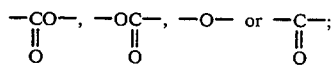

and $X_3'$ denotes

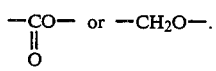

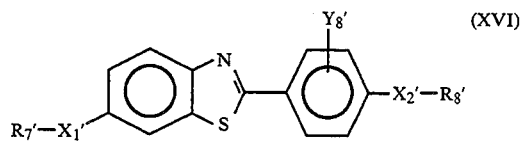

wherein $Y_8'$ is H or F; and $X_1'$ and $X_2'$ respectively denote a single bond,

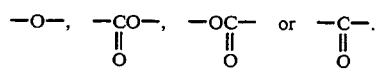

In the above formula (XV), preferred compounds thereof may include those represented by the following formulas (XVa) and (XVb):

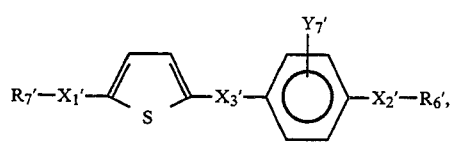

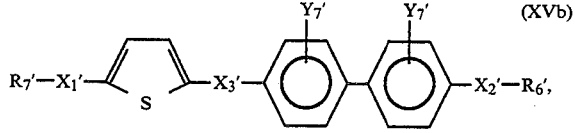

and

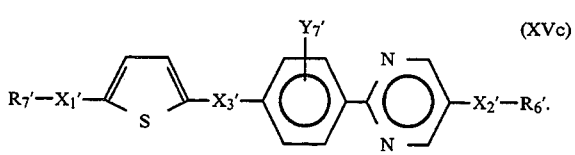

In the formula (XVI), preferred compounds thereof may include those represented by the following formulas (XVI) and (XVI).

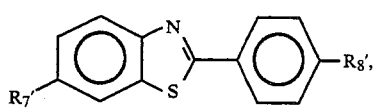

and

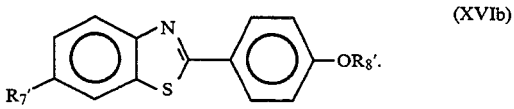

More preferred compounds of the formula (XV) may include those represented by the formulas (XVaa) to (XVcb):

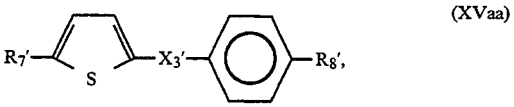

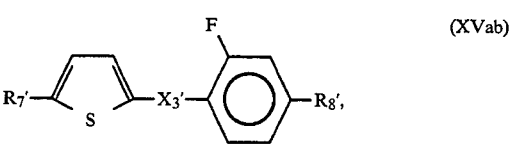

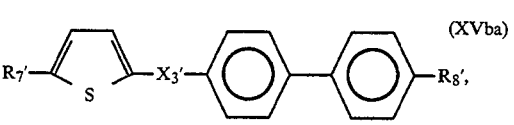

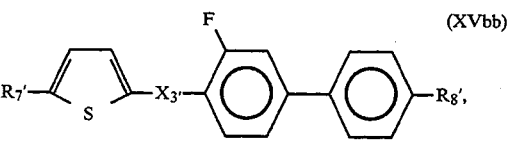

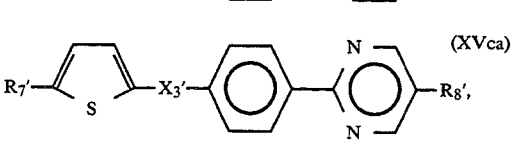

and

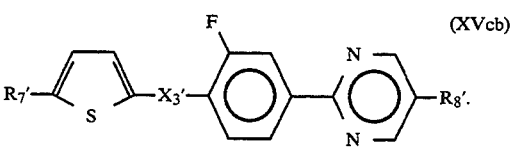

Herein, $R_7'$ and $R_8'$ respectively denote a linear or branched alkyl group having 1-18 carbon atoms capable of including one or non-neighboring two or more methylene groups which can be replaced with —CH halogen— and capable of further including one or two or more non-neighboring methylene groups other than those directly connected to $X_1'$ or $X_2'$ which can be replaced with at least one species of

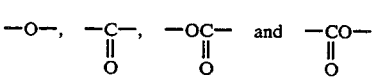

with proviso that $R_7'$ and $R_8'$ respectively do not connect to a ring structure by a single bond when $R_7'$ and $R_8'$ respectively denote a halogenated alkyl group containing one methylene group replaced with —CH halogen—.

Further, preferred examples of $R_7'$ and $R_8'$ may respectively include those represented by the following groups (i) to (v):

i) a linear alkyl group having 1–15 carbon atoms;

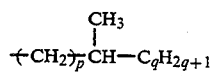   ii)

wherein p denotes an integer of 0–5 and q denotes an integer of 2–11 (optically active or inactive);

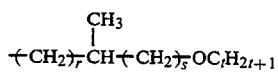   iii)

wherein r denotes an integer of 0–6, s denotes 0 or 1, and t denotes an integer of 1–14 (optically active or inactive);

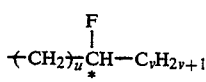   iv)

wherein u denotes an integer of 0 or 1 and v denotes an integer of 1–16; and

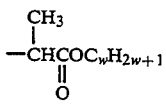   v)

wherein w denotes an integer of 1–15 (optically active or inactive).

In formulating the liquid crystal composition according to the present invention, the liquid crystal composition may desirably contain 1–80 wt. %, preferably 1–60 wt. %, more preferably 1–40 wt. % of a mesomorphic compound represented by the formula (I).

Further, when two or more species of the mesomorphic compounds represented by the formula (I) are used, the liquid crystal composition may desirably contain 1–80 wt. %, preferably 1–60 wt. %, more preferably 1–40 wt. %, of the two or more species of the mesomorphic compounds represented by the formula (I).

The liquid crystal device according to the present invention may preferably be prepared by heating the liquid crystal composition assuming a chiral smectic phase prepared as described above into an isotropic liquid under vacuum, filling a blank cell comprising a pair of oppositely spaced electrode plates with the composition, gradually cooling the cell to form a liquid crystal layer and restoring the normal pressure.

FIG. 1 is a schematic sectional view of an embodiment of the liquid crystal device utilizing ferroelectricity prepared as described above for explanation of the structure thereof.

Referring to FIG. 1, the liquid crystal device includes a liquid crystal layer 1 assuming a chiral smectic phase disposed between a pair of glass substrates 2 each having thereon a transparent electrode 3 and an insulating alignment control layer 4. Lead wires 6 are connected to the electrodes so as to apply a driving voltage to the liquid crystal layer 1 from a power supply 7. Outside the substrates 2, a pair of polarizers 8 are disposed so as to modulate incident light $I_0$ from a light source 9 in cooperation with the liquid crystal 1 to provide modulated light I.

Each of two glass substrates 2 is coated with a transparent electrode 3 comprising a film of $In_2O_3$, $SnO_2$ or ITO (indium-tin-oxide) to form an electrode plate. Further thereon, an insulating alignment control layer 4 is formed by rubbing a film of a polymer such as polyimide with gauze or acetate fiber-planted cloth so as to align the liquid crystal molecules in the rubbing direction. Further, it is also possible to compose the alignment control layer of two layers, e.g., by first forming an insulating layer of an inorganic material, such as silicon nitride, silicon nitride containing hydrogen, silicon carbide, silicon carbide containing hydrogen, silicon oxide, boron nitride, boron nitride containing hydrogen, cerium oxide, aluminum oxide, zirconium oxide, titanium oxide, or magnesium fluoride, and forming thereon an alignment control layer of an organic insulating material, such as polyvinyl alcohol, polyimide, polyamide-imide, polyester-imide, polyparaxylylene, polyester, polycarbonate, polyvinyl acetal, polyvinyl chloride, polyvinyl acetate, polyamide, polystyrene, cellulose resin, melamine resin, urea resin, acrylic resin, or photoresist resin. Alternatively, it is also possible to use a single layer of inorganic insulating alignment control layer or organic insulating alignment control layer. An inorganic insulating alignment control layer may be formed by vapor deposition, while an organic insulating alignment control layer may be formed by applying a solution of an organic insulating material or a precursor thereof in a concentration of 0.1 to 20 wt. %, preferably 0.2–10 wt. %, by spinner coating, dip coating, screen printing, spray coating or roller coating, followed by curing or hardening under prescribed hardening condition (e.g., by heating). The insulating alignment control layer may have a thickness of ordinarily 10 Å–1 micron, preferably 10–3000 Å, further preferably 10–1000 Å. The two glass substrates 2 with transparent electrodes 3 (which may be inclusively referred to herein as "electrode plates") and further with insulating alignment control layers 4 thereof are held to have a prescribed (but arbitrary) gap with a spacer 5. For example, such a cell structure with a prescribed gap may be formed by sandwiching spacers of silica beads or alumina beads having a prescribed diameter with two glass plates, and then sealing the periphery thereof with, e.g., an epoxy adhesive. Alternatively, a polymer film or glass fiber may also be used as a spacer. Between the two glass plates, a liquid crystal assuming a chiral smectic phase is sealed up to provide a liquid crystal layer 1 in a thickness of generally 0.5 to 20 μm, preferably 1 to 5 μm.

The transparent electrodes 3 are connected to the external power supply 7 through the lead wires 6. Further, outside the glass substrates 2, polarizers 8 are applied. The device shown in FIG. 1 is of a transmission type and is provided with a light source 9.

FIG. 2 is a schematic illustration of a liquid crystal cell (device) utilizing ferroelectricity for explaining operation thereof. Reference numerals 21a and 21b denote substrates (glass plates) on which a transparent electrode of, e.g., $In_2O_3$, $SnO_2$, ITO (indium-tin-oxide), etc., is disposed, respectively. A liquid crystal of an SmC*-phase (chiral smectic C phase) or SmH*-phase (chiral smectic H phase) in which liquid crystal molecular layers 22 are aligned perpendicular to surfaces of the glass plates is hermetically disposed therebetween. Full lines 23 show liquid crystal molecules. Each liquid crystal molecule 23 has a dipole moment (P⊥) 24 in a direction perpendicular to the axis thereof. The liquid crystal molecules 23 continuously form a helical structure in the direction of extension of the substrates. When a voltage higher than a certain threshold level is applied between electrodes formed on the substrates 21a and 21b, a helical structure of the liquid crystal molecule 23 is unwound or released to change the alignment direction of respective liquid crystal molecules 23 so that the dipole moments (P⊥) 24 are all directed in the direction of the electric field. The liquid crystal molecules 23 have an elongated shape and show refractive anisotropy between the long axis and the short axis thereof. Accordingly, it is easily understood that when, for instance, polarizers arranged in a cross nicol relationship, i.e., with their polarizing directions crossing each other, are disposed on the upper and the lower surfaces of the glass plates, the liquid crystal cell thus arranged functions as a liquid crystal optical modulation device of which optical characteristics vary depending upon the polarity of an applied voltage.

Further, when the liquid crystal cell is made sufficiently thin (e.g., less than about 10 microns), the helical structure of the liquid crystal molecules is unwound to provide a non-helical structure even in the absence of an electric field, whereby the dipole moment assumes either of the two states, i.e., Pa in an upper direction 34a or Pb in a lower direction 34b as shown in FIG. 3, thus providing a bistable condition. When an electric field Ea or Eb higher than a certain threshold level and different from each other in polarity as shown in FIG. 3 is applied to a cell having the above-mentioned characteristics by using voltage application means 31a and 31b, the dipole moment is directed either in the upper direction 34a or in the lower direction 34b depending on the vector of the electric field Ea or Eb. In correspondence with this, the liquid crystal molecules are oriented in either of a first stable state 33a and a second stable state 33b.

When the above-mentioned ferroelectric liquid crystal is used as an optical modulation element, it is possible to obtain two advantages. First is that the response speed is quite fast. Second is that the orientation of the liquid crystal shows bistability. The second advantage will be further explained, e.g., with reference to FIG. 3. When the electric field Ea is applied to the liquid crystal molecules, they are oriented in the first stable state 33a. This state is stably retained even if the electric field is removed. On the other hand, when the electric field Eb of which direction is opposite to that of the electric field Ea is applied thereto, the liquid crystal molecules are oriented to the second stable state 33b, whereby the directions of molecules are changed. This state is similarly stably retained even if the electric field is removed. Further, as long as the magnitude of the electric field Ea or Eb being applied is not above a certain threshold value, the liquid crystal molecules are placed in the respective orientation states.

Figure 4:
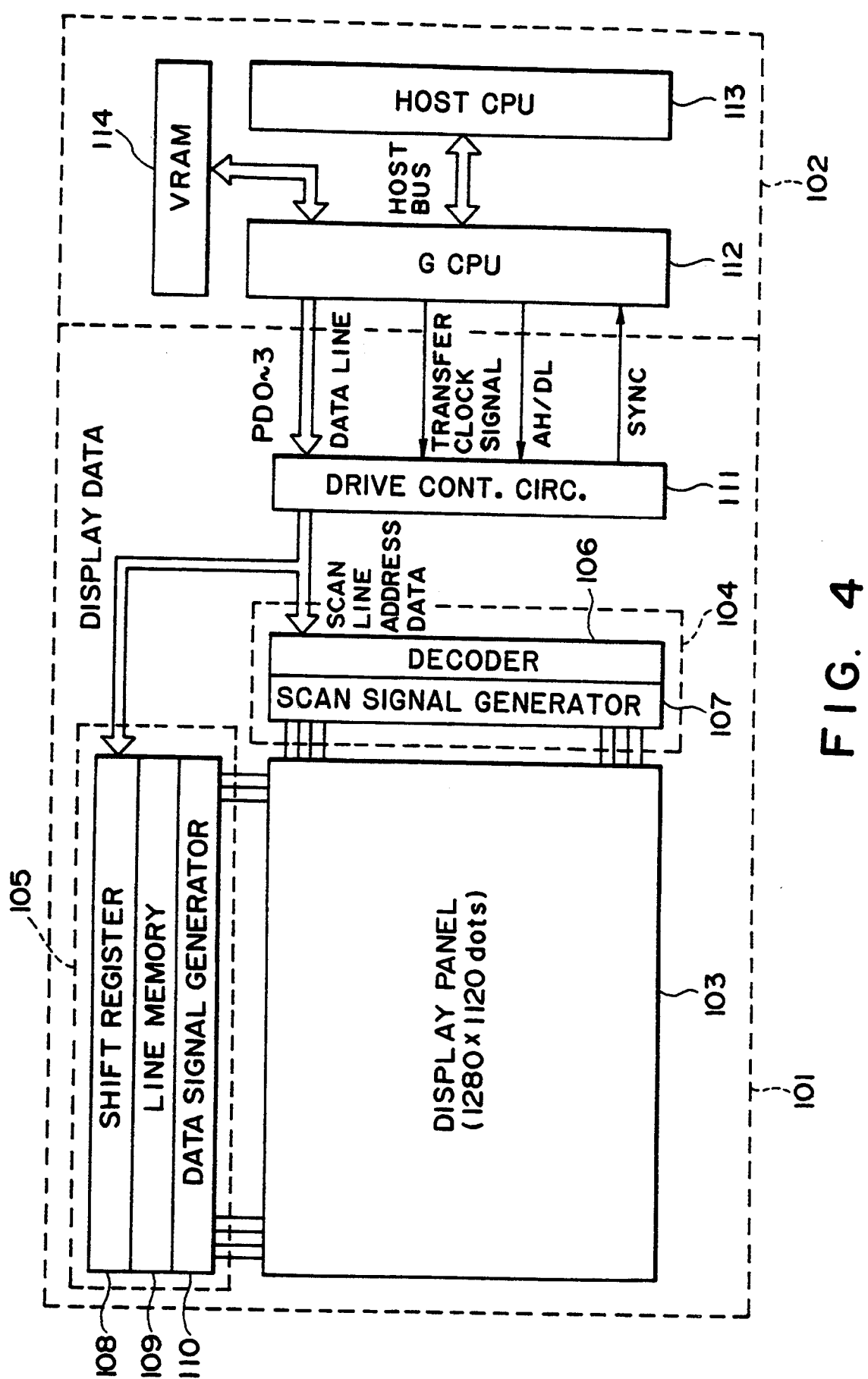
FIG. 4 is a block diagram showing a display apparatus comprising a liquid crystal device utilizing ferroelectricity of a liquid crystal composition and a graphic controller.
Figure 5:
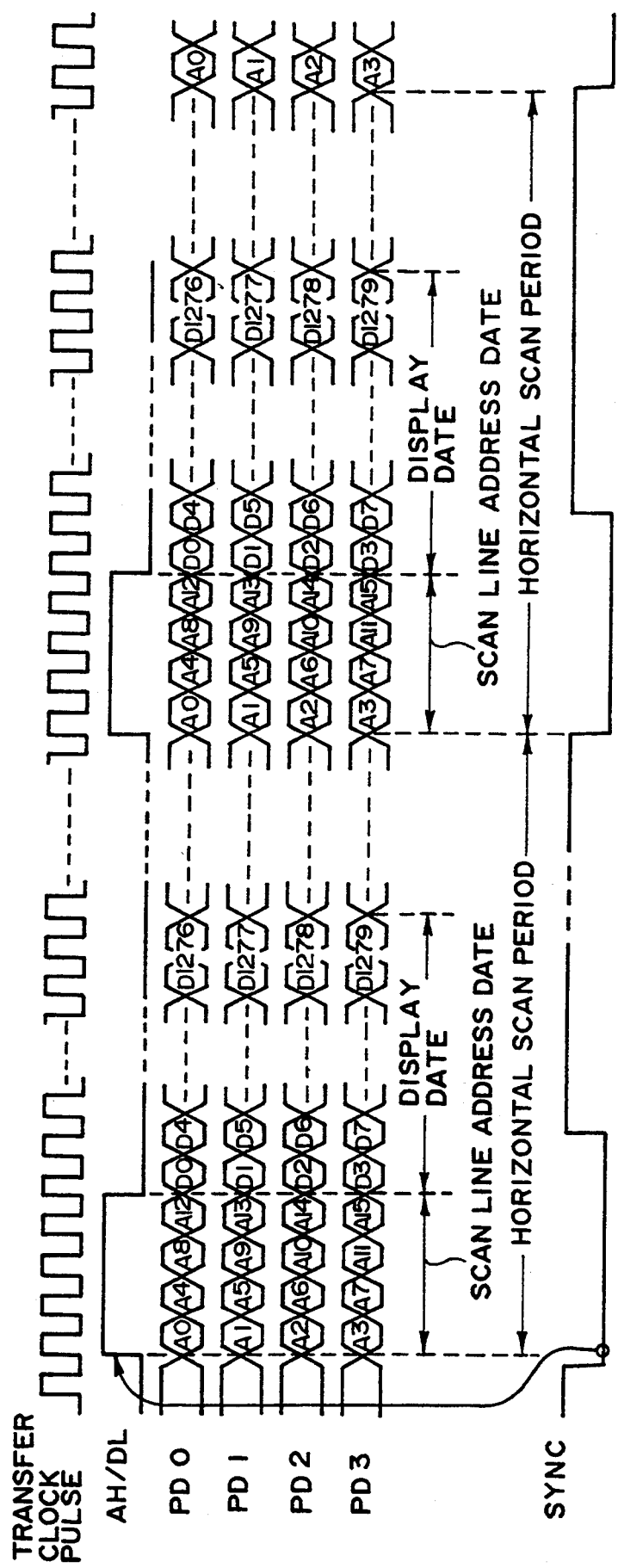
FIG. 5 is a time chart of image data communication showing time correlation between signal transfer and driving with respect to a liquid crystal display apparatus and a graphic controller.

Based on an arrangement appearing hereinbelow and data format comprising image data accompanied with scanning line address data and by adopting communication synchronization using a SYNC signal as shown in FIGS. 4 and 5, there is provided a liquid crystal display apparatus of the present invention which uses the liquid crystal device according to the present invention as a display panel portion.

Referring to FIG. 4, the ferroelectric liquid crystal display apparatus 101 includes a graphic controller 102, a display panel 103, a scanning line drive circuit 104, a data line drive circuit 105, a decoder 106, a scanning signal generator 107, a shift resistor 108, a line memory 109, a data signal generator 110, a drive control circuit 111, a graphic central processing unit (GCPU) 112, a host central processing unit (host CPU) 113, and an image data storage memory (VRAM) 114.

Image data are generated in the graphic controller 102 in an apparatus body and transferred to a display panel 103 by signal transfer means shown in FIGS. 4 and 5. The graphic controller 102 principally comprises a CPU (central processing unit, hereinafter referred to as "GCPU") 112 and a VRAM (video-RAM, image data storage memory) 114 and is in charge of management and communication of image data between a host CPU 113 and the liquid crystal display apparatus (FLCD) 101. The control of the display apparatus is principally realized in the graphic controller 102. A light source is disposed at the back of the display panel 103.

Hereinbelow, the present invention will be explained more specifically with reference to examples. It is however to be understood that the present invention is not restricted to these examples.

EXAMPLE 1

4-(5-decylpyrimidine-2-yl)phenyl 2-octylindan-5-carboxylate (Example Compound No. I-43) was synthesized through the following reaction steps (1) and (2).

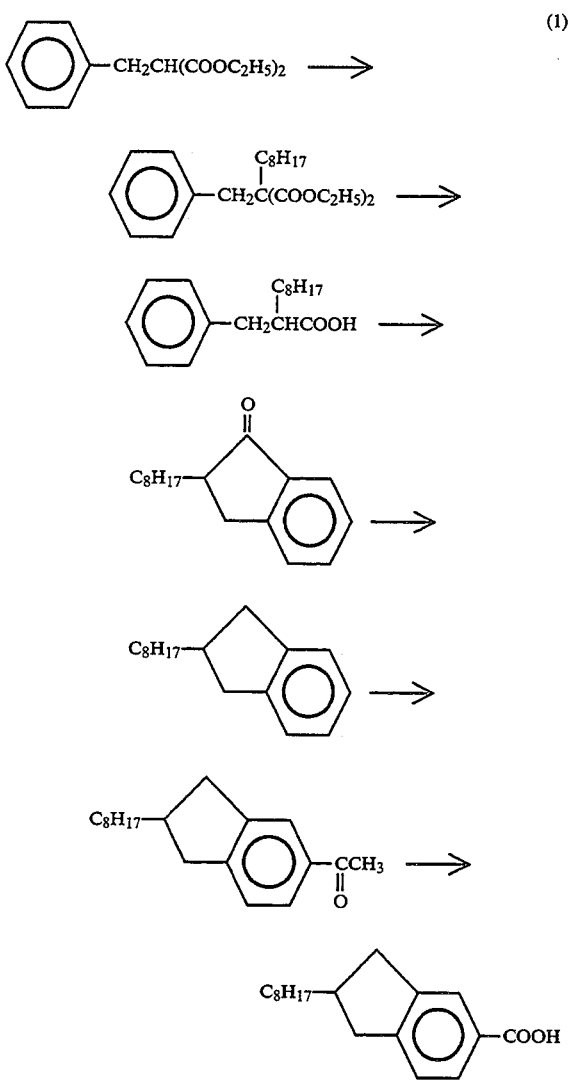

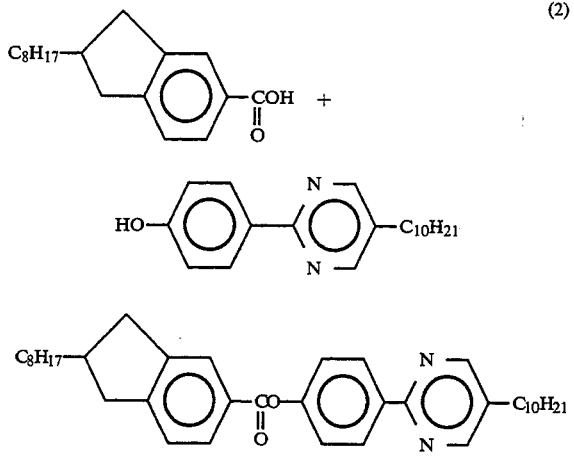

(1) Production of 2-octylindan-5-carboxylic acid

In a 3 liter-reaction vessel, 46 g (2 mol(M)) of metal sodium which had been cut small was added to 1100 ml of anhydrous ethanol and dissolved therein. To the solution, 500 g (2M) of diethyl benzylmalonate was added dropwise in 30 minutes at 40°–50° C. and 348 g (1.8M) of n-octylbromide was further added thereto in 10 minutes at 40°–50° C., followed by heat-refluxing for 3 hours. After the reaction, about 750 ml of ethanol was distilled off from the reaction mixture. 750 ml of water was added to the residue and 1 liter of benzene was further added thereto to effect extraction. After the benzene layer was washed with saturated aqueous solution of common salt until the benzene layer showed neutrality, the resultant mixture was dried with anhydrous sodium sulfate, followed by distilling-off of benzene to obtain 666 g of a crude product of diethyl 2-benzyl-2-n-octylmalonate.

Then, in a 5 liter-reaction vessel, 660 g of the above-prepared diethyl 2-benzyl-2-n-octyl malonate and 1540 ml of methanol were placed. Under stirring, 836 g (7.29M) of 50%-potassium hydroxide aqueous solution was added dropwise to the above mixture in 10 minutes, followed by heat-refluxing for 7 hours and then cooling. To the reaction mixture, 1500 g of 30%-sulfuric acid aqueous solution was added dropwise to acidify the reaction mixture. After cooling to room temperature, the acidified reaction mixture was subjected to extraction with 1500 ml of ether. The ether layer was washed three times with 1500 ml of saturated aqueous solution of common salt and dried with anhydrous sodium sulfate, followed by distilling-off of ether to obtain a residue. The residue was placed in a 1 liter-reaction vessel and stirred for 5 hour at 150° C. After cooling, the resultant crude product was purified by silica gel column chromatography (eluent: n-hexane/ethyl acetate=20/1) to obtain 154 g of 2-benzyldecanoic acid.

115 g (4.39×10⁻¹M) of the above-prepared 2-benzyldecanoic acid and 575 g of polyphosphoric acid were placed in a 1 liter-reaction vessel and stirred for 5 hours at 80° C. After the reaction, the reaction mixture was poured into 2 liters of ice water to decompose the 2-benzyldecanoic acid. The resultant reaction mixture was subjected to extraction with 600 ml of benzene. The benzene layer was washed two time with 600 ml of saturated aqueous solution of common salt and washed with 600 ml of 2% sodium hydroxide aqueous solution, followed by further washing with saturated aqueous solution of common salt until the benzene layer showed neutrality. The resultant benzene layer was dried with anhydrous sodium sulfate, followed by distilling-off of benzene to obtain 102.5 g of 2-octyl-1-indanone.

Then, 1140 ml of tetrahydrofuran (THF) was placed in a 3 liter-reaction vessel. Under stirring, 361.4 g (2.7M) of anhydrous aluminum chloride was added to the above THF in 25 minutes below 20° C. To the mixture, 34.3 g (9.03×10⁻¹M) of lithium aluminum hydride was added in 10 minutes below 20° C. Further, to the resultant mixture, a solution of 100 g (4.1×10⁻¹M) of the above-prepared 2-octyl-1-indanone in 430 ml of THF was added dropwise in 40 minutes below 5° C., followed by stirring for 30 minutes below 5° C., and heat-refluxing for 1 hour. After the reaction, the reaction mixture was cooled and washed with ethyl acetate and water in this order to decompose the 2-octyl-1-indanone. The resultant reaction mixture was poured into 2 liters of ice water and subjected to extraction with ethyl acetate, followed by washing with saturated aqueous solution of common salt, drying with anhydrous magnesium sulfate and distilling-off of the solvent to obtain 93.0 g of 2-octylindan.

Subsequently, 450 ml of dry dichloromethane and 68.7 g (5.15×10⁻¹M) of anhydrous aluminum chloride were placed in a 1 liter-reaction vessel and cooled below 0° C. To the mixture, 37.2 g (4.74×10⁻¹M) of acetyl chloride was added dropwise in 10 minutes below 0° C. and then 90 g (3.91×10⁻¹M) of the above prepared 2-octylindan was added dropwise below 0° C., followed by stirring for 2 hours below 0° C. and further stirring for 2 hours at room temperature. After the reaction, the reaction mixture was poured into 1 liter of ice water and 90 ml of concentrated sulfuric acid was added. The dichloromethane layer was separated from the above mixture and washed with water, followed by drying with anhydrous magnesium sulfate and distilling-off of the solvent to obtain a crude product. The crude product was purified by silica gel column chromatography (eluent: n-hexane/ethyl acetate=20/1) to obtain 57.6 g of 2-octyl-5-acetylindan.

In a 3 liter-reaction vessel, 50 g (1.84×10⁻¹M) of the above-prepared 2-octyl-5-acetylindan and 500 ml of 1,4-dioxane were placed and warmed to 25° C. To the mixture, a mixture solution of 482 g of 10% -sodium hypochlorite aqueous solution and 178 g of 25%-sodium hydroxide aqueous solution was added dropwise in 30 minutes at about 30° C., followed by stirring for 6 hours at 60° C. After the reaction, the reaction mixture was cooled to 40° C. and then a solution of 22 g of sodium sulfite in 750 ml of water was added thereto, followed by stirring for 30 minutes. To the resultant mixture, 380 ml of concentrated sulfuric acid was added to precipitate a crystal. The crystal was recovered by filtration and washed with water, followed by drying and recrystallization from ethanol to obtain 37.0 g of 2-octylindan-5-carboxylic acid.

(2) Production of 4-(5-decylpyrimidine-2-yl)phenyl 2-octylindan-5-carboxylate 1.00 g (3.64 mM) of 2-octylindan-5-carboxylic acid and 1.13 g (3.62 mM) of 5-decyl-2-(4-hydroxyphenyl)-pyrimidine were dissolved in 30 ml of dichloromethane. To the solution, 0.74 g (3.59 mM) of N,N'-dicyclohexylcarbodiimide (DCC) and 0.05 g of 4-pyrrolidinopyridine were added, followed by stirring for 5 hours. The resultant N,N'-dicyclohexylurea was recovered by filtration, washed with dichloromethane, and added to the filtrate. The resultant dichloromethane solution was subjected to distillation under reduced pressure. The residue was purified by silica gel column chromatography (eluent: toluene) and recrystallized from a mixture solvent (toluene/methanol) to obtain 1.23 g of 4-(5-decylpyrimidine-2-yl)phenyl 2-octylindan-5-carboxylate (Yield: 60.3%).

Phase transition temperature (° C.)

Cry. $\underset{40}{\overset{66}{\rightleftarrows}}$ SmC $\underset{73}{\overset{74}{\rightleftarrows}}$ N $\underset{137}{\overset{138}{\rightleftarrows}}$ Iso Herein, the respective symbols denote the following phase; Iso: isotropic phase; Ch: cholesteric phase; N: nematic phase; SmA: smectic A phase; SmC: smectic C phase; SmC*: chiral smectic C phase; Sm3: smectic phase other than SmA and SmC; and Cry.: crystal.

EXAMPLE 2

2-octyl-5-(5-octyloxypyrimidine-2-yl)indan (Ex. Comp. No. I-392) was synthesized through the following reaction steps (1) and (2).

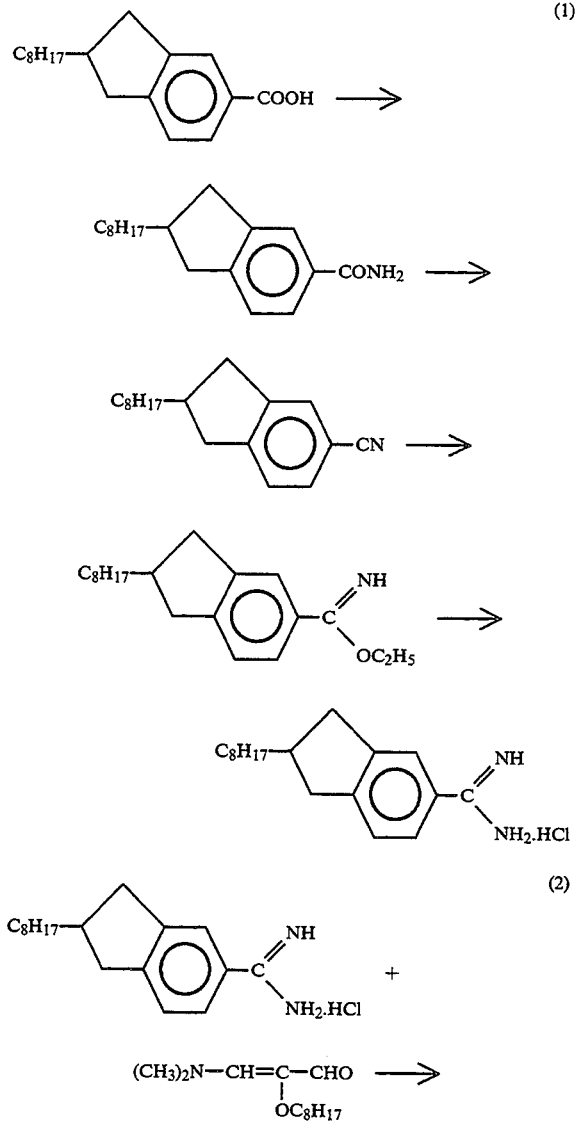

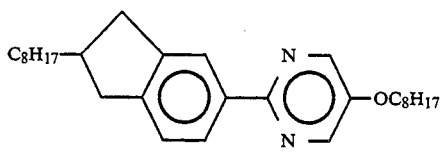

(1) Production of 2-octyl-5-amidinoindan hydrochloride

In a 50 ml-round bottomed flask, 5.00 g (18.2 mM) of 2-octylindan-5-carboxylic acid was placed and 7.0 ml of thionyl chloride and one drop of N,N'-dimethylformamide (DMF) were added thereto, followed by heat-refluxing for 30 minute. An excessive thionyl chloride was distilled off under reduced pressure from the above mixture to obtain 2-octylindan-5-carbonyl chloride. A solution of the above-obtained 2-octylindan-5-carbonyl chloride in 50 ml of THF was gradually added dropwise to 45 ml of 30%-ammonia water which had been cooled to about 0° C. on an ice-common salt bath under stirring. After the addition, the resultant mixture was stirred for 4.5 hours at room temperature. After the reaction, 300 ml of water was added to the reaction mixture to precipitate a crystal. The crystal was recovered by filtration and successively washed with water and methanol to obtain 4.59 g of 2-octyl-5-carbamoylindan (Yield: 92.1%).

Subsequently, 8.71 g (33.2 mM) of triphenylphosphine, 25 ml of carbon tetrachloride and 15 ml of THF were placed in 200 ml-three necked flask. Under stirring at room temperature, 4.55 g (16.6 mM) of the above-prepared 2-octyl-5-carbamoylindan was gradually added to the above mixture, followed by washing with 10 ml, of THF and stirring for 3 hours at 45°–50.4° C. to precipitate a crystal. After the reaction, the crystal was removed from the reaction mixture by filtration and the filtrate was evaporated under reduced pressure to obtain a residue. The residue was purified silica gel column chromatography (eluent: toluene/ethyl acetate=100/1) and recrystallized from methanol to obtain 4.24 g of 2-octyl-5-cyanoindan (Yield: 99.8%).

Then, 4.24 g (16.6 mM) of 2-octyl-5-cyanoindan, 0.90 g (19.5 mM) of ethanol and 48 ml of chloroform were placed in a 100 ml-three necked flask and dissolved. On an ice-common salt bath, a hydrogen chloride gas was blown in the solution for 3.5 hours at −9.5° to −3° C. under stirring to saturate the solution and the interior of the flask. The flask containing the mixture was left standing in a refrigerator for 4 days. The resultant mixture was poured into 220 ml of 5N-NaOH aqueous solution which had been iced, followed by extraction with chloroform. The organic layer was washed two times with saturated common salt aqueous solution and dried with anhydrous sodium sulfate, followed by distilling-off of the solvent to obtain an ethyl imidate. To the ethyl imidate, 0.93 g (17.4 mM) of ammonium chloride and 18 ml of 75% ethanol were added, followed by heat-refluxing for 3 hours under stirring. After the reaction, the reaction mixture was cooled on an ice water both. The resultant insoluble matter was removed from the reaction mixture by filtration and the filtrate was evaporated to obtain a residue. To the residue, an appropriate amount of acetone was added to precipitate a crystal. The crystal was recovered by filtration to obtain 2.92 g of 2-octyl-5-amidinoindan hydrochloride (Yield: 56.9%).

(2) Production of 2-octyl-5-(5-octylpyrimidine-2-yl) indan 0.80 g (2.59 mM) of 2-octyl-5-amidinoindan hydrochloride, 0.30 g (5.55 mM) of sodium methylate, 0.62 g (2.73 mM) of α-octyloxy-β-dimethylaminoacrolein and 12 ml of methanol were placed in a 30 ml-round bottomed flask, followed by refluxing for 18 hours and 20 minutes under stirring. After the reaction, the reaction mixture was cooled on an ice water bath to precipitate a crystal. The crystal was recovered by filtration and purified by silica gel column chromatography (eluent: toluene), followed by recrystallization from a mixture solvent (acetone/methanol) to obtain 0.57 g of 2-octyl-5-(5-octylpyrimidine-2-yl) indan (Yield: 50.4%).

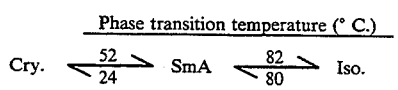

EXAMPLE 3

2-octyl-5-(5-ethoxypyrimidine-2-yl) indan (Ex. Comp. No. I-387) was synthesized through the following reaction step.

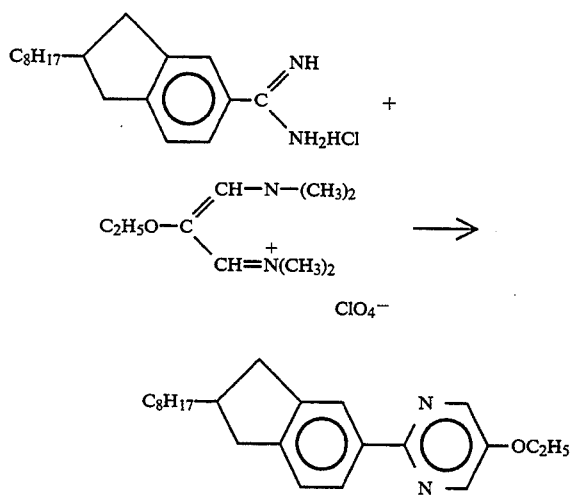

1.10 g (3.56 mM) of 2-octyl-5-amidinoindan hydrochloride, 0.57 g (10.7 mM) of sodium methylate, 0.96 g (4.1 mM) of 3-dimethylamino-2-ethoxy-N,N-dimethylpropene-(2)-ammonium perchlorate and 20 ml of methanol were placed in a 50 ml-round bottomed flask and heat-refluxed for 7 hours under stirring. After the reaction, an appropriate amount of water was poured into the reaction mixture and the resultant insoluble matter was recovered by filtration, followed by washing with water and drying with anhydrous sodium sulfate. After distilling-off of the solvent, the resultant crude product was recrystallized two times from ethanol to obtain 0.72 g of 2-octyl-5-(5-ethoxypyrimidine-2-yl) indan (Yield: 58%).

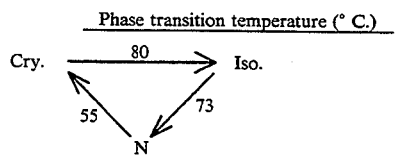

EXAMPLE 4

6-octyl-2-(2-octylindan-5-yl)benzothiazole (Ex. Comp. No. I-129) was synthesized through the following reaction steps (1) and (2).

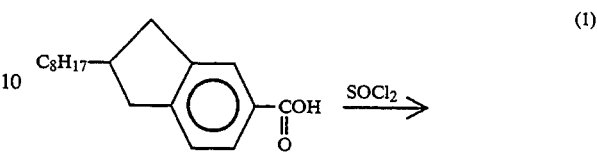

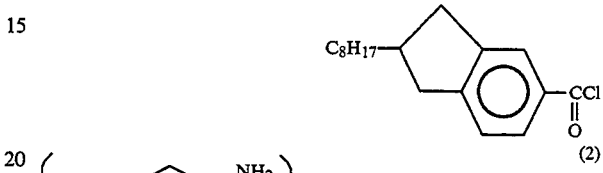

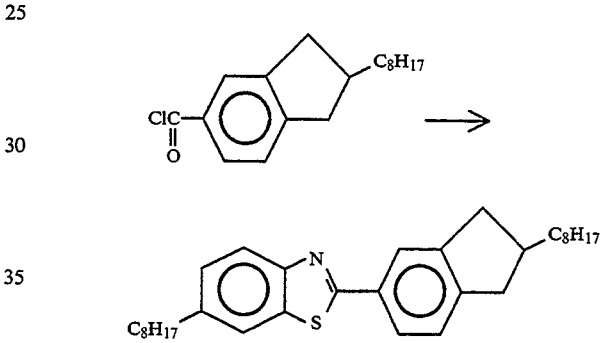

(1) Production of 2-octylindan-5-carbonyl chloride 4.8 g of thionyl chloride was added to 1.10 g (4.00 mM) of 2-octylindan-5-carboxylic acid, followed by refluxing for 1 hour. After the refluxing, an excessive thionyl chloride was distilled off under reduced pressure, followed by further distillation with benzene to obtain 2-octylindan-5-carbonyl chloride.

(2) Production of 6-octyl-2-(2-octylindan-5-yl) benzothiazole

To the above-prepared 2-octylindan-5-carbonyl chloride, 1.06 g (1.97 mM) of zinc 5-octyl-2-aminobenzenethiolate was added, followed by stirring for 30 minutes at 200° C. After the reaction, the reaction mixture was cooled and then a dilute sodium hydroxide aqueous solution was added thereto, followed by extraction with benzene. The resultant extract was washed with water and dried with anhydrous magnesium sulfate, followed by distilling-off of the solvent to obtain a crude product. The crude product was purified by silica gel column chromatography (eluent: toluene) and treated with activated carbon, followed by two times of recrystallization from a mixture solvent (ethanol/toluene) to obtain 0.75 g of 6-octyl-2-(2-octylindan-5-yl) benzothiazole (Yield: 80.6%).

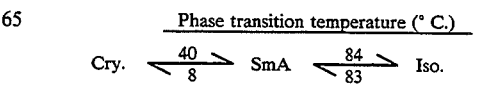

EXAMPLE 5

2-octyl-5-[5-(4-hexyloxyphenyl)pyrimidine-2-yl]indan (Ex. Comp. No. I-726) was synthesized through the following reaction steps (1) and (2).

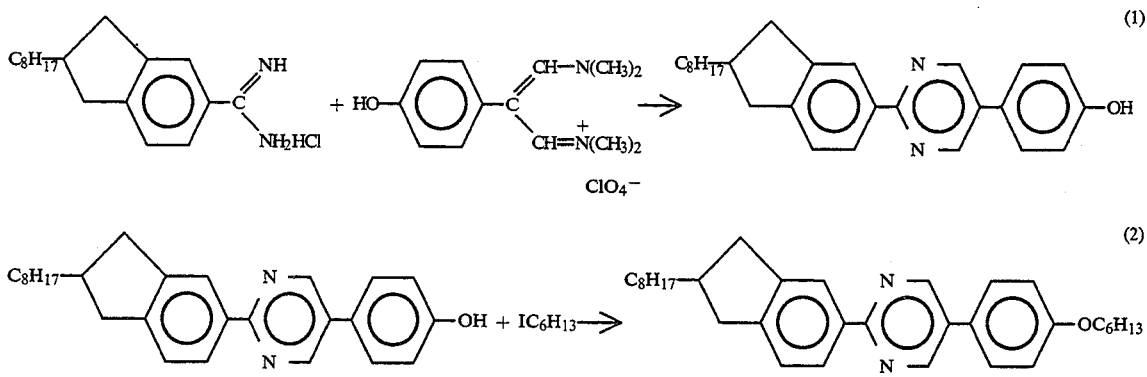

(1) Production of 2-octyl-5-[5-(4-hydroxyphenyl)-pyrimidine-2-yl]indan 1.00 g (3.24 mM) of 2-octyl-5-amidinoindan hydrochloride, 0.70 g (13.7 mM) of sodium methylate, 1.04 g (3.26 mM) of 3-dimethylamino-2-(4-hydroxyphenyl)-N,N-dimethylpropene-(2)-ammonium perchlorate and 20 ml of methanol were placed in a 50 ml-round bottomed flask and heat-refluxed for 14.5 hours under stirring. After the reaction, an appropriate amount of water was poured into the reaction mixture and 0.66 ml of concentrated sulfuric acid was further added thereto under cooling with ice water, followed by stirring. The resultant insoluble matter was recovered by filtration, followed by washing with water and drying with anhydrous sodium sulfate. The resultant insoluble was purified by silica gel column chromatography (eluent: toluene) and recrystallized from a mixture solvent (acetone/methanol) to obtain 0.98 g of 2-octyl-5-[5-(4-hydroxyphenyl)pyrimidine-2-yl]indan (Yield: 75.6%).

(2) Production of 2-octyl-5-[5-(4-hexyloxyphenyl)-pyrimidine-2-yl]indan 0.25 g (0.62 mM) of 2-octyl-5-[5-(4-hydroxyphenyl)-pyrimidine-2-yl]indan, 0.07 g of 85% -potassium hydroxide, 0.2 ml of hexyl iodide and 5 ml of n-butanol were placed in a 20 ml-round bottomed flask, followed by heat-refluxing for 3.5 hours under stirring. After the reaction, the reaction mixture was poured into ice water. The resultant insoluble matter was recovered by filtration and dissolved in toluene, followed by washing with 3%-sodium thiosulfate aqueous solution. The water layer was subjected to extraction with toluene and the resultant toluene layer was added to the organic layer, followed by washing with saturated common salt aqueous solution, drying with anhydrous sodium sulfate and distilling-off of the solvent. The resultant crude product was purified by silica gel column chromatography (eluent: toluene) and recrystallized from a mixture solvent (toluene/methanol) to obtain 0.23 g of 2-octyl-5-[5-(4-hexyloxyphenyl)pyrimidine-2-yl]indan (Yield: 76.0%).

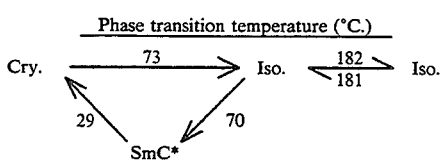

EXAMPLE 6

Optically active 2-octyl-5-[5-{4-(2-fluorooctyloxy)-phenyl}pyrimidine-2-yl]indan (Ex. Comp. No. I-144) was synthesized through the following reaction step.

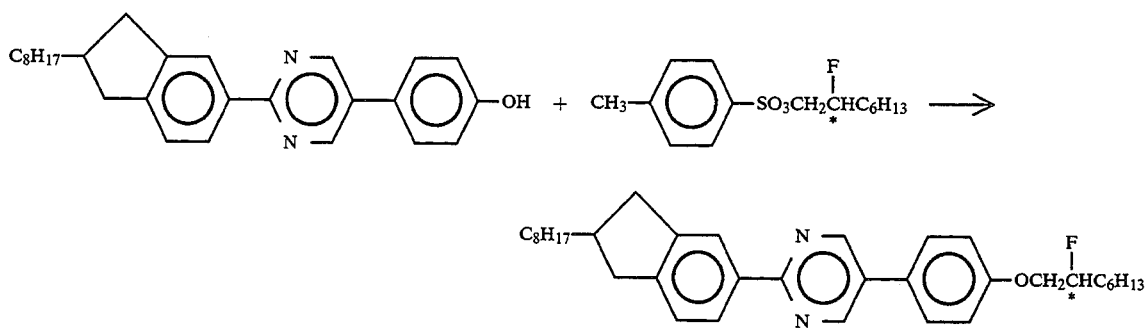

0.25 g (0.62 mM) of 2-octyl-5-[5-(4-hydroxyphenyl)-pyrimidine-2-yl]indan, 0.05 g (0.76 mM) of 85%-potassium hydroxide, 0.23 g (0.76 mM) of 2-fluorooctyl p-toluenesulfonate and 5 ml of n-butanol were placed in a 20 ml-round bottomed flask, followed by heat-refluxing for 7 hours under stirring. After the reaction, the reaction mixture was poured into ice water. The resultant insoluble matter was recovered by filtration and washed with methanol, followed by purification by silica gel column chromatography (eluent: toluene) and recrystallized from a mixture solvent (toluene/methanol) to obtain 0.21 g of 2-octyl-5-[5-{4-(2-fluorooctyloxy)-phenyl)pyrimidine-2-yl]indan (Yield: 63.4%).

Phase transition temperature (°C.)

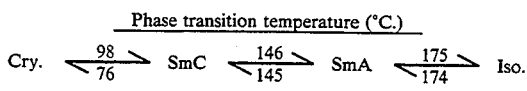

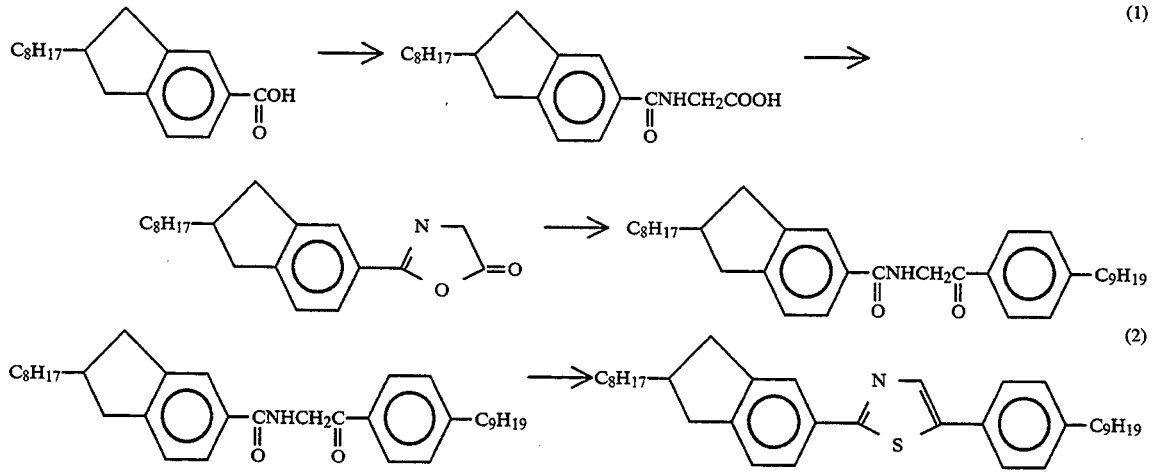

EXAMPLE 8

2-(2-octylindan-5-yl)-5-(4-nonylphenyl)-1,3-thiazole (Ex. Comp. No. I-161) was synthesized through the following reaction steps (1) and (2).

(1) Production of 2-octylindan-5-carbonyl-4'-nonylphenacrylamine 1.10 g (14.7 mM) of glycine, 0.29 (7.25 mM) of NaOH, 5.8 ml of distilled water were placed in a 100 ml-three necked flask and dissolved to prepare a solution. To the solution, 5.8 ml of dioxane was added, followed by stirring or a ice-common salt bath. To the mixture, a solution of 0.29 g (7.25 mM) of NaOH in 2.5 ml of distilled water and a solution of 2.14 g (7.29 mM) of 2-octylindan-5-carbonyl chloride in 10 ml of dioxane were gradually added dropwise at the same time at −1° to 3° C. by means of a dropping funnel, respectively, followed by stirring for 30 minutes at 1°-2° C. After the reaction, 0.87 ml of concentrated HCl was added to the reaction mixture to precipitate a crystal. The crystal was recovered by filtration and washed with water, followed by drying and recrystallization from methanol to obtain 1.61 g of N-(2-octylindan-5-carbonyl)glycin (Yield: 66.6%).

Subsequently, 1.55 g (4.68 mM) of N-(2-octylindan-5-carbonyl)glycine and 25 ml of dry benzene were placed in a 50 ml-three necked flask. Under stirring at room temperature, 0.66 ml (4.74 mM) of triethylamine and 0.46 ml (4.81 mM) were successively added to the above mixture, followed by further stirring for 23 minutes at room temperature to precipitate a crystal. After the reaction, the precipitated triethylamine hydrochloride was removed by filtration and the filtrate was evapo-

EXAMPLE 7

2-octyl-5-[5-(4-heptanoyloxyphenyl)pyrimidine-2-yl]indan (Ex. Comp. No. I-146) was synthesized through the following reaction step.

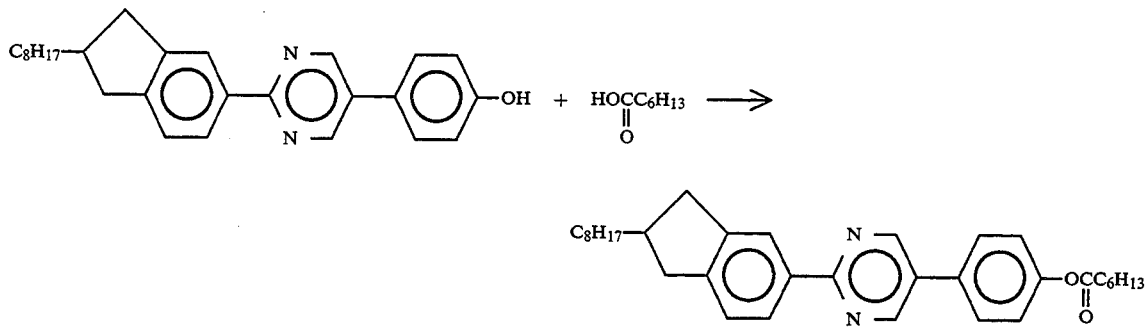

0.15 g (0.37 mM) of 2-octyl-5-[5-(4-hydroxyphenyl)-pyrimidine-2-yl]indan, 0.05 g (0.38 mM) of heptanoic acid, 0.08 g (0.39 mM) of DCC, 0.01 g of 4-dimethylaminopyridine and 3 ml of methylene chloride were mixed and stirred for 5 hours at room temperature. The resultant N,N'-dichlorhexylurea was recovered by filtration, washed with dichloromethane, and added to the filtrate. The resultant dichloromethane solution was subjected to distillation under reduced pressure. The residue was purified by silica gel column chromatography (eluent: toluene/ethyl acetate=100/1) and recrystallized from a mixture solvent (toluene/methanol) to obtain 0.14 g of 2-octyl-5-[5-(4-heptanoyloxyphenyl)-pyrimidine-2-yl]indan (Yield: 72.9%).

Phase transition temperature (°C.)

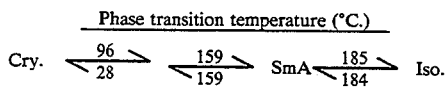

rated under reduced pressure to obtain a residue. The residue was dried under reduced pressure to obtain 2-(2-octylindan-5-yl)-5-oxazolone.

Separately, 10 ml of dry nonylbenzene was placed in a 100 ml-three necked flask and 1.87 g (14.0 mM) of powdered aluminum chloride anhydride was added thereto on an ice water bath under stirring. The above-prepared 2-(2-octylindan-5-yl)-5-oxazolone was dissolved in dry nonylbenzene and the resultant solution was gradually added to the above mixture under the above condition. After the addition, the ice water bath was removed and the resultant mixture was stirred for 5.5 hours at room temperature. After the reaction, the reaction mixture was poured into a mixture of 40 g of ice and 10.3 ml of HCl, followed by addition of ethylacetate and toluene successively and then stirring at room temperature. The resultant organic layer was recovered and washed with water and dried with anhydrous sodium sulfate, followed by evaporation under reduced pressure. To the resultant residue, hexane was added to precipitate a crystal. The crystal was recovered by filtration and washed with hexane to obtain 1.15 g of 2-octylindan-5-carboxyl-4'-nonylphenacrylamine (Yield: 47.5%).

(2) Production of 2-(2-octylindan-5-yl)-5-(4-nonylphenyl)-1,3-thiazole 1.10 g (2.12 mM) of the above-prepared 2-octylindan-5-carbonyl-4'-nonylphenacrylamine, 1.03 g (2.55 mM) of a Lawesson's reagent, 10 ml of THF were placed in a 30 ml-round bottomed flask and refluxed for 70 minutes under stirring. After the reaction, the reaction mixture was poured into a solution of 0.79 g of NaOH in 50 ml of ice water to precipitate a crystal. The crystal was recovered by filtration and washed with water. The resultant crystal was dissolved in toluene and washed with water, followed by drying with anhydrous sodium sulfate and distilling-off of the solvent under reduced pressure. The resultant residue was purified by silica gel column chromatography (eluent: toluene/ethyl acetate=100/1) and treated with activated carbon, followed by two times of recrystallization from a mixture solvent (toluene/methanol) to obtain 0.89 g of 2-(2-octylindan-5-yl)-5-(4-nonylphenyl)-1,3-thiazole (Yield: 81.2%).

Phase transition temperature (°C.)

Cry. ⇌ 43/12 SmA ⇌ 135/134 Iso.

EXAMPLE 9

Optically active 2-octyl-5-{{4-(tetrahydro-2-furancarbonyloxy)phenyl}pyrimidine-2-yl]indan (Ex. Comp. No. I-151) was synthesized through the following reaction step.

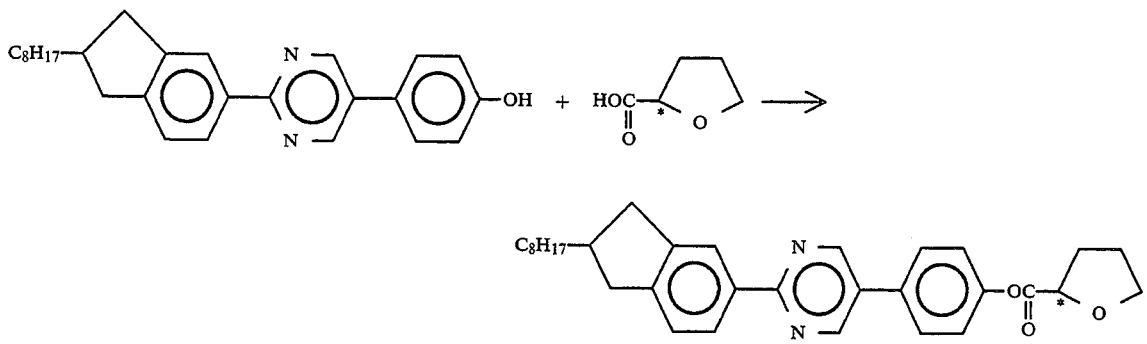

0.30 g (0.75 mM) of 2-octyl-5-[5-(4-hydroxyphenyl)-pyrimidine-2-yl]indan, 0.09 g (0.75 mM) of s-(—)-tetrahydro-2-fluorocarboxylic acid, 0.15 g (0.75 mM) of DCC, 0.01 g of 4-dimethylaminopyridine and 10 ml of methylene chloride were mixed and stirred for 6 hours at room temperature. The resultant N,N'-dichlorhexylurea was recovered by filtration, washed with dichloromethane, and added to the filtrate. The resultant dichloromethane solution was subjected to distillation under reduced pressure. The residue was purified by silica gel column chromatography (eluent: toluene/ethyl acetate=100/1) and recrystallized from a mixture solvent (toluene/ethanol) to obtain 0.21 g of 2-octyl-5-[5-{4-(tetrahydro-2-furancarbonyloxy)phenyl}pyrimidine-2-yl]indan (Yield: 56.7%).

Phase transition temperature (°C.)

Cry. ⇌ 149/111 Ch. ⇌ 159/159 Iso.

EXAMPLE 10

2-octyl-5-[5-(tetrahydro-2-furancarbonyloxy)pyrimidine-2-yl]indan (Ex. Comp. No. I-202) was synthesized through the following reaction steps (1) and (2).

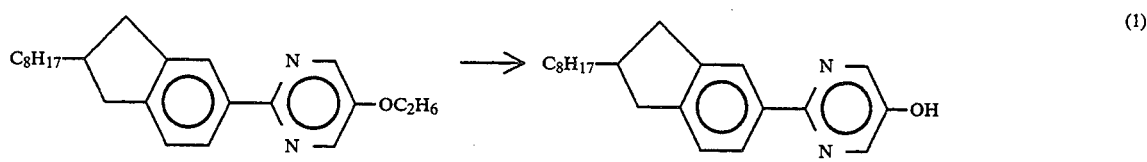

(1)

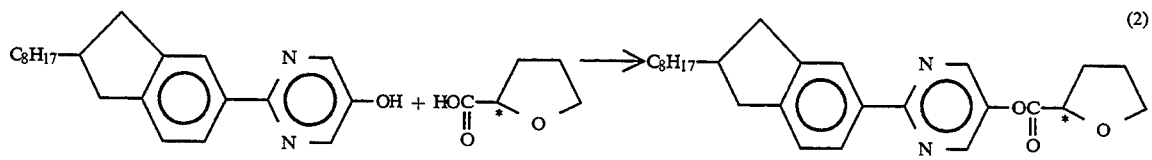

(1) Production of 2-octyl-5-(5-hydroxypyrimidine-2-yl)indan 0.5 g (1.42 mM) of 2-octyl-5-(5-ethoxypyrimidine-2-yl)indan, 1.0 g (25 mM) of NaOH and 10 ml of diethylene glycol were mixed and refluxed for 3 hours under stirring. After the reaction, the reaction mixture was poured into water and acidified with HCl to precipitate a crystal. The crystal was recovered by filtration and washed with water. The resultant crystal was dissolved in toluene and washed with water, followed by drying with anhydrous sodium sulfate and distilling-off of the solvent to obtain a residue. The residue was purified by silica gel column chromatography (eluent: toluene-/ethyl acetate=1/10) to obtain 0.41 g of 2-octyl-5-(5-hydroxypyrimidine-2-yl)indan (Yield: 89.0%).

(2) Production of 2-octyl-5-[5-(tetrahydro-2-furancarbonyloxy)pyrimidine-2-yl]indan 0.2 g (0.60 mM) of 2-octyl-5-(5-hydroxypyrimidine-2-yl)indan, 0.07 g (0.62 mM) of s-(−)-tetrahydro-2-furancarboxylic acid, 0.13 g (0.62 mM) of DCC, 0.01 g of 4-dimethylaminopyridine and 10 ml of methylene chloride were mixed and stirred for 6 hours at room temperature. The resultant N,N'-dichlorhexylurea was recovered by filtration, washed with dichloromethane, and added to the filtrate. The resultant dichloromethane solution was subjected to distillation under reduced pressure. The residue was purified by silica gel column chromatography (eluent: ethyl acetate/methylene chloride=1/10) and recrystallized from a mixture solvent (toluene/ethanol) to obtain 0.15 g of 2-octyl-5-[5-(tetrahydro-2-furancarbonyloxy))pyrimidine-2-yl]indan (Yield: 82.7%).

Phase transition temperature (°C.)

Cry. ⇌(84/69) Iso.

EXAMPLE 11

2-octyl-5-(5-decylpyrimidine-2-yl)indan (Ex. Comp. No. I-248) was synthesized through the following reaction step.

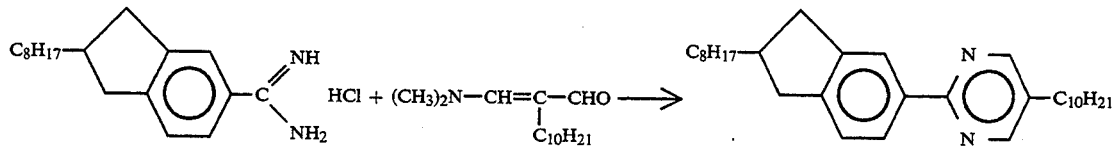

1.00 g (3.24 mM) of 2-octyl-5-amidinoindan hydrochloride, 0.40 g (7.40 mM) of sodium methylate, 0.82 g (3.43 mM) of α-octyloxy-β-dimethylaminoacrolein and 15 ml of methanol were placed in a 30 ml-round bottomed flask, followed by refluxing for 10.5 hours under stirring. After the reaction, the reaction mixture was left standing in a refrigerator for 2 days to precipitate a crystal. The crystal was recovered by filtration and dissolved in toluene, followed by drying with anhydrous sodium sulfate and filtration. The filtrate was evaporated to obtain a residue. The residue was purified by silica gel column chromatography (eluent: toluene-/ethyl acetate=100/1) and recrystallized from a mixture solvent (toluene/methanol) to obtain 0.79 g of 2-octyl-5-(5-decylpyrimidine-2-yl)indan (Yield: 54.4%).

Phase transition temperature (°C.)

Cry. ⇌(42/18) SmA ⇌(64/63) Iso.

EXAMPLE 12

2-octyl-5-[5-(4-octylphenyl)pyrimidine-2-yl)indan (Ex. Comp. No. I-560) was synthesized through the following reaction step.

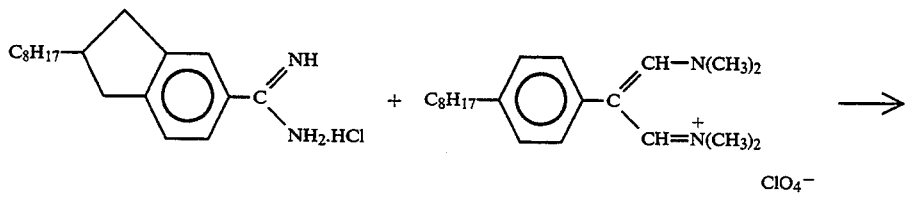

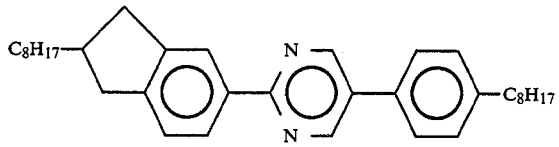

2-octyl-5-[5-(4-octylphenyl)pyrimidine-2-yl)indan was prepared in the same manner as in Example 5 except that 3-dimethylamino-2-(4-octylphenyl)-N,N-dimethylpropene-(2)-ammonium perchlorate was used instead of 3-dimethylamino-2-(4-hydroxyphenyl)-N,N-dimethylpropene-(2)-ammonium perchlorate.

Phase transition temperature (°C.)

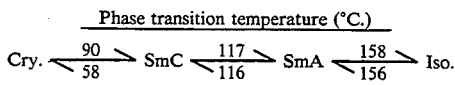

EXAMPLE 13

A liquid crystal composition A was prepared by mixing the following compounds including the compound (Ex. Comp. No. I-726) prepared in Example 5 in the respectively indicated proportions.

| Structure formula | wt. parts |
|---|---|
| $C_6H_{13}$—[pyrimidine]—[phenyl]—$OC_{12}H_{25}$ | 4.0 |
| $C_8H_{17}$—[pyrimidine]—[phenyl]—$OC_9H_{19}$ | 8.0 |
| $C_8H_{17}$—[pyrimidine]—[phenyl]—$OC_{10}H_{21}$ | 8.0 |
| $C_9H_{19}$—[pyrimidine]—[phenyl]—$OC_8H_{17}$ | 4.0 |
| $C_{10}H_{21}O$—[phenyl]—CO—O—[phenyl]—$OCH_2CH(CH_3)C_2H_5$ | 26.0 |
| $C_6H_{13}$—[benzothiazole]—[phenyl]—$OC_8H_{17}$ | 10.0 |
| $C_5H_{11}$—[phenyl]—CH=N-N=CH—[phenyl]—$C_5H_{11}$ (thiadiazole) | 5.0 |
| $C_6H_{13}$—[phenyl]—CH=N-N=CH—[phenyl]—$C_4H_9$ (thiadiazole) | 5.0 |
| $C_{11}H_{23}$—[pyridine]—[phenyl]—O—CO—[thiophene]—$C_4H_9$ | 6.7 |

| Structure formula | wt. parts |
|---|---|
| C₁₁H₂₃—[pyrimidine]—[phenyl(F)]—OC(=O)CH=CH—[thiophene]—C₄H₉ | 3.3 |
| C₁₀H₂₁—[pyrimidine]—[phenyl]—OCH₂C*HFC₆H₁₃ | 10.0 |
| I-726  C₆H₁₃O—[phenyl]—[pyrimidine]—[indane]—C₈H₁₇ | 10.0 |

The liquid crystal composition A showed the following phase transition series.

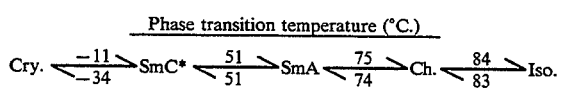

EXAMPLE 14

Two 0.7 mm-thick glass plates were provided and respectively coated with an ITO film to form an electrode for voltage application, which was further coated with an insulating layer of vapor-deposited SiO₂. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyimide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 Å-thick film. The coating film was rubbed with acetate fiber-planted cloth. The thus treated two glass plates were washed with isopropyl alcohol. After alumina beads with an average particle size of 2.0 microns were dispersed on one of the glass plates, the two glass plates were applied to each other with a bonding sealing agent (Lixon Bond, available from Chisso K.K.) so that their rubbed directions were parallel to each other and heated at 100° C. for 60 min. to form a blank cell. The cell gap was found to be about 2 microns as measured by a Berek compensator.

Then, the liquid crystal composition A prepared in Example 13 was heated into an isotropic liquid, and injected into the above prepared cell under vacuum and, after sealing, was gradually cooled at a rate of 20° C./hour to 25° C. to prepare a ferroelectric liquid crystal device.

Each of the ferroelectric liquid crystal devices was subjected to measurement of the magnitude of spontaneous polarization Ps and an optical response time (time from voltage application until the transmittance change reaches 90% of the maximum under the application of a peak-to-peak voltage Vpp of 20 V in combination with right-angle cross-nicol polarizers).

The results are shown below.

|  | 10° C. | 30° C. | 40° C. |
|---|---|---|---|
| Response time (μsec) | 208 | 76 | 51 |
| Ps (nC/cm²) | 10.8 | 7.5 | 5.2 |

EXAMPLE 15

A liquid crystal composition B was prepared by mixing the following compounds in the respectively indicated proportions.

| Structural formula | wt. parts |
|---|---|
| C₇H₁₅—[pyrimidine]—[phenyl]—OC₉H₁₉ | 12 |
| C₁₁H₂₃—[pyrimidine]—[phenyl]—OC₆H₁₃ | 10 |

| Structural formula | wt. parts |
|---|---|
| 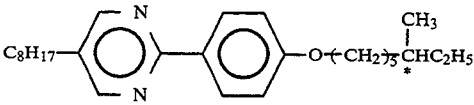 | 10 |
| 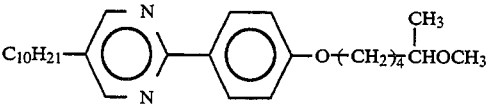 | 3 |
| 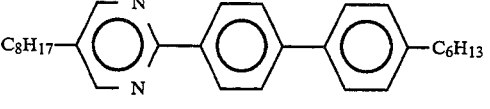 | 8 |
| 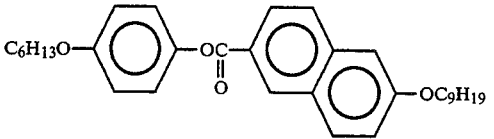 | 4 |
| 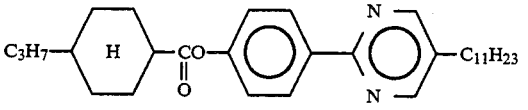 | 6 |
| 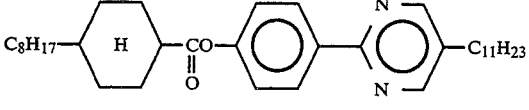 | 2 |
| 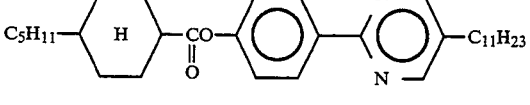 | 8 |
| 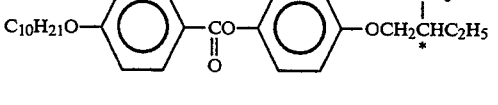 | 15 |
| 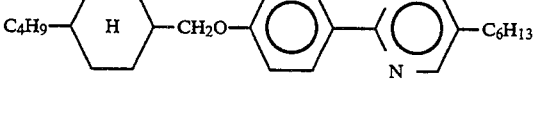 | 7 |
| 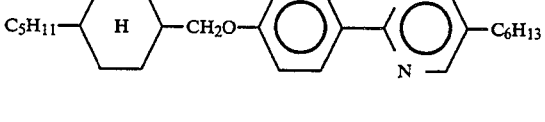 | 7 |
| 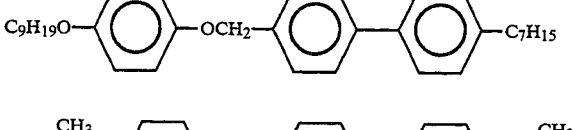 | 4 |
|  | 2 |

-continued

| Structural formula | wt. parts |
|---|---|
| 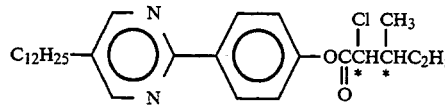 | 2 |

The liquid crystal composition B was further mixed with the following compounds in the proportions indicated below to provide a liquid crystal composition C.

|  | 10° C. | 25° C. | 40° C. |
|---|---|---|---|
| Response time (μsec) | 540 | 269 | 150 |

COMPARATIVE EXAMPLE 1

A ferroelectric liquid crystal device was prepared and subjected to measurement of response time in the same manner as in Example 15 except for injecting the composition B alone into the cell, whereby the following results were obtained.

| Ex. Comp. No. | Structural Formula | wt. parts |
|---|---|---|
| I-1 | 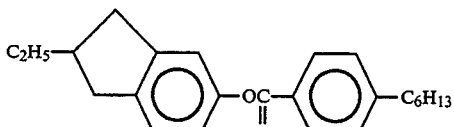 | 3 |
| I-10 | 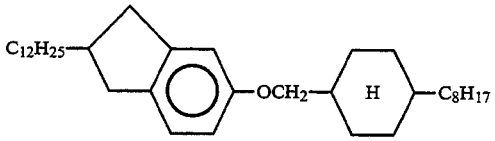 | 2 |
| I-11 | 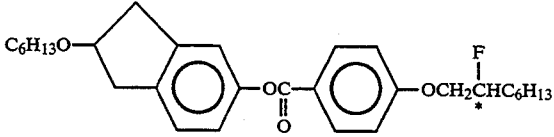 | 2 |
| Composition B | | 93 |

A ferroelectric liquid crystal device was prepared in the same manner as in Example 14 except for using the composition C. The ferroelectric liquid crystal device was subjected to measurement of response time in the same manner as in Example 14, whereby the following results were obtained.

|  | 10° C. | 25° C. | 40° C. |
|---|---|---|---|
| Response time (μsec) | 784 | 373 | 197 |

EXAMPLE 16

A liquid crystal composition D was prepared by mixing the following Example Compounds instead of those of (I-1), (I-10) and (I-11) used in Example 15 in the indicated proportions with the liquid crystal composition B.

| Ex. Comp. No. | Structural formula | wt. parts |
|---|---|---|
| I-17 | 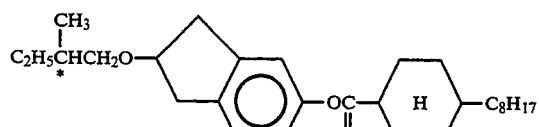 | 3 |

-continued

| Ex. Comp. No. | Structural formula | wt. parts |
|---|---|---|
| I-21 | C₁₆H₃₃-indane-CH₂O-pyridine-C₁₂H₂₅ | 3 |
| I-30 | C₆H₁₃-indane-CO-O-phenyl-phenyl-OCH₃ | 2 |
| Composition B | | 92 |

A ferroelectric liquid crystal device was prepared in the same manner as in Example 14 except that the above indicated proportions with the liquid crystal composition B.

| Ex. Comp. No. | Structural formula | wt. parts |
|---|---|---|
| I-40 | $C_8H_{17}O$-indane-OC(O)-phenyl-cyclohexyl(H)-$C_8H_{17}$ | 1 |
| I-100 | $C_6H_{13}O$-indane-pyrimidine-$C_5H_{11}$ | 3 |
| I-111 | $C_6H_{13}$-indane-thiadiazole-$C_{10}H_{21}$ | 3 |
| Composition B | | 93 | liquid crystal composition D was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 633 | 308 | 172 |

EXAMPLE 17

A liquid crystal composition E was prepared by mixing the following Example Compounds instead of those of (I-1), (I-10) and (I-11) used in Example 15 in the A ferroelectric liquid crystal device was prepared in the same manner as in Example 14 except that the above liquid crystal composition E was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 497 | 250 | 142 |

EXAMPLE 18

A liquid crystal composition F was prepared by mixing the following compounds in the indicated proportions.

| Structural formula | wt. parts |
|---|---|
| 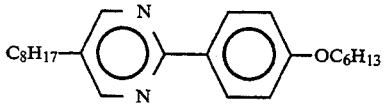 | 10 |
| 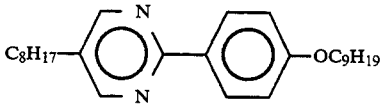 | 5 |
| 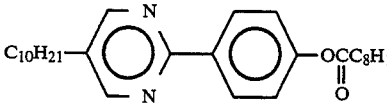 | 7 |
| 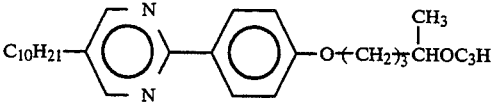 | 7 |
| 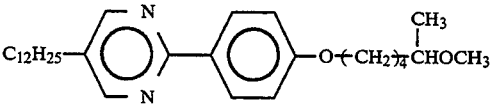 | 6 |
|  | 5 |
|  | 5 |
|  | 8 |
| 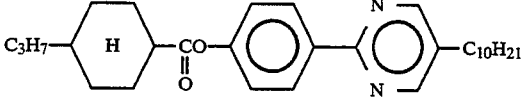 | 8 |
| 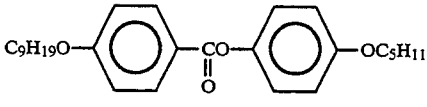 | 20 |
| 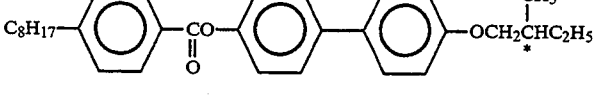 | 5 |
| 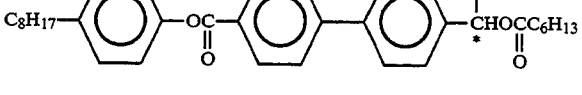 | 5 |
|  | 6 |

-continued

| Structural formula | wt. parts |
|---|---|
| C$_{12}$H$_{25}$—[pyrimidine]—[phenyl]—OCH$_2$CHC$_6$H$_{13}$ with F on chiral carbon | 3 |

The liquid crystal composition F was further mixed with the following compounds in the proportions indicated below to provide a liquid crystal composition G.

| Ex. Comp. No. | Structural Formula | wt. parts |
|---|---|---|
| I-54 | C$_8$H$_{17}$—[indane]—CO—O—[phenyl]—[thiadiazole]—C$_6$H$_{13}$ | 1 |
| I-230 | C$_6$H$_{13}$—[indane]—[pyrimidine]—C$_8$H$_{17}$ | 3 |
| I-117 | C$_{10}$H$_{21}$O—[indane]—[thiadiazole]—CH$_2$CHC$_4$H$_9$ with CF$_3$ on chiral carbon | 3 |
| Composition F | | 93 |

A ferroelectric liquid crystal device was prepared in the same manner as in Example 14 except that the above liquid crystal composition G was used, and the device was subjected to measurement of optical response time and observation of switching states. In the device, a monodomain with a good and uniform alignment characteristic was observed. The results of the measurement are shown below.

| | 10° C. | 25° C. | 40° C. |
|---|---|---|---|
| Response time (μsec) | 414 | 212 | 115 |

Further, when the device was driven, a clear switching action was observed, and good bistability was shown after the termination of the voltage application.

COMPARATIVE EXAMPLE 2

A ferroelectric liquid crystal device was prepared and subjected to measurement of response time in the same manner as in Example 18 except for injecting the composition F alone into the cell, whereby the following results were obtained.

| | 10° C. | 25° C. | 40° C. |
|---|---|---|---|
| Response time (μsec) | 653 | 317 | 159 |

EXAMPLE 19

A liquid crystal composition H was prepared by mixing the following Example Compounds instead of those of (I-54), (I-230) and (I-117) used in Example 18 in the indicated proportions with the liquid crystal composition F.

| Ex. Comp. No. | Structural formula | wt. parts |
|---|---|---|
| I-66 | C$_4$H$_9$—[indane]—CO—O—[phenyl]—[thiophene]—C$_{10}$H$_{21}$ | 2 |

| Ex. Comp. No. | Structural formula | wt. parts |
|---|---|---|
| I-93 | $C_6H_{13}$—indane—pyridine—$C_5H_{11}$ | 3 |
| I-143 | $C_{12}H_{25}$—indane—pyrimidine—phenyl—$C_{16}H_{33}$ | 2 |
| Composition F | | 93 |

A ferroelectric liquid crystal device was prepared in the same manner as in Example 14 except that the above indicated proportions with the liquid crystal composition G.

| Ex. Comp. No. | Structural formula | wt. parts |
|---|---|---|
| I-74 | $C_2H_5CH(CH_3)CH_2$—indane—CO-O—pyridine—thiazole—$C_{10}H_{21}$ | 2 |
| I-96 | $C_8H_{17}CH(F)CH_2O$*—indane—pyridine—$C_{10}H_{21}$ | 3 |
| I-153 | $C_{10}H_{21}$—indane—phenyl—pyrimidine—$OC_6H_{13}$ | 2 |
| Composition G | | 93 | liquid crystal composition H was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 511 | 253 | 135 |

EXAMPLE 20

A liquid crystal composition I was prepared by mixing the following Example Compounds instead of those of (I-54), (I-230) and (I-117) used in Example 18 in the A ferroelectric liquid crystal device was prepared in the same manner as in Example 14 except for using the composition I was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 474 | 239 | 128 |

EXAMPLE 21

A liquid crystal composition J was prepared by mixing the following compounds in the indicated proportions.

| Structural formula | wt. parts |
|---|---|
| 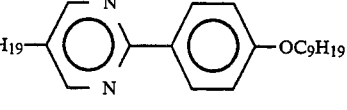 | 6 |
| 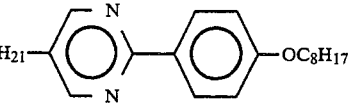 | 6 |
| 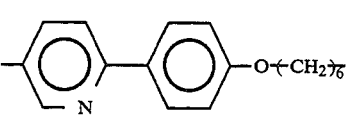 | 7 |
| 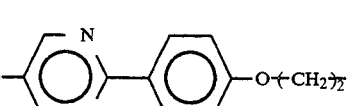 | 14 |
| 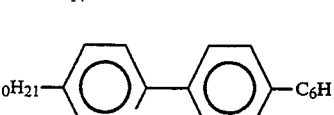 | 8 |
| 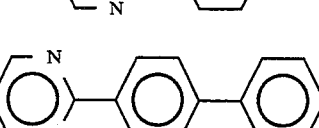 | 4 |
|  | 2 |
| 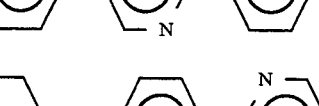 | 10 |
| 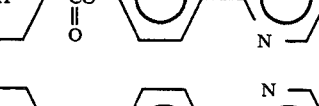 | 5 |
| 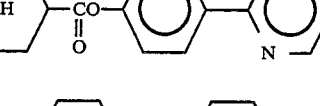 | 10 |
| 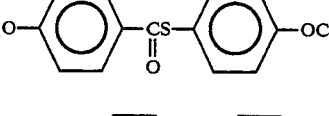 | 7 |
| 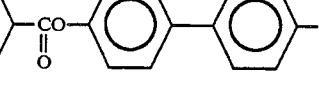 | 7 |
| 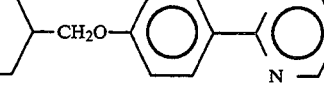 | 5 |

| Structural formula | wt. parts |
|---|---|
| 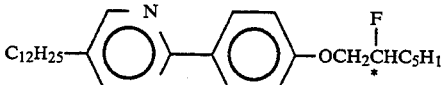 | 2 |
| 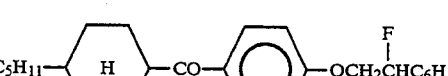 | 2 |
| 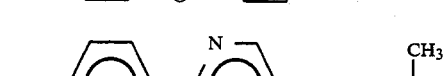 | 2 |
| 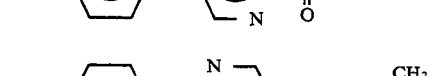 | 3 |

The liquid crystal composition J was further mixed with the following compounds in the proportions indicated below to provide a liquid crystal composition K.

A ferroelectric liquid crystal device was prepared in the same manner as in Example 14 except that the above liquid crystal composition K was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 527 | 274 | 155 |

COMPARATIVE EXAMPLE 3

A ferroelectric liquid crystal device was prepared and subjected to measurement of response time in the same manner as in Example 21 except for injecting the composition J alone into the cell, whereby the following results were obtained.

| Ex. Comp. No. | Structural formula | wt. parts |
|---|---|---|
| I-147 | | 3 |
| I-182 | | 2 |
| I-202 | | 1 |
| Composition J | | 94 |

|  | 10° C. | 25° C. | 40° C. |
|---|---|---|---|
| Response time (μsec) | 668 | 340 | 182 |

EXAMPLE 22

A liquid crystal composition L was prepared by mixing the following Example Compounds instead of those of (I-147), (I-182) and (I-202) used in Example 21 in the indicated proportions with the liquid crystal composition J.

| Ex. Comp. No. | Structural formula | wt. parts |
|---|---|---|
| I-29 | 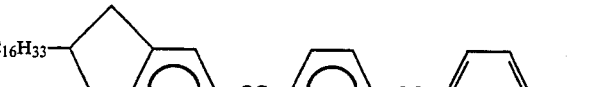 | 1 |
| I-102 |  | 3 |
| I-158 |  | 2 |
| Composition J |  | 94 |

A ferroelectric liquid crystal device was prepared in the same manner as in Example 14 except that the above liquid crystal composition L was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 501 | 262 | 143 |

EXAMPLE 23

A liquid crystal composition M was prepared by mixing the following Example Compounds instead of those of (I-147), (I-182) and (I-202) used in Example 21 in the indicated proportions with the liquid crystal composition J.

| Ex. Comp. No. | Structural formula | wt. parts |
|---|---|---|
| I-85 | 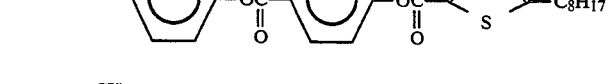 | 1 |
| I-125 |  | 3 |
| I-162 |  | 2 |
| Composition J |  | 94 |

A ferroelectric liquid crystal device was prepared in the same manner as in Example 14 except that the above liquid crystal composition M was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 555 | 282 | 160 |

As apparent from the above Examples 15 to 23, the ferroelectric liquid crystal device containing the liquid crystal compositions C, D, E, G, H, I, K, L and M according to the present invention provided improved operation characteristic at a lower temperature, high speed responsiveness and a decreased temperature dependence of response speed.

EXAMPLE 24

A blank cell was prepared in the same manner as in Example 14 by using a 2% aqueous solution of polyvinyl alcohol resin (PVA-117, available from Kuraray K.K.) instead of the 1.5%-solution of polyimide resin precursor in dimethylacetoamide on each electrode plate. A ferroelectric liquid crystal device was prepared by filling the blank cell with the liquid crystal composition C prepared in Example 15. The liquid crystal device was subjected to measurement response time in the same manner as in Example 14. The results are shown below.

|  | 10° C. | 25° C. | 40° C. |
|---|---|---|---|
| Response time (μsec) | 542 | 268 | 149 |

EXAMPLE 25

A blank cell was prepared in the same manner as in Example 14 except for omitting the $SiO_2$ layer to form an alignment control layer composed of the polyimide resin layer alone on each electrode plate. A ferroelectric liquid crystal devices were prepared by filling such a blank cell with liquid crystal composition C prepared in Example 15. The liquid crystal device was subjected to measurement of response time in the same manner as in Example 14. The results are shown below.

|  | 10° C. | 25° C. | 40° C. |
|---|---|---|---|
| Response time (μsec) | 538 | 268 | 149 |

As is apparent from the above Examples 24 and 25, also in the case of a different device structure, the device containing the ferroelectric liquid crystal composition C according to the present invention provided an improved low-temperature operation characteristic and a decreased temperature dependence of response speed similarly as in Example 15.

EXAMPLES 26–40

Mesomorphic compounds of Examples 26 to 40 were prepared in the same manner as in Example 11.

The mesomorphic compounds were represented by the following formulas and showed the following phase transition series.

| Ex. No. | Structural formula | Ex. Comp. No. | Phase transition temperature (°C.) |
|---|---|---|---|
| 26 | $C_6H_{13}$—[indane]—[phenyl]—[pyrimidine N,N]—$C_9H_{19}$ | (I-231) | Cryst $\underset{15}{\overset{52}{\rightleftarrows}}$ SmA $\underset{57}{\overset{58}{\rightleftarrows}}$ Iso |
| 27 | $C_6H_{13}$—[indane]—[phenyl]—[pyrimidine N,N]—$C_{10}H_{21}$ | (I-232) | Cryst $\overset{50}{\rightarrow}$ SmA $\underset{58}{\overset{60}{\rightleftarrows}}$ Iso, 13 ↘ SmC ↗ 26 |
| 28 | $C_6H_{13}$—[indane]—[phenyl]—[pyrimidine N,N]—$C_{12}H_{25}$ | (I-233) | Cryst $\underset{18}{\overset{41}{\rightleftarrows}}$ Sm3 $\underset{44}{\overset{48}{\rightleftarrows}}$ SmA $\underset{51}{\overset{56}{\rightleftarrows}}$ Iso |
| 29 | $C_8H_{17}$—[indane]—[phenyl]—[pyrimidine N,N]—$C_6H_{13}$ | (I-244) | Cryst $\overset{47}{\rightarrow}$ Iso, 31 ↘ N ↗ 43 |

| Ex. No. | Structural formula | Ex. Comp. No. | Phase transition temperature (°C.) |
|---|---|---|---|
| 30 | C8H17–[indane]–[pyrimidine]–C8H17 | (I-246) | Cryst $\xrightleftharpoons[23]{39}$ SmA $\xrightleftharpoons[50]{51}$ N $\xrightleftharpoons[53]{54}$ Iso |
| 31 | C8H17–[indane]–[pyrimidine]–C9H19 | (I-247) | Cryst $\xrightleftharpoons[26]{48}$ SmA $\xrightleftharpoons[59]{61}$ Iso |
| 32 | C8H17–[indane]–[pyrimidine]–C11H23 | (I-248) | Cryst $\xrightleftharpoons[21]{52}$ SmA $\xrightleftharpoons[67]{69}$ Iso |
| 33 | C8H17–[indane]–[pyrimidine]–C12H25 | (I-250) | Cryst $\xrightarrow{47}$ SmA $\xrightleftharpoons[65]{66}$ Iso; SmC $\xrightarrow{43}$ SmA; Cryst $\xleftarrow{29}$ SmC |
| 34 | C8H17–[indane]–[pyrimidine]–C13H27 | (I-833) | Cryst $\xrightarrow{55}$ SmA $\xrightleftharpoons[66]{68}$ Iso; SmC $\xrightarrow{51}$ SmA; Cryst $\xleftarrow{24}$ SmC |
| 35 | C8H17–[indane]–[pyrimidine]–C16H33 | (I-834) | Cryst $\xrightarrow{63}$ SmA $\xrightleftharpoons[69]{71}$ Iso; SmC $\xrightarrow{56}$ SmA; Cryst $\xleftarrow{30}$ SmC |
| 36 | C10H21–[indane]–[pyrimidine]–C8H17 | (I-262) | Cryst $\xrightarrow{51}$ Iso; Iso $\xrightarrow{48}$ N $\xrightarrow{40}$ Cryst |
| 37 | C10H21–[indane]–[pyrimidine]–C9H19 | (I-263) | Cryst $\xrightleftharpoons[37]{50}$ SmA $\xrightleftharpoons[61]{62}$ Iso |
| 38 | C10H21–[indane]–[pyrimidine]–C10H21 | (I-264) | Cryst $\xrightleftharpoons[30]{47}$ SmA $\xrightleftharpoons[63]{65}$ Iso |

-continued

| Ex. No. | Structural formula | Ex. Comp. No. | Phase transition temperature (°C.) |
|---|---|---|---|
| 39 | C₁₀H₂₁–[indane]–[pyrazine]–C₁₁H₂₃ | (I-265) | Cryst $\underset{29}{\overset{45}{\rightleftarrows}}$ SmA $\underset{68}{\overset{70}{\rightleftarrows}}$ Iso |
| 40 | C₁₀H₂₁–[indane]–[pyrazine]–C₁₂H₂₅ | (I-266) | Cryst $\underset{37}{\overset{50}{\rightleftarrows}}$ SmA $\underset{64}{\overset{65}{\rightleftarrows}}$ Iso |

EXAMPLES 41 AND 42

Mesomorphic compounds of Examples 41 and 42 were prepared in the same manner as in Example 2.

EXAMPLES 43 AND 44

Mesomorphic compounds of Examples 43 and 44 were prepared in the same manner as in Example 12.

| Ex. No. | Structural formula | Ex. Comp. No. | Phase transition temperature (°C.) |
|---|---|---|---|
| 41 | C₁₀H₂₁–[indane]–[pyrazine]–OC₈H₁₇ | (I-416) | Cryst $\underset{21}{\overset{51}{\rightleftarrows}}$ SmA $\underset{79}{\overset{80}{\rightleftarrows}}$ Iso |
| 42 | C₁₀H₂₁–[indane]–[pyrazine]–OC₁₀H₂₁ | (I-418) | Cryst $\underset{27}{\overset{50}{\rightleftarrows}}$ Sm3 $\underset{62}{\overset{63}{\rightleftarrows}}$ SmA $\underset{85}{\overset{86}{\rightleftarrows}}$ Iso |

| Ex. No. | Structural formula | Ex. Comp. No. | Phase transition temperature (°C.) |
|---|---|---|---|
| 43 | C₆H₁₃–[indane]–[pyrazine]–[phenyl]–C₈H₁₇ | (I-536) | Cryst $\underset{74}{\overset{93}{\rightleftarrows}}$ SmC $\underset{115}{\overset{116}{\rightleftarrows}}$ SmA $\underset{158}{\overset{159}{\rightleftarrows}}$ Iso |
| 44 | C₁₀H₂₁–[indane]–[pyrazine]–[phenyl]–C₈H₁₇ | (I-584) | Cryst $\underset{50}{\overset{88}{\rightleftarrows}}$ SmA $\underset{152}{\overset{154}{\rightleftarrows}}$ Iso |

EXAMPLE 45

2-octyl-5-[4-(5-decyloxypyrimidine-2-yl)phenyl]indan (Ex. Comp. No. I-910) was synthesized through the following reaction steps (1) and (2).

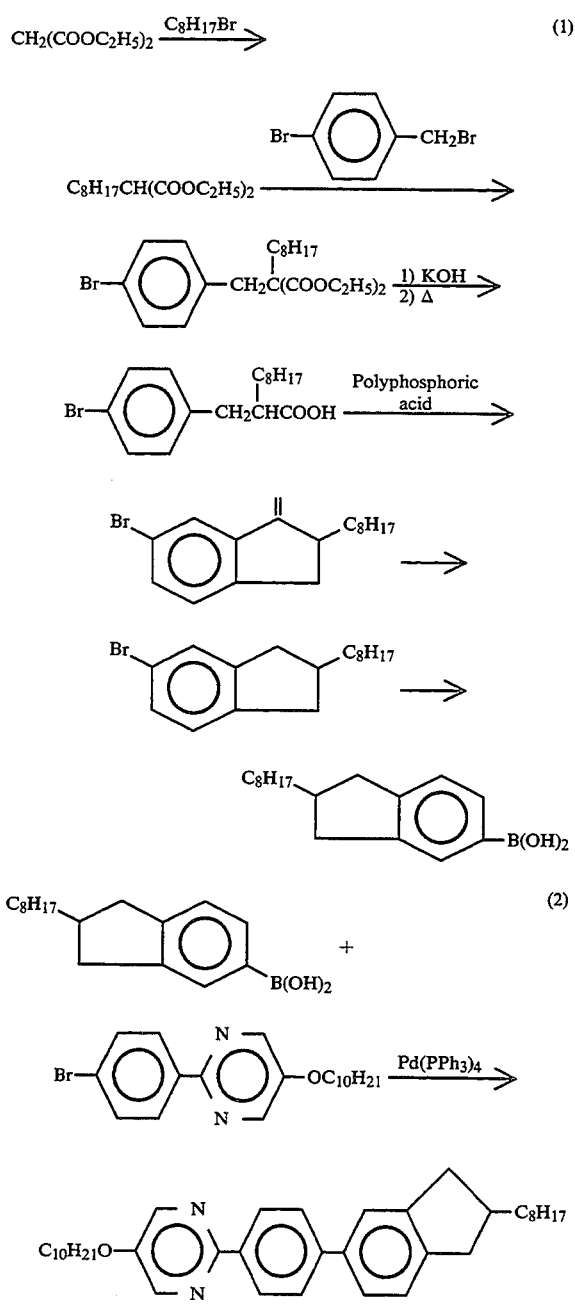

(1) Production of 2-octylindan-5-boronic acid (2-octyl-indan-5-yl(dihydroxyborate))

In a 10 liter-reaction vessel, 3.1 liters of anhydrous (or absolute) ethanol was placed and then 143 g (6.2M) which had been cut small was dissolved therein. To the solution, 1025 g (6.4M) of diethyl malonate was added dropwise in 30 minutes at 40°-50° C. and further 1200 g (6.2M) of n-octyl bromide was added dropwise in 10 minutes at 40°-50° C., followed by heat-refluxing for 23 hours. After the reaction, about 2.5 liters of ethanol was distilled off from the reaction mixture and 2.5 liters of water was added to the residue, followed by extraction with ether. After the ether layer was washed with saturated common salt aqueous solution until the ether layer showed neutrality, the resultant ether layer was dried with anhydrous sodium sulfate. After distilling-off of the solvent, 1672 g of a crude product was obtained, followed by vacuum distillation to obtain 1333 g of n-2-octyldiethylmalonate (Yield: 78.8%, b.p.=146° C./4 mmHg).

In a 10 liter-reaction vessel, 2.3 liters of anhydrous (or absolute) ethanol was placed and then 95.6 g (4.2M) which had been cut small was dissolved therein. To the solution, 130 g (4.2M) of n-2-octyldiethylmalonate was added dropwise in 30 minutes at 40°-50° C. and further 933 g (3.73M) of p-bromobenzyl bromide was added dropwise in 10 minutes at 40°-50° C., followed by heat-refluxing for 22 hours. After the reaction, about 1.5 liters of ethanol was distilled off from the reaction mixture and 1.5 liters of water was added to the residue, followed by extraction with ether. After the ether layer was washed with saturated common salt aqueous solution until the ether layer showed neutrality, the resultant ether layer was dried with anhydrous sodium sulfate, followed by distilling-off of the solvent to obtain 1652 g of 2-(p-bromobenzyl)-2-n-octyldiethylmalonate (purity (by gas chromatography)=91%).

Then, 1650 g of 2-(p-bromobenzyl)-2-n-octyl diethylmalonate and 3.8 liters of methanol were placed in a 10 liter-reaction vessel. To the mixture, 1792 g of 50%-KOH aqueous solution was added dropwise in 20 minutes under stirring, followed by heat-refluxing for 9 hours. After the reaction, the reaction mixture was cooled and 30%-$H_2SO_4$ aqueous solution was added dropwise thereto so as to acidify the reaction mixture. After cooling to room temperature, the above reaction mixture was subjected to extraction with ether and the ether layer was washed three times with saturated common salt aqueous solution, followed by drying with anhydrous sodium sulfate. After distilling-off of the ether, the residue was placed in a 3 liter-reaction vessel, followed by stirring for 8 hours at 160° C. to obtain 1199 g of 2-(p-bromobenzyl)decanoic acid.

In a 5 liter-reaction vessel, 690 g of 2-(p-bromobenzyl)decanoic acid and 2200 g of polyphosphoric acid were placed, followed by stirring for 24 hours at 140° C. After the reaction, the reaction mixture was poured into 2.5 liters of ice water to be decomposed, followed by extraction with benzene. The benzene layer was washed sucessively with saturated common salt aqueous solution, 2%-NaOH aqueous solution and saturated common salt aqueous solution. The resultant benzene layer was dried with anhydrous sodium sulfate, followed by distilling-off of the solvent and purification by silica gel column chromatography (eluent: n-hexane/-chloroform=10/1) to obtain 190 g of 6-bromo-2-n-octyl-1-indanone.

Subsequently, 45.9 g (0.14M) of 6-bromo-2-n-octyl-1-indanone and 162.4 g (1.42M) of trifluoroacetic acid were placed in a 500 ml-reaction vessel. To the mixture, 41.4 g (3.57×10⁻¹M) of triethylsilane was added dropwise in 15 minutes at room temperature. After the addition, the resultant mixture was heat-refluxed for 3.5 hours. After the reaction, the reaction mixture was poured into ice water and subjected to extraction with toluene, followed by successive washing with water and NaHCO₃ aqueous solution, drying with anhydrous magnesium sulfate and distilling-off of the solvent. The resultant residue was subjected to vacuum distillation to obtain 40.3 g of 5-bromo-2-n-octylindan (Yield: 93.1%).

In a 200 ml-reaction vessel, 3.16 g (1.02×10⁻²M) of 5-bromo-2-n-octylindan and 45 ml of dry THF were placed. To the mixture, 1.5M-solution of n-butyllithium in 7.2 ml of hexane was added dropwise in 20 minutes at −70° C. under argon atmosphere, followed by stirring for 2 hours at −70° C. To the above mixture, a solution of 4.14 g (2.20×10⁻²M) of triisopropylborate in 9 ml of dry THF was added dropwise in 20 minutes below −70° C., followed by stirring for 1 hour at the same temperature, gradual restoration to room temperature and further stirring for 20 hours. After the reaction, 15 ml of 10%-HCl aqueous solution was added dropwise to the reaction mixture to be decomposed under cooling, followed by extraction with ether. The ether layer was washed with water and dried with anhydrous sodium sulfate, followed by distilling-off of the solvent and purification by silica gel column chromatography to obtain 1.96 g of 2-octylindan-5-boronic acid (Yield: 70%).

(2) Production of 2-octyl-5-[4-(5-decyloxypyrimidine-2-yl)phenyl]indan 0.30 g (1.09 mM) of 2-octylindan-5-boronic acid, 0.37 g (0.95 mM) of 5-decyloxy-2-(4-bromophenyl)pyrimidine, 1.8 ml of ethanol, 2.5 ml of benzene, 1.5 ml of 2M-sodium carbonate aqueous solution and 0.05 g of tetrakis (triphenylphosphine) palladium (O) were mixed and heat-refluxed for 4 hours under stirring. After the reaction, the reaction mixture was poured into ice water to precipitate a crystal. The crystal was recovered by filtration under reduced pressure and dissolved in toluene, followed by drying with anhydrous sodium sulfate. Then, the sodium sulfate was removed from the mixture and the resultant mixture was evaporated to obtain a residue. The residue was purified by silica gel column chromatography (eluent: toluene/ethyl acetate=100/1) and recrystallized two times from a mixture solvent (toluene/acetone) to obtain 0.42 g of 2-octyl-5-[4-(5-decyloxypyrimidine-2-yl)phenyl]indan (Yield: 82.1%).

Phase transition temperature (°C.)

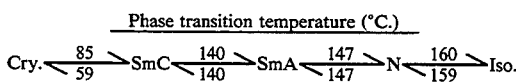

EXAMPLES 46–52

Mesomorphic compounds of Examples 46–52 were prepared in the same manner as in Example 45. The mesomorphic compounds were represented by the following formulas and showed the following phase transition series.

| Ex. No. | Structural formula | Ex. Comp. No. | Phase transition temperature (°C.) |
|---|---|---|---|
| 47 | C₈H₁₇–[indan]–[phenyl]–[pyrimidine]–C₁₀H₂₁ | (I-908) | Cry. ⇌(56/38) SmC ⇌(121/119) SmA ⇌(129/128) N ⇌(139/138) Iso. |
| 48 | C₈H₁₇–[indan]–[phenyl]–[pyrimidine]–C₆H₁₃ | (I-871) | Cry. ⇌(74/46) SmC ⇌(139/138) Iso. |
| 49 | C₆H₁₃–[indan]–[phenyl]–[pyrimidine]–C₆H₁₃ | (I-869) | Cry. ⇌(87/64) N ⇌(143/142) Iso. |
| 50 | C₆H₁₃–[indan]–[phenyl]–[pyrimidine]–C₈H₇ | (I-890) | Cry. ⇌(69/36) SmC ⇌(95/94) N ⇌(144/143) Iso. |
| 51 | C₆H₁₃–[indan]–[phenyl]–[pyrimidine]–C₁₀H₂₁ | (I-907) | Cry. ⇌(60/45) SmC ⇌(117/115) SmA ⇌(123/122) N ⇌(140/139) Iso. |

-continued

| Ex. No. | Structural formula | Ex. Comp. No. | Phase transition temperature (°C.) |
|---|---|---|---|
| 52 |  | (I-921) | Cry. $\underset{50}{\overset{66}{\rightleftarrows}}$ SmC $\underset{125}{\overset{127}{\rightleftarrows}}$ SmA $\underset{133}{\overset{133}{\rightleftarrows}}$ N $\underset{139}{\overset{139}{\rightleftarrows}}$ Iso. |

EXAMPLES 53 AND 54

Mesomorphic compounds of Examples 53 and 54 were prepared in the same manner as in Example 2.

1.0 g (3.01 mM) of 2-octyl-5-(5-hydroxypyrimidine-2-yl)indan, 0.24 g (3.6 mM) of 85%-KOH, 0.91 g (3.01 mM) of 2-fluorooctyl p-toluenesulfonate and 20 ml of butanol was placed in a 50 ml-round bottomed flask and heat-refluxed for 7 hours under stirring. After the reaction, the reaction mixture was poured into ice water and the insoluble matter was recovered by filtration, followed by washing with methanol. The resultant insoluble matter was purified by silica gel column chromatography (eluent: toluene) and recrystallized from a mixture solvent (toluene/methanol) to obtain 0.87 g of 2-octyl-5-[5-(2-fluorooctyloxy)pyrimidine-2-yl]indan (Yield: 66.4%).

| Ex. No. | Structural formula | Ex. Comp. No. | Phase transition temperature (°C.) |
|---|---|---|---|
| 53 | $C_{10}H_{21}$—[indan]—[pyrimidine]—$OC_6H_{13}$ | (I-414) | Cry. $\underset{44}{\overset{58}{\rightleftarrows}}$ SmA $\underset{62}{\overset{62}{\rightleftarrows}}$ N $\underset{72}{\overset{73}{\rightleftarrows}}$ Iso. |
| 54 | $C_{12}H_{25}$—[indan]—[pyrimidine]—$C_{10}H_{21}$ | (I-280) | Cry. $\underset{44}{\overset{58}{\rightleftarrows}}$ SmA $\underset{62}{\overset{64}{\rightleftarrows}}$ Iso. |

EXAMPLE 55

2-octyl-5-[5-(2-fluorooctyloxy)pyrimidine-2-yl]indan (Ex. Comp. No. I-1411) was synthesized through the following reaction step.

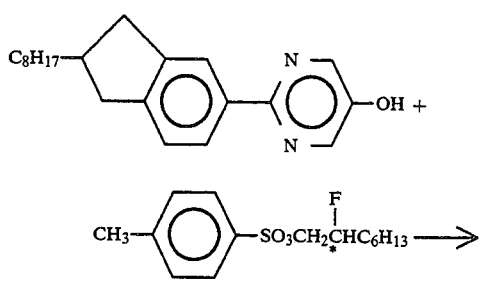

Phase transition temperature (°C.)

Cry. $\underset{23}{\overset{59}{\rightleftarrows}}$ SmA $\underset{73}{\overset{75}{\rightleftarrows}}$ Iso.

EXAMPLE 56

2-decyl-5-[5-(4-fluorobenzoyloxy)pyrimidine-2-yl]indan (Ex. Comp. No. I-197) was synthesized through the following step.

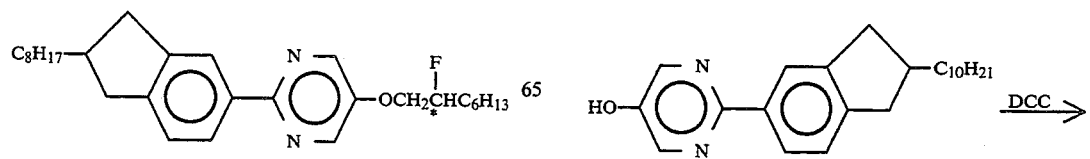

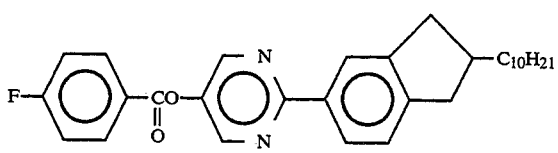

0.70 g (3.0 mM) of 2-octyl-5-(5-hydroxypyrimidine-2-yl)indan, 0.42 g (3.0 mM) of 4-fluorobenzoic acid, 0.62 g (3.0 mM) of DCC, 0.02 g of 4-dimethylaminopyridine and 20 ml of methylene chloride were mixed and stirred for 7 hours at room temperature to precipitate N,N'-dicyclohexaurea. The N,N'-dicyclohexylurea was recovered by filtration and washed with dichloromethane to be added to the filtrate. The resultant dichloromethane solution was evaporated into a residue under reduced pressure. The residue was purified by silica gel column chromatography (eluent: toluene) and recrystallized from a mixture solvent (toluene/methanol) to obtain 0.70 g of 2-decyl-5-[5-(4-fluorobenzoyloxy)-pyrimidine-2-yl]indan (Yield: 66.0%).

Phase transition temperature (°C.)

Cry. ⇌(111/80) SmA ⇌(146/145) N ⇌(150/150) Iso.

EXAMPLE 57

2-octyl-5-[4-(2-octylpyrimidine-5-yl)phenyl]indan (Ex. Comp. No. I-149) was synthesized through the following reaction steps (1) and (2).

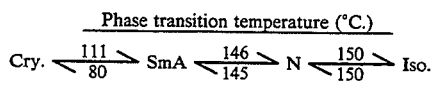

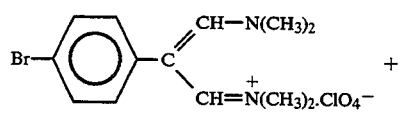

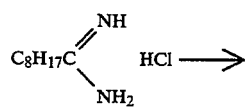

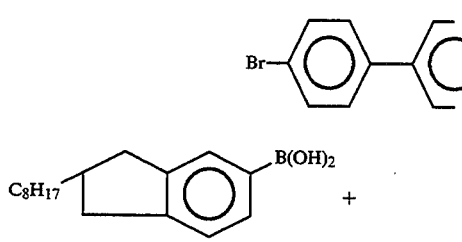

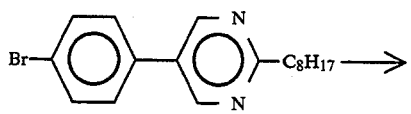

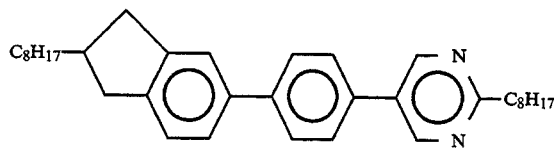

(1) Production of 2-octyl-5-(4-bromophenyl)pyrimidine
1.00 g (5.19 mM) of amidinooctane hydrochloride, 1.15 g (21.3 mM) of sodium methylate, 1.98 g (5.19 mM) of 3-dimethylamino-2-(4-bromophenyl)-N,N-dimethyl-propene-(2)-ammonium perchlorate and 50 ml of ethanol were mixed and heat-refluxed for 8.5 hours under stirring. After the reaction, an appropriate amount of water was poured into the reaction mixture and the resultant insoluble matter was recovered by filtration, followed by washing with water and drying to obtain 1.25 g of 2-octyl-5-(4-bromophenyl)pyrimidine.

(2) Production of 2-octyl-5-[4-(2-octylpyrimidine-5-yl)phenyl]indan 0.41 g (1.50 mM) of 2-octylindan-5-boronic acid, 0.45 g (1.30 mM) of 2-octyl-5-(4-bromophenyl)pyrimidine, 2.2 ml of ethanol, 4.2 ml of benzene, 2.1 ml of 2M-sodium carbonate aqueous solution and 0.07 g of tetrakis (triphenylphosphine) palladium (O) were mixed and heat-refluxed for 200 minutes under stirring. After the reaction, the reaction mixture was poured into ice water and subjected to extraction with ethyl acetate, followed by washing with saturated common salt aqueous solution. The organic layer was dried with anhydrous sodium sulfate. Then, the sodium sulfate was removed from the organic layer and the resultant organic layer was evaporated to obtain a residue. The residue was purified by silica gel column chromatography (eluent: toluene/ethyl acetate=100/1) and recrystallized from a mixture solvent (toluene/acetone) and ethyl acetate to obtain 0.46 g of 2-octyl-5-[4-(2-octylpyrimidine-5-yl)phenyl]indan (Yield: 71.5%).

Phase transition temperature (°C.)

Cry. ⇌(87/81) Sm3 ⇌(96/94) SmA ⇌(169/167) Iso.

EXAMPLE 58

2-hexyl-5-(5-decanoylpyridine-2-yl)indan (Ex. Comp. No. I-1076) was synthesized through the following reaction steps (1) and (2).

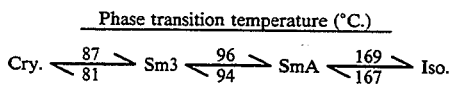

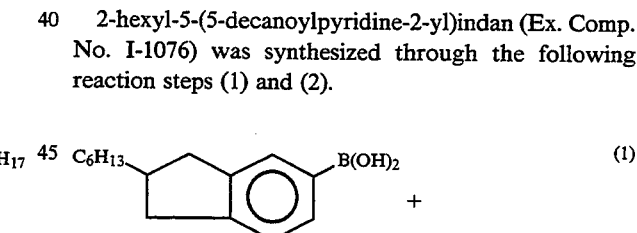

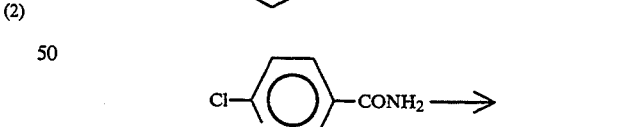

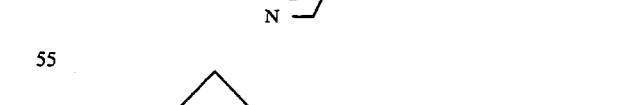

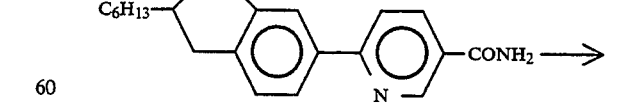

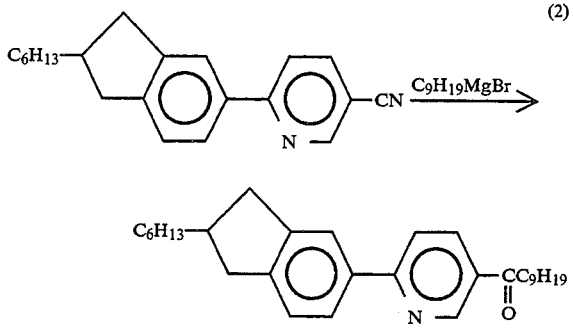

(1) Production of 2-hexyl-5-(5-cyanopyridine-2-yl)indan 5.00 g (20.3 mM) of 2-hexylindan-5-boronic acid, 2.79 g (17.8 mM) of 6-chloronicotinamide, 20 ml of ethanol, 30 ml of benzene, 27.9 ml of 2M-sodium carbonate aqueous solution and 1.19 g of tetrakis (triphenylphosphine) palladium (O) were mixed and heat-refluxed for 2 hours under stirring. After the reaction, the reaction mixture was poured into water to obtain an insoluble matter. The insoluble matter was recovered by filtration. Separately, the filtrate was subjected to vacuum distillation to remove the organic solvent and poured into water to obtain an insoluble matter. The insoluble matter was added to the above-prepared insoluble matter. To the resultant mixture, 100 ml of acetone was added, followed by cooling with ice to precipitate a crystal. The crystal was recovered by filtration and washed with acetone, followed by drying to obtain 5.30 g of 2-hexyl-5-(5-carbamoylpyridine-2-yl)indan (Yield: 92.2%).

Then, 2.00 g (6.20 mM) of 2-hexyl-5-(5-carbamoylpyridine-2-yl)indan was dissolved in 20 ml of dry THF. To the solution, a solution of 4.89 g (18.6 mM) of triphenylphosphine in 15 ml of carbon tetrachloride was added, followed by stirring 10 hours to obtain an insoluble matter. The insoluble matter was recovered by filtration and washed with toluene. The resultant mixture was added to the filtrate and evaporated under reduced pressure to obtain a residue. The residue was purified by silica gel column chromatography (eluent: toluene/hexane=100/1), followed by distilling-off of the solvent and addition of methanol to obtain an insoluble matter. The insoluble matter was recovered by filtration to obtain 0.69 g of 2-hexyl-5-(5-cyanopyridine-2-yl)indan (Yield: 36.5%).

Phase transition temperature (°C.)

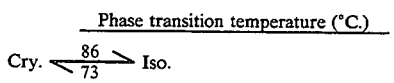

(2) Production of 2-hexyl-5-(5-decanoylpyridine-2-yl)indan

To 0.43 g (17.6M) of magnesium, a solution of 3.50 ml (18.3 mM) of nonyl bromide in 10 ml of anhydrous ether was added dropwise, followed by refluxing for 20 minutes and cooling with ice. Under cooling, a solution of 2.70 g (8.87 mM) of 2-hexyl-5-(5-cyanopyridine-2-yl)indan in 35 ml of anhydrous ether was added dropwise to the above mixture in 10 minutes, followed by washing with 15 ml of anhydrous ether. The resultant mixture was stirred for 1 hour at room temperature and refluxed for 20 minutes. After the reaction, ice was added to the reaction mixture and a sulfuric acid aqueous solution (3 ml of 20% (w/v) sulfuric acid and 4.5 ml of water) was added thereto, followed by stirring at room temperature. After stirring, the above mixture was subjected to extraction with ethyl acetate and washed with saturated common salt aqueous solution, followed by drying with anhydrous sodium sulfate. The sodium sulfate was removed by filtration, the filtrate was subjected to vacuum distillation to obtain a residue. Methanol was added to the residue to obtain an insoluble matter through filtration. The insoluble matter was recrystallized from acetone and purified by silica gel column chromatography (eluent: toluene/ethyl acetate=100/1), followed by recrystallization from ethyl acetate to obtain 2.21 g of 2-hexyl-5-(5-decanoylpyridine-2-yl)indan (Yield: 57.5%).

Phase transition temperature (°C.)

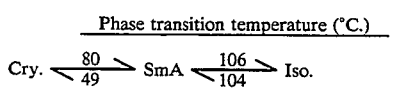

EXAMPLE 59

2-hexyl-5-(5-decylpyridine-2-yl)indan (Ex. Comp. No. I-1085) was synthesized through the following reaction step.

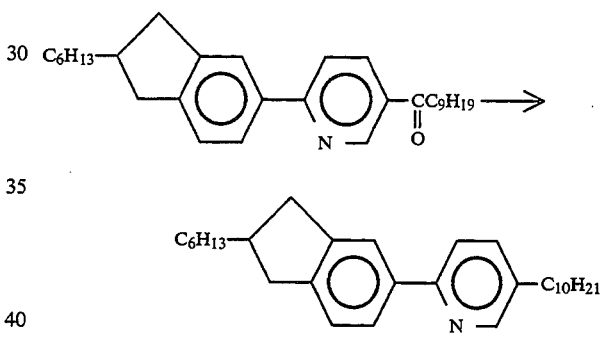

0.50 g (1.15 mM) of 2-hexyl-5-(5-decanoylpyridine-2-yl) indan, 3.5 ml of diethylene glycol, 0.18 ml (2.96 mM) of 80%-hydrazine hydrate (density: 1.03), and 0.23 g (3.48 mM) of 85%-KOH were mixed and heat-stirred for 1 hour at 144°-216° C. After the reaction, the reaction mixture was poured into water, followed by addition of ethyl acetate and saturated common salt aqueous solution and stirring at room temperature to obtain an insoluble matter through filtration under reduced pressure. The insoluble matter was dissolved in toluene and dried with anhydrous sodium sulfate. The filtrate was subjected to extraction with ethyl acetate and washed with saturated common salt aqueous solution, followed by drying with anhydrous sodium sulfate. Each of the sodium sulfate was removed by filtration and each of the filtrate (toluene solution and ethyl acetate solution) was evaporated into a residue. The thus-prepared two-species of residues were mixed and purified by silica gel column chromatography (eluent: toluene), followed by concentration. To the concentrated matter, methanol was added, followed by cooling in a refrigerator. After the cooling, the resultant insoluble matter was recovered by filtration to obtain 0.18 g of 2-hexyl-5-(5-decylpyridine-2-yl)indan (Yield: 37.2%).

Phase transition temperature (°C.)

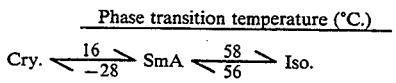

EXAMPLE 60

2-hexyl-5-(5-decyloxypyridine-2-yl)indan (Ex. Comp. No. I-1087) was synthesized through the following reaction steps (1) and (2).

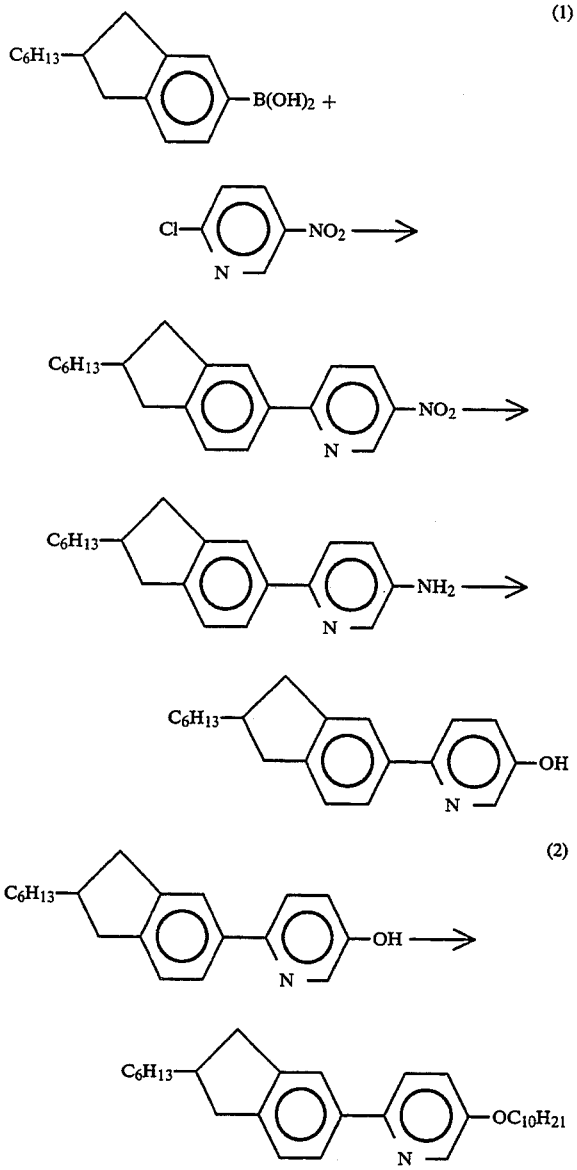

(1) Production of 2-hexyl-5-(5-hydroxypyridine-2-yl)indan 1.00 g (4.06 mM) of 2-hexylindan-5-boronic acid, 0.64 g (4.04 mM) of 2-chloro-5-nitropyrimidine, 5 ml of ethanol, 6 ml of benzene, 5.6 ml of 2M-sodium carbonate aqueous solution and 0.24 g of tetrakis (triphenylphosphine) palladium (O) were mixed and heat-refluxed for 30 minutes under stirring. After the reaction, the reaction mixture was subjected to filtration under reduced pressure to obtain an insoluble matter. The insoluble matter was washed with ethyl acetate and recrystallized from acetone to obtain 1.02 g of 2-hexyl-5-(5-nitropyridine-2-yl)indan (Yield: 77.4%).

Subsequently, 1.01 g (3.11 mM) of 2-hexyl-5-(5-nitropyridine-2-yl)indan, 0.19 g of activated carbon and 0.02 g ferric chloride hexahydrate were mixed and stirred at room temperature. To the mixture, 0.96 ml of 80%-hydrazine hydrate (density: 1.03) was added dropwise, followed by stirring for 40 minutes at 70°–71.5° C. The resultant insoluble matter was removed by filtration and the filtrate was concentrated under reduced pressure, followed by addition of methanol and cooling in a refrigerator to obtain an insoluble matter. The insoluble matter was recovered by filtration to obtain 0.71 g of 2-hexyl-5-(5-aminopyridine-2-yl)indan (Yield: 77.5%).

Then, a solution of 0.70 g (2.38 mM) of 2-hexyl-5-(5-aminopyridine-2-yl)indan in 2 ml of dimethyl sulfoxide (DMSO) was warmed and 2.9 ml of fluoroboric acid (min. 42%) was gradually added dropwise thereto, followed by cooling to 10° C. on a common salt-ice bath. Under stirring, 1.5 g of ice was added to the above mixture. When the temperature of the mixture showed −3° C., 0.21 g of sodium nitrite was added to the above mixture at a stretch, followed by a gradual increase in stirring speed. 2 or 3 minutes later, a yellow crystal was precipitated and the temperature of the mixture was increased to reach 10° C., followed by further stirring for 1 hour at 10° C. The resultant crystal was recovered by filtration and successively washed with 2 ml of 5%-fluoroboric acid solution, cooled methanol and ether, followed by drying to obtain a diazonium fluoroborate derivative.

The diazonium fluoroborate derivative was stirred for 30 minutes on an ice water bath and 30 ml of concentrated sulfuric acid was added dropwise thereto in 12 minutes. The temperature of the mixture was increased to show 57.5° C. Then, the temperature of the mixture was gradually increased to the boiling point thereof and a small amount of ethanol was added thereto, followed by refluxing 30 minutes. After the reaction, the reaction mixture was poured into water and 2M-sodium carbonate aqueous solution was added thereto until the reaction mixture was alkalized (pH≈9), followed by further addition of toluene and ethyl acetate. After stirring at room temperature, the resultant insoluble matter was removed by filtration and the water layer was subjected to extraction with ethyl acetate. The ethyl acetate layer was added to the above organic layer and washed with saturated common salt aqueous solution, followed by distilling-off of the solvent under reduced pressure. An appropriate amount of methanol was added to the resultant residue, followed by cooling for 3 days in a refrigerator. The resultant insoluble matter was removed by filtration and the filtrate was concentrated into a residue. The residue was purified by silica gel column chromatography (eluent: toluene/ethyl acetate=3/1), followed by distilling-off of the solvent and addition of hexane. Under cooling with ice, the resultant crystal was recovered by filtration to obtain 0.148 g of 2-hexyl-5-(5-hydroxypyridine-2-yl)indan (Yield: 21.0%).

(2) Production of 2-hexyl-5-(5-decyloxypyridine-2-yl)indan 0.045 g (0.15 mM) of 2-hexyl-5-(5-hydroxypyridine-2-yl)indan, 0.05 ml (0.23 mM) of decyl iodide, 0.013 g (0.20 mM) of 85%-KOH and 1 ml of n-butanol were mixed and heat-refluxed for 130 minutes under stirring. After the reaction, methanol was added to the reaction mixture, followed by filtration under cooling with ice to obtain an insoluble matter. The insoluble matter was dried and purified by silica gel column chromatography (eluent: toluene/ethyl acetate=100/1), followed by recrystallization from acetone to obtain 0.026 g of 2-hexyl-5-(5-decyloxypyridine-2-yl)indan (Yield: 39.2%).

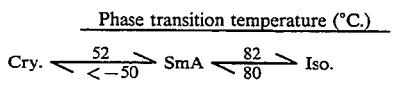

EXAMPLE 61

2-octyl-5-[4-(trans-4-pentylcyclohexyl)phenyl]indan (Ex. Comp. No. I-1313) was synthesized through the following reaction step.

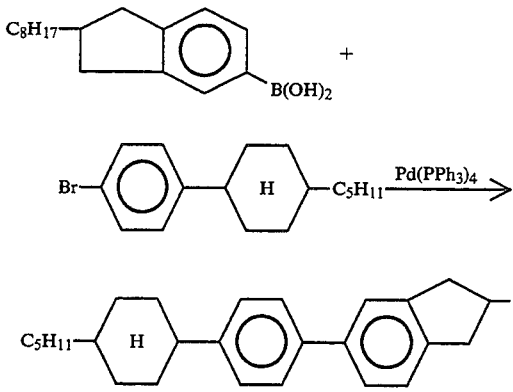

1.78 g (6.5 mM) of 2-octylindan-5-boronic acid, 2.0 g (6.5 mM) of 4-(trans-4-pentylcyclohexy)phenyl bromide, 4 ml of ethanol, 8 ml of benzene, 8 ml of 2M-sodium carbonate aqueous solution and 0.24 g of tetrakis (triphenylphosphine) palladium (O) were mixed and heat-refluxed for 5 hours under stirring. After the reaction, the reaction mixture was poured into ice water, followed by extraction with toluene, washing with water and drying with anhydrous sodium sulfate. Then, the sodium sulfate was removed from the mixture and the resultant mixture was evaporated to obtain a residue. The residue was purified by silica gel column chromatography (eluent: hexane) and recrystallized from a mixture solvent (toluene/methanol) to obtain 1.52 g of 2-octyl-5-[4-(trans-4-pentylcyclohexyl)phenyl]indan (Yield: 51.0%).

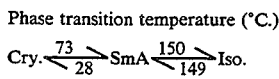

EXAMPLE 62

2-octyl-5-[4-(4-decylphenyl)phenyl]indan (Ex. Comp. No. I-1374) was synthesized through the following reaction steps (1) and (2).

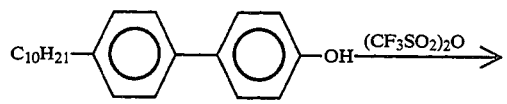

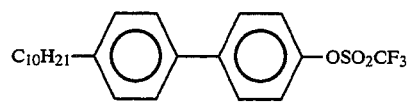

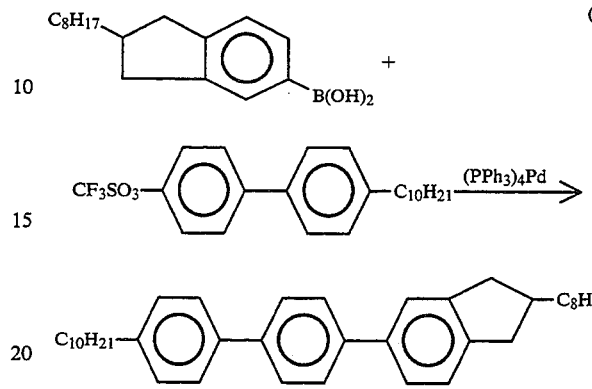

(1) Production of 4-(4-decylphenyl)phenyl trifluoromethanesulfonic ester (or 4-(4-decylphenyl)phenyl triflate)

1.00 g (3.22 mM) of 4-(4-decylphenyl)phenol, 1.6 ml of pyridine were mixed and stirred on a common salt-ice bath. To the mixture, 0.60 ml (3.57 mM) of anhydrous trifluoromethanesulfonic acid was added dropwise and stirred for 18 minutes, followed by further stirring for 70 minutes at room temperature. After the reaction, the reaction mixture was poured into ice water, followed by extraction with isopropyl ether. The isopropyl ether layer was successively washed with a common salt aqueous solution, 12%-HCl and a common salt aqueous solution, followed by drying with anhydrous sodium sulfate. The sodium sulfate was removed by filtration and the filtrate was concentrated into a solid product, whereby 1.41 g of 4-(4-decylphenyl)phenyl triflate (Yield: 98.9%).

(2) Production of 2-octyl-5-[4-(4-decylphenyl)phenyl]indan 0.55 g (2.01 mM of 2-octylindan-5-boronic acid, 0.80 g (1.81 mM) of 4-(4-decylphenyl)phenyl triflate, 1.5 ml of ethanol, 2.8 ml of toluene, 2.8 ml of 2M-sodium carbonate aqueous solution and 0.09 g of tetrakis(triphenylphosphine)palladium (O) were mixed and heat-refluxed for 4 hours under stirring. After the reaction, the reaction mixture, water and toluene were added to followed by filtration under reduced pressure. The toluene layer was washed with a common salt aqueous solution followed by drying with anhydrous sodium sulfate. Then, the sodium sulfate was removed from the mixture and the resultant mixture was evaporated to obtain a residue. Ethyl acetate was added to the residue and cooled with ice water to precipitate a crystal. The crystal was recovered by filtration and purified by silica gel column chromatography (eluent: toluene) and recrystallized from a mixture solvent (toluene/ethyl acetate). The resultant crystal was further purified by silica gel column chromatography (eluent: toluene/hexane=2/1) and recrytallized from a mixture solvent (toluene/hexane) to obtain 0.39 g of 2-octyl-5-[4-(4-decylphenyl)phenyl]indan (Yield: 41.3%).

Phase transition temperature (°C.)

Cry. $\xrightarrow[93]{97}$ Sm3 $\xrightarrow[119]{119}$ SmC $\xrightarrow[125]{126}$ SmA $\xrightarrow[158]{159}$ Iso.

EXAMPLE 63

2-octyl-5-[2-fluoro-4-(5-decylpyrimidine-2-yl)phenyl]indan (Ex. Comp. No. I-1011) was synthesized through the following reaction steps (1) and (2).

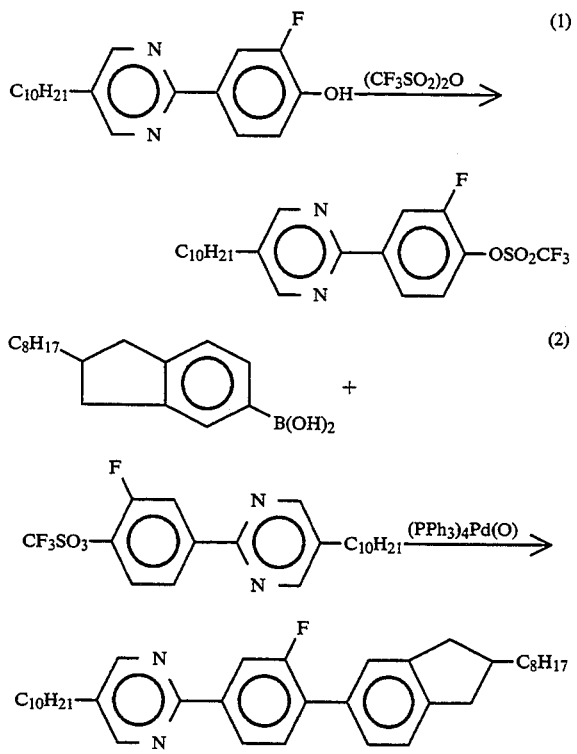

(1) Production of 2-fluoro-4-(5-decylpyrimidine-2-yl)phenyl triflate 1.00 g (3.03 mM) of 2-fluoro-4-(5-decylpyrimidine-2-yl)phenol, 3 ml of pyridine were mixed and stirred on a common salt-ice bath. To the mixture, 1.00 ml (5.94 mM) of anhydrous trifluoromethanesulfonic acid was added dropwise and stirred for 20 minutes, followed by further stirring for 70 minutes at room temperature. After the reaction, the reaction mixture was left standing overnight and then was poured into ice water, followed by extraction with isopropyl ether. The isopropyl ether layer was successively washed with a common salt aqueous solution, 12%-HCl and a common salt aqueous solution, followed by drying with anhydrous sodium sulfate. The sodium sulfate was removed by filtration and the filtrate was concentrated into a solid product, whereby 1.32 g of 2-fluoro-4-(5-decylpyrimidine-2-yl)phenyl triflate (Yield: 94.3%).

(2) Production of 2-octyl-5-[2-fluoro-4-(5-decylpyrimidine-2-yl)phenyl]indan 0.53 g (1.93 mM of 2-octylindan-5-boronic acid, 0.80 g (1.73 mM) of 2-fluoro-4-(5-decylpyrimidine-2-yl)phenyl triflate, 1.5 ml of ethanol, 2.7 ml of toluene, 2.7 ml of 2M-sodium carbonate aqueous solution and 0.09 g of tetrakis (triphenylphosphine) palladium (0) were mixed and heat-refluxed for 130 minutes under stirring. After the reaction, the reaction mixture, water and toluene were added to followed by filtration under reduced pressure. The toluene layer was washed with a common salt aqueous solution followed by drying with anhydrous sodium sulfate. Then, the sodium sulfate was removed from the mixture and the resultant mixture was evaporated to obtain a residue. The residue was purified by silica gel column chromatography (eluent: toluene) and recrystallized from a mixture solvent (toluene/methanol) to obtain 0.81 g of 2-octyl-5-[2-fluoro-4-(5-decylpyrimidine-2-yl)phenyl]indan (Yield: 86.3%).

Phase transition temperature (°C.)

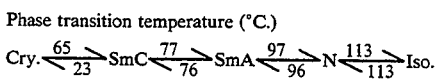

EXAMPLE 64

2-octyl-5-[3-fluoro-4-(5-decylpyrimidine-2-yl)phenyl]indan (Ex. Comp. No. I-1012) was synthesized through the following reaction steps (1) and (2).

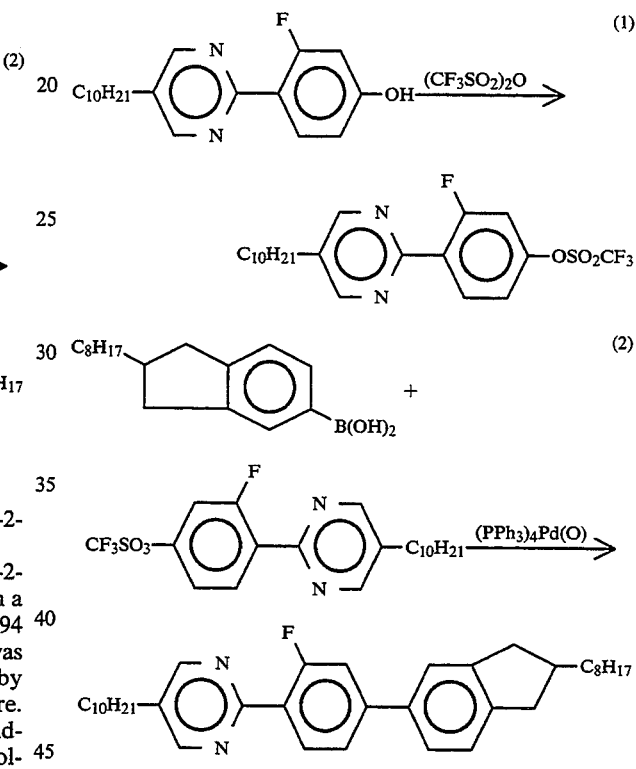

(1) Production of 3-fluoro-4-(5-decylpyrimidine-2-yl)phenyl triflate 1.80 g (2.42 mM) of 3-fluoro-4-(5-decylpyrimidine-2-yl)phenol, 2.42 ml of pyridine were mixed and stirred on a common salt-ice bath. To the mixture, 0.80 ml (4.76 mM) of anhydrous trifluoromethanesulfonic acid was added dropwise and stirred for 20 minutes, followed by further stirring for 140 minutes at room temperature. After the reaction, the reaction mixture was poured into ice water, followed by extraction with isopropyl ether. The isopropyl ether layer was successively washed with a common salt aqueous solution, 12%-HCl and a common salt aqueous solution, followed by drying with anhydrous sodium sulfate. The sodium sulfate was removed by filtration and the filtrate was concentrated into a solid product, whereby 1.11 g of 3-fluoro-4-(5-decylpyrimidine-2-yl)phenyl triflate (Yield: 99.1%).

(2) Production of 2-octyl-5-[3-fluoro-4-(5-decylpyrimidine-2-yl)phenyl]indan 0.40 g (1.46 mM of 2-octylindan-5-boronic acid, 0.60 g (1.30 mM) of 3-fluoro-4-(5-decylpyrimidine-2-yl)phenyl triflate, 1.2 ml of ethanol, 2 ml of toluene, 2 ml of 2M-sodium carbonate aqueous solution and 0.07 g of tetrakis (triphenylphosphine) palladium (O) were mixed and heat-refluxed for 200 minutes under stirring. After the reaction, the reaction mixture, water and toluene were added to followed by filtration under reduced pressure. The toluene layer was washed with a common salt aqueous solution followed by drying with anhydrous sodium sulfate. Then, the sodium sulfate was removed from the mixture and the resultant mixture was evaporated to obtain a residue. The residue was purified by silica gel column chromatography (eluent: toluene/ethyl acetate=100/1) and treated with activated carbon, followed by recrystallization from acetone to obtain 0.52 g of 2-octyl-5-[3-fluoro-4-(5-decylpyrimidine-2-yl)phenyl]indan (Yield: 73.8%).

Phase transition temperature (°C.)

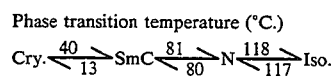

EXAMPLE 65

2-octyl-5-(6-octylpyridazine-3-yl)indan (Ex. Comp. No. I-1768) was synthesized through the following reaction step.

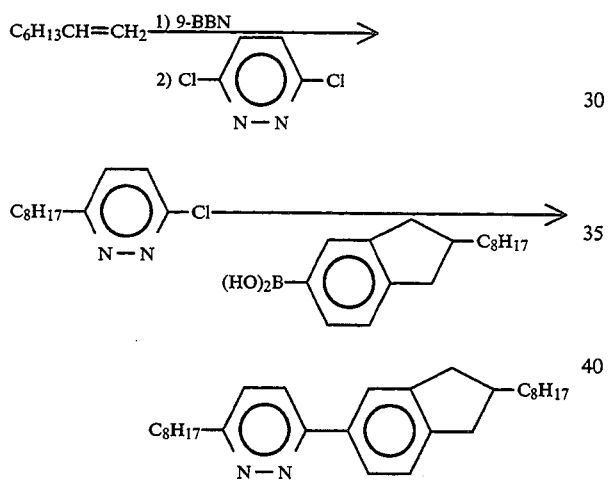

1.12 g (10.0 mM) of 1-octene, 20 ml of a solution of 0.5M-9-borabicyclo[3,3,1]nonane in THF and 5 ml of THF were mixed at 0° C. under nitrogen atmosphere and the temperature of the mixture was gradually increased to room temperature, followed by stirring for 6 hours. Subsequently, 2.2 g (15 mM) of 3,9-dichloropyridazine, 0.31 g of tetrakis (triphenylphosphine)palladium (O), 15 ml of 3M-NaOH aqueous solution and 20 ml of THF were added to the above mixture, followed by heat-refluxed for 3 hours under stirring. After the reaction, 50 ml of benzene was added to the reaction mixture, followed by washing two times with a common salt aqueous solution. After drying, the resultant mixture was concentrated and purified by silica gel column chromatography (eluent: toluene) to obtain 1.60 g (7.06 mM) of 3-chloro-6-octylpyridazine (Yield: 71%).

Then, 0.82 g (3.0 mM) of 2-octylindan-5-boronic acid, 0.68 g (3.0 mM) of 3-chloro-6-octylpyridazine, 2 ml of ethanol, 4 ml of benzene, 4 ml of 2M-sodium carbonate aqueous solution and 0.12 g of tetrakis (triphenylphosphine) palladium (O) were mixed and heat-refluxed for 2 hours under stirring. After the reaction, the reaction mixture was poured into ice water to precipitate a crystal. The crystal was recovered by filtration under reduced pressure and purified by silica gel column chromatography (eluent: toluene) and recrystallized from a mixture solvent (toluene/methanol) to obtain 0.92 g (2.19 mM) of 2-octyl-5-(6-octylpyridazine-3-yl)indan (Yield: 73%).

Phase transition temperature (°C.)

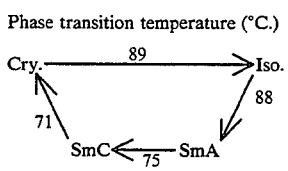

EXAMPLE 66

5,5'-bi-2-octylindan (Ex. Comp. No. I-1664) was synthesized through the following reaction step.

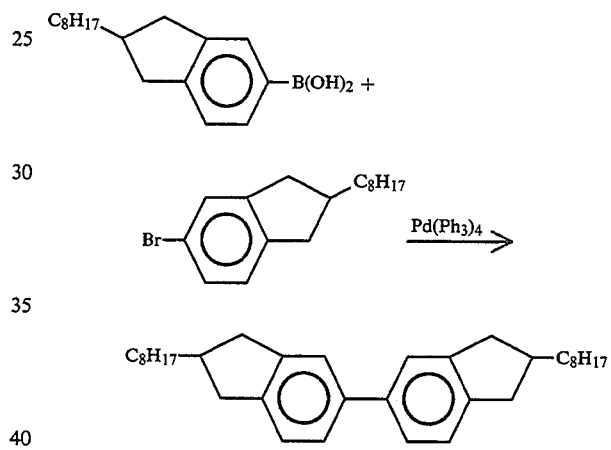

Then, 0.89 g (3.2 mM) of 2-octylindan-5-boronic acid, 1.00 g (3.2 mM) of 5-bromo-2-octylindan, 2 ml of ethanol, 4 ml of benzene, 4 ml of 2M-sodium carbonate aqueous solution and 0.12 g of tetrakis(triphenylphosphine)palladium (O) were mixed and heat-refluxed for 1.5 hours under stirring. After the reaction, the reaction mixture was poured into ice water to precipitate a crystal. The crystal was recovered by filtration under reduced pressure and purified by silica gel column chromatography (eluent: toluene) and recrystallized from a mixture solvent (toluene/methanol) to obtain 1.22 g (2.66 mM) of 5,5'-bi-2-octyl)indan (Yield: 83%).

Phase transition temperature (°C.)

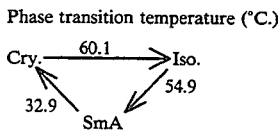

EXAMPLE 67

5,5'-bi-2-hexylindan (Ex. Comp. No. I-1663) was prepared in the same manner as in Example 66 through the following reaction step (Yield: 81%, m.p.=59° C.).

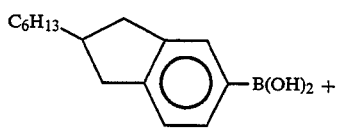

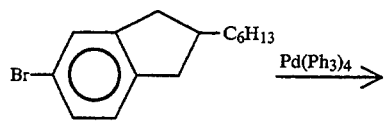

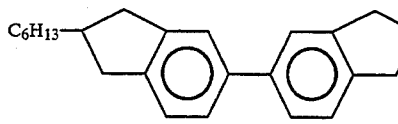

Phase transition temperature (°C.)

Cry. $\underset{44}{\overset{59}{\rightleftarrows}}$ Iso.

EXAMPLE 68

3,6-bis(2-hexylindan-5-yl)pyridazine (Ex. Comp. No. I-1688) was synthesized through the following reaction step.

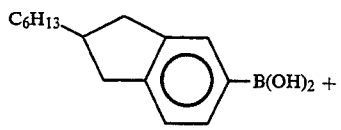

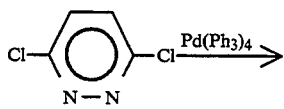

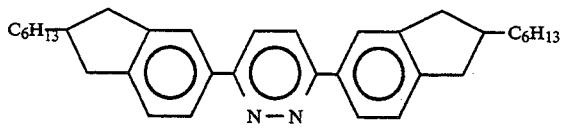

0.74 g (3.0 mM) of 2-hexylindan-5-boronic acid, 0.22 g (1.5 mM) of 3,6-dichloropyridazine, 2 ml of ethanol, 4 ml of benzene, 4 ml of 2M-sodium carbonate aqueous solution and 0.21 g of tetrakis (triphenylphosphine) palladium (O) were mixed and heat-refluxed for 2 hours under stirring. After the reaction, the reaction mixture was poured into ice water to precipitate a crystal. The crystal was recovered by filtration under reduced pressure and purified by silica gel column chromatography (eluent: toluene) and recrystallized from a mixture solvent (toluene/ethyl acetate) to obtain 0.57 g (1.19 mM) of 3,6-bis(2-hexylindan-5-yl)pyridazine (Yield: 79%).

Phase transition temperature (°C.)

Cry. $\underset{111}{\overset{133}{\rightleftarrows}}$ SmC $\underset{165}{\overset{168}{\rightleftarrows}}$ SmA $\underset{177}{\overset{179}{\rightleftarrows}}$ Iso.

EXAMPLE 69

3,6-bis(2-octylindan-5-yl)pyridazine (Ex. Comp. No. I-1694) was prepared in the same manner as in Example 68 through the following reaction step. (Yield: 76%).

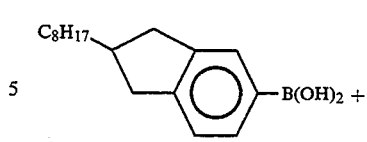

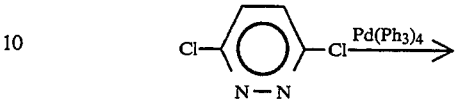

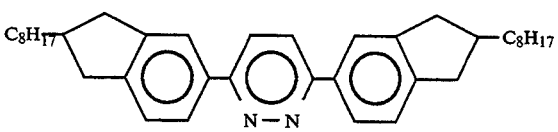

EXAMPLE 70

2,5-bis(2-octylindan-5-yl)thiophene (Ex. Comp. No. I-1708) was synthesized through the following reaction step.

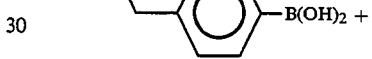

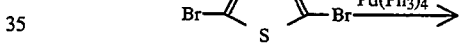

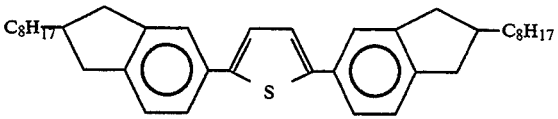

0.82 g (3.0 mM) of 2-octylindan-5-boronic acid, 0.36 g (1.5 mM) of 2,5-dibromothiophene, 2 ml of ethanol, 4 ml of benzene, 4 ml of 2M-sodium carbonate aqueous solution and 0.12 g of tetrakis (triphenylphosphine)palladium (O) were mixed and heat-refluxed for 1 hour under stirring. After the reaction, the reaction mixture was poured into ice water to precipitate a crystal. The crystal was recovered by filtration under reduced pressure and purified by silica gel column chromatography (eluent: hexane/toluene=2/1) and recrystallized from a mixture solvent (toluene/methanol) to obtain 0.74 g (1.37 mM) of 2,5-bis(2-octylindan-5-yl)thiophene (Yield: 91%).

Phase transition temperature (°C.)

Cry. $\underset{59}{\overset{90}{\rightleftarrows}}$ Sm3 $\underset{94}{\overset{95}{\rightleftarrows}}$ SmA $\underset{134}{\overset{136}{\rightleftarrows}}$ Iso.

EXAMPLE 71

2,5-bis(2-pentylindan-5-yl)pyrimidine (Ex. Comp. No. I-1677) was synthesized through the following reaction step.

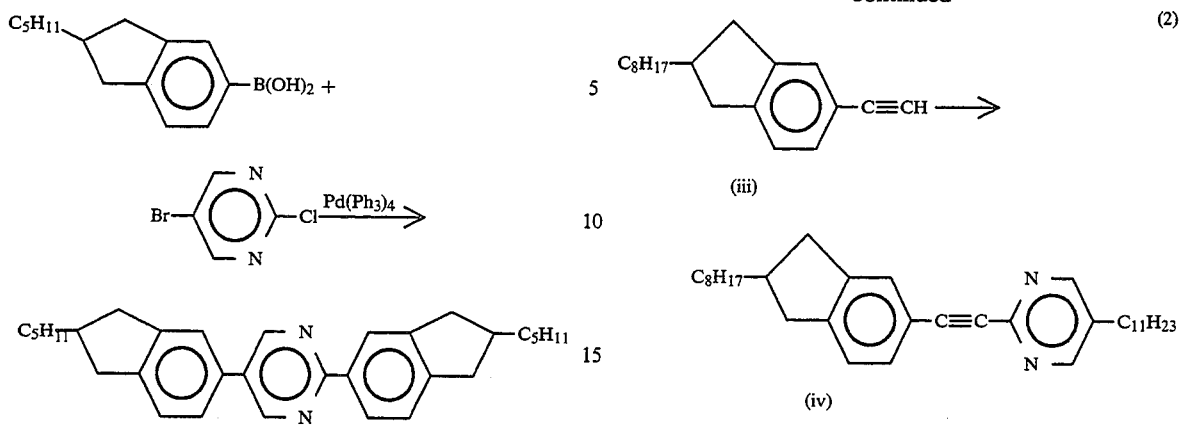

1.0 g (4.3 mM) of 2-pentylindan-5-boronic acid, 0.42 g (2.16 mM) of 5-bromo-2-chloropyrimidine, 4 ml of ethanol, 6 ml of benzene, 6 ml of 2M-sodium carbonate aqueous solution and 0.18 g of tetrakis (triphenylphosphine)palladium (O) were mixed and heat-refluxed for 2 hours under stirring. After the reaction, the reaction mixture was poured into ice water to precipitate a crystal. The crystal was recovered by filtration under reduced pressure and purified by silica gel column chromatography (eluent: toluene) and recrystallized from a mixture solvent (toluene/methanol) to obtain 0.63 g (1.40 mM) of 2,5-bis(2-pentylindan-5-yl)pyrimidine (Yield: 65%).

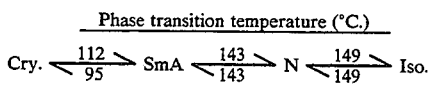

EXAMPLE 72

5-undecylpyrimidine-2-yl-2-octylindan-5-yl ethyne (Ex. Comp. No. I-1460) was synthesized through the following reaction steps (1) and (2).

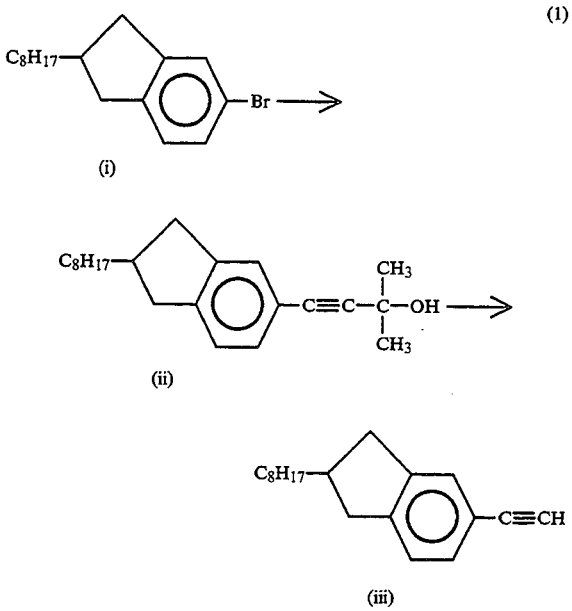

(1) Production of the Compound (iii)

0.88 g (2.85 mM) of 5-bromo-2-octylindan (Compound (i)), 0.33 ml (3.41 mM) of 2-methyl-3-butyne-2-ol, 2.8 ml of triethylamine, 75 mg of tetrakis (triphenylphosphine) palladium (O) and 14 mg of copper (I) iodide were placed in a 20 ml-round bottomed flask and refluxed for 130 minutes under stirring and nitrogen atmosphere. After the reaction, to the reaction mixture, water and isopropyl ether were added. The resultant organic layer was washed with a common salt aqueous solution and dried with anhydrous sodium sulfate, followed by evaporation under reduced pressure to obtain a compound (ii). To the compound (ii), 10 ml of toluene and 0.35 g of NaOH which had been crushed in a mortar were added, followed by refluxing for 1 hour. After the reaction, the reaction mixture was subjected to vacuum distillation to obtain a compound (iii).

(2) Production of 5-undecylpyrimidine-2-yl-2-octylindan (Compound (iv))

75 mg of tetrakis(triphenylphosphine)palladium (O), 15 mg of copper (I) iodide, 0.76 g (2.83 mM) of 2-chloro-5-undecylpyrimidine and 3 ml of triethylamine were added to the above-prepared compound (iii) and refluxed for 2 hours under stirring and nitrogen atmosphere. After the reaction, water and ethyl acetate were added to the reaction mixture. The resultant organic layer was washed with water and dried with anhydrous sodium sulfate, followed by evaporation under reduced pressure. The resultant residue was purified by silica gel column chromatography (eluent: toluene/ethyl acetate=100/1) and recrystallized from a mixture solvent (toluene/methanol) to obtain 5-undecylpyrimidine-2-yl-octylindan.

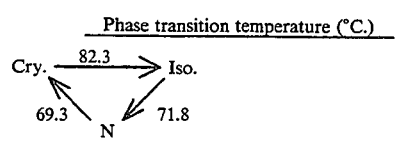

EXAMPLE 73

5-decylpyrimidine-2-yl-2-octylindan-5-yl ethyne (Ex. Comp. No. I-1459) was prepared in the same manner as in Example 73.

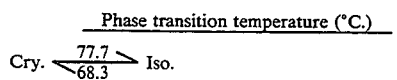

EXAMPLE 74

A liquid crystal composition N was prepared by mixing the following Example Compounds in the indicated proportions with the liquid crystal composition B used in Example 15.

|  | 10° C. | 25° C. | 40° C. |
|---|---|---|---|
| Response time (μsec) | 480 | 238 | 134 |

| Ex. Comp. No. | Structural formula | wt. parts |
|---|---|---|
| I-846 |  | 2 |
| I-1474 | 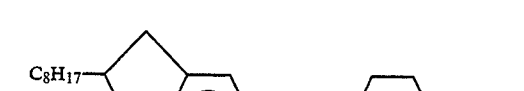 | 2 |
| I-1111 |  | 3 |
| | Composition B | 93 |

A ferroelectric liquid crystal device was prepared in the same manner as in Example 14 except that the above liquid crystal composition N was used, and the device was subjected to measurement of optical response time and observation of switching states. In the device, a monodomain with a good and uniform alignment characteristic was observed. The results of the measurement are shown below.

EXAMPLE 75

A liquid crystal composition O was prepared by mixing the following Example Compounds in the indicated proportions with the liquid crystal composition B used in Example 15.

| Ex. Comp. No. | Structural formula | wt. parts |
|---|---|---|
| I-1379 | 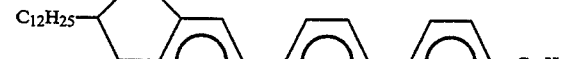 | 1 |
| I-1573 |  | 2 |
| I-1413 |  | 3 |
| | Composition B | 94 |

A ferroelectric liquid crystal device was prepared in the same manner as in Example 14 except that the above liquid crystal composition O was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time (μsec) | 472 | 231 | 130 |

EXAMPLE 76

A liquid crystal composition P was prepared by mixing the following Example Compounds in the indicated proportions with the liquid crystal composition F used in Example 18.

| Ex. Comp. No. | Structural formula | wt. parts |
| --- | --- | --- |
| I-1429 | C$_6$H$_{13}$—[indane]—[pyridazine]—[phenyl]—C$_8$H$_{17}$ | 2 |
| I-1449 | C$_{12}$H$_{25}$—[indane]—C≡C—[fluorophenyl]—OC$_8$H$_{17}$ | 1 |
| I-1776 | C$_{10}$H$_{21}$—[indane]—[pyrimidine]—C$_{12}$H$_{25}$ | 4 |
| Composition F | | 93 |

A ferroelectric liquid crystal device was prepared in the same manner as in Example 14 except that the above liquid crystal composition P was used, and the device was subjected to measurement of optical response time and observation of switching states. In the device, a monodomain with a good and uniform alignment characteristic was observed. The results of the measurement are shown below.

|  | 10° C. | 25° C. | 40° C. |
| --- | --- | --- | --- |
| Response time (μsec) | 422 | 207 | 115 |

EXAMPLE 77

A liquid crystal composition Q was prepared by mixing the following Example Compounds in the indicated proportions with the liquid crystal composition F used in Example 18.

| Ex. Comp. No. | Structural formula | wt. parts |
| --- | --- | --- |
| I-289 | C$_{13}$H$_{27}$—[indane]—[pyridazine]—C$_{11}$H$_{23}$ | 4 |
| I-526 | C$_5$H$_{11}$—[indane]—[pyridazine]—[phenyl]—C$_{10}$H$_{21}$ | 2 |
| I-1483 | C$_{10}$H$_{21}$—[indane]—[phenyl]—C≡C—[pyridazine]—C$_{12}$H$_{25}$ | 1 |
| Composition F | | 93 |

A ferroelectric liquid crystal device was prepared in the same manner as in Example 14 except that the above liquid crystal composition Q was used, and the device was subjected to measurement of optical response time and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 420 | 210 | 120 |

EXAMPLE 78

A liquid crystal composition R was prepared by mixing the following Example Compounds in the indicated proportions with the liquid crystal composition J used in Example 21.

and observation of switching states. In the device, a monodomain with a good and uniform alignment characteristic was observed. The results of the measurement are shown below.

|  | 10° C. | 25° C. | 40° C. |
|---|---|---|---|
| Response time (μsec) | 515 | 264 | 147 |

EXAMPLE 79

A liquid crystal composition S was prepared by mixing the following Example Compounds in the indicated proportions with the liquid crystal composition J used in Example 21.

| Ex. Comp. No. | Structural formula | wt. parts |
|---|---|---|
| I-429 | [structure: $C_{11}H_{23}$–indane–pyrimidine–$OC_9H_{19}$] | 3 |
| I-1324 | [structure: $C_8H_{17}$–indane–difluorophenyl–cyclohexyl–$C_8H_{17}$] | 1 |
| I-1629 | [structure: $C_8H_{17}$–pyrimidine–indane–phenyl–$C_8H_{17}$] | 2 |
| Composition J |  | 94 |

| Ex. Comp. No. | Structural formula | wt. parts |
|---|---|---|
| I-1184 | [structure: $C_8H_{17}$–indane–phenyl–pyridine–$C_4H_9$] | 2 |
| I-1553 | [structure: $C_{10}H_{21}$–indane–$CH_2CH_2$–pyrimidine–$C_{10}H_{21}$] | 3 |
| I-1763 | [structure: $C_9H_{19}$, $C_8H_{17}$–indane–CH=N–N=CH–indane–$C_{10}H_{21}$ with S] | 1 |
| Composition J |  | 94 |

A ferroelectric liquid crystal device was prepared in the same manner as in Example 14 except that the above liquid crystal composition R was used, and the device was subjected to measurement of optical response time A ferroelectric liquid crystal device was prepared in the same manner as in Example 14 except that the above liquid crystal composition S was used, and the device was subjected to measurement of optical response time and observation of switching states. In the device, a monodomain with a good and uniform alignment characteristic was observed. The results of the measurement are shown below.

|                      | 10° C. | 25° C. | 40° C. |
| -------------------- | ------ | ------ | ------ |
| Response time (μsec) | 521    | 274    | 154    |

As apparent from the above Examples 74 to 79, the ferroelectric liquid crystal device containing the liquid crystal compositions N, O, P, Q, R and S according to the present invention provided improved operation characteristic at a lower temperature, high speed responsiveness and a decreased temperature dependence of response speed.

As described hereinabove, according to the present invention, there is provided a mesomorphic compound which can effectively be applied to a liquid crystal device utilizing ferroelectricity when the compound per se assumes a chiral smectic phase. Further, there is also provided a liquid crystal composition containing the compound and assuming a chiral smectic phase, whereby a liquid crystal device comprising the composition can be operated by utilizing ferroelectricity of the composition. The present invention provides a liquid crystal device using such a composition which shows a good switching characteristic, an improved low-temperature operation characteristic and a decreased temperature-dependence of response speed. The present invention further provides a display apparatus and a display method which employ such a device as a display unit, whereby good display characteristics can be obtained in combination with a light source, a drive circuit, etc.

What is claimed is:

1. A mesomorphic compound represented by the following formula (I):

$$R_1-A_1-X_1-A_2-X_2-A_3-R_2 \quad (I),$$

wherein $R_1$ and $R_2$ independently denote hydrogen, halogen,

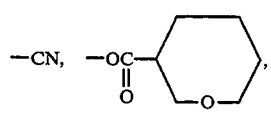

or a linear or branched alkyl group having 1-18 carbon atoms capable of including one or non-neighboring two or more —CH$_2$— groups which can be replaced with

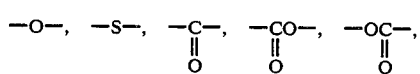

—CH=CH— or —C≡C—, said linear or branched alkyl group being capable of including hydrogen which can be replaced with fluorine;

$X_1$ and $X_2$ independently denote a single bond,

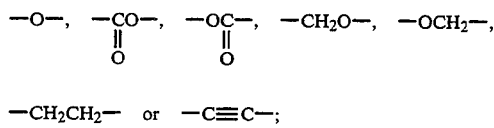

—CH$_2$CH$_2$— or —C≡C—;

$A_1$, $A_2$ and $A_3$ independently denote a single bond,

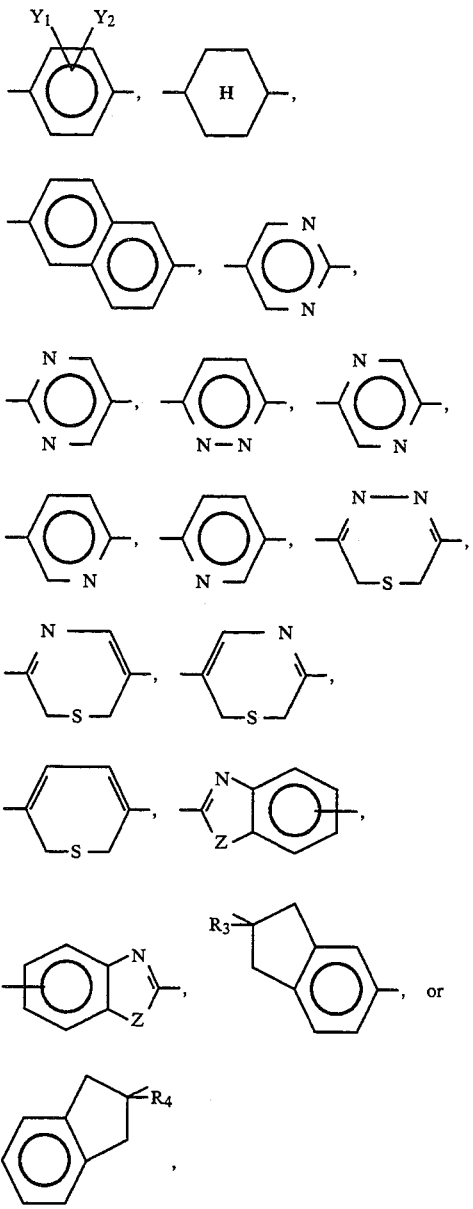

wherein $R_3$ and $R_4$ independently denote hydrogen, halogen, —CN or a linear or branched alkyl group having 1-18 carbon atoms capable of including one or non-neighboring two or more —CH$_2$— groups which can be replaced with

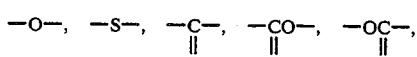

—CH=CH— or —C≡C—, said linear or branched alkyl group being capable of including hydrogen which can be replaced with fluorine; $Y_1$ and $Y_2$ independently denote, H, F, Cl, Br, —$CH_3$, —$CF_3$ or —CN; Z denotes O or S; and at least one of $A_1$, $A_2$ and $A_3$ is

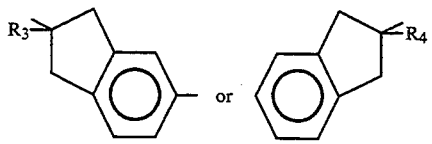

and the remaining two of $A_1$, $A_2$ and $A_3$ cannot be a single bond simultaneously; and
with the proviso that:

(i) —$A_1$—$X_1$—$A_2$—$X_2$—$A_3$— is not

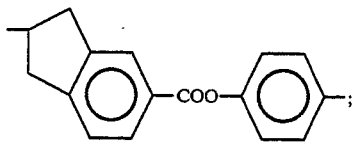

(ii) $X_1$ and $X_2$ are not an ester group simultaneously when $A_1$ is

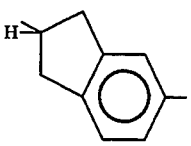

and $A_2$ and $A_3$ are

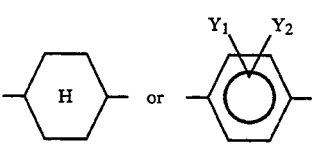

(iii) $X_1$ and $X_2$ are not an ester group simultaneously when $A_3$ is

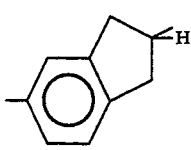

and $A_1$ and $A_2$ are

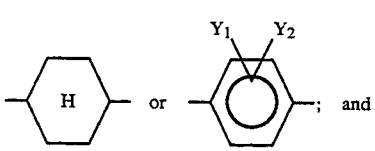

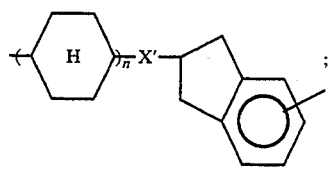

wherein n is 1 or 2 and X' denotes $X_1$ or $X_2$.

2. A mesomorphic compound according to claim 1, which is represented by any one of the following formula (Ia) to (It):

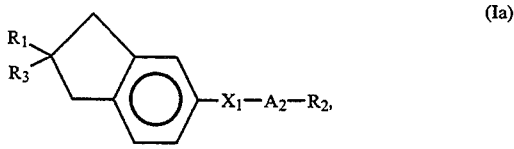 (Ia)

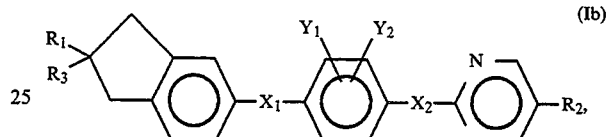 (Ib)

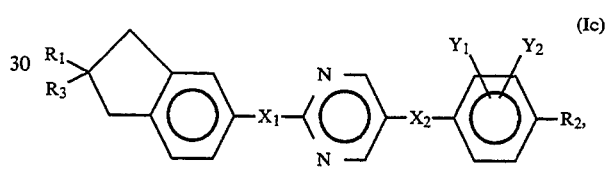 (Ic)

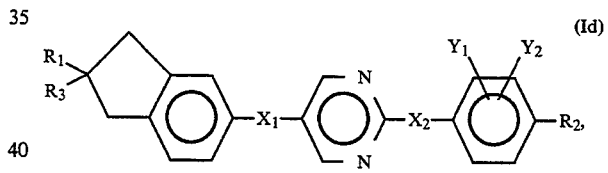 (Id)

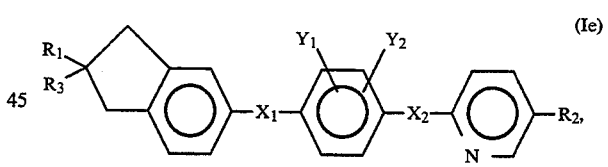 (Ie)

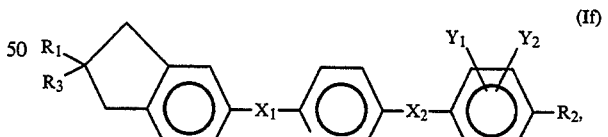 (If)

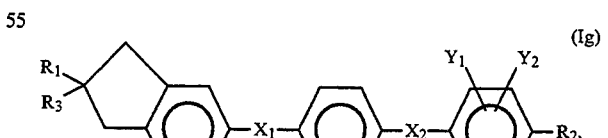 (Ig)

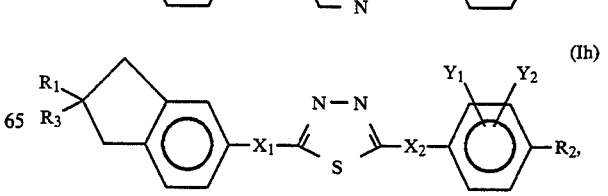 (Ih)

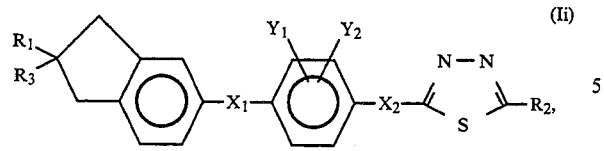 (Ii)

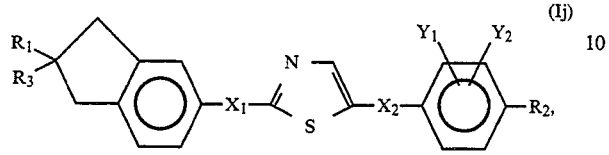 (Ij)

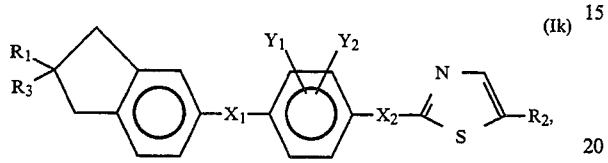 (Ik)

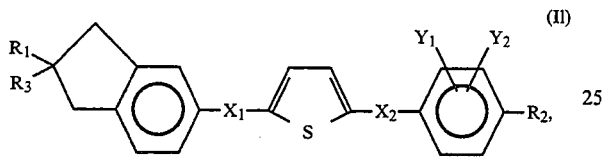 (Il)

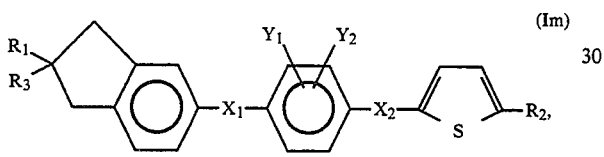 (Im)

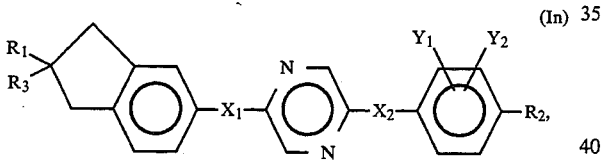 (In)

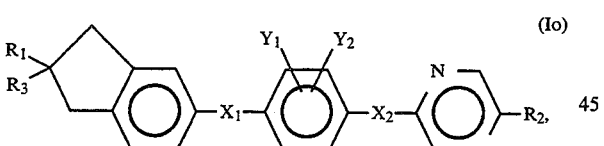 (Io)

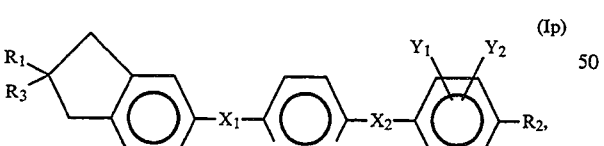 (Ip)

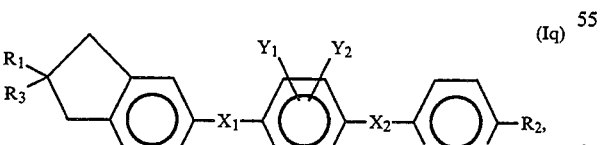 (Iq)

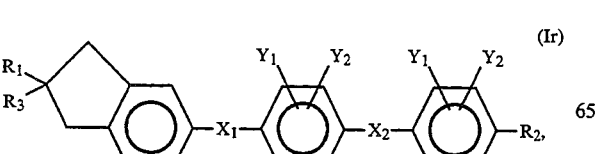 (Ir)

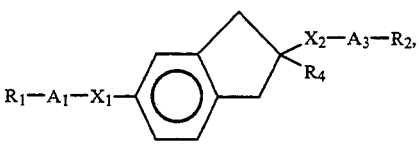 (Is)

and

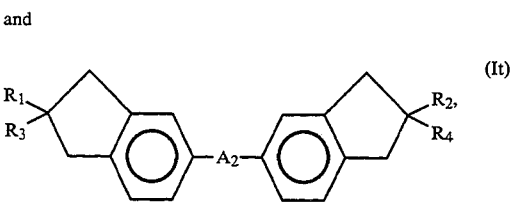 (It)

wherein $R_1$ and $R_2$ independently denote hydrogen, halogen,

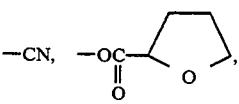

or a linear or branched alkyl group having 1–18 carbon atoms capable of including one or non-neighboring two or more —CH$_2$— groups which can be replaced with

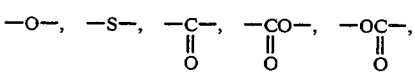

—CH=CH— or —C≡C—, said linear or branched alkyl group being capable of including hydrogen which can be replaced with fluorine;

$X_1$ and $X_2$ independently denote a single bond,

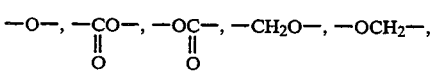

—CH$_2$CH$_2$— or —C≡C—;

$A_1$, $A_2$ and $A_3$ independently denote a single bond

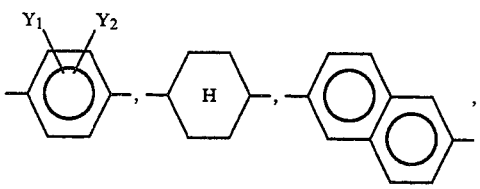

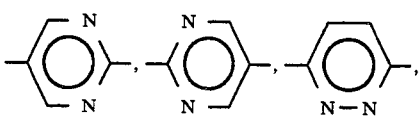

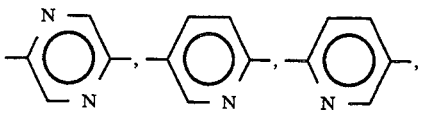

-continued

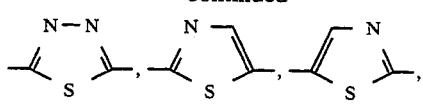

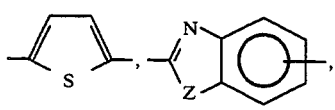

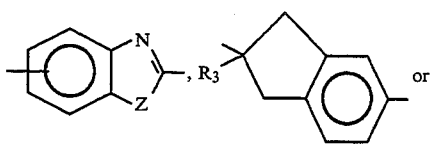

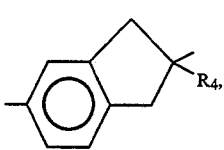

wherein R₃ and R₄ independently denote hydrogen, halogen, —CN or a linear or branched alkyl group having 1-18 carbon atoms capable of including one or non-neighboring two or more —CH₂— groups which can be replaced with

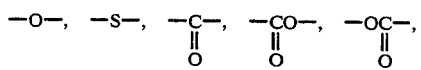

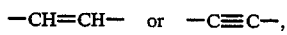

said linear or branched alkyl group being capable of including hydrogen which can be replaced with fluorine; $Y_1$ and $Y_2$ independently denote, H, F, Cl, Br, —CH₃, —CF₃ or —CN; Z denotes O or S; and at least one of $A_1$, $A_2$ and $A_3$ is

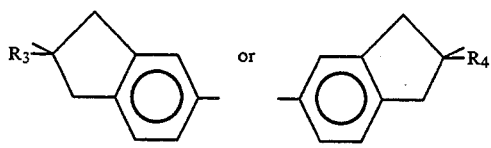

and the remaining two of $A_1$, $A_2$ and $A_3$ cannot be a single bond simultaneously; and
with the proviso that:
(i) —A₁—X₁—A₂—X₂—A₃— is not

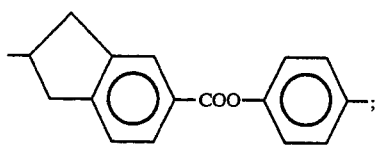

(ii) X₁ and X₂ are not an ester group simultaneously when A₁ is

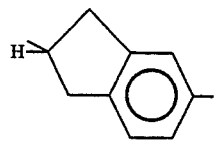

and A₂ and A₃ are

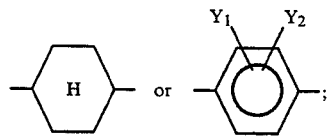

and
(iii) X₁ and X₂ are not an ester group simultaneously when A₃ is

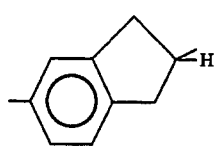

and A₁ and A₂ are

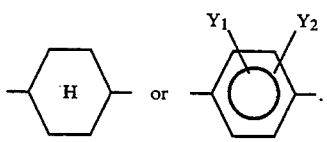

3. A mesomorphic compound according to claim 1, which is represented by any one of the following formulas (Iaa) to (Itg):

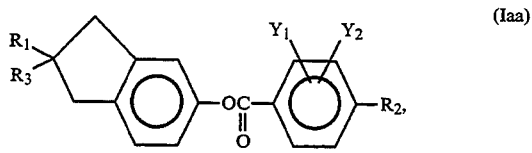
(Iaa)

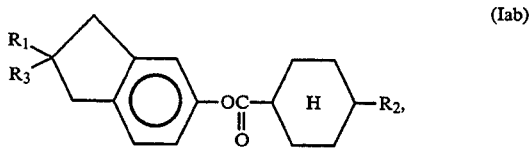
(Iab)

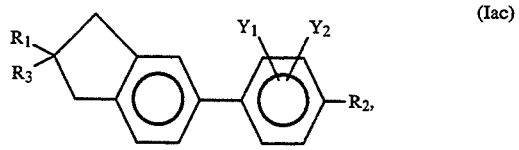
(Iac)

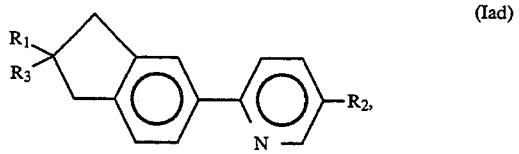
(Iad)

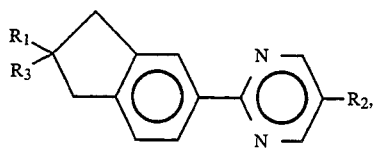 (Iae)
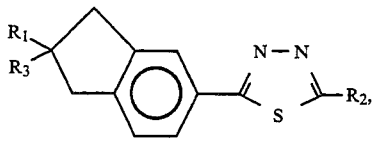 (Iaf)
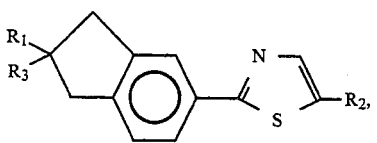 (Iag)
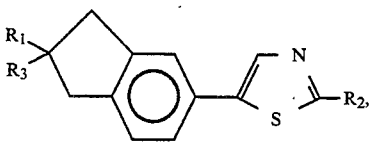 (Iah)
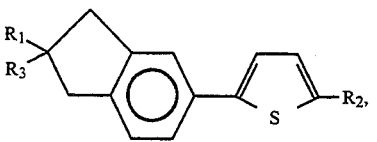 (Iai)
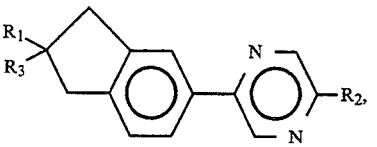 (Iaj)
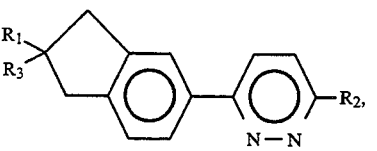 (Iak)
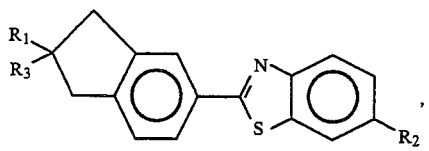 (Ial)
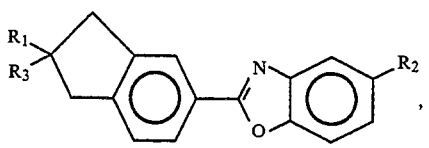 (Iam)
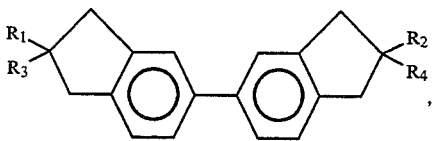 (Ian)
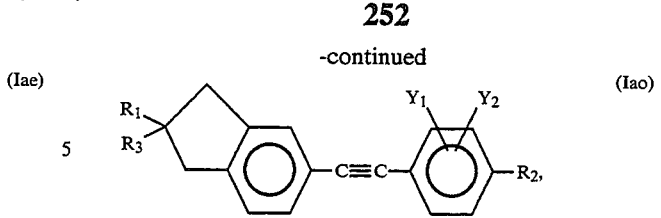 (Iao)
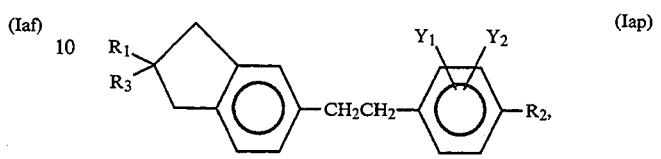 (Iap)
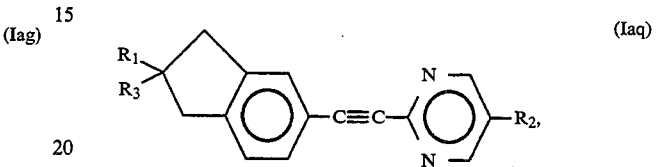 (Iaq)
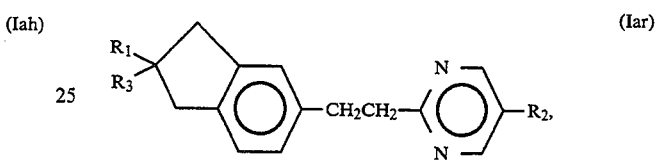 (Iar)
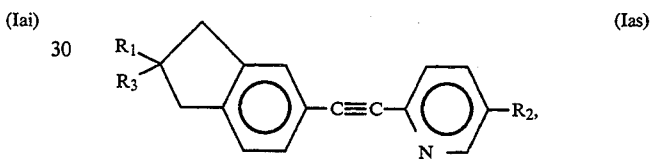 (Ias)
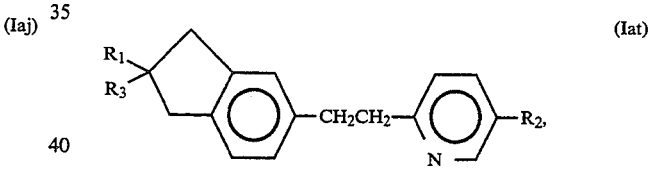 (Iat)
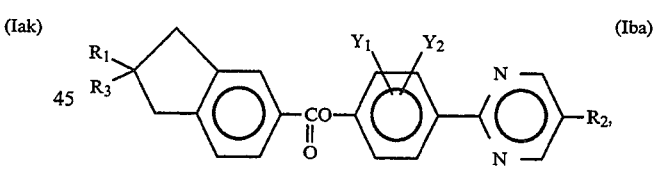 (Iba)
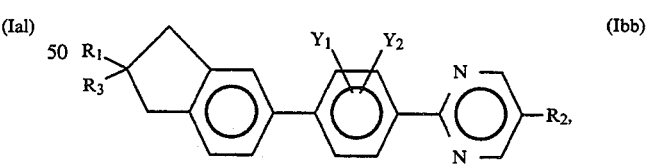 (Ibb)
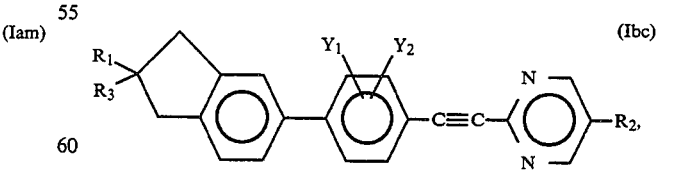 (Ibc)
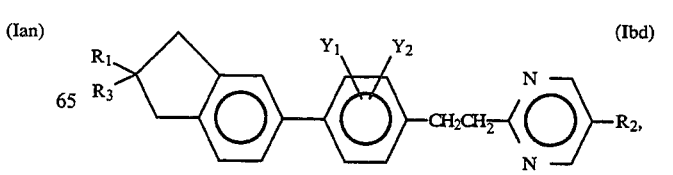 (Ibd)

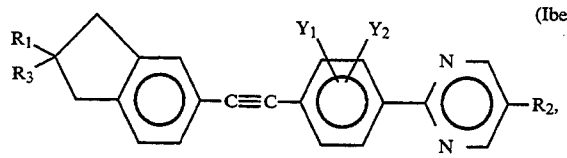 (Ibe)
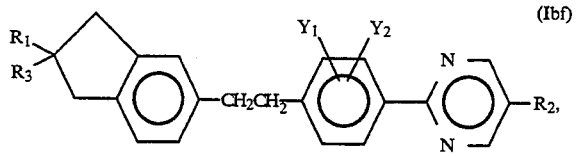 (Ibf)
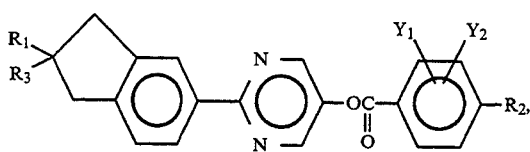 (Ica)
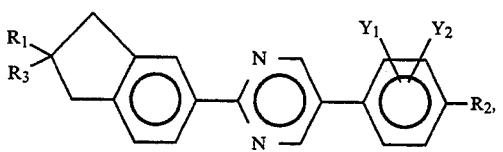 (Icb)
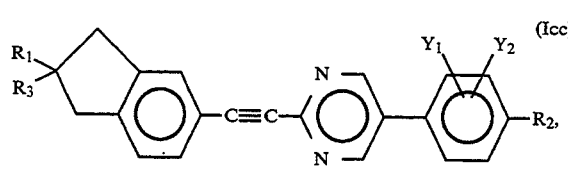 (Icc)
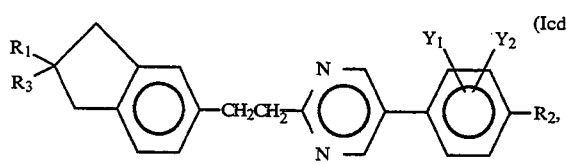 (Icd)
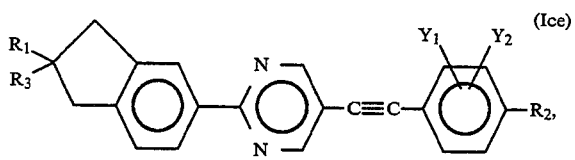 (Ice)
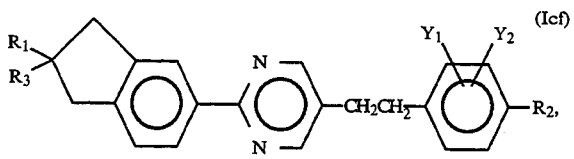 (Icf)
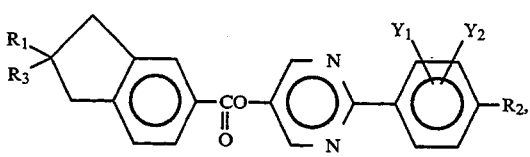 (Ida)
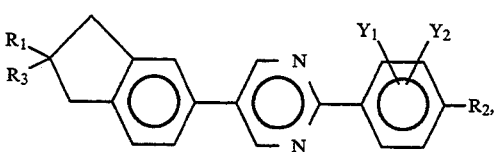 (Idb)
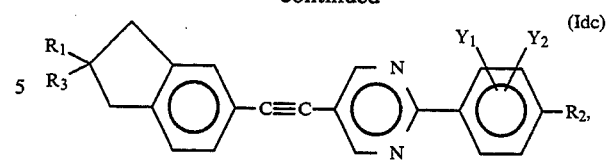 (Idc)
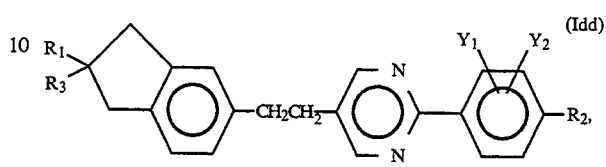 (Idd)
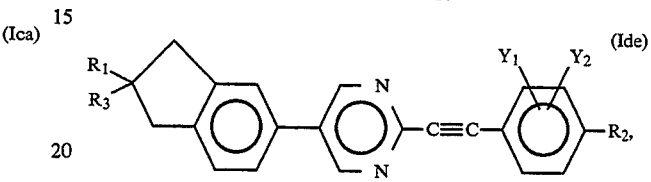 (Ide)
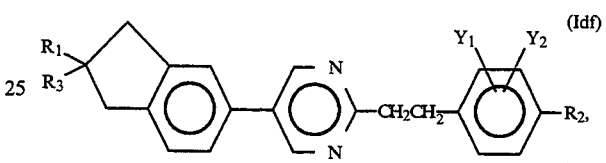 (Idf)
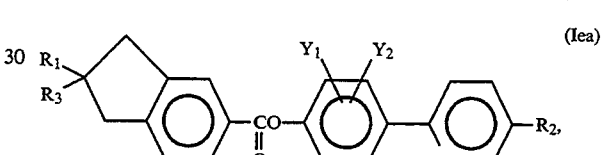 (Iea)
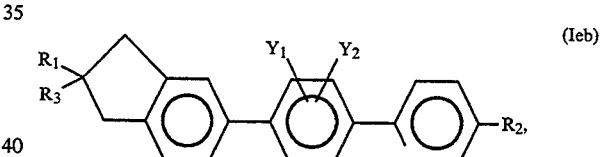 (Ieb)
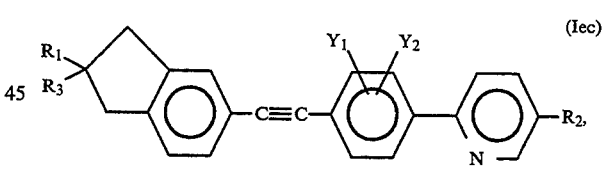 (Iec)
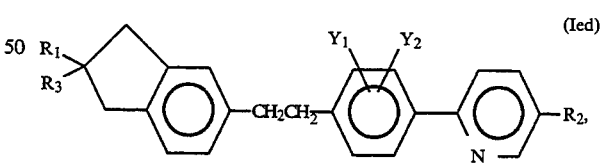 (Ied)
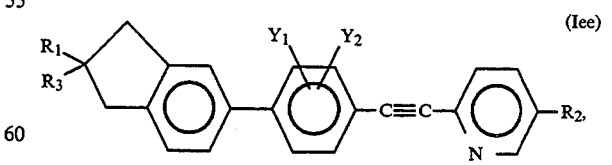 (Iee)
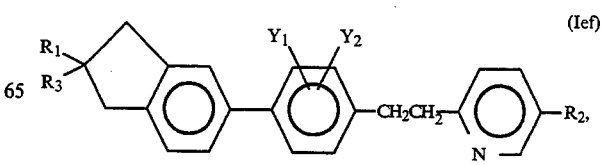 (Ief)

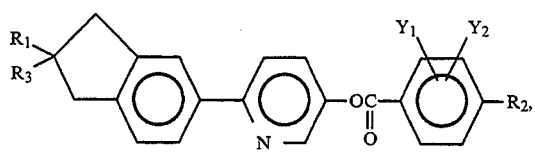
(Ifa)
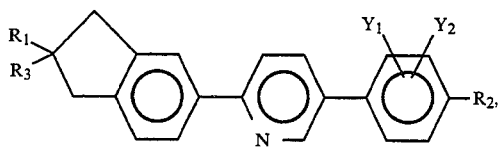
(Ifb)
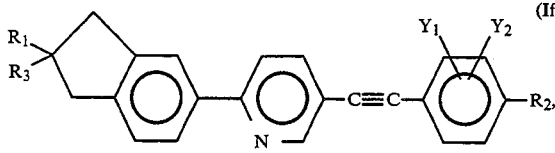
(Ifc)
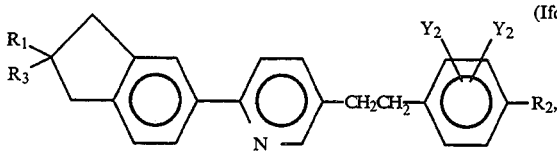
(Ifd)
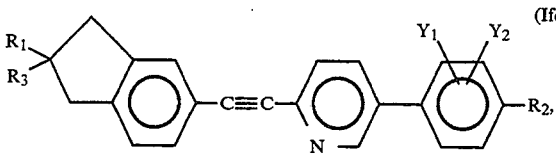
(Ife)
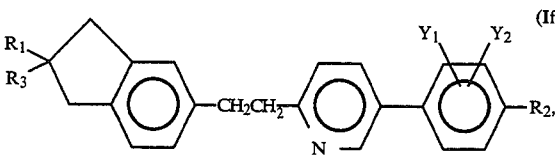
(Iff)
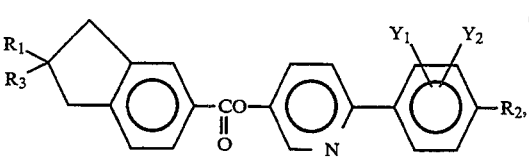
(Iga)
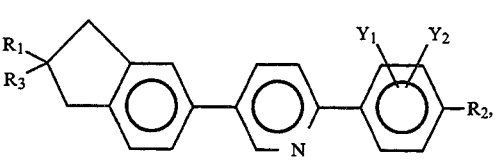
(Igb)
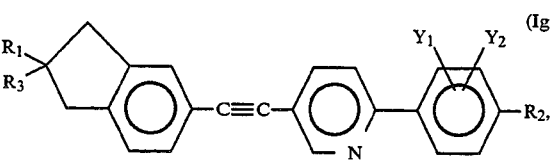
(Igc)
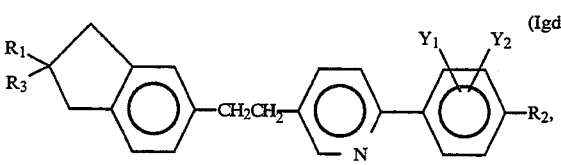
(Igd)
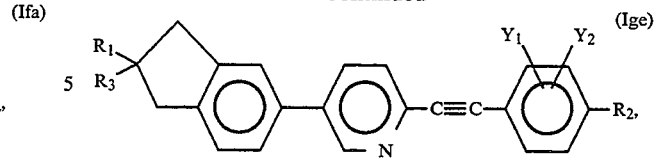
(Ige)
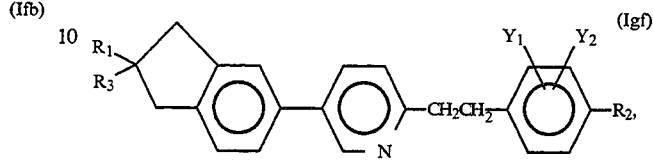
(Igf)
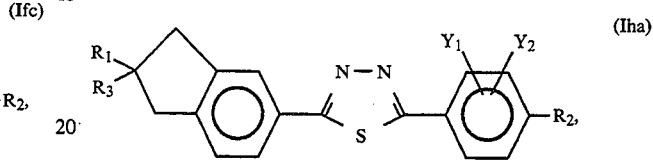
(Iha)
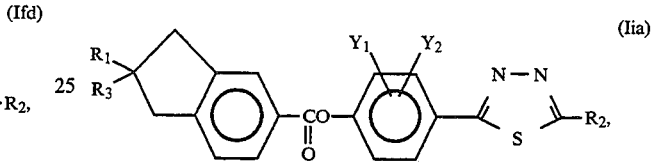
(Iia)
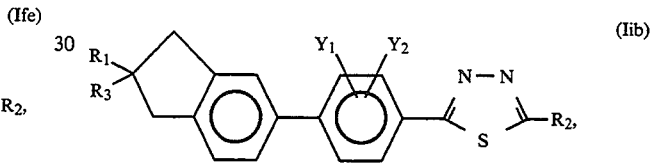
(Iib)
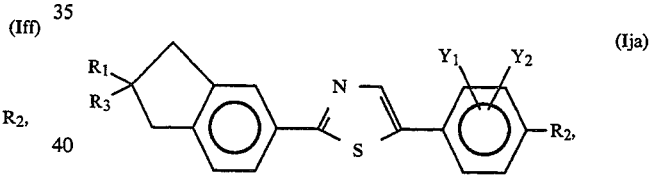
(Ija)
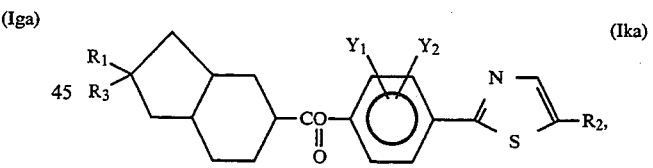
(Ika)
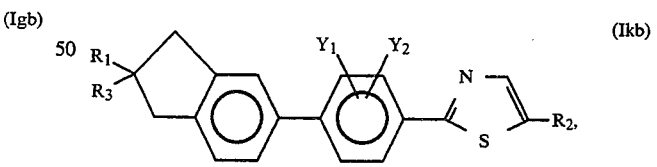
(Ikb)
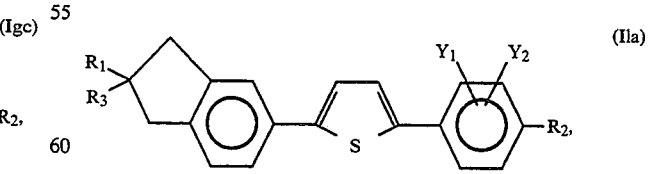
(Ila)
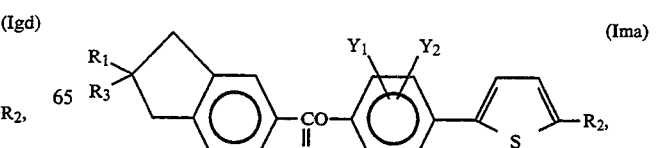
(Ima)

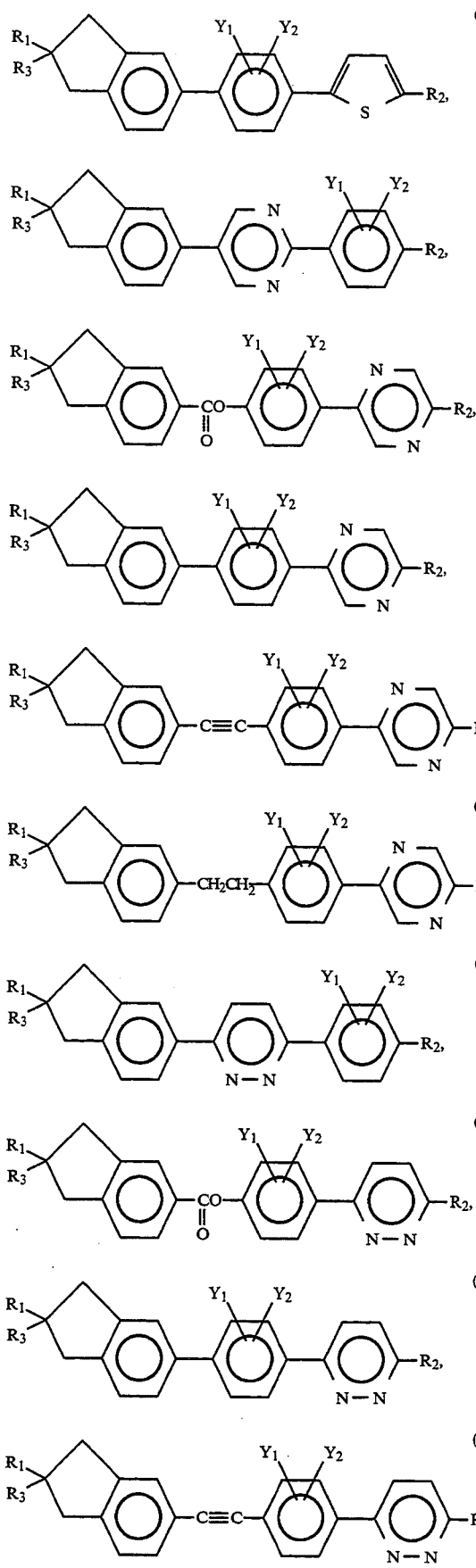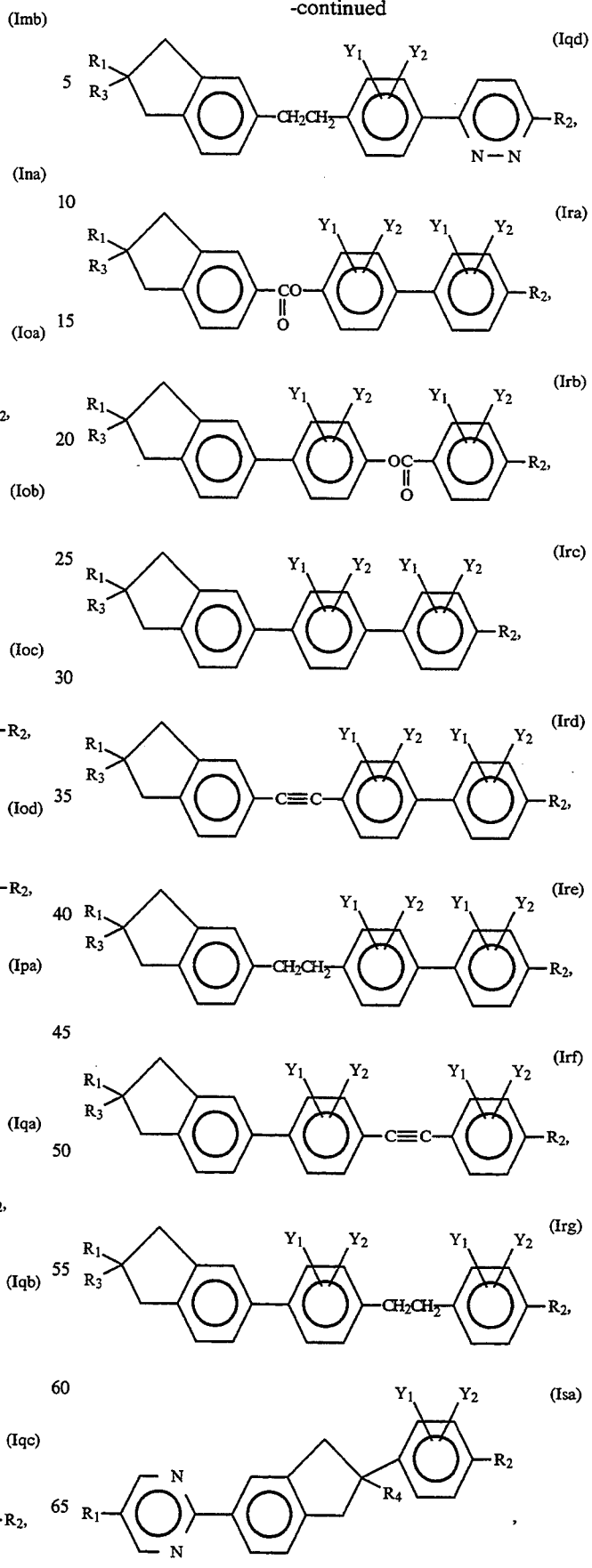

-continued

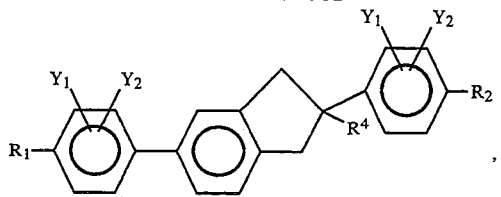 (Isb)

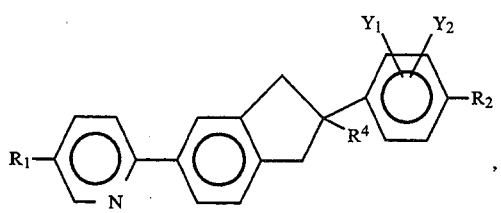 (Isc)

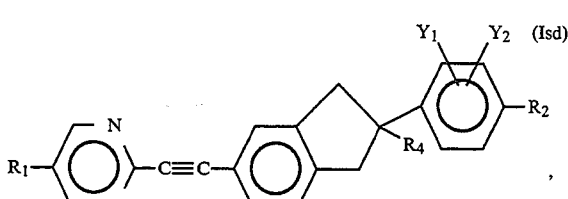 (Isd)

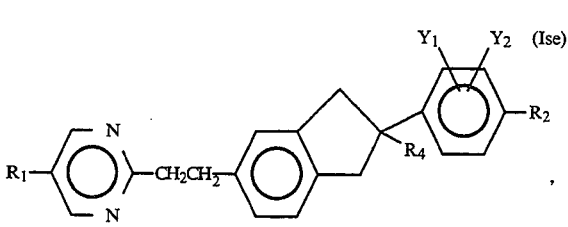 (Ise)

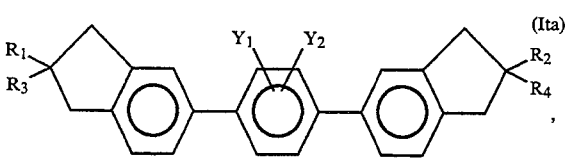 (Ita)

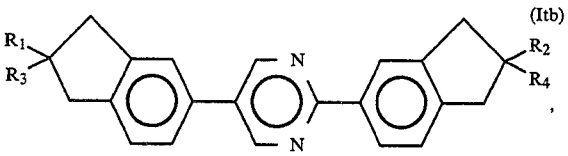 (Itb)

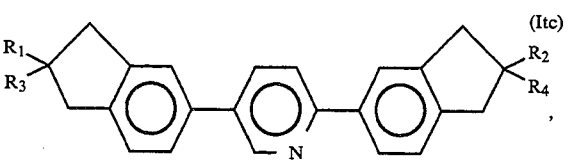 (Itc)

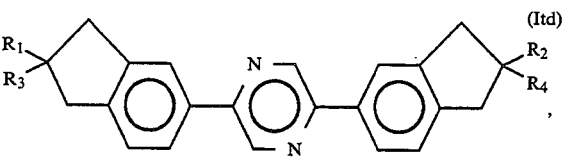 (Itd)

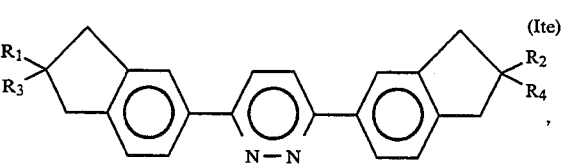 (Ite)

-continued

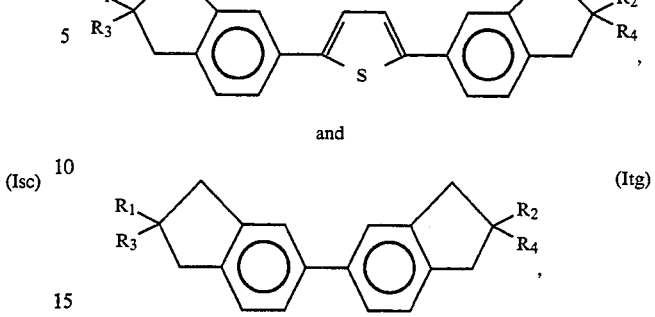 (Itf)

and

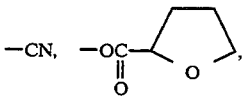 (Itg)

wherein $R_1$ and $R_2$ independently denote hydrogen, halogen

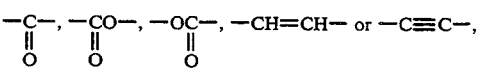

or a linear or branched alkyl group having 1–18 carbon atoms capable of including one or non-neighboring two or more —CH$_2$— groups which can be replaced with —O—, —S—,

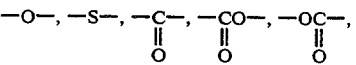

said linear or branched alkyl group being capable of including hydrogen which can be replaced with fluorine;

$R_3$ and $R_4$ independently denote hydrogen, halogen, —CN or a linear or branched alkyl group having 1–18 carbon atoms capable of including one or non-neighboring two or more —CH$_2$— groups which can be replaced with $$-O-, -S-, -\underset{\underset{O}{\|}}{C}-, -\underset{\underset{O}{\|}}{CO}-, -\underset{\underset{O}{\|}}{OC}-,$$

—CH=CH— or —C≡C—, said linear or branched alkyl group being capable of including hydrogen which can be replaced with fluorine; and $Y_1$ and $Y_2$ independently denote, H, F, Cl, Br, —CH$_3$, —CF$_3$ or —CN.

4. A mesomorphic compound according to claim 1, wherein $R_1$ in the formula (I) is represented by any one of the following groups (i) to (vi):

 (i)

 (ii)

 (iii)

 (iv)

-continued

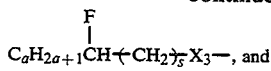

H, (vi)

wherein l is an integer of 1–17; m, r and y is an integer of 0–7; n, t and x is an integer of 1–8, s is 0 or 1, a is an integer of 1–15; and $X_3$ denotes a single bond,

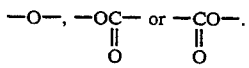

5. A mesomorphic compound according to claim 1, wherein $R_2$ in the formula (I) is represented by any one of the following groups (i) to (vii):

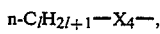 (i)

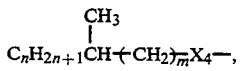 (ii)

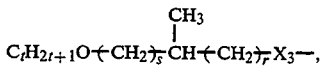 (iii)

$C_xF_{2x+1}(CH_2)_yX_4$, (iv)

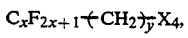 (v)

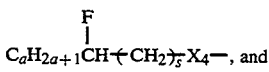 and

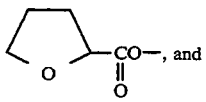 (vi)

F, (vii)

wherein l is an integer of 1–17; m, r and y is an integer of 0–7; n, t and x is an integer of 1–8, s is 0 or 1, a is an integer of 1–15; and $X_4$ denotes a single bond,

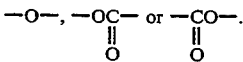

6. A mesomorphic compound according to claim 1, wherein $R_3$ and $R_4$ in the formula (I) are hydrogen.

7. A mesomorphic compound according to claim 1, which is an optically active compound.

8. A mesomorphic compound according to claim 1, which is an optically inactive compound.

9. A liquid crystal composition comprising at least two compounds, at least one of which is mesomorphic compound of the formula (I) according to claim 1.

10. A liquid crystal composition according to claim 9, which comprises 1–80 wt. % of a mesomorphic compound of the formula (I).

11. A liquid crystal composition according to claim 9, which comprises 1–60 wt. % of a mesomorphic compound of the formula (I).

12. A liquid crystal composition according to claim 9, which comprises 1–40 wt. % of a mesomorphic compound of the formula (I).

13. A liquid crystal composition according to claim 9, which has a chiral smectic phase.

14. A liquid crystal device, comprising a pair of electrode plates and a liquid crystal composition according to claim 9 disposed between the electrode plates.

15. A liquid crystal device according to claim 14, which further comprises an insulating alignment control layer.

16. A liquid crystal device according to claim 15, wherein the insulating alignment control layer has been subjected to rubbing.

17. A liquid crystal device according to claim 14, wherein the liquid crystal composition is disposed in a thickness suppressing formation of a helical structure of liquid crystal molecules between the electrode plates.

18. A display apparatus comprising a liquid crystal device according to claim 14, and voltage application means for driving the liquid crystal device.

19. A display apparatus according to claim 18, which further comprises a drive circuit.

20. A display apparatus according to claim 18, which further comprises a light source.

21. A display method, comprising:
providing a liquid crystal composition comprising at least two compounds, at least one of which is a mesomorphic compound of the formula (I) according to claim 1; and
switching the alignment direction of liquid crystal molecules by applying voltages to the liquid crystal composition to effect display.

22. A display method, comprising:
providing a liquid crystal composition comprising at least two compounds, at least one of which is a mesomorphic compound of the formula (I) according to claim 2; and
switching the alignment direction of liquid crystal molecules by applying voltages to the liquid crystal composition to effect display.

23. A display method, comprising:
providing a liquid crystal composition comprising at least two compounds, at least one of which is a mesomorphic compound of the formula (I) according to claim 3; and
switching the alignment direction of liquid crystal molecules by applying voltages to the liquid crystal composition to effect display.

24. A display method, comprising:
providing a liquid crystal composition comprising at least two compounds, at least one of which is a mesomorphic compound of the formula (I) according to claim 4; and
switching the alignment direction of liquid crystal molecules by applying voltages to the liquid crystal composition to effect display.

25. A display method, comprising:
providing a liquid crystal composition comprising at least two compounds, at least one of which is a mesomorphic compound of the formula (I) according to claim 5; and
switching the alignment direction of liquid crystal molecules by applying voltages to the liquid crystal composition to effect display.

26. A display method according to claim 21, wherein $R_3$ and $R_4$ in the formula (I) are hydrogen.

27. A display method according to claim 21, wherein the mesomorphic compound of the formula (I) is an optically active compound.

28. A display method according to claim 21, wherein the mesomorphic compound of the formula (I) is an optically inactive compound.

29. A display method according to claim 21, wherein the liquid crystal composition comprises 1–80 wt. % of a mesomorphic compound of the formula (I).

30. A display method according to claim 21, wherein the liquid crystal composition comprises 1–60 wt. % of a mesomorphic compound of the formula (I).

31. A display method according to claim 21, wherein the liquid crystal composition comprises 1–40 wt. % of a mesomorphic compound of the formula (I).

32. A display method according to claim 21, wherein the liquid crystal composition has a chiral smectic phase.

33. A display method, comprising:
providing a liquid crystal device comprising a pair of electrode plates and a liquid crystal composition disposed therebetween comprising at least two compounds, at least one of which is a mesomorphic compound of the formula (I) according to claim 1; and
switching the alignment direction of liquid crystal molecules by applying voltages to the liquid crystal composition disposed between the electrode plates to effect display.

34. A mesomorphic compound represented by the following formula (II):

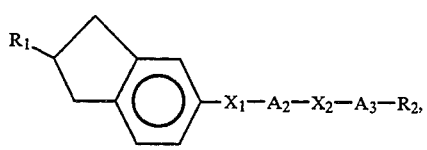

(II)

wherein
$R_1$ and $R_2$ independently denote hydrogen, halogen,

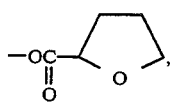

or a linear or branched alkyl group having 1–18 carbon atoms capable of including one or non-neighboring two or more —CH$_2$— groups which can be replaced with

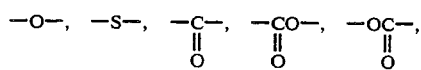

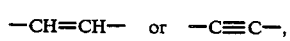

said linear or branched alkyl group being capable of including hydrogen which can be replaced with fluorine;

$X_1$ and $X_2$ independently denote a single bond,

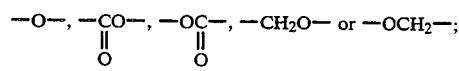

$A_2$ denotes

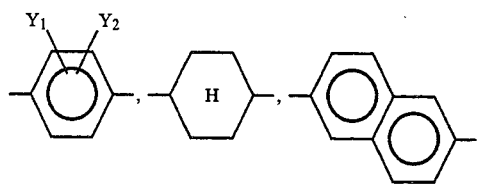

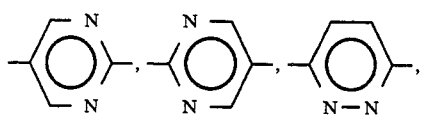

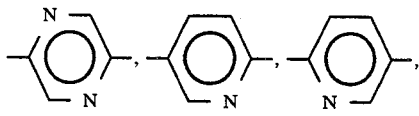

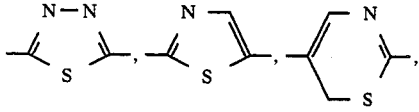

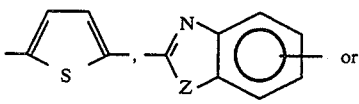

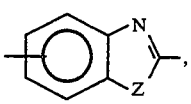

wherein $Y_1$ and $Y_2$ independently denote, H, F, Cl, Br, —CH$_3$, —CF$_3$ or —CN; and Z denotes O or S;
$A_3$ denotes a single bond or $A_2$; and
with the proviso that:
(i) $A_2$ is not

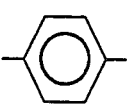

when $X_1$ is —COO— and $A_3$ is a single bond, and
(ii) $X_1$ and $X_2$ are not an ester group simultaneously when $A_2$ and $A_3$ are

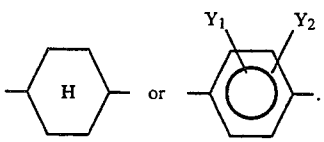

35. A mesomorphic compound represented by the following formula (III):

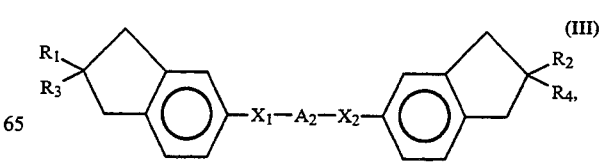

(III)

wherein $R_1$, $R_2$, $R_3$ and $R_4$ independently denote hydrogen, halogen, —CN, or a linear or branched alkyl group having 1-18 carbon atoms capable of including one or non-neighboring two or more —CH$_2$— groups which can be replaced with

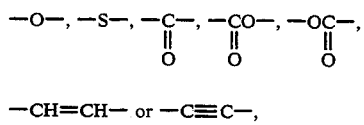

—CH=CH— or —C≡C—, said linear or branched alkyl group being capable of including hydrogen which can be replaced with fluorine;

$X_1$ and $X_2$ independently denote a single bond,

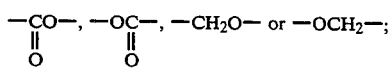

$A_2$ denotes a single bond,

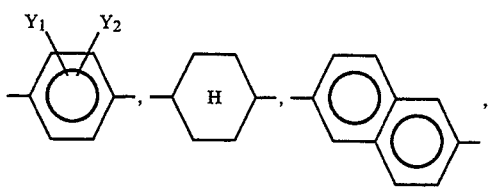

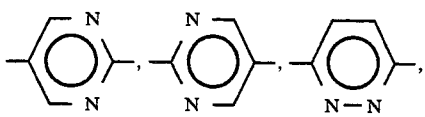

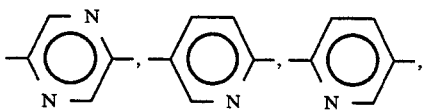

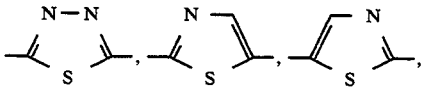

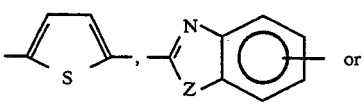

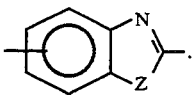

wherein $Y_1$ and $Y_2$ independently denote, H, F, Cl, Br, —CH$_3$, —CF$_3$ or —CN; and Z denotes O or S.

36. A mesomorphic compound represented by the following formula (IV):

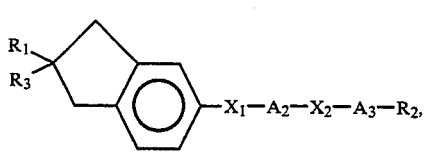

wherein $R_1$ and $R_2$ independently denote hydrogen, halogen,

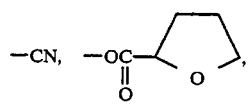

or a linear or branched alkyl group having 1-18 carbon atoms capable of including one or non-neighboring two or more —CH$_2$— groups which can be replaced with

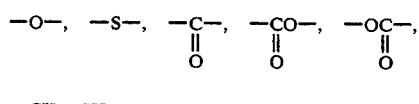

—CH=CH— or —C≡C—, said linear or branched alkyl group being capable of including hydrogen which can be replaced with fluorine;

$R_3$ denotes hydrogen, halogen, —CN, or a linear or branched alkyl group having 1-18 carbon atoms;

$X_1$ and $X_2$ independently denote a single bond,

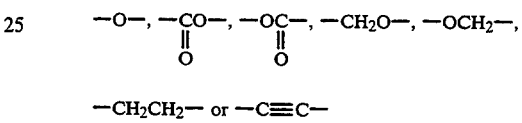

—CH$_2$CH$_2$— or —C≡C— with the proviso that at least one species of $X_1$ and $X_2$ is —C≡C—;

$A_2$ denotes

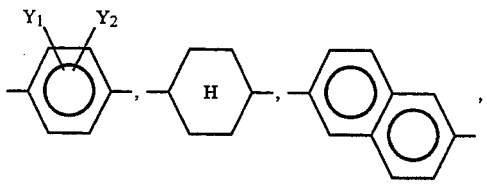

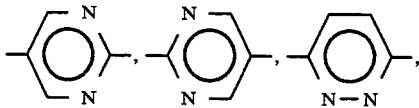

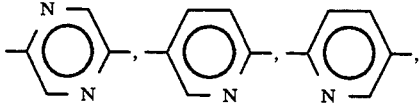

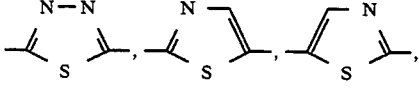

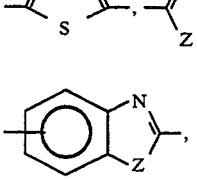

or wherein $Y_1$ and $Y_2$ independently denote, H, F, Cl, Br, —CH$_3$, —CF$_3$ or —CN; and Z denotes O or S; and $A_3$ denotes a single bond or $A_2$.

* * * * *

UNITED STATES PATENT AND TRADEMARK OFFICE
CERTIFICATE OF CORRECTION

PATENT NO. : 5,385,692
DATED : January 31, 1995
INVENTOR(S) : TAKASHI IWAKI, ET AL.

It is certified that error appears in the above-indentified patent and that said Letters Patent is hereby corrected as shown below:

TITLE PAGE

[30] Foreign Application Priority Data

"Nov. 12, 1991  [JP]  Japan ........2-95684
     Oct. 30, 1992  [JP]  Japan ........3-16329" should read --Nov. 12, 1991  [JP]  Japan ........3-295684
     Oct. 30, 1992  [JP]  Japan ........4-316329--.

[56] References Cited

FOREIGN PATENT DOCUMENTS, "079647  6/1981  Japan
                                           083448  7/1981  Japan
                                           069055  4/1985  Japan" should be deleted.

[57] Abstract

Line 2, "for" should read --for a--.

COLUMN 3

Line 34, "an" should read --a--; and

Line 43, "particularly" should read --particularly,--.

COLUMN 7

Line 4, "examples-of" should read --examples of--.

UNITED STATES PATENT AND TRADEMARK OFFICE
CERTIFICATE OF CORRECTION

PATENT NO. : 5,385,692
DATED : January 31, 1995
INVENTOR(S) : TAKASHI IWAKI, ET AL.

It is certified that error appears in the above-indentified patent and that said Letters Patent is hereby corrected as shown below:

COLUMN 17

In (Ika) " 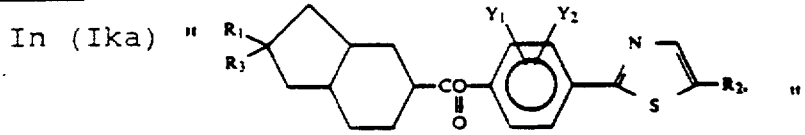 "

should read -- 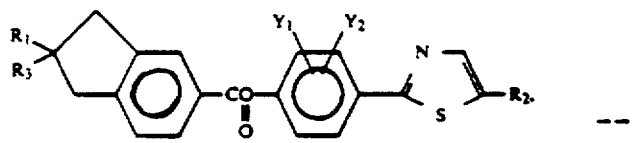 --

COLUMN 26

Line 55, "denotes" should read --denote--.

COLUMN 71

In (I-615) " 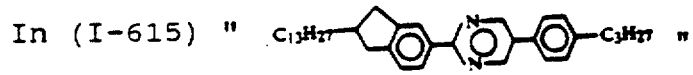 "

should read --  --

UNITED STATES PATENT AND TRADEMARK OFFICE
CERTIFICATE OF CORRECTION

PATENT NO. : 5,385,692
DATED : January 31, 1995
INVENTOR(S) : TAKASHI IWAKI, ET AL.

It is certified that error appears in the above-indentified patent and that said Letters Patent is hereby corrected as shown below:

COLUMN 130

Formula (I-1492), "  "

should read

COLUMN 134

Formula (I-1543), " 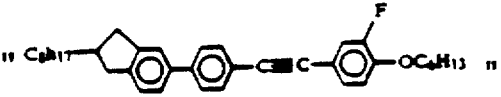 "

should read

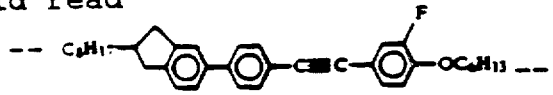

COLUMN 141

Formula (I-1652), " 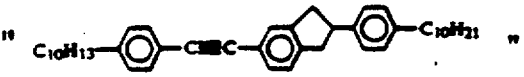 "

should read

UNITED STATES PATENT AND TRADEMARK OFFICE
CERTIFICATE OF CORRECTION

PATENT NO. : 5,385,692
DATED : January 31, 1995
INVENTOR(S) : TAKASHI IWAKI, ET AL.

It is certified that error appears in the above-indentified patent and that said Letters Patent is hereby corrected as shown below:

COLUMN 150

Line 55, "g+h 0" should read --g+h=0--.

COLUMN 167

Line 62, "(XVI) and (XVI)" should read --(XVIa) and (XVIb)--.

COLUMN 173

Line 65, "time" should read --times--.

COLUMN 176

Line 15, "minute." should read --minutes.--; and

Line 62, "both." should read --bath.--.

COLUMN 188

Line 21, "Structure" should read --Structural--.

COLUMN 209

Line 33, "149" should read --152--.

COLUMN 210

Line 6, "A ferroelectric-" should read --Ferroelec- --.

UNITED STATES PATENT AND TRADEMARK OFFICE
CERTIFICATE OF CORRECTION

PATENT NO. : 5,385,692
DATED : January 31, 1995
INVENTOR(S) : TAKASHI IWAKI, ET AL.

It is certified that error appears in the above-indentified patent and that said Letters Patent is hereby corrected as shown below:

COLUMN 228

Line 48, "to" should be deleted.

COLUMN 229

Line 63, "to" should be deleted.

COLUMN 231

Line 5, "to" should be deleted.

COLUMN 234

Line 20, beneath "EXAMPLE 70" add

--Phase transition temperature (°C.)

Cry. $\underset{107}{\overset{123}{\rightleftarrows}}$ SmC $\underset{168}{\overset{170}{\rightleftarrows}}$ SmA $\underset{174}{\overset{175}{\rightleftarrows}}$ Iso.--

COLUMN 245

Line 65, "and" should read --and
¶ (iv) - $A_1$ -$X_1$ -$A_2$ - $X_2$ -$A_3$ is not--.

UNITED STATES PATENT AND TRADEMARK OFFICE
CERTIFICATE OF CORRECTION

PATENT NO. : 5,385,692
DATED : January 31, 1995
INVENTOR(S) : TAKASHI IWAKI, ET AL.

It is certified that error appears in the above-indentified patent and that said Letters Patent is hereby corrected as shown below:

COLUMN 256
  Line 45, Formula (Ika), " 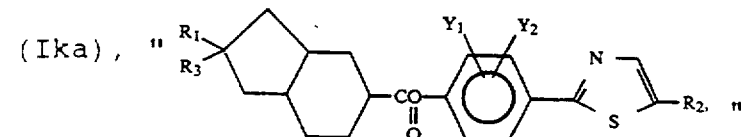

should read -- 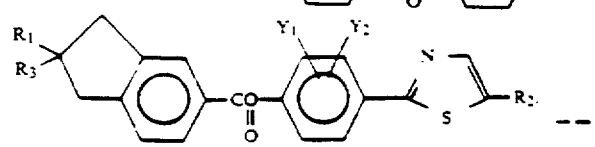 --

COLUMN 262
  Line 3, "claim 9" should read --claim 9,--.

Signed and Sealed this

Thirteenth Day of June, 1995

*Attest:*

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,385,692

DATED : January 31, 1995

INVENTORS : TAKASHI IWAKI, ET AL.

It is certified that error appears in the above-identified patent and that said Letters Patent is hereby corrected as shown below:

Column 243, line 50, change "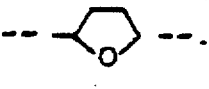" to --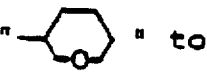--.

Column 244, lines 30-40, change "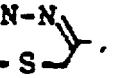, , , " to --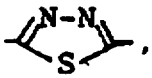, , 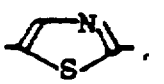, 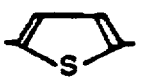--.

Signed and Sealed this

Third Day of October, 1995

Attest:

BRUCE LEHMAN

*Attesting Officer*     *Commissioner of Patents and Trademarks*